(12) United States Patent
Cochran et al.

(10) Patent No.: US 6,221,361 B1
(45) Date of Patent: Apr. 24, 2001

(54) RECOMBINANT SWINEPOX VIRUS

(75) Inventors: Mark D. Cochran, Carlsbad; David E. Junker, San Diego, both of CA (US)

(73) Assignee: Syntro Corporation, Lenexa, KS (US)

(*) Notice: Subject to any disclaimer, the term of this patent is extended or adjusted under 35 U.S.C. 154(b) by 0 days.

(21) Appl. No.: 08/686,968

(22) Filed: Jul. 25, 1996

Related U.S. Application Data

(63) Continuation-in-part of application No. PCT/US96/01485, filed on Jan. 19, 1996, which is a continuation-in-part of application No. 08/472,679, filed on Jun. 7, 1995, and a continuation-in-part of application No. 08/488,237, filed on Jun. 7, 1995, and a continuation-in-part of application No. 08/480,640, filed on Jun. 7, 1995, now Pat. No. 6,033,904, which is a continuation-in-part of application No. 08/375,992, filed on Jan. 19, 1995, said application No. 08/472,679, is a continuation-in-part of application No. 08/375,992, filed on Jan. 19, 1995, said application No. 08/488,237, is a continuation-in-part of application No. 08/375,992, filed on Jan. 19, 1995, said application No. 08/480,640, is a continuation-in-part of application No. 08/375,992.

(51) Int. Cl.[7] .......................... A61K 39/275; C12N 7/01; C12N 15/86

(52) U.S. Cl. ..................................... 424/199.1; 435/320.1; 435/235.1; 424/232.1

(58) Field of Search .............................. 435/235.1, 320.1; 424/199.1, 232.1; 935/68

(56) References Cited

PUBLICATIONS

Massung et al, Virology 197:511–528, 1993.*

* cited by examiner

*Primary Examiner*—Mary E. Mosher
(74) *Attorney, Agent, or Firm*—John P. White; Cooper & Dunham LLP

(57) ABSTRACT

This invention provides a recombinant swinepox virus comprising a foreign DNA inserted into a swinepox virus genomic DNA, wherein the foreign DNA is inserted into an EcoRI site within the approximately 3.2 Kb subfragment of the HindIII K fragment of the swinepox virus genomic DNA and is capable of being expressed in a swinepox virus infected host cell. The invention further provides a recombinant swinepox virus designated S-SPV-120, S-SPV-121, S-SPV-122, S-SPV-127, and S-SPV-128. The invention further provides vaccines and methods of immunization of the recombinant swinepox virus.

44 Claims, 55 Drawing Sheets

FIGURE 2B

Figure 1A:
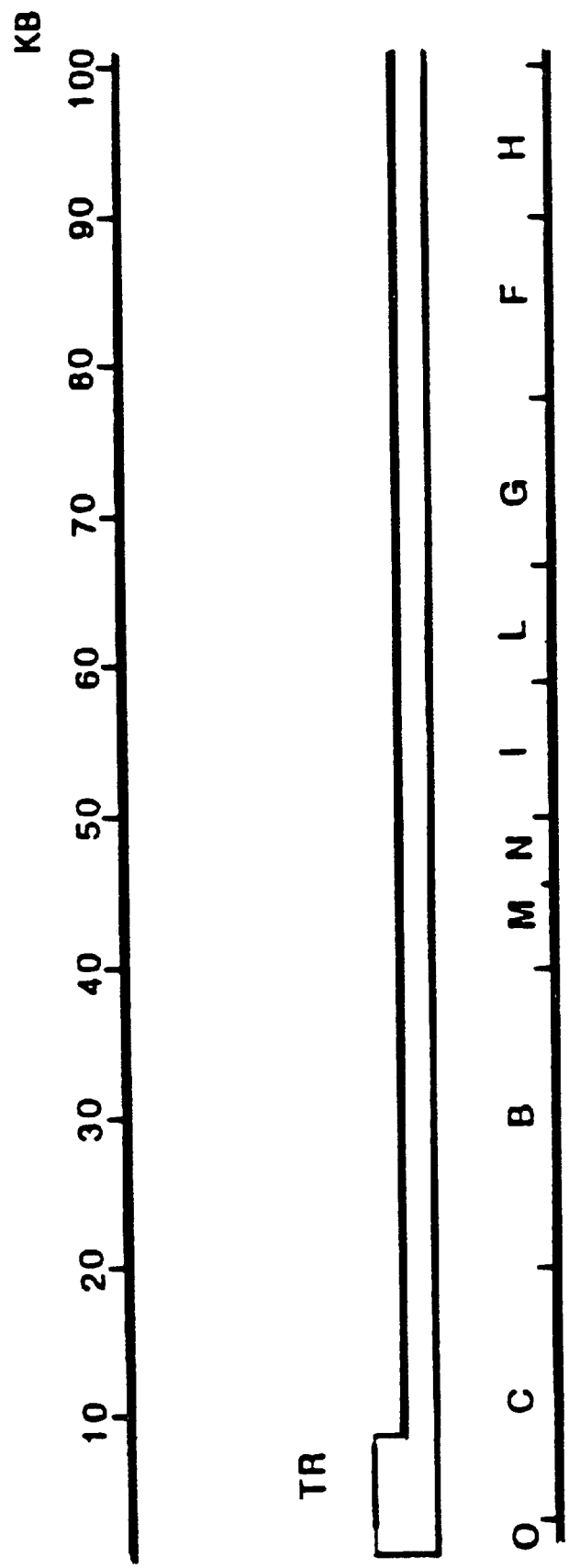

```
                    10         20         30         40         50         60         70
                    *          *          *          *          *          *          *
(A) VV      MFMYPEFARKALSKLISKKLNIEKVSSKHQLVLLDYGLHGLLPKSLYLEAINSDILNVRFFPPEIINVT
 orf 01L     ::: ::  :: ::  :  ::   ::  :::::   ::     ::   :   ::  ::  ::    ::
(B) SPV     MPSYMYPKNARKVISKIISL

FIGURE 2C

```
                        570          580          590          600          610
                         *            *            *            *            *
(C) VV orf O1L      VLNDQYAKIVIFFNTIIEYIIATIYYRLTVLNNYTNVKHFVSKVLHTVMEA
                    :::  ::::::::  :  ::: :::  ::  ::  :::  :
(D) SPV EcoRV-EcoRI SLNEYYSKIVILINVILEYMISILILYRILIVKRFNNIKEFISKVVNTVLES
                                              |
                                            EcoRV 620          630          640          650          660         TERM
                         *            *            *            *            *            |
(C) VV orf O1L      CGVLFSYIKVNDKIEHELEEMVDKGTVPSYLYHLSINVISIILDDINGTR-
                    :  :      ::         :   :            :
(D) SPV EcoRV-EcoRI SGIYFCQMRVHEQIELEIDELIINGSMPVQLMHLLLKVATIILEEIKEI- ─→ EcoRI
                                                                            |
                                                                           TERM
```

FIGURE 4C

JUNCTION C  GTA TCG GCG GAA ATC CAG CTG AGC=GCC GGT CGC TAC CAT=TAC CAG TTG GTC TGG=TGT
            Val Ser Ala Glu Ile Gln Leu Ser Ala Gly Arg Tyr His Tyr Gln Leu Val Trp Cys

PvuII pJF751→

PstI  SalI
CAA=AAA GAT CCA TAA TTA=ATT AAC CCG GCC GCC=TGC AGG TGG ACT
Gln Lys Asp Pro --- lacZ (1024)

BglII
XbaI
CT AGA AAA AAT TGA=AAA ACT ATT CTA ATT=TAT TGC ACG GAG ATC=T

EP1

EcoRI
TT TTT TTT TTT=TTT TTT GGC ATA TAA=ATG AAT TCG CTC GCA=GCG CTA TTG GCG GCG
                                    MET Asn Ser Leu Ala Ala Leu Leu Ala Ala

LP2                                → gp50(3)
                                             → PRV BamHI #7

FIGURE 5C

JUNCTION C

```
                    Pvu II
GAA ATC  CAG CTG  AGC GCC GGT CGC TAC CAT TAC CAG TTG GTC TGG TGT CAA AAA GAT
Glu Ile  Gln Leu  Ser Ala Gly Arg Tyr His Tyr Gln Leu Val Trp Cys Gln Lys Asp
         →                                                    →
         pJF 751                                               E. coli Lac Z (1024)
```

JUNCTION C (CONT.)

```
                              Sal I    Xba I
CCA TAA TTA ATT AAC CCG  GTC GAC   TCT AGA  TTT TTT TTT TTT TTT TTG GCA TAT AAA
Pro ·
                                            LP2
```

JUNCTION C (CONT.)

```
     Bgl II                                                Eco R I              [Nco I]
TAG  ATC  TGT ATC CTA AAA TTG AAT TGT AAT TAT CGA TAA TAA ATG AAT TCC GGC ATG GCC TCG
                                                          MET Asn Ser Gly Met Ala Ser
          EP2                                                                    →
                                                                                 PRV gpC (1)
```

| DNA | Origin | Sites | Size |
|---|---|---|---|
| Vector | pSP64 | Hind III–Bam HI | ~2972 BP |
| Fragment 1 | SPV Hind III M | Bgl II–Acc I | ~1484 BP |
| Fragment 2 | chicken MGF | EcoR I†–Acc I | ~640 BP |
| Fragment 3 | pJF751 | Bam HI–Pvu II | ~3002 BP |
| Fragment 4 | SPV Hind III M | Acc I–Hind III | ~2149 BP |

†Restriction sites introduced by PCR cloning

| DNA | Origin | Sites | Size |
| --- | --- | --- | --- |
| Vector | pSP64 | Hind III–Bam HI | ~2972 BP |
| Fragment 1 | SPV Hind III M | Bgl II–Acc I | ~1484 BP |
| Fragment 2 | chicken IFN | EcoR I†–Bgl II† | ~577 BP |
| Fragment 3 | pJF751 | Bam HI–Pvu II | ~3002 BP |
| Fragment 4 | SPV Hind III M | Acc I–Hind III | ~2149 BP |

†Restriction sites introduced by PCR cloning

FIGURE 9D

Junction D

```
                Pvu II
GAA ATC  CAG CTG  AGC GCC GGT CGC TAC CAT TAC CAG TTG GTC TGG TGT CAA AAA GAT
         └──────┘
            ↓                                                    ↓
          pJF 751                                       E. coli Lac Z (1024)
```

Junction D Continued

```
             Asc I                            Sal I                  Not I              [Acc I]
CCA TAA TTA ATT AAC CCG GGT CGA GGT CGA CCT GCA GGC GGC CGC TAT AC
            └─────────────┘                 └───────┘        └───────┘                  ↑
                                                                                    SPV Hind III M
```

Junction E

```
                                      HindIII
TAA TGT ATC TAT AAT GGT ATA  AAG CTT  GTA TTC TAT AGT GTC ACC TAA ATC
                             └──────┘
                                ↑                    ↓
                              pSP64             SPV Hind III M
```

Junction A

Junction B

FIGURE 10C

Junction C

Pvu II
TCC AGC TGA GCG CCG GTC GCT ACC ATT ACC AGT TGG TCT GGT GTC AAA AAG ATC CAT AAT
       └──── pJF 751 ────→                                    ←──── E. coli lacZ (1024)

Junction C
Continued

Sal I   Xba I
TAA TTA ACC AGC GGC CGC CTG CAG GTC GAC TCT AGA TTT TTT TTT TTT TTG GCA
                                                    LP2

Junction C
Continued

Bgl II                                                          EcoRI    BamHI
TAT AAA TAG ATC TGT ATC CTA AAA TTG AAT TGT AAT TAT CGA TAA ATG AAT TCG GAT CCA
                            EP2

Junction C
Continued

Sal I           Pst I  Not I                    Sal I
TAA TTA ATT AAT TTT TAT CCC GGC GCG CCG CCT GCA GGC CGC TGG CGC GTC GAC AAA GAT
                                                                        SPV Hind III M ↑

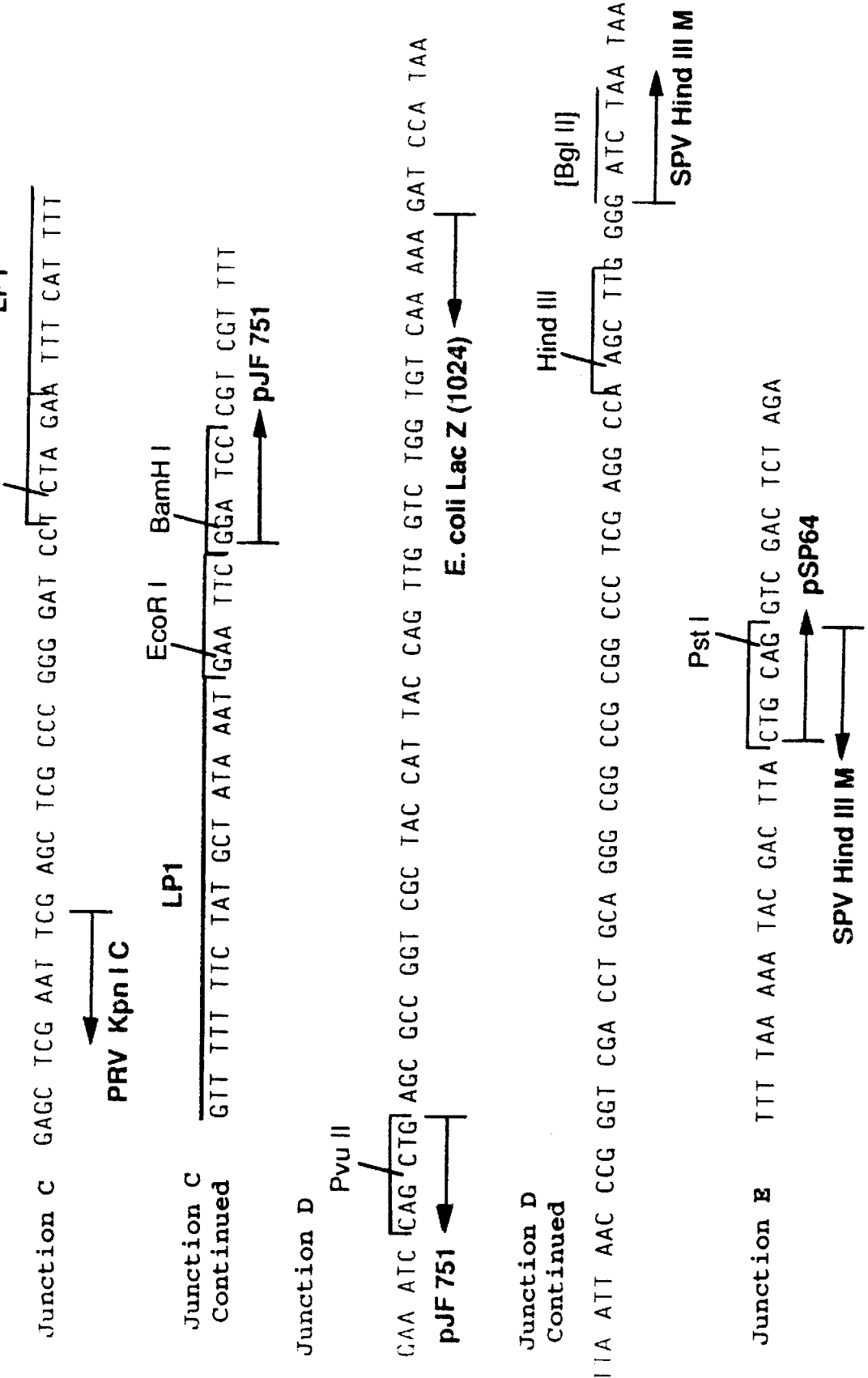

FIGURE 13B 789-41.7
SPV-052

[BgI II, BamH I]

Junction A

GCC CGG GGA TCT TGA AGA TGA ATG CAT
                    →
               pSP64   SPV Hind III M

Junction B

[Acc I]
                ATT TGG TCT GCT GCA GGT CGA CTC TAG AAA AAA TTG AAA AAC TAT TCT AAT TTA TTG CAC
                ↓                    Pst I
         SPV Hind III M                                        EP1LP2

Junction B continued

GGA GAT CTT TTT TTT TTT TGG CAT ATA AAT GAA TTC GCT CGC AGC GCT
                  [Stu I]                              EcoRI      ↑
         EP1LP2    AGG GAC TCT AGA GGA TCC ATA ATT AAT TAA TTA ATT TTT
                      ←
                PRV Bam HI #7                            PRV Bam HI #7

Junction C

GCG TGC ACC ACG
              Pst I
              [Acc I]
          CCT GCA GTC TAC ATG GAA ATC TAC CAG
                            →
                      SPV Hind III M

Junction C continued

ATC CCG GGT CGA

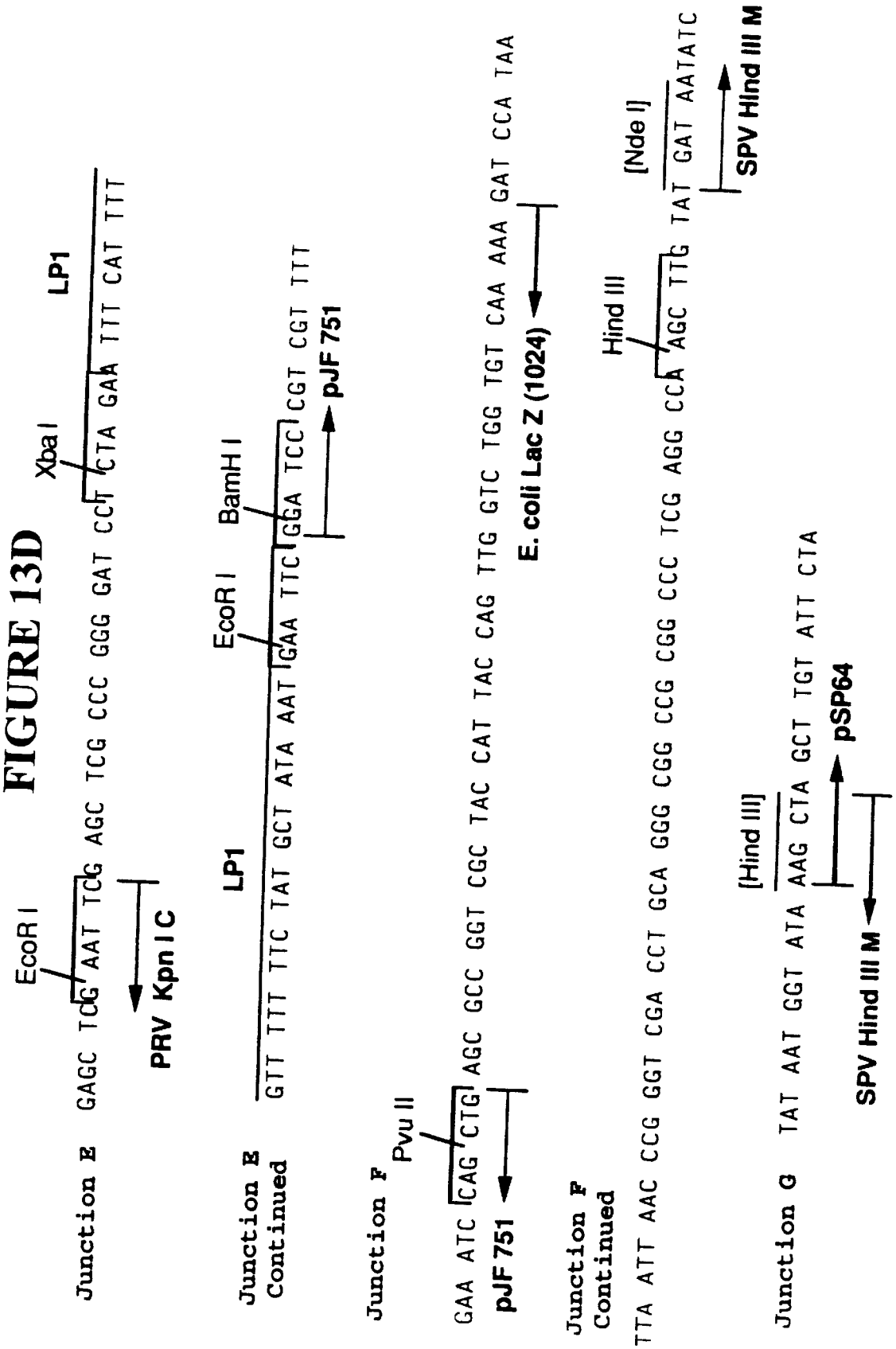

| DNA | Origin | Sites | Size |
| --- | --- | --- | --- |
| Vector | pSP64 | Hind III–BamH I | ~2972 BP |
| Fragment 1 | SPV Hind III M | Hind III–Nde I | ~1560 BP |
| Fragment 2 | PRV Kpn I C | Sma I–EcoR I | ~3500 BP |
| Fragment 3 | pJF751 | Bam HI–Pvu II | ~3010 BP |
| Fragment 4 | SPV Hind III M | Nde I–Acc I | ~48 BP |
| Fragment 5 | PRV BamH I #2 & #9 | Nco I–Nco I | ~2378 BP |
| Fragment 6 | SPV Hind III M | Acc I–Bgl II | ~1484 BP |

FIGURE 14D

Junction E  Pst I  Xba I
[Acc I]
TGT AGG CTG CAG GTC GAC TCT AGA AAA AAT TGA AAA ACT ATT CTA ATT TAT TGC ACG GAG ATC
↓                                                                                    
SPV                              EP1LP2                                            Bgl II
Hind III M              EP1LP2

Junction E
Continued
TTT TTT TTT TTT TTT GGC ATA TAA ATG AAT TCC GGC ATG GCC TCG CTC GCG CGT
                                        EcoR I        [Nco I]      →
                                                              PRV BamH I #2 & #9

Junction F
[Nco I]
CCA TGC TCT AGA GGA TCC CCG GGC GAG CTC GAA TTC GGA TCC ATA ATT AAT TAA TTA
←
PRV
BamH I #2 & #9

Junction F                                                Pst I
Continued      ATT TTT ATC CCG GGT CGA CCT GCA GTA GAC CAA
                                                 [Acc I]    ↑
                                                       SPV Hind III M

[Bgl II, BamH I]
Junction G  CAT TCA TCT TCA AGA TCC CCG GGC GAG CTC GAA TTC
                         ←———————→
                    SPV Hind III M  pSP 64

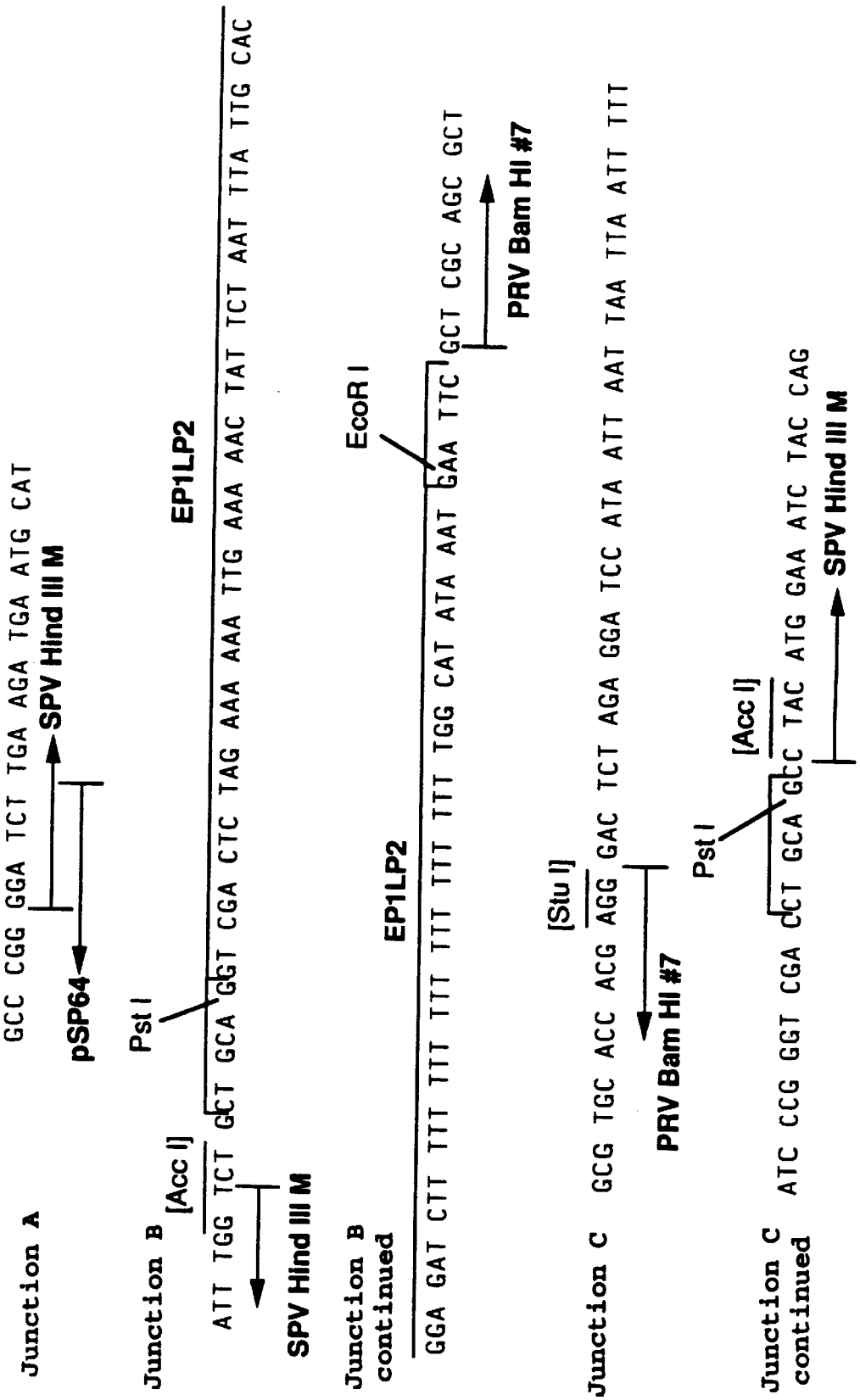

FIGURE 16B 789-41.73
SPV-055

Junction A

[Bgl II, BamH I]

GCC CGG GGA TCT TGA AGA TGA ATG CAT
              pSP64 →    ← SPV Hind III M

Junction B

[Acc I]
ATT TGG TCT GCT GCA GGT ATA GCT CGA CTC TAG ATT TTT TTT TTT TTT GGC ATA TAA ATA
         SPV Hind III M ↓    Pst I                              LP2EP2

Junction B continued

GAT CTG TAT CCT AAA ATT GAA TTG TAA TTA TCG ATA ATA AAT GAA TTC GCT CGC AGC GCT
                         LP2EP2                            EcoR I        PRV Bam HI #7 →

RECOMBINANT SWINEPOX VIRUS

This application is a continuation-in-part of PCT International Application PCT/US96/01485, filed Jan. 19, 1996, which is a continuation-in-part application of U.S. Ser. No. 08/472,679, filed Jun. 7, 1995, and a continuation-in-part application of U.S. Ser. No. 08/488,237, filed Jun. 7, 1995, and a continuation-in-part application of U.S. Ser. No. 08/480,640, filed Jun. 7, 1995, U.S. Pat. No. 6,033,904; U.S. Ser. Nos. 08/472,679, 08/488,237, and 08/480,640 are all continuation-in-part applications of U.S. Ser. No. 08/375,992, filed Jan. 19, 1995, the contents of which are incorporated by reference into the present application.

Within this application several publications are referenced by arabic numerals within parentheses. Full citations for these publications may be found at the end of the specification immediately preceding the claims. The disclosures of these publications are hereby incorporated by reference into this application.

BACKGROUND OF THE INVENTION

Swinepox virus (SPV) belongs to the family Poxviridae. Viruses belonging to this group are large, double-stranded DNA viruses that characteristically develop in the cytoplasm of the host cell. SPV is the only member of the genus Suipoxvirus. Several features distinguish SPV from other poxviruses. SPV exhibits species specificity (18) compared to other poxviruses such as vaccinia which exhibit a broad host range. SPV infection of tissue culture cell lines also differs dramatically from other poxviruses (24). It has also been demonstrated that SPV does not exhibit antigenic cross-reactivity with vaccinia virus and shows no gross detectable homology at the DNA level with the ortho, lepori, avi or entomopox virus groups (24). Accordingly, what is known and described in the prior art regarding other poxviruses does not pertain a priori to swinepox virus.

SPV is only mildly pathogenic, being characterized by a self-limiting infection with lesions detected only in the skin and regional lymph nodes. Although the SPV infection is quite limited, pigs which have recovered from SPV are refractory to challenge with SPV, indicating development of active immunity (18).

The present invention concerns the use of SPV as a vector for the delivery of vaccine antigens and therapeutic agents to swine. The following properties of SPV support this rationale: SPV is only mildly pathogenic in swine, SPV is species specific, and SPV elicits a protective immune response. Accordingly, SPV is an excellent candidate for a viral vector delivery system, having little intrinsic risk which must be balanced against the benefit contributed by the vector's vaccine and therapeutic properties.

The prior art for this invention stems first from the ability to clone and analyze DNA while in bacterial plasmids. The techniques that are available are detailed for the most part in Maniatis et al., 1983 and Sambrook et al., 1989. These publications teach state of the art general recombinant DNA techniques.

Among the poxviruses, five (vaccinia, fowlpox, canarypox, pigeon, and raccoon pox) have been engineered, previous to this disclosure, to contain foreign DNA sequences. Vaccinia virus has been used extensively to vector foreign genes (25) and is the subject of U.S. Pat. Nos. 4,603,112 and 4,722,848. Similarly, fowlpox has been used to vector foreign genes and is the subject of several patent applications EPA 0 284 416, PCT WO 89/03429, and PCT WO 89/12684. Raccoon pox (10) and Canarypox (31) have been utilized to express antigens from the rabies virus. These examples of insertions of foreign genes into poxviruses do not include an example from the genus Suipoxvirus. Thus, they do not teach methods to genetically engineer swinepox viruses, that is, where to make insertions and how to get expression in swinepox virus.

The idea of using live viruses as delivery systems for antigens has a very long history going back to the first live virus vaccines. The antigens delivered were not foreign but were naturally expressed by the live virus in the vaccines. The use of viruses to deliver foreign antigens in the modern sense became obvious with the recombinant vaccinia virus studies. The vaccinia virus was the vector and various antigens from other disease causing viruses were the foreign antigens, and the vaccine was created by genetic engineering. While the concept became obvious with these disclosures, what was not obvious was the answer to a more practical question of what makes the best candidate virus vector. In answering this question, details of the pathogenicity of the virus, its site of replication, the kind of immune response it elicits, the potential it has to express foreign antigens, its suitability for genetic engineering, its probability of being licensed by regulatory agencies, etc, are all factors in the selection. The prior art does not teach these questions of utility.

The prior art relating to the use of poxviruses to deliver therapeutic agents relates to the use of a vaccinia virus to deliver interleukin-2 (12). In this case, although the interleukin-2 had an attenuating effect on the vaccinia vector, the host did not demonstrate any therapeutic benefit.

The therapeutic agent that is delivered by a viral vector of the present invention must be a biological molecule that is a by-product of swinepox virus replication. This limits the therapeutic agent in the first analysis to either DNA, RNA or protein. There are examples of therapeutic agents from each of these classes of compounds in the form of anti-sense DNA, anti-sense RNA (16), ribozymes (34), suppressor tRNAs (2), interferon-inducing double stranded RNA and numerous examples of protein therapeutics, from hormones, e.g., insulin, to lymphokines, e.g., interferons and interleukins, to natural opiates. The discovery of these therapeutic agents and the elucidation of their structure and function does not make obvious the ability to use them in a viral vector delivery system.

SUMMARY OF THE INVENTION

This invention provides a recombinant swinepox virus comprising a foreign DNA inserted into a swinepox virus genomic DNA, wherein the foreign DNA is inserted into an EcoRI site within the approximately 3.2 Kb subfragment of the HindIII K fragment of the swinepox virus genomic DNA and is capable of being expressed in a swinepox virus infected host cell. The invention further provides a recombinant swinepox virus designated S-SPV-120, S-SPV-121, S-SPV-122, S-SPV-127, and S-SPV-128. The invention further provides vaccines and methods of immunization of the recombinant swinepox virus.

BRIEF DESCRIPTION OF THE INVENTION

Figure 1B:
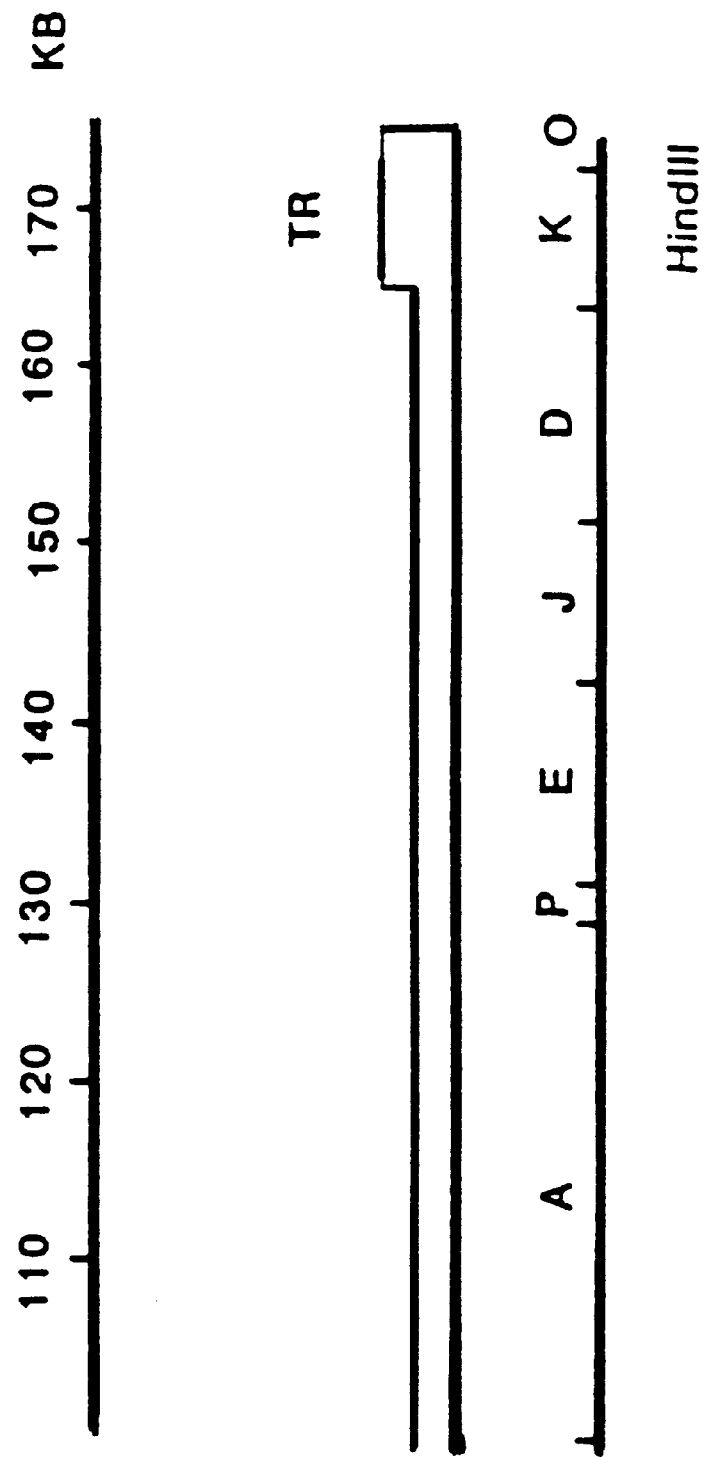

FIGS. 1A–1B: Show a detailed diagram of SPV genomic DNA (Kasza strain) including the unique long and Terminal repeat (TR) regions. A restriction map for the enzyme HindIII is indicated (23). Fragments are lettered in order of decreasing size. Note that the terminal repeats are greater than 2.1 kb but less than 9.7 kb in size.

Figure 2A:
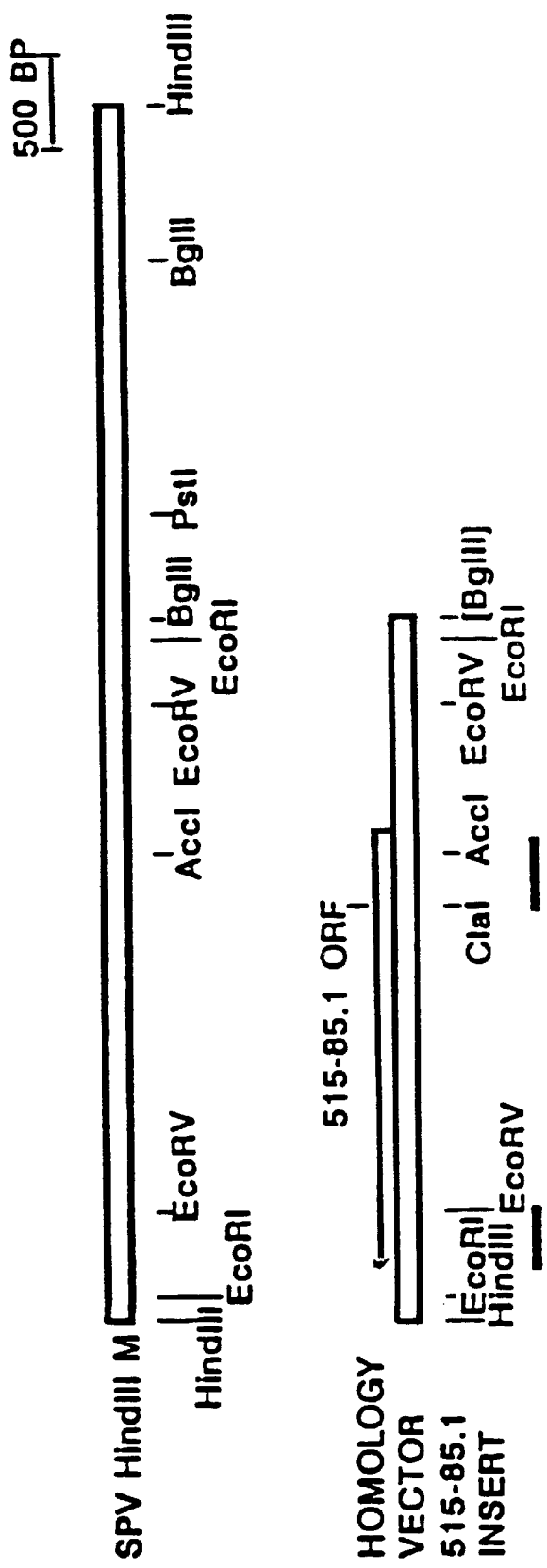

FIGS. 2A–2C: Show the homology which exists between the 515.85.1 ORF and the Vaccinia virus 01L ORF. FIG. 2A shows two maps: The first line of FIG. 2A is a restriction map of the SPV HindIII M fragment and the second is a restriction map of the DNA insertion in plasmid 515-85.1. The location of the 515-85.1. [VV 01L-like] ORF is also indicated on the map. The locations of the DNA sequences shown in FIGS. 2B and 2C are indicated below the map by heavy bars in FIG. 2A. FIG. 2B shows the homology between the VV 01L ORF and the 515-85.1 ORF at their respective. N-termini (SEQ ID NOS: 101 and 102 respectively). FIG. 2C shows the homology between the VV 01L ORF and the 515-85.1 ORF at their respective C-termini (SEQ ID NOS: 103 and 104 respectively).

Figure 3A:
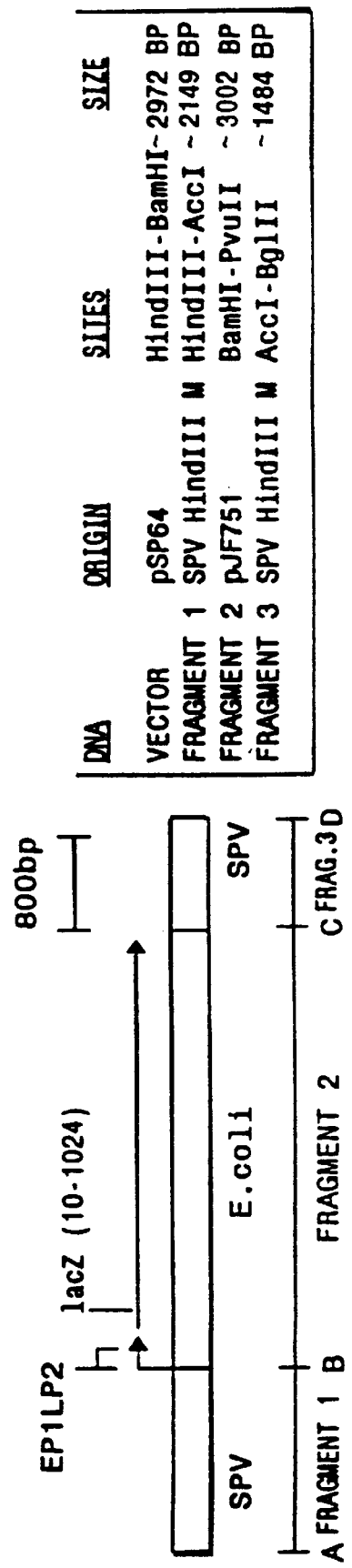
Figure 3B:
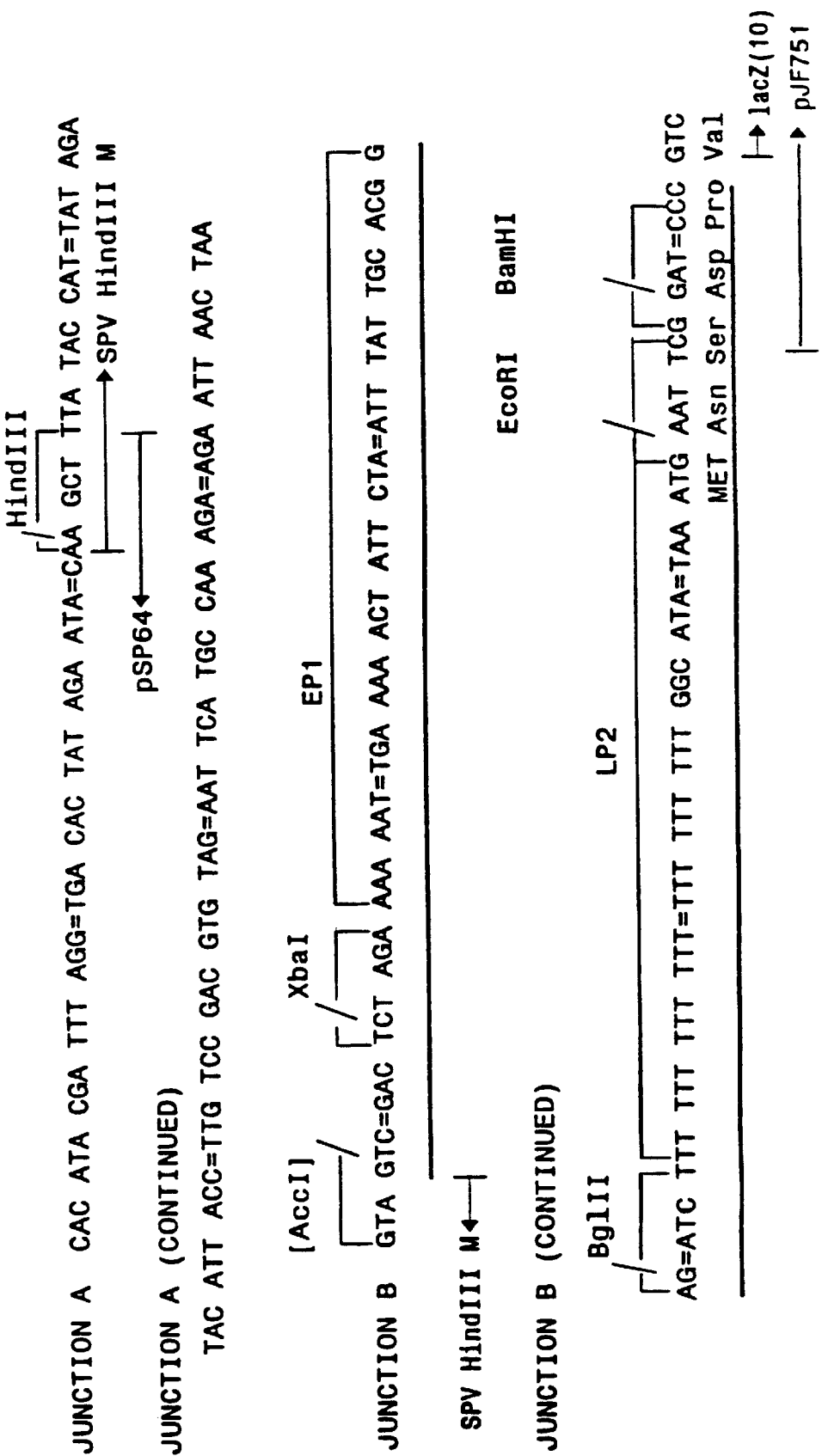
Figure 3C:
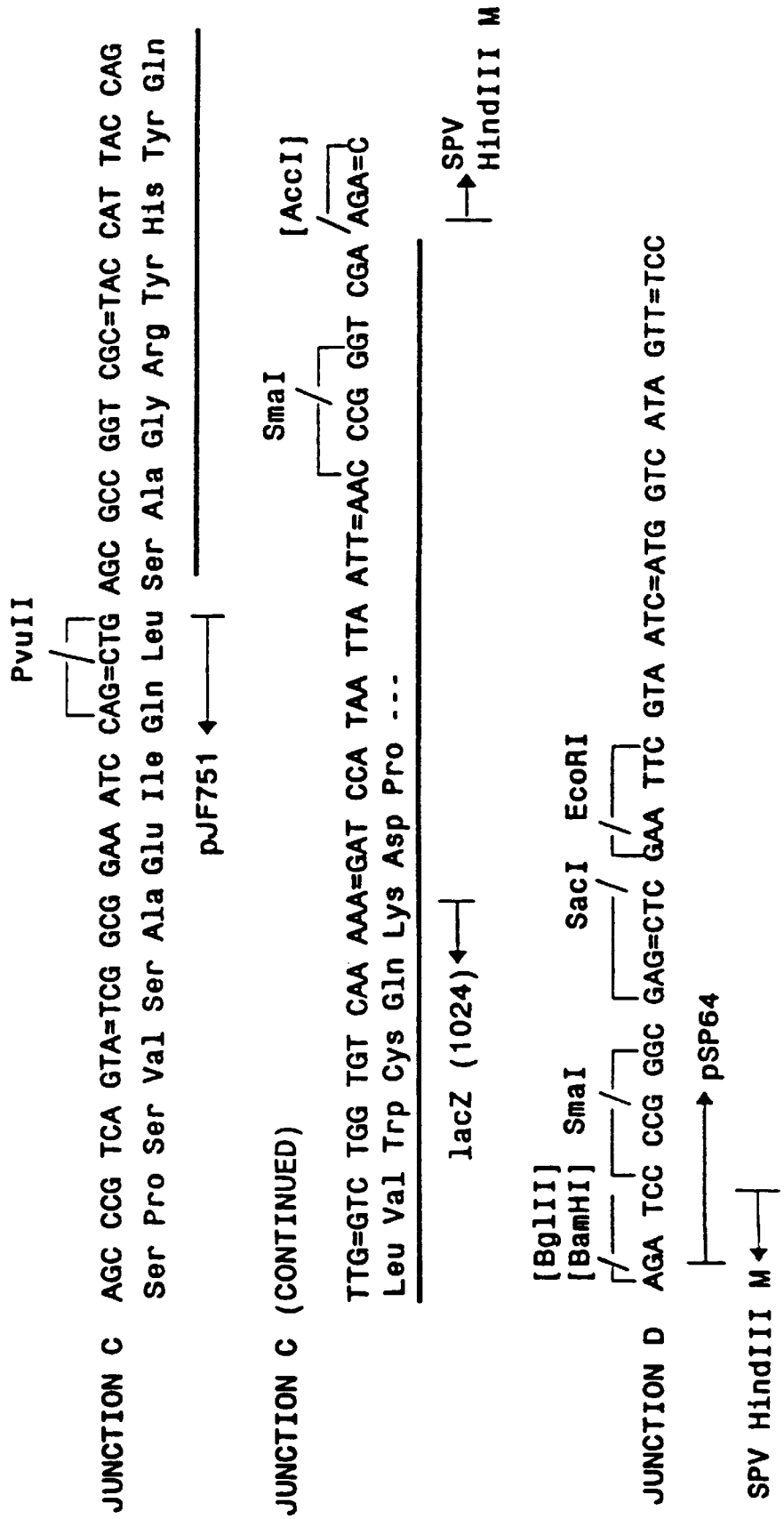

FIGS. 3A–3C: Show a description of the DNA insertion in Homology Vector 520-17.5. FIG. 3A contains a diagram showing the orientation of DNA fragments assembled in plasmid 520-17.5 and table indicating the origin of each fragment. FIG. 3B shows the sequences located at each of the junctions A (SEQ ID NO: 105) and B (SEQ ID NO: 106) between fragments, and FIG. 3C shows the sequences located at Junctions C (SEQ ID NO: 107) and D (SEQ ID NO: 108). FIGS. 3B and 3C further describe the restriction sites used to generate each fragment as well as the synthetic linker sequences which were used to join the fragments are described for each junction. The synthetic linker sequences are underlined by a heavy bar. The location of several gene coding regions and regulatory elements are also given. The following two conventions are used: numbers in parenthesis ( ) refer to amino acids, and restriction sites in brackets [ ] indicate the remnants of sites which were destroyed during construction. The following abbreviations are used, swinepox virus (SPV), early promoter 1 (EP1), late promoter 2 (LP2), lactose operon Z gene (lacZ), and *Escherichia coli* (*E. coli*).

Figure 4A:
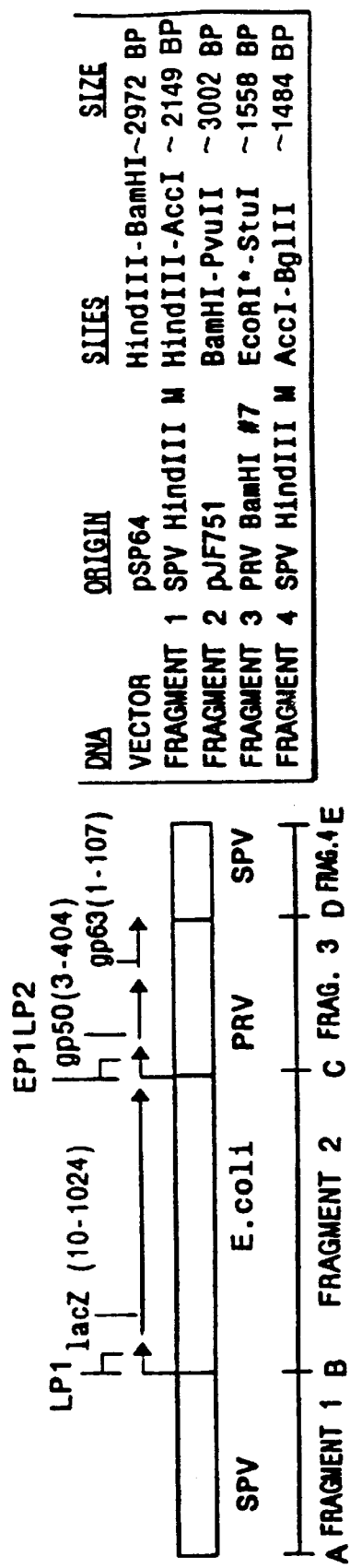
Figure 4B:
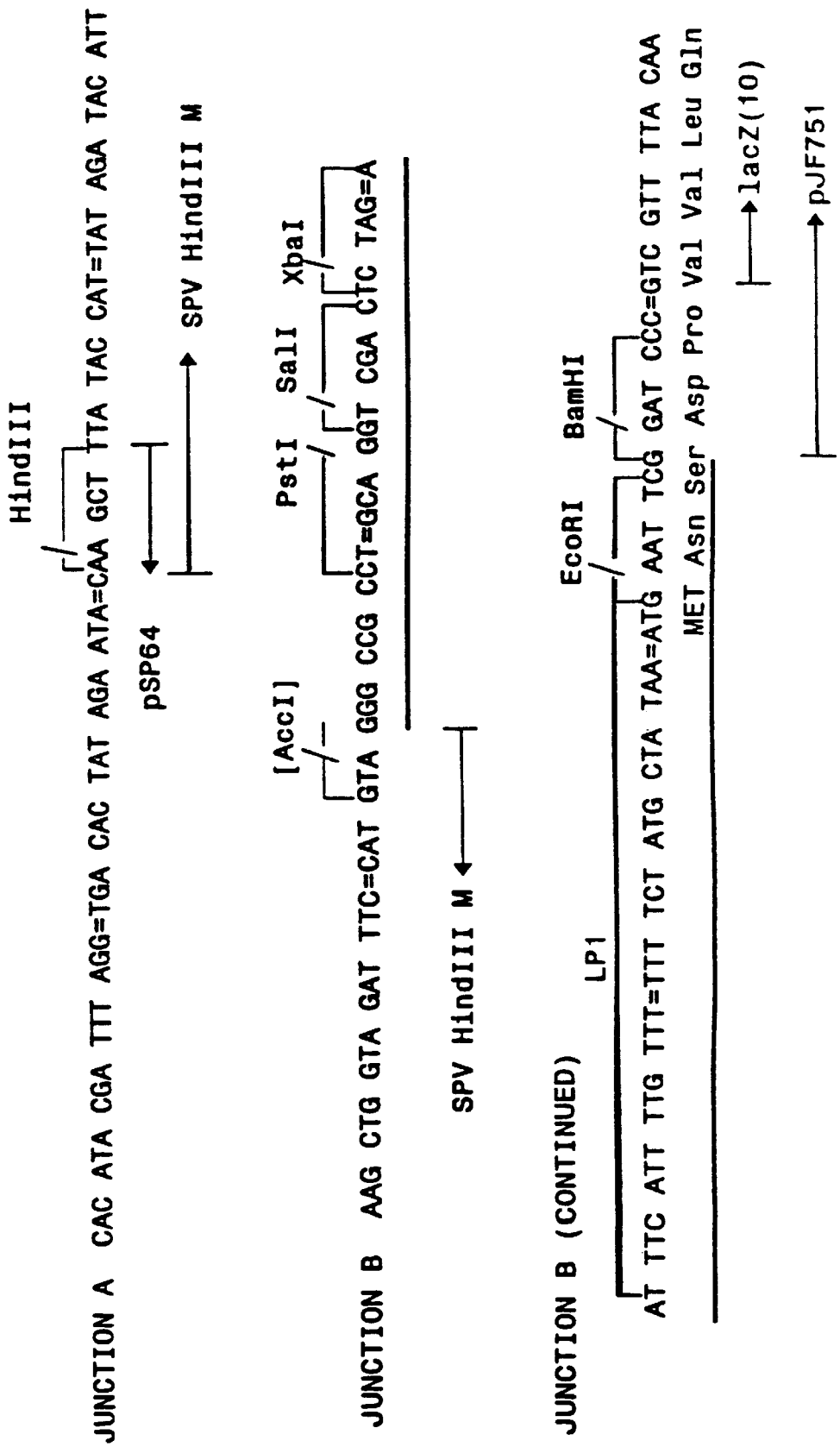
Figure 4D:
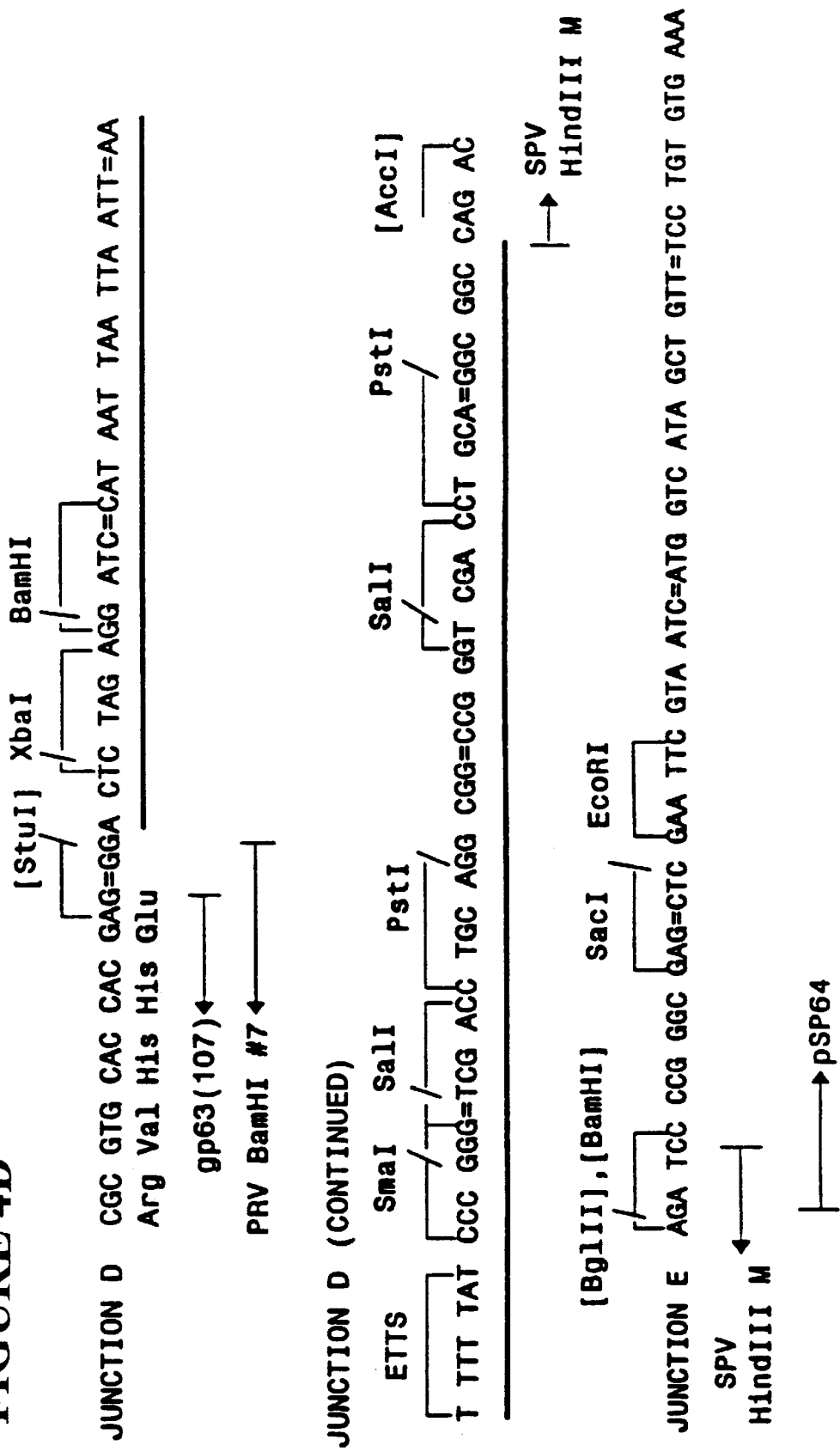

FIGS. 4A–4D: Show a detailed description of the DNA insertion in Homology Vector 538-46.16. FIG. 4A contains a diagram showing the orientation of DNA fragments assembled in plasmid 538-46.16 and a table indicating the origin of each fragment. FIG. 4B shows the sequences located at Junctions A (SEQ ID NO: 109) and B (SEQ ID NO: 110) between fragments, FIG. 4C shows sequences located. at Junction C (SEQ ID NO: 111) and FIG. 4D shows sequences located at Junctions D (SEQ ID NO: 112) and E (SEQ ID NO: 113). FIGS. 4B to 4D also describe the restriction sites used to generate each fragment as well as the synthetic linker sequences which were used to join the fragments are described for each junction. The synthetic linker sequences are underlined by a heavy bar. The location of several gene coding regions and regulatory elements is also given. The following two conventions are used: numbers in parenthesis ( ) refer to amino acids, and restriction sites in brackets [ ] indicate the remnants of sites which were destroyed during construction. The following abbreviations are used, swinepox virus (SPV), pseudorabies virus (PRV), g50 (gD), glycoprotein 63 (g63), early promoter 1 (EP1), late promoter 1 (LP1), late promoter 2 (LP2), lactose operon Z gene (lacZ), and *Escherichia coli* (*E. coli*).

Figure 5A:
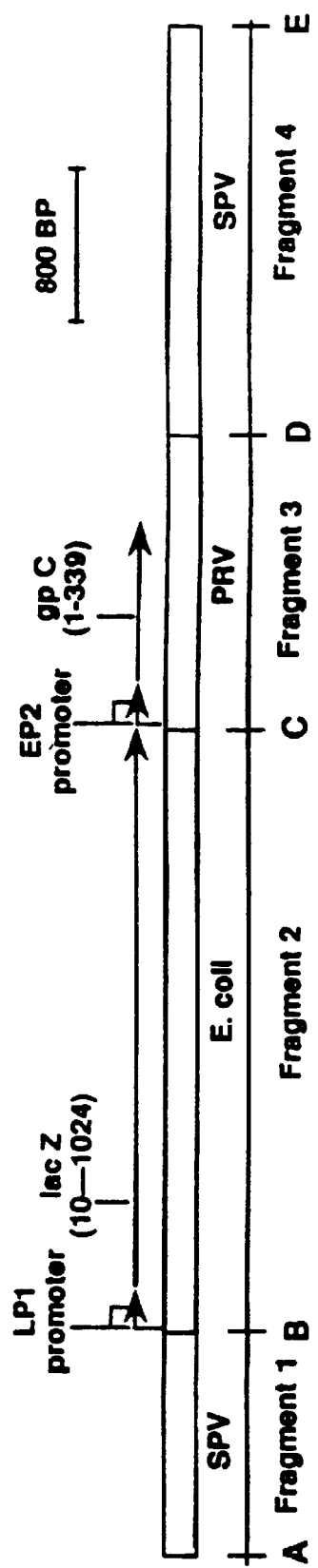
Figure 5B:
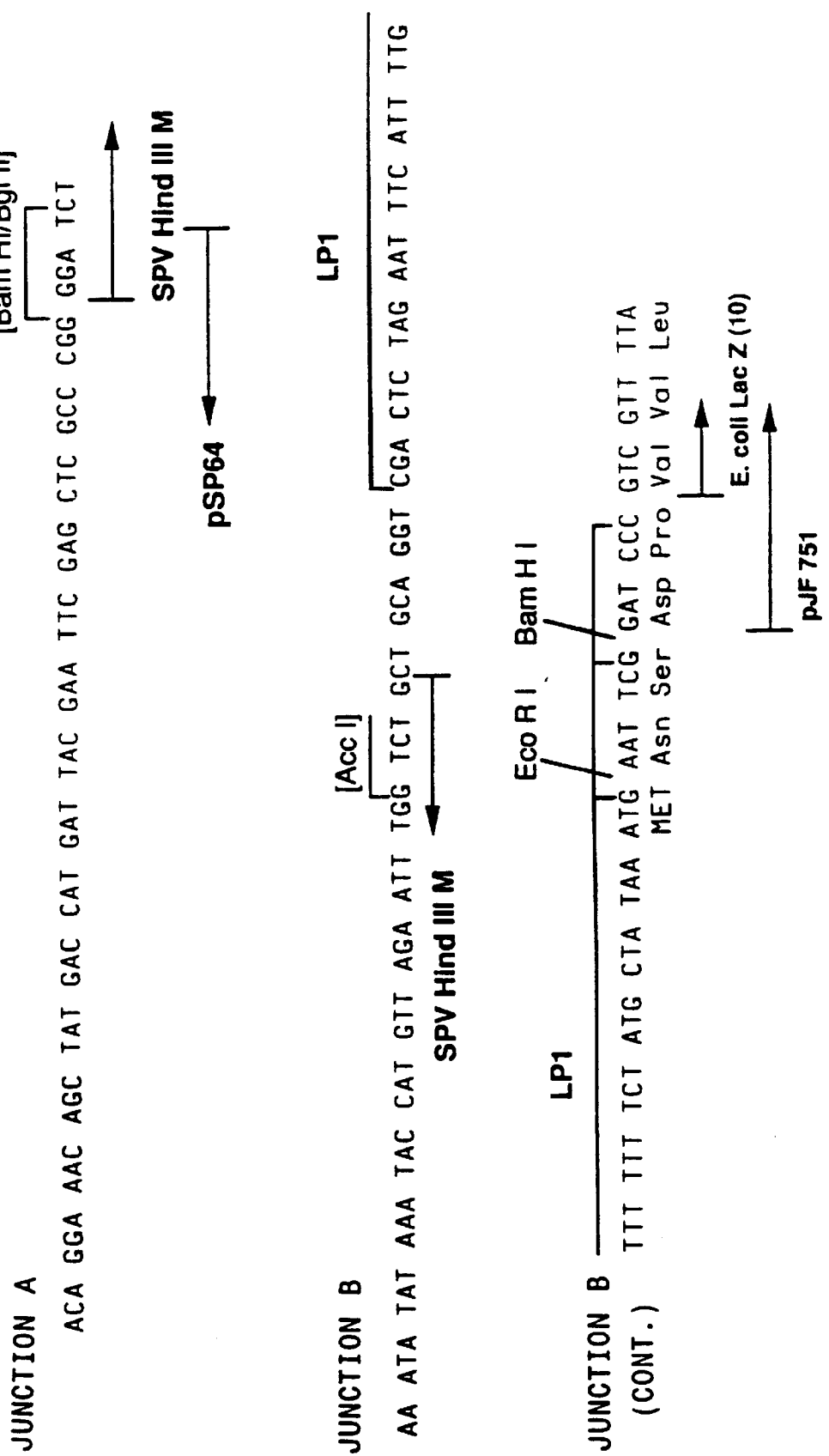
Figure 5D:
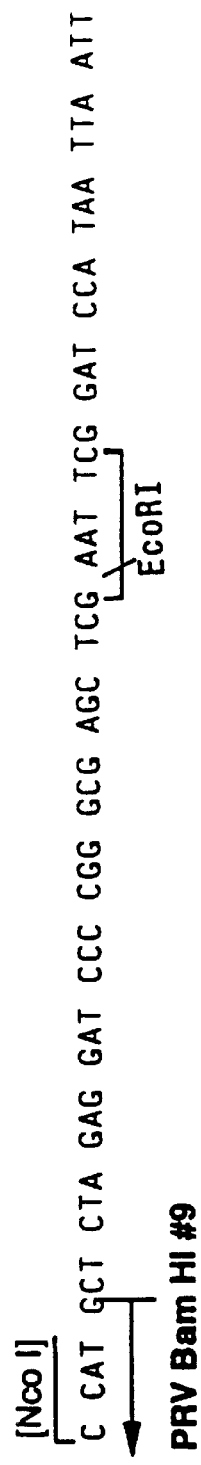
Figure 5D:
Figure 5D:
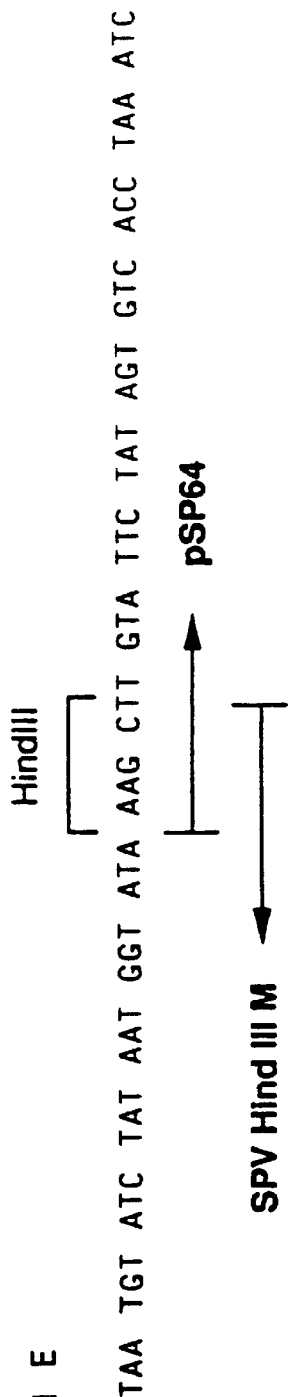

FIGS. 5A–5D: Show a detailed description of Swinepox Virus S-PRV-013 and the DNA insertion in Homology Vector 570-91.64. FIG. 5A contains a diagram showing the orientation of DNA fragments assembled in plasmid 570-91.64 and a table indicating the origin of each fragment. Figure SB shows the sequences located at Junctions A (SEQ ID NO: 114) and B (SEQ ID NO: 115) between fragments, FIG. 5C shows the sequences located at Junction C (SEQ ID NO: 116), and FIG. 5D shows the sequences located at Junctions D (SEQ ID NO: 117) and E (SEQ ID NO: 118). The restriction sites used to generate each fragment as well as synthetic linker sequences which are used to join the fragments are described for each junction in FIGS. 5B to 5D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 1 (LP1), pox synthetic late promoter 2 early promoter 2 (LP2EP2), gIII (gC) base pairs (BP).

Figure 6:
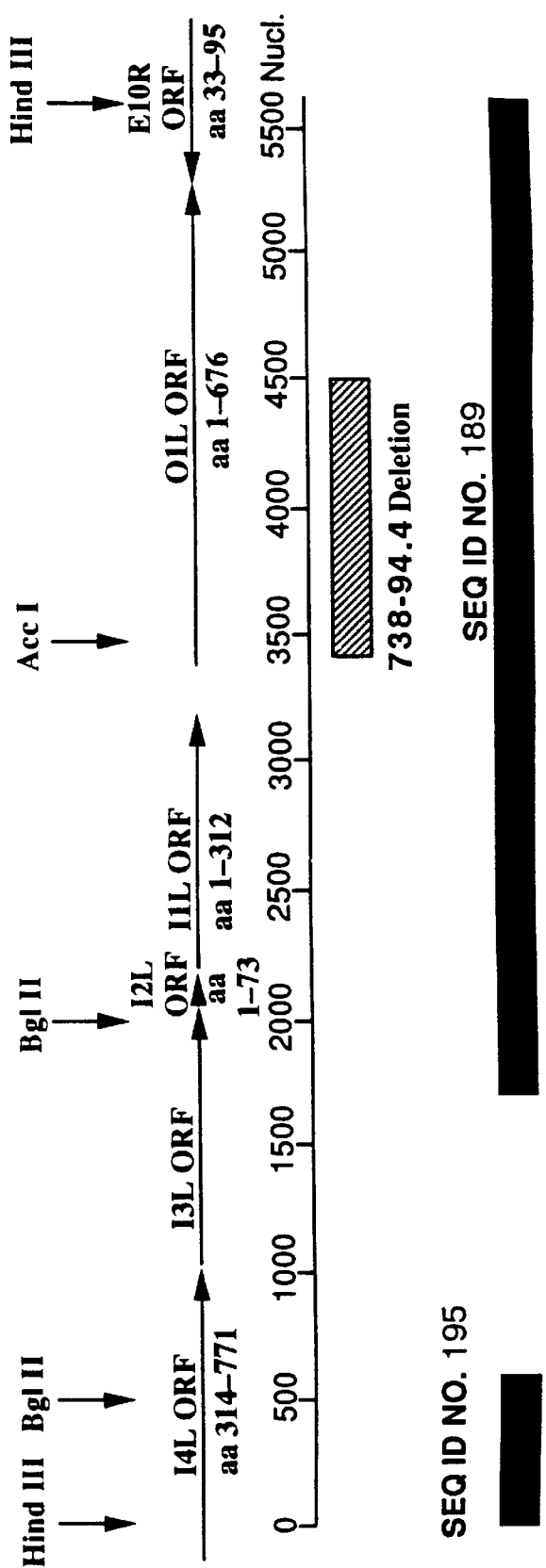

FIG. 6: Map showing the 5.6 kilobase pair HindIII M swinepcx virus genomic DNA fragment. Open reading frames (ORF) are shown with the number of amino acids coding in each open reading frame. The swinepox virus ORFs show significant sequence identities to the vaccinia virus ORFs and are labeled with the vaccinia virus nomenclature (56 and 58). The I4L ORF (SEQ ID NO: 196) shows amino acid sequence homology to ribonucleotide reductase large subunit (57), and the 01L ORF (SEQ ID NO: 193) shows amino acid sequence homology to a leucine zipper motif characteristic of certain eukaryotic transcriptional regulatory proteins (13). The BglII site in the I4L ORF and the AccI site in the 01L ORF are insertion sites for foreign DNA into non-essential regions of the swinepox genome. The homology vector 738-94.4 contains a deletion of SPV DNA from nucleotides 1679 to 2452 (SEQ ID NO: 189). The black bar at the bottom indicates regions for which the DNA sequence is known and references the SEQ ID NOs: 189 and 195. Positions of restriction sites AccI, BglII, and HindIII are shown. I3L ORF (SEQ ID NO: 190), I2L ORF (SEQ ID NO: 191) and E1OR ORF (SEQ ID NO: 194) are shown. SEQ ID NO 221 contains the complete 5785 base pair sequence of the HindIII M fragment. Open. reading frames within the SPV HindIII M fragment are the partial I4L ORF (445 AA; Nucl 2 to 1336); I3L ORF (275 AA; Nucl 1387 to 2211); I2L ORF (75 AA; Nucl 2215 to 2439); I1L ORF (313 AA; Nucl 2443 to 3381); 01L ORF (677 AA; Ncl 3520 to 5550); partial E1OR ORF (64 AA; Nucl 5787 to 5596).

Figure 7A:
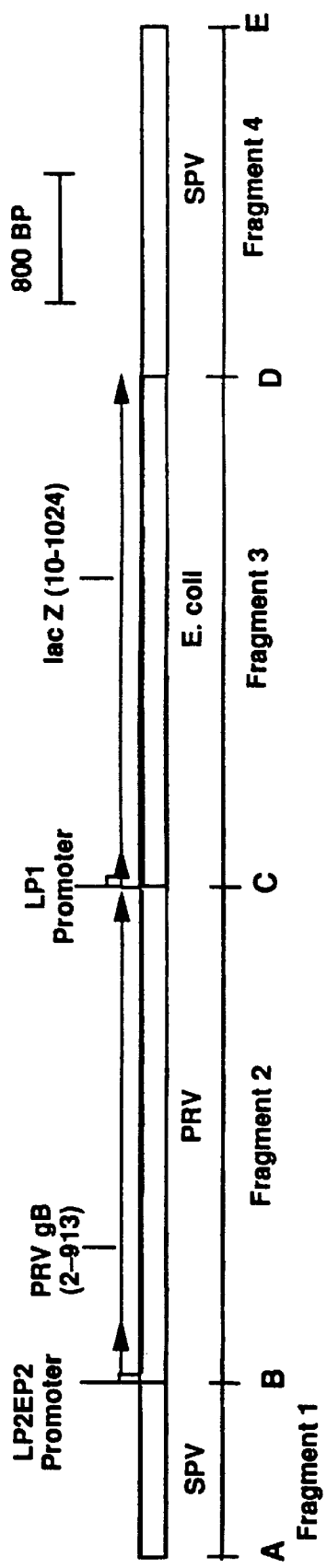
Figure 7B:
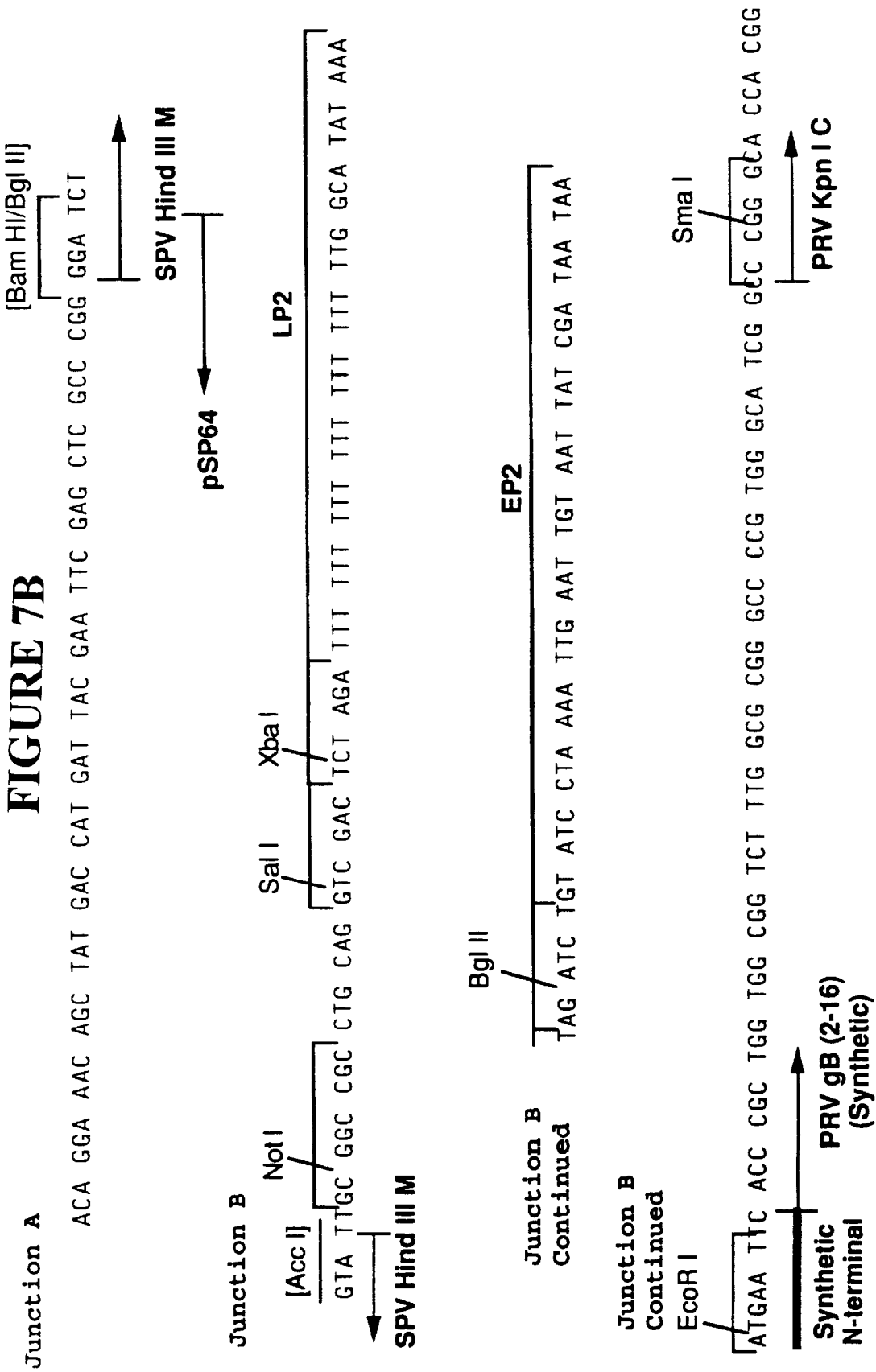
Figure 7C:
Figure 7C:
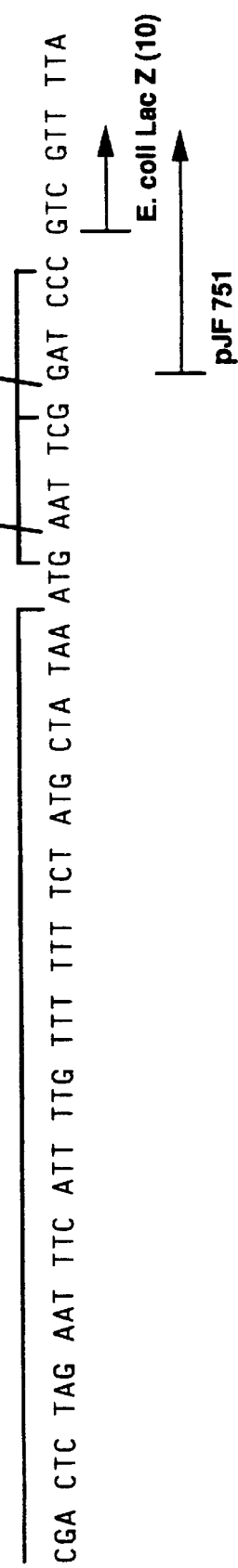
Figure 7D:
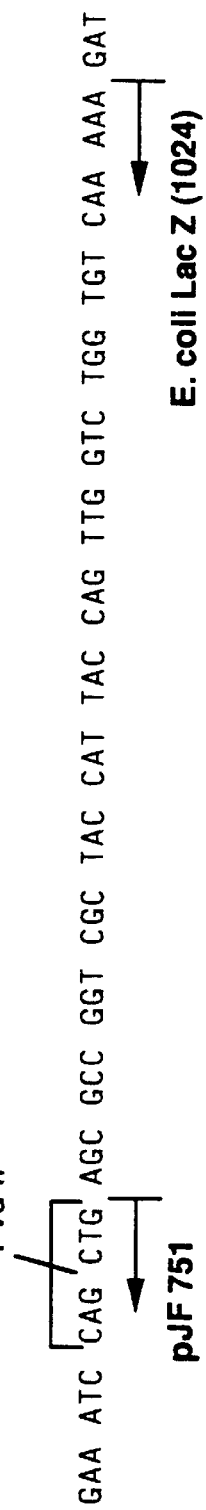
Figure 7D:
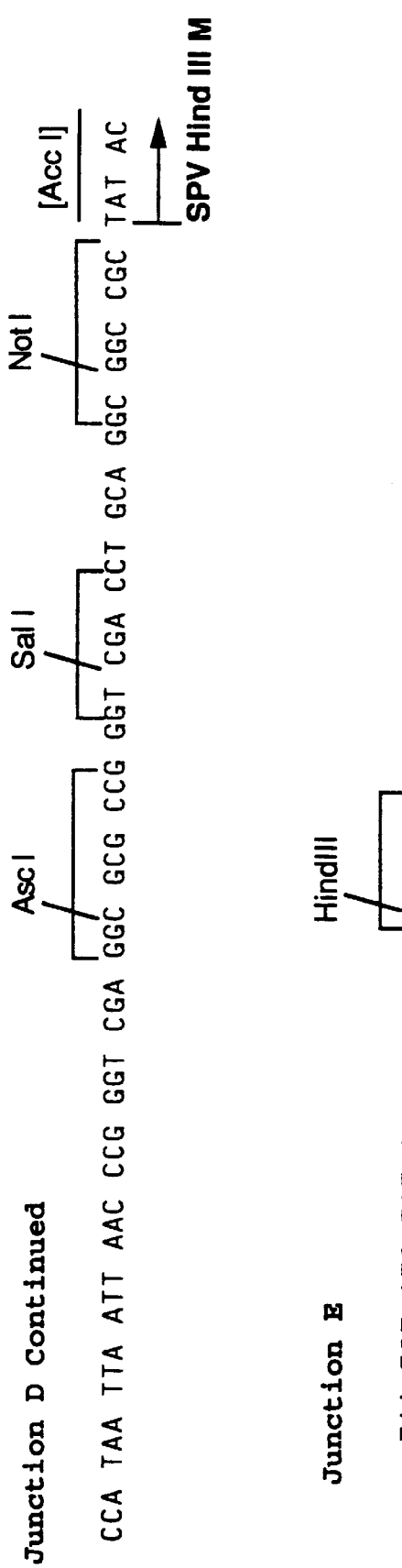
Figure 7D:
Figure 8A:
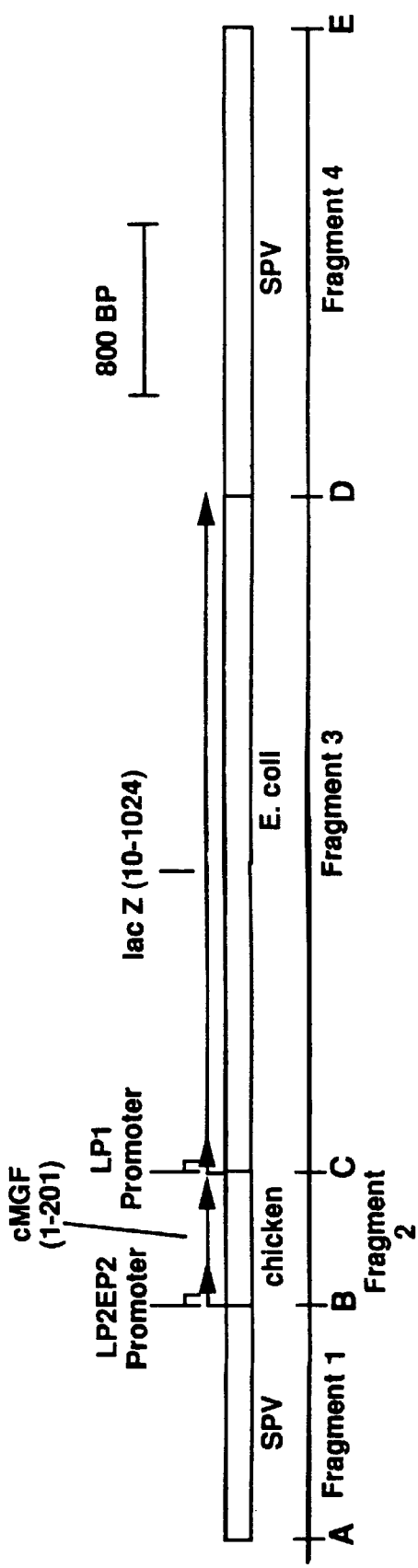
Figure 8B:
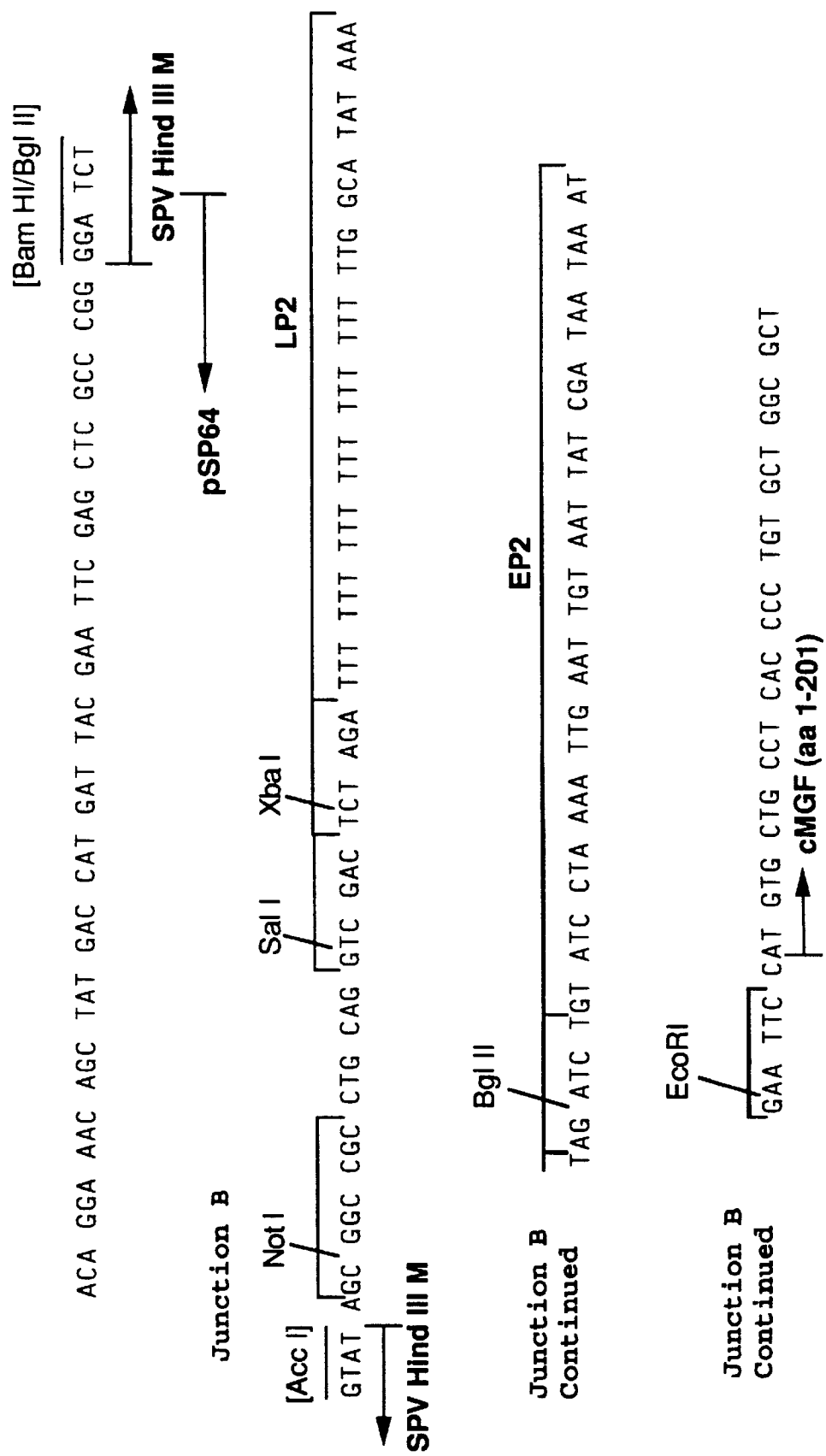
Figure 8C:
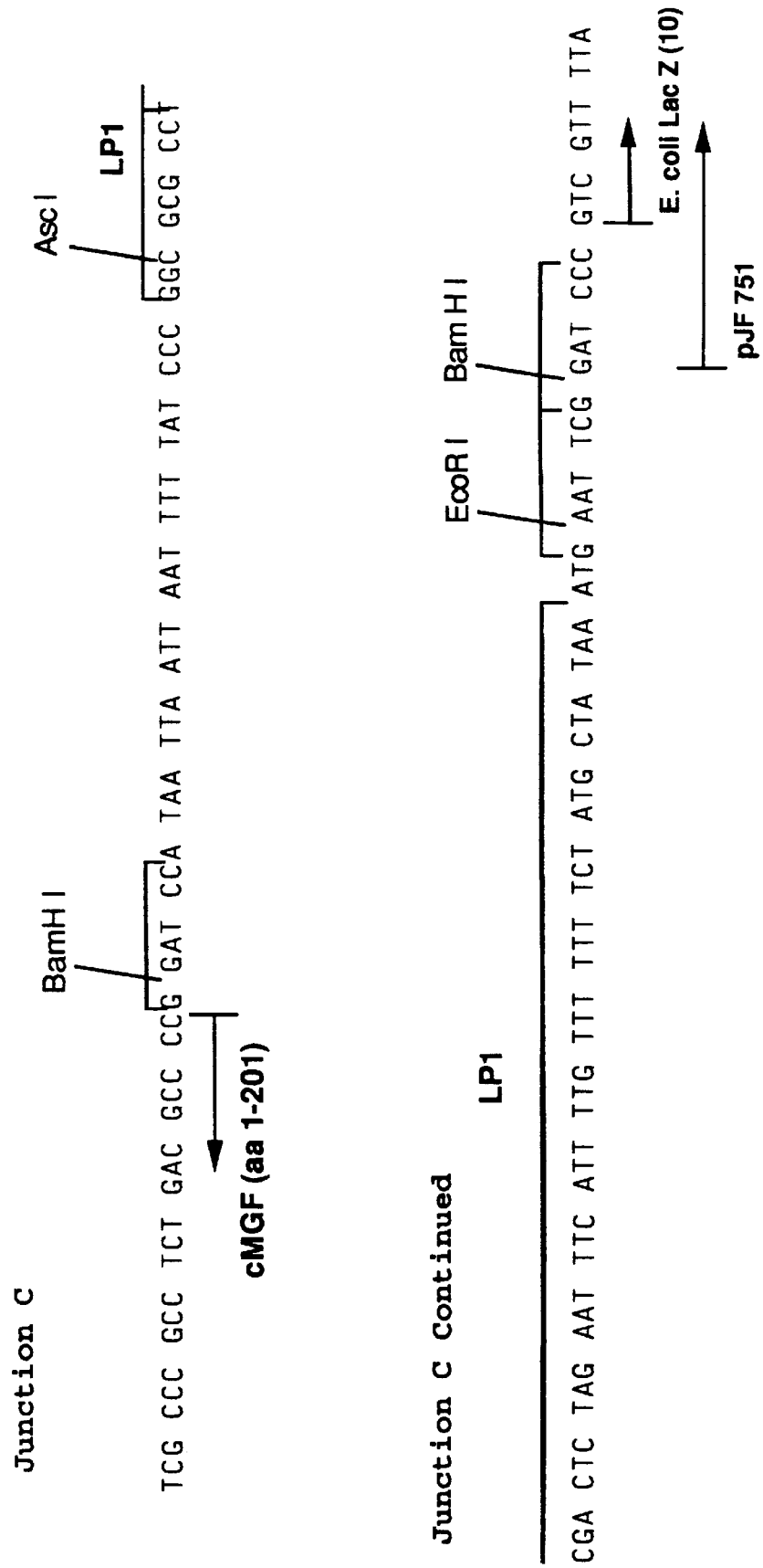
Figure 8D:
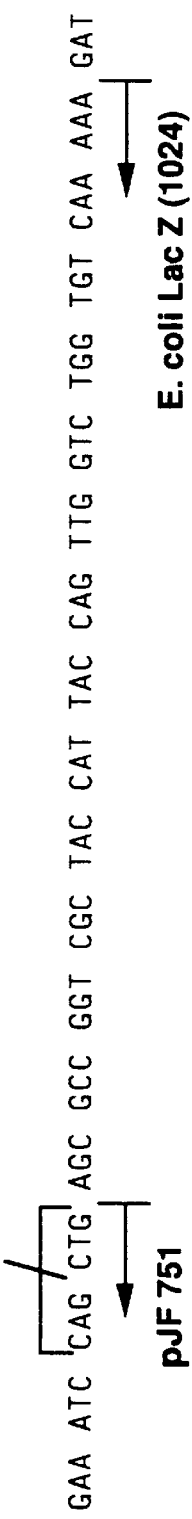
Figure 8D:
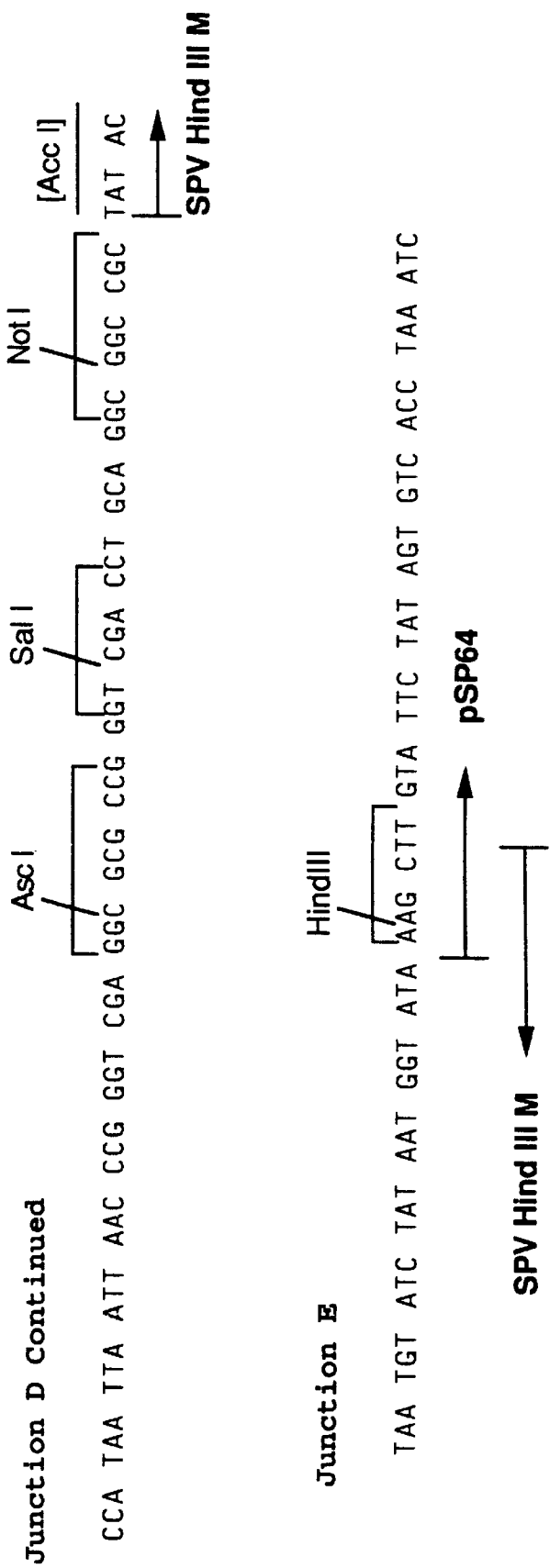
Figure 9A:
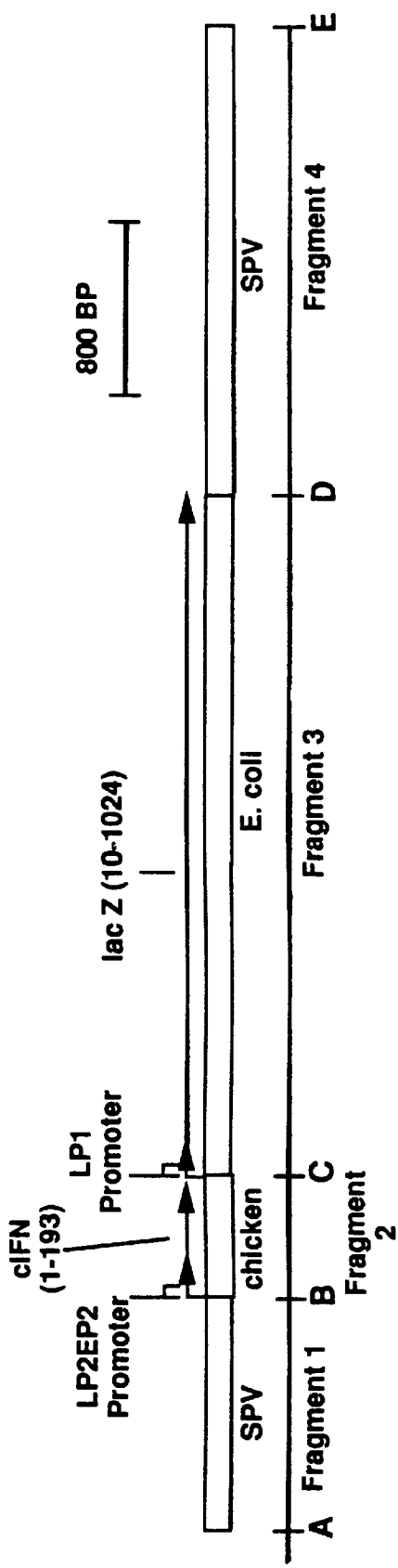
Figure 9B:
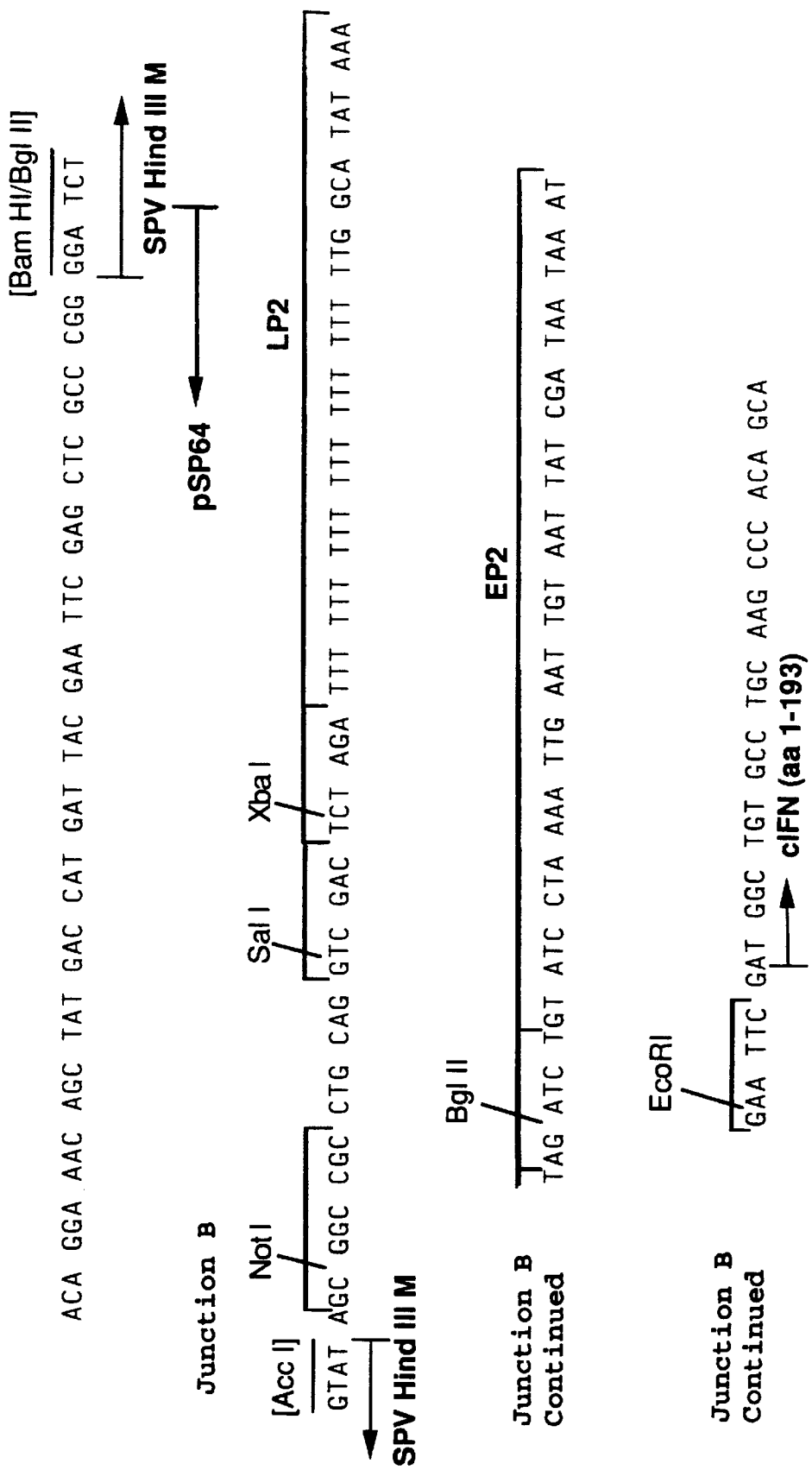
Figure 9C:
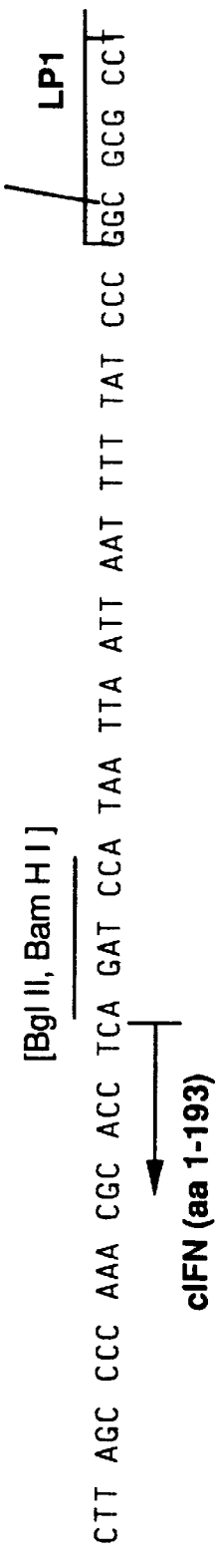
Figure 9C:
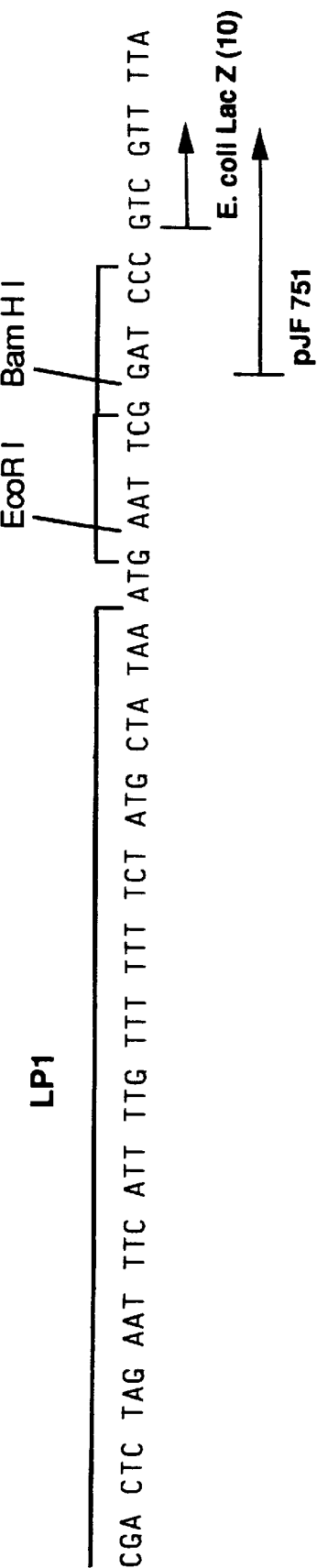
Figure 10A:
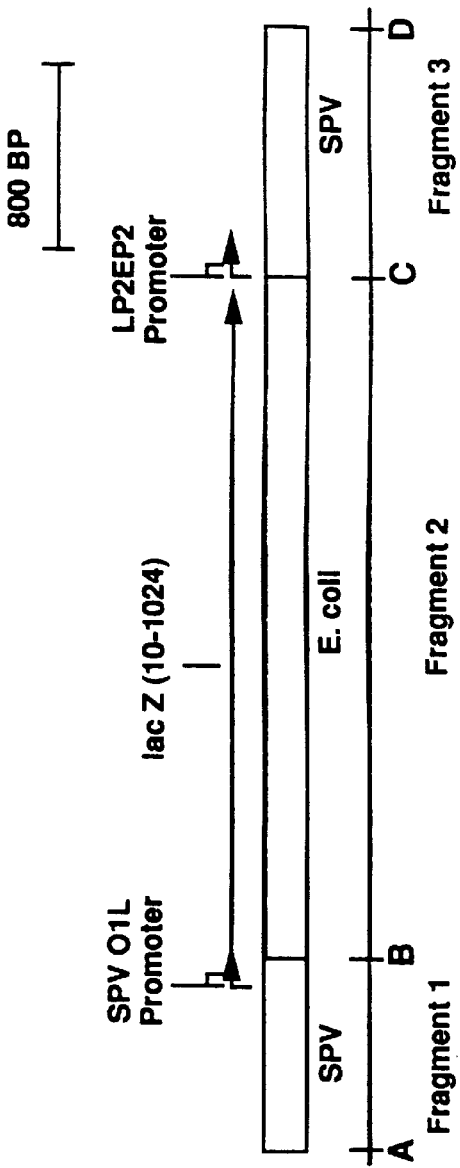
Figure 10B:
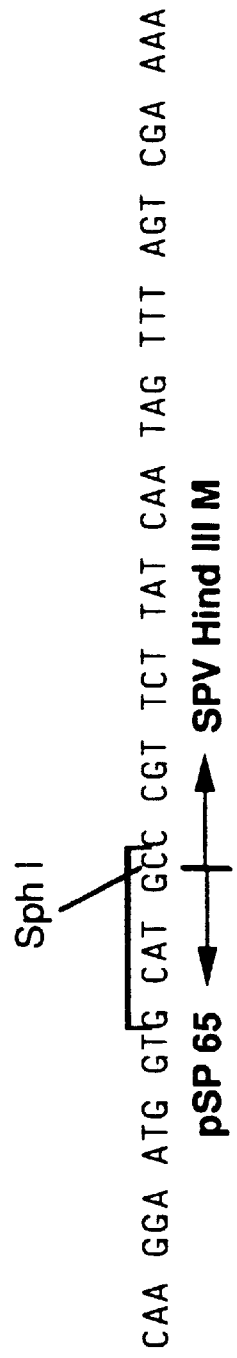
Figure 10B:
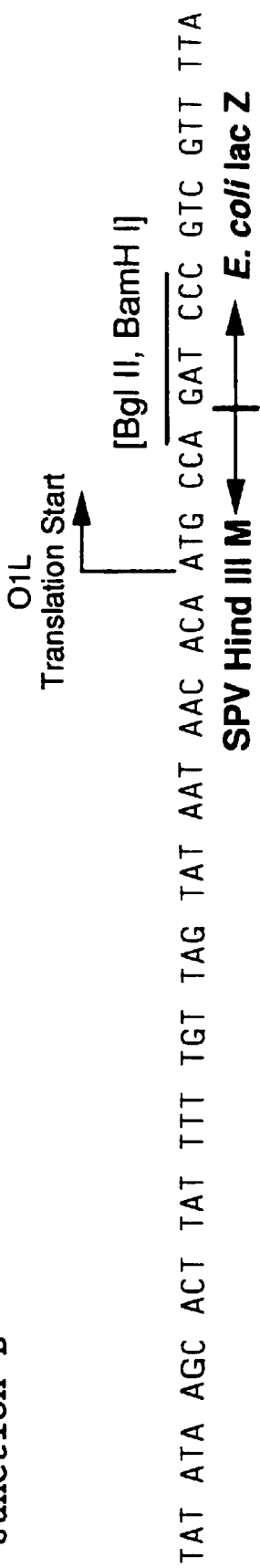
Figure 10D:
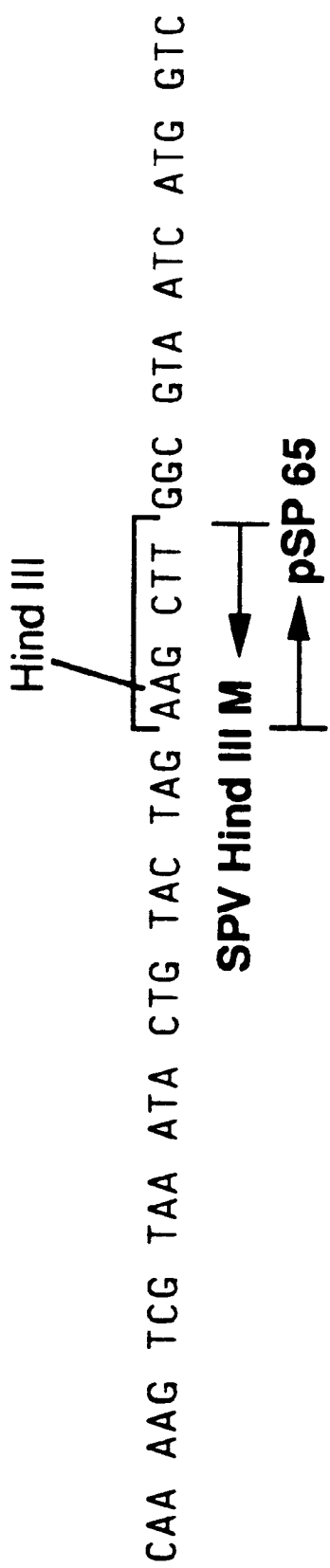

FIGS. 7A–7D: Show a detailed description of Swinepox Virus S-SPV-015 and the DNA insertion in Homology Vector 727-54.60. FIG. 7A contains a diagram showing the orientation of DNA fragments assembled in plasmid 727-54.60 and a table indicating the origin of each fragment. FIG. 7B shows the sequences located at Junctions A (SEQ ID NO: 119) and B (SEQ ID NO: 120) between fragments, FIG. 7C shows the sequences located at Junction C (SEQ ID NO: 121), and FIG. 7D shows the sequences located at Junctions D (SEQ ID NO: 123) and E (SEQ ID NO: 123). The restriction sites used to generate each fragment as well as synthetic linker sequences which are used to join the fragments are described for each junction in FIGS. 7B to 7D. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 1 (LP1), pox synthetic late promoter 2 early promoter 2 (LP2EP2), glycoprotein B (gB), base pairs (BP).

FIGS. 8A–8D: Detailed description of Swinepox Virus S-SPV-042 and the DNA insertion in Homology Vector 751-07.A1. Diagram showing the orientation of DNA fragments assembled in plasmid 751-07.A1. The origin of each fragment is indicated in the table. The sequence located at each of the junctions between fragments is also shown. The restriction sites used to generate each fragment as well as synthetic linker sequences which are used to join the fragments are described for each junction. FIGS. 8A–8D show the sequences located at Junction A (SEQ ID NOS: 197), B (SEQ ID NO: 198), C (SEQ ID NO: 199), D (SEQ ID NO: 200) and E (SEQ ID NO: 201) between fragments and the sequences located at the junctions. The location of several gene coding. regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), chicken myelomonocytic growth factor (cMGF), *Escherichia coli* (*E. coli*), pox synthetic late promoter 1 (LP1), pox synthetic late promoter 2 early promoter 2 (LP2EP2), polymerase chain reaction (PCR), base pairs (BP).

FIGS. 9A–9D: Detailed description of Swinepox Virus S-SPV-043 and the DNA insertion in Homology Vector 751-56.A1. Diagram showing the orientation of DNA fragments assembled in plasmid 751-56.A1. The origin of each fragment is indicated in the table. The sequences located at each of the junctions between fragments is. also shown. FIGS. 9A–9D show the sequences located at Junction A (SEQ ID NOS: 202), B (SEQ ID NO: 203), C (SEQ ID NO: 204), D (SEQ ID NO: 205) and E (SEQ ID NO: 206) between fragments and the sequences located at the junctions. The restriction sites used to generate each fragment as well as synthetic linker sequences which are used to join the several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), chicken interferon (cIFN), *Escherichia coli* (*E. coli*), pox synthetic late promoter 1 (LP1), pox synthetic late promoter 2 early promoter 2 (LPE2EP2), polymerase chain reaction (PCR), base pairs (BP).

FIGS. 10A–10D: Detailed description of Swinepox Virus S-SPV-037 and the DNA insertion in Homology Vector 752-22.1. Diagram showing the orientation of DNA fragments assembled in plasmid 752-22.1. The origin of each fragment is indicated in the table. The sequences located at each of the junctions between fragments is also shown. FIGS. 10A–10D show the sequences located at Junction A (SEQ ID NOS: 207), B (SEQ ID NO: 208), C (SEQ ID NO: 209), and D (SEQ ID NO: 210) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: swinepox virus (SPV), *Escherichia coli* (*E. coli*), pox synthetic late promoter 2 early promoter 2 (LP2EP2), polymerase chain reaction (PCR), base pairs (BP).

Figure 11A:
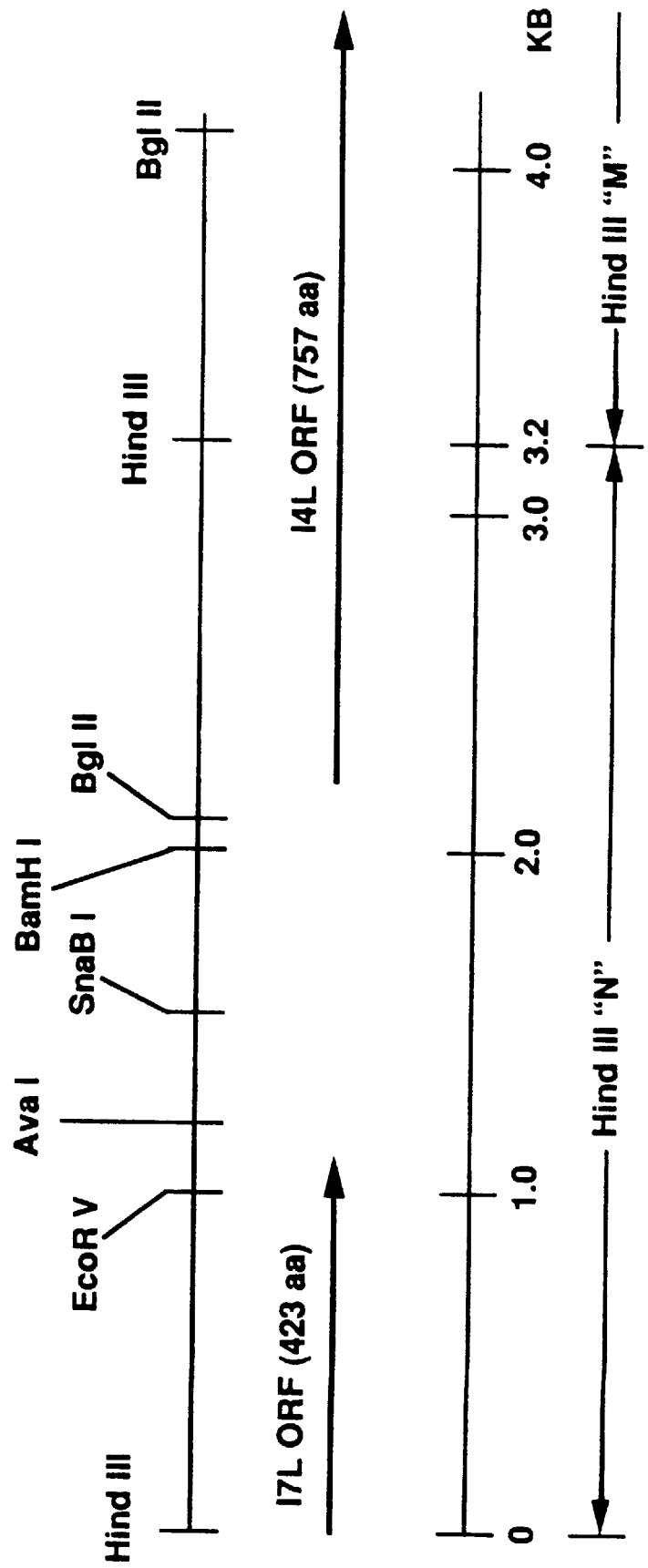
Figure 11B:
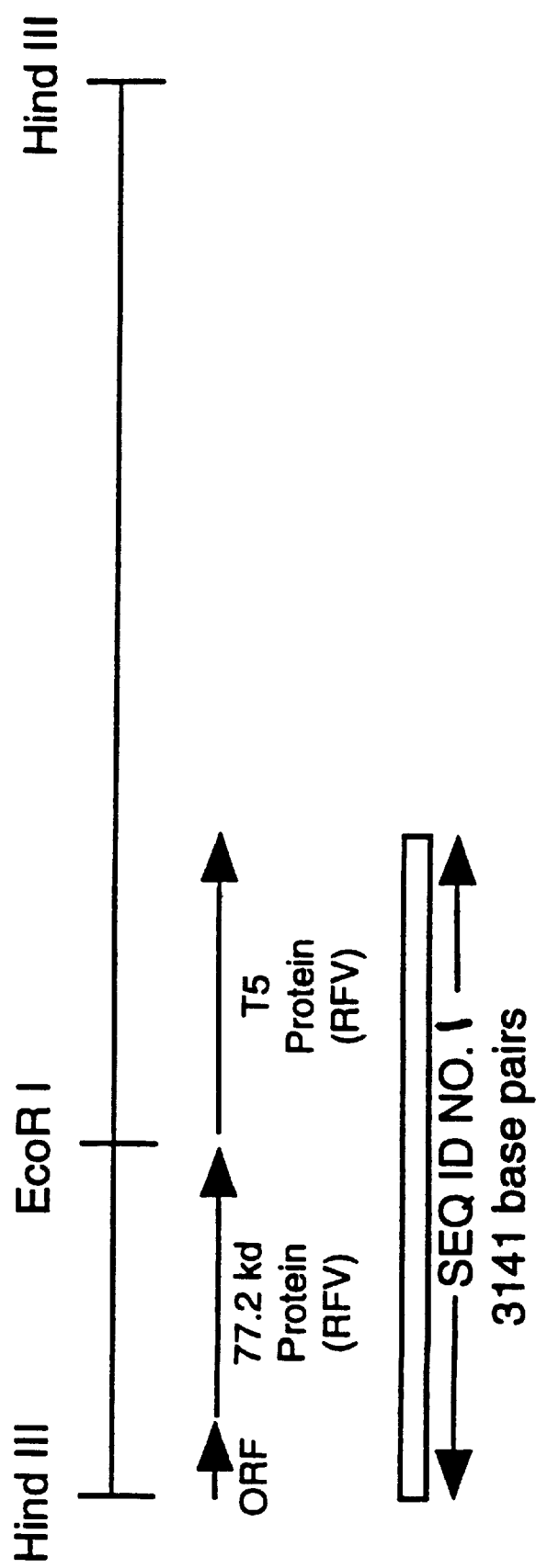

FIGS. 11A–11B: FIG. 11A: Restriction Endonuclease Map and Open Reading Frames in the SPV HindIII N fragment and part of SPV HindIII M fragment. Insertions of a foreign gene into a non-essential site of the swinepox virus Hind III N and Hind III M genomic DNA include the EcoR V site (S-SPV-060), SnaB I site (S-SPV-061), Bgl II site in Hind III N (S-SPV-062), and the Bgl II site in Hind III M (S-SPV-047). Insertions of a foreign gene into the I7L ORF (SEQ ID NO. 230) and I4L ORF (SEQ ID NO. 231) indicates that the sequence of the entire open reading frame is non-essential for replication of the swinepox virus and suitable for insertion of foreign genes. Additional sites for insertion of foreign genes include, but are not limited to the two Hind III sites, Ava I site, and the BamHI site.

FIG. 11B: Restriction Endonuclease Map and Open Reading Frames in the SPV Hind III K genomic fragment. Insertion of a foreign gene into a non-essential site of the swinepox virus Hind III K genomic DNA includes, but is not limited to the unique EcoR I site (S-SPV-059). Three open reading frames (ORFs) were identified within an approximately 3.2 kB region (SEQ ID NO. 1) of the approximately 6.7 kb SPV HindIII K fragment. Insertions of a foreign DNA into a unique EcoRI site within the SPV HindIII K genomic fragment indicates that the sequence is non-essential for replication of the swinepox virus and suitable for insertion of foreign genes. The unique EcoRI site is located between the 77.2 kd protein ORF and the T5 protein ORF in an intergenic region indicating that the intergenic region contains suitable sites for insertion of foreign DNA. Also identified are the 77.2 kd protein )RF (SEQ ID NO:3) and the T5 protein ORF (SEQ ID NO. 4) and an ORF of unknown function (SEQ ID NO. 2) which are suitable sites for insertion of a foreign DNA. The SPV 77.2 kd protein ORF (SEQ ID NO. 3) has amino acid sequence homology to rabbit fibroma virus (RFV) 77.2 kd protein. The SPV T5 protein ORF has amino acid sequence homology to rabbit fibroma virus (RFV) T5 protein. The identified open reading frames are within an approximately 3141 base pair segment of the SPV Hind III K fragment (SEQ ID NO. 1). The remaining approximately 3500 base pairs of the SPV Hind III K fragment has been sequenced previously (R. F. Massung, et al. Virology 197, 511–528 (1993)).

Figure 12A:
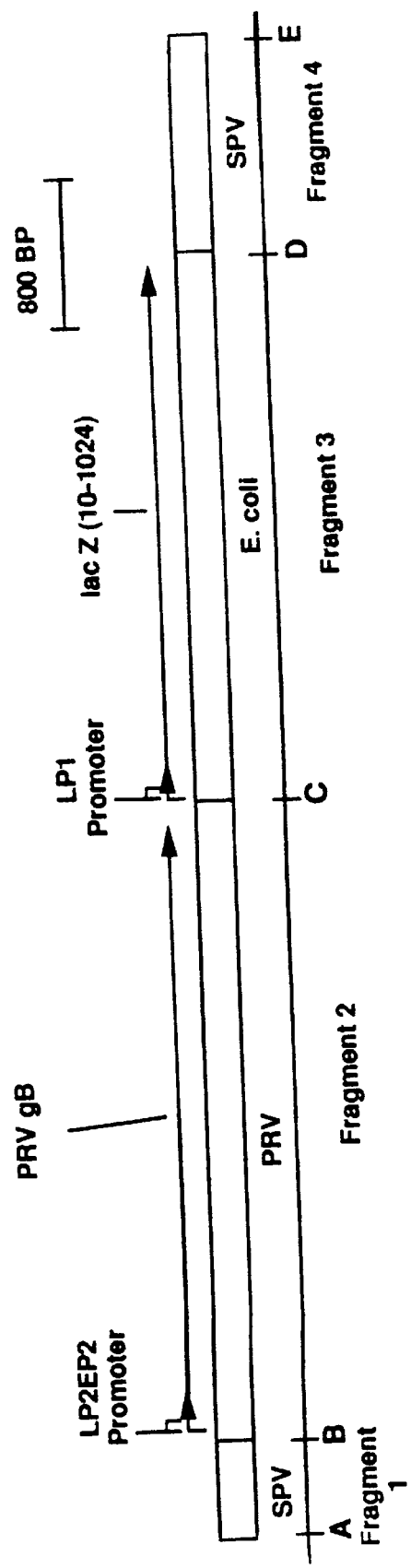
Figure 12B:
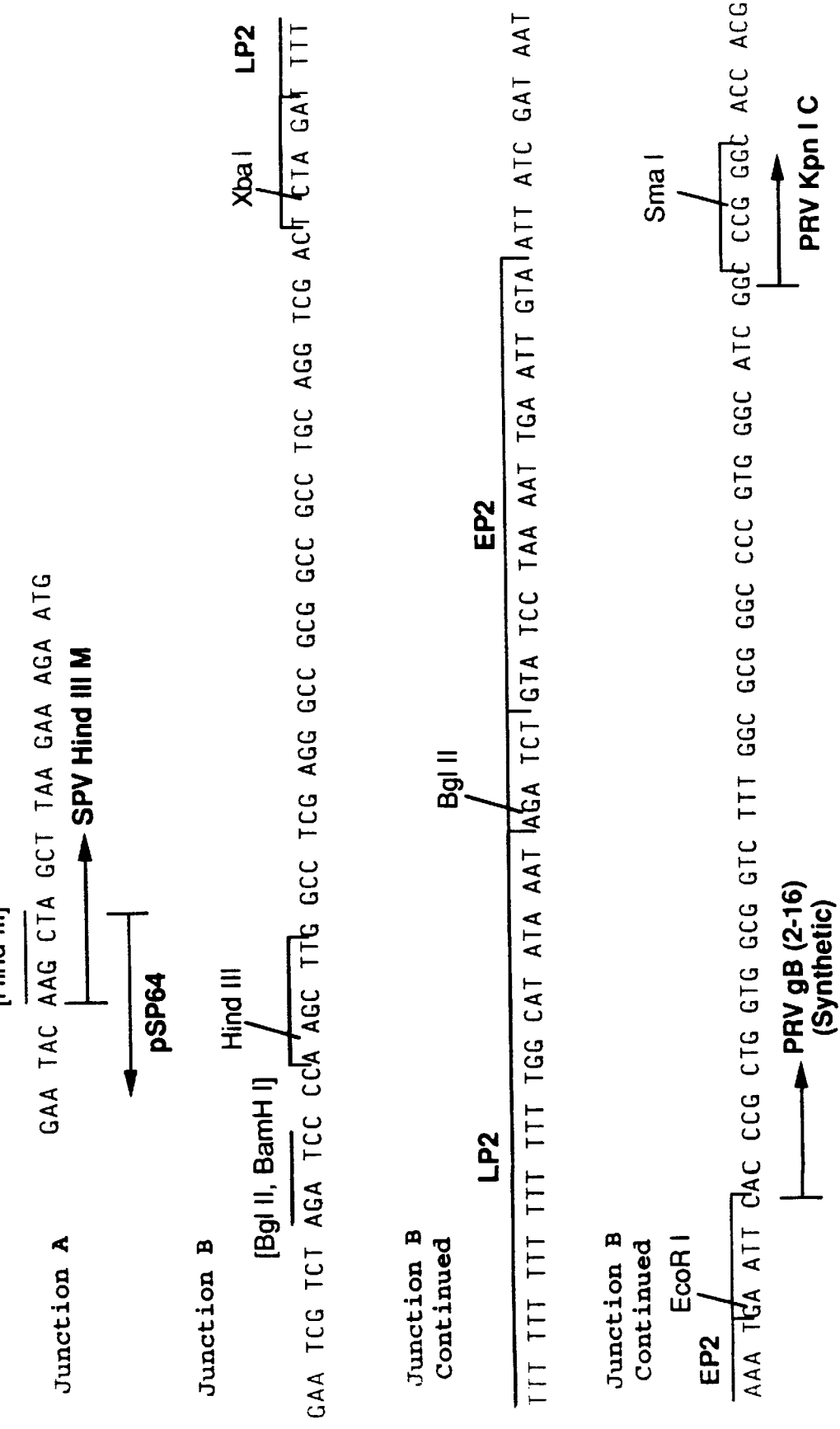
Figure 13A:
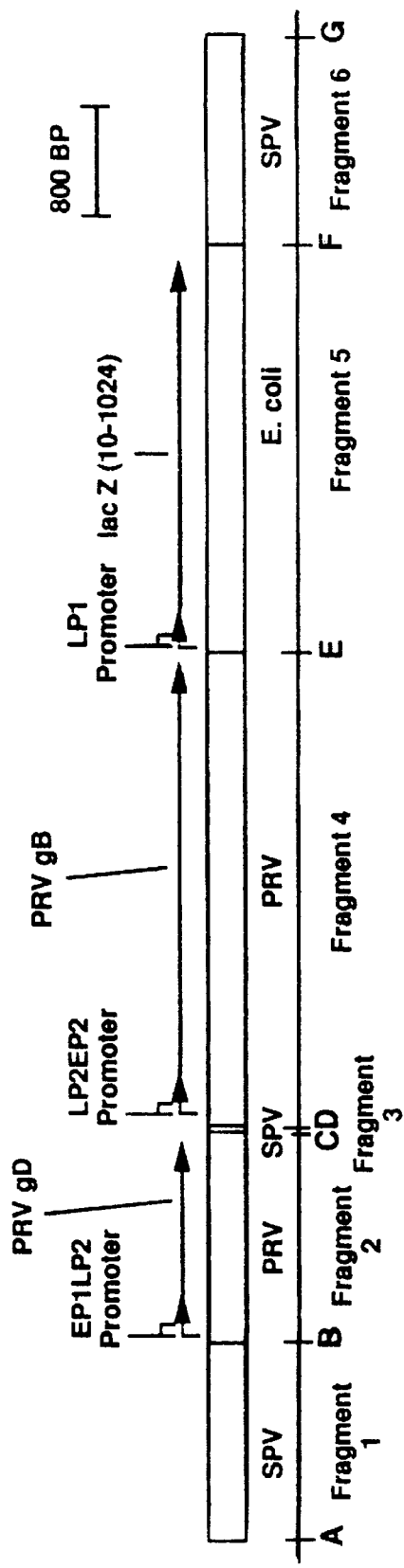
Figure 13C:
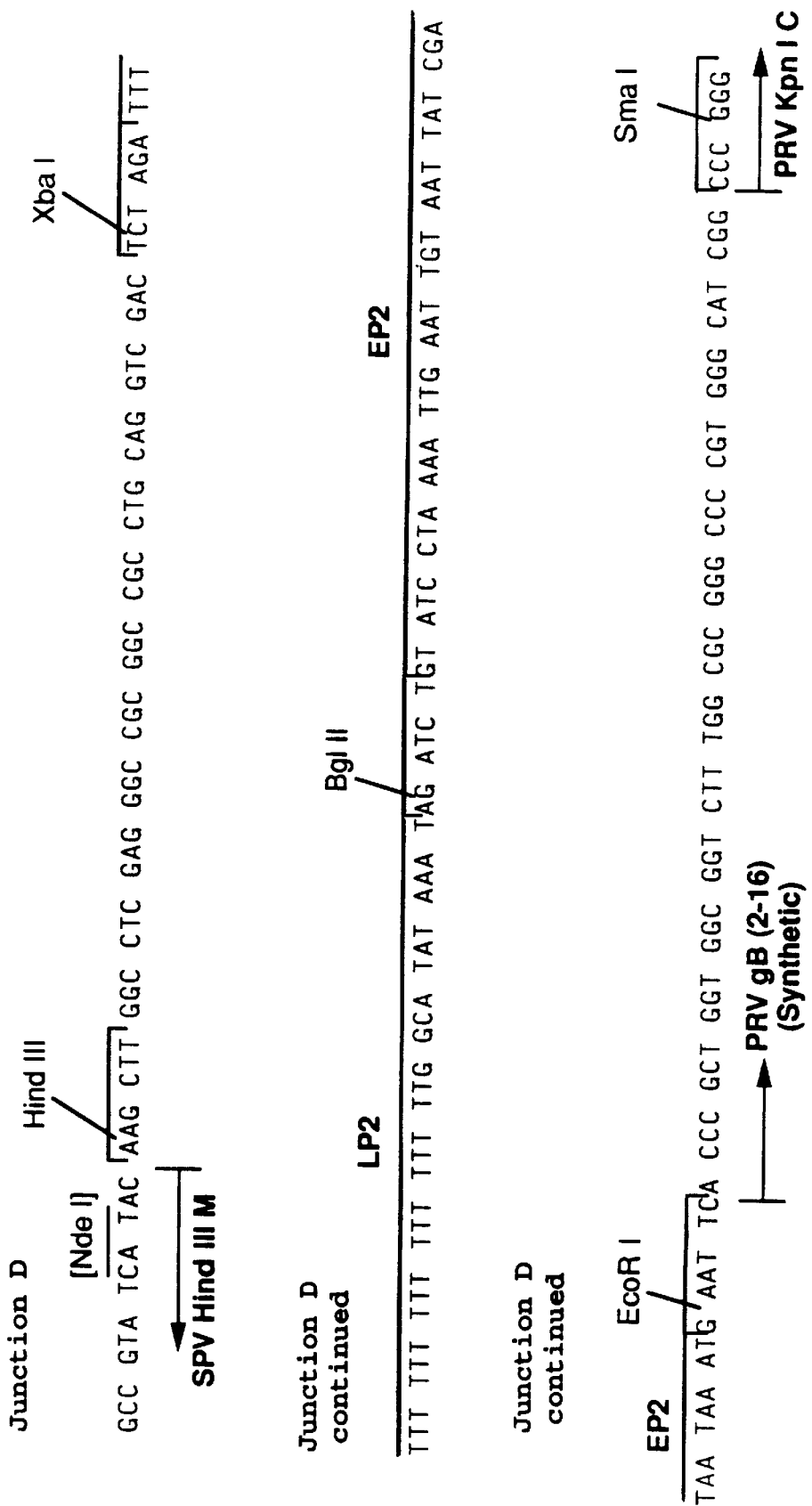
Figure 14A:
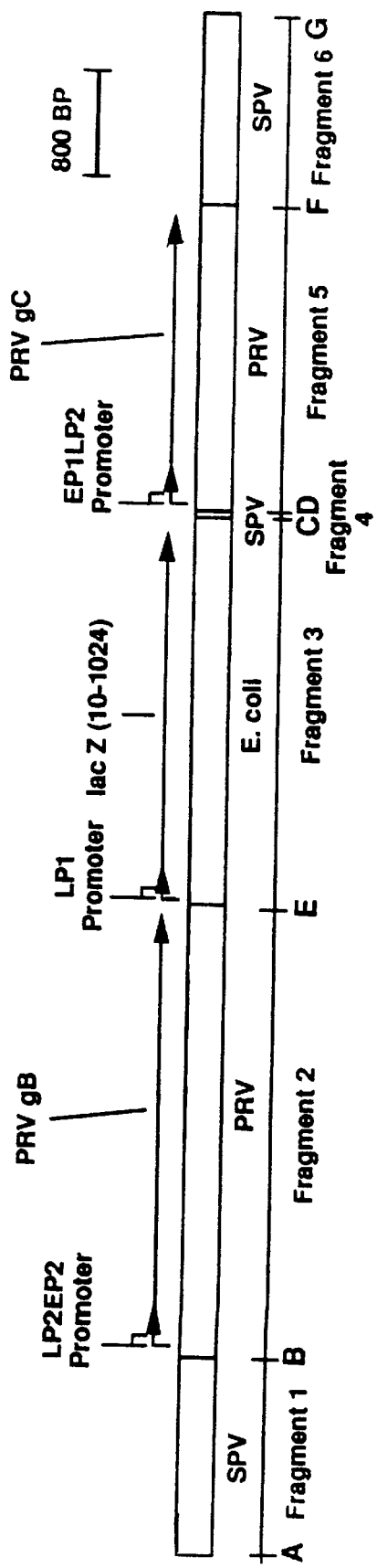
Figure 14B:
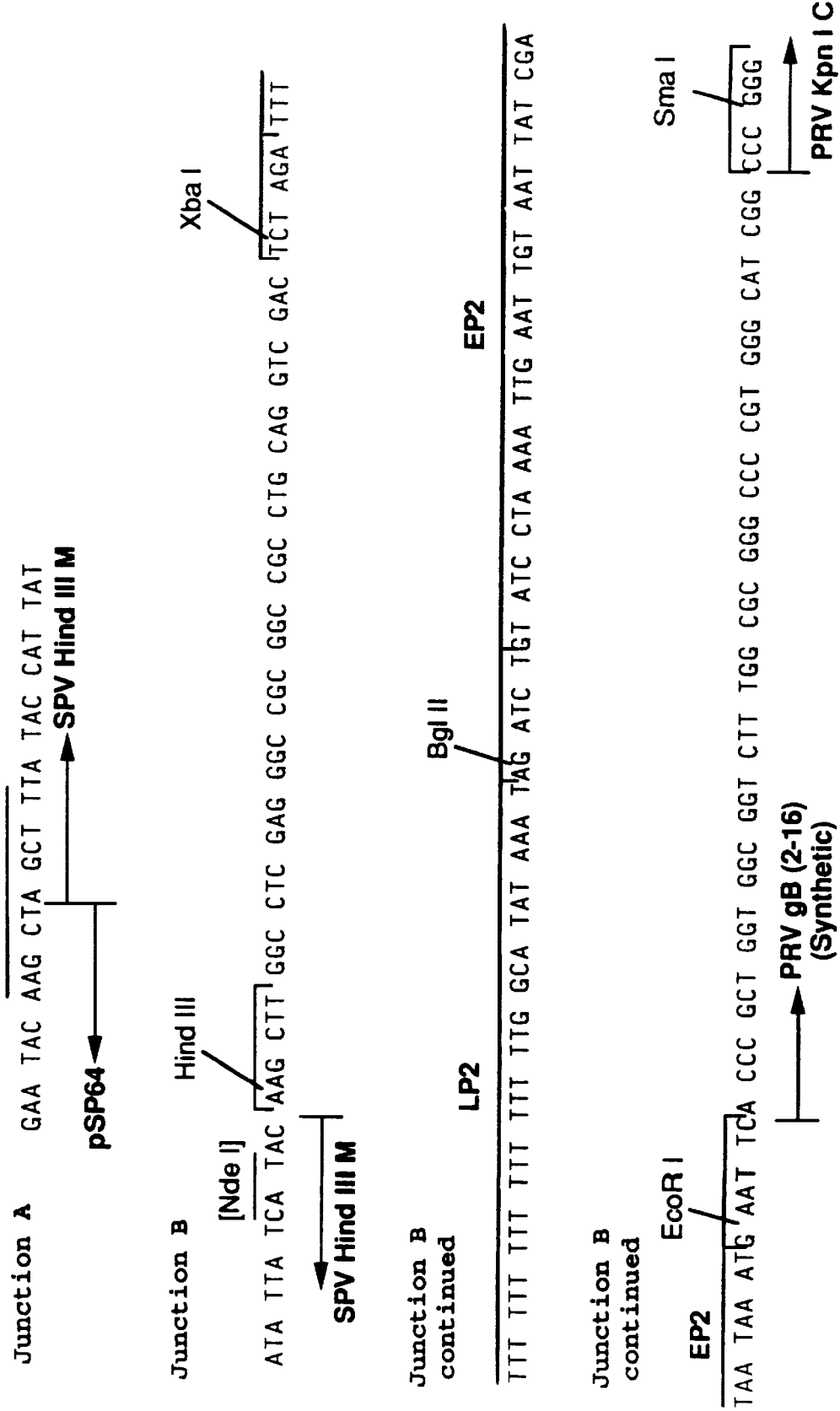
Figure 14C:
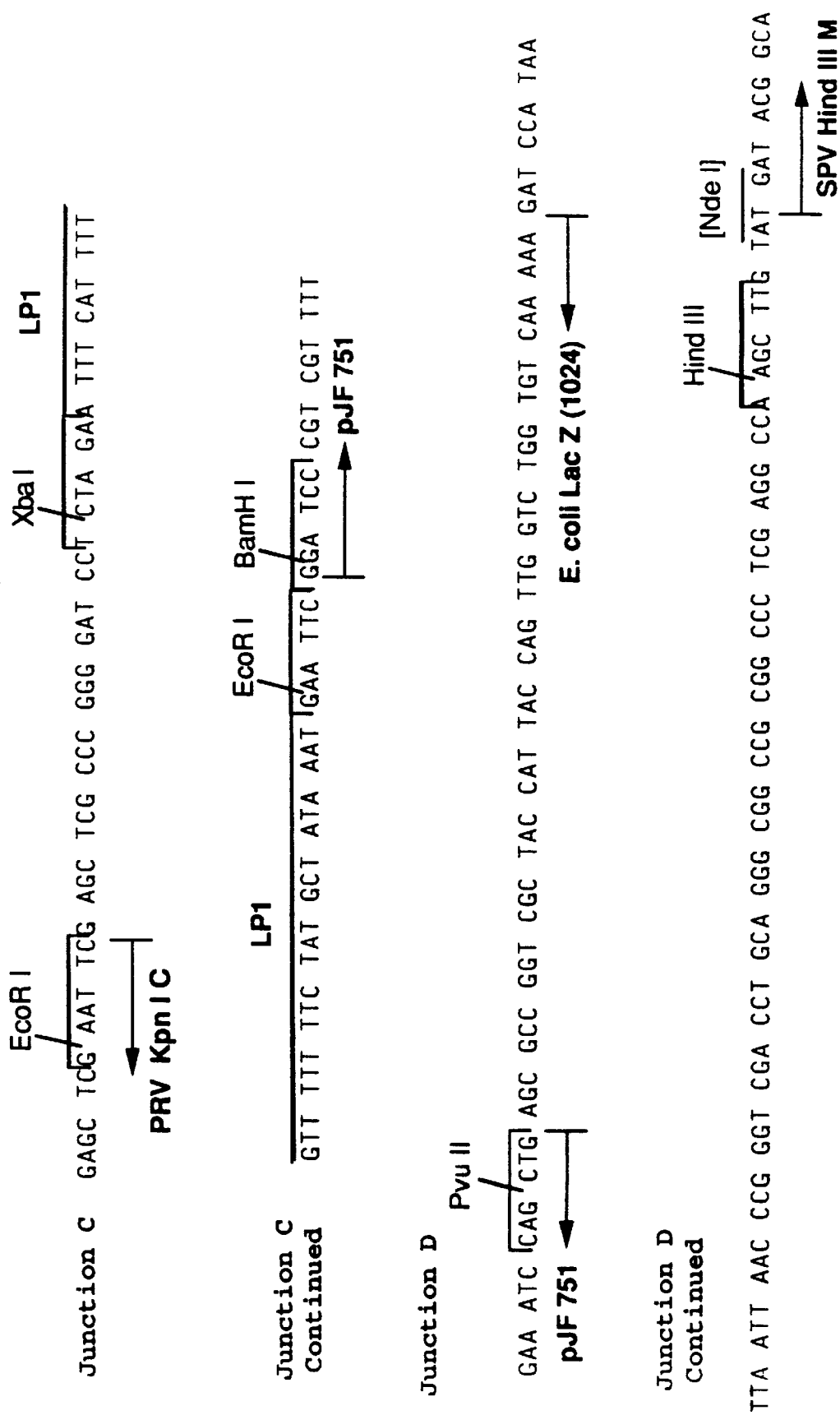
Figure 15A:
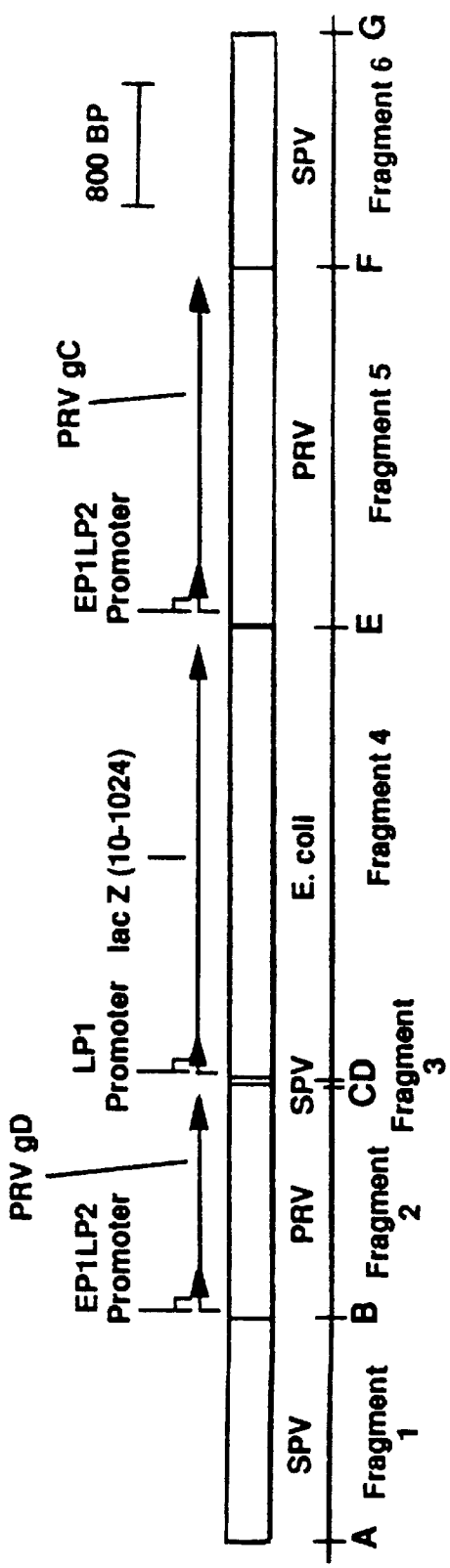
Figure 15C:
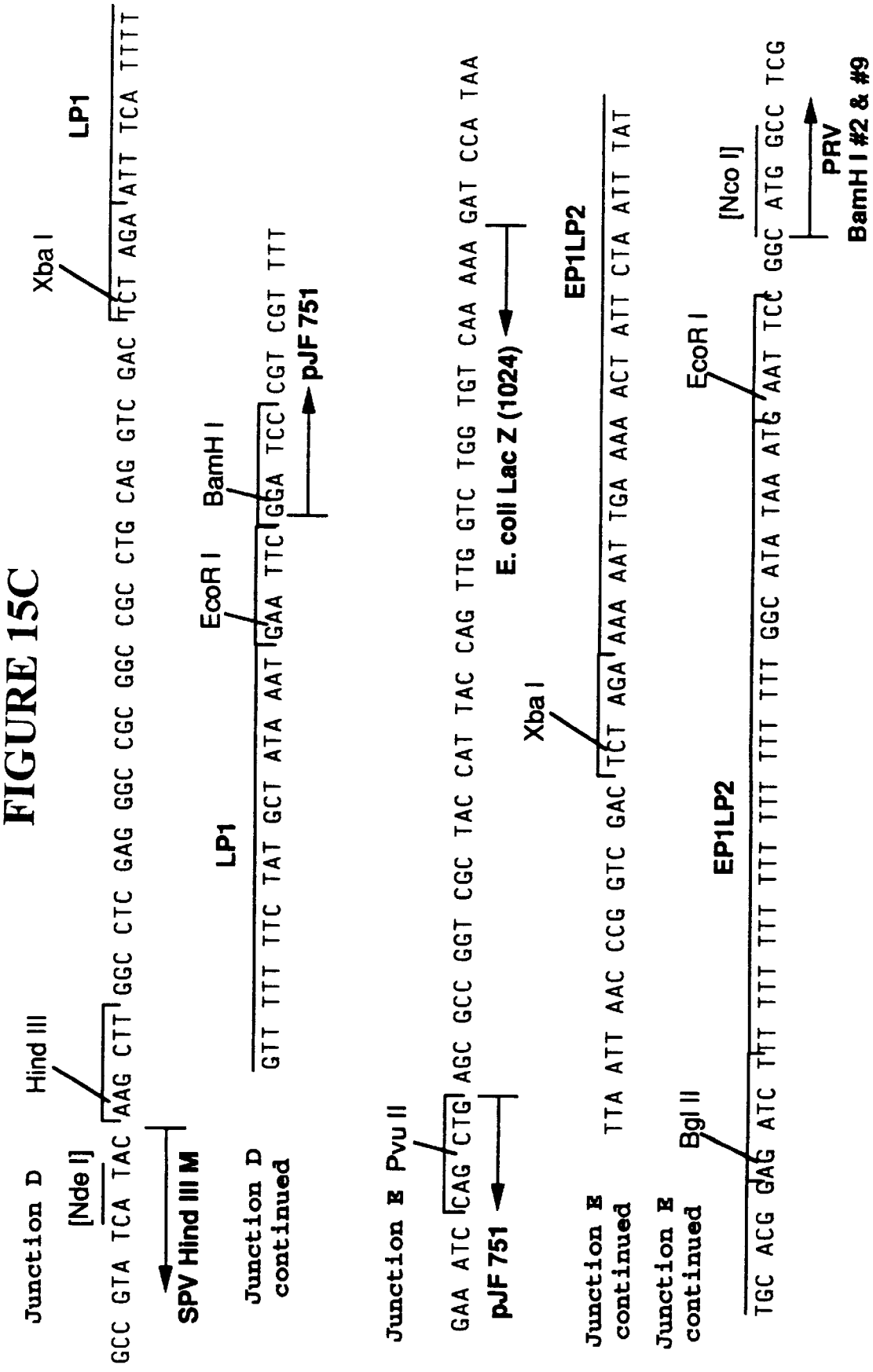
Figure 15D:
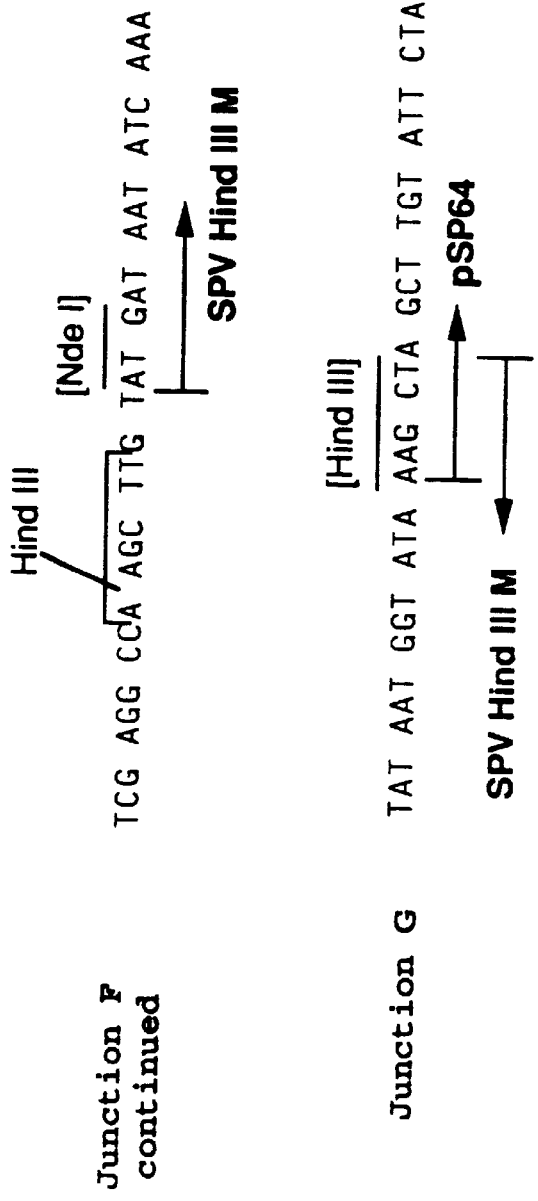
Figure 16A:
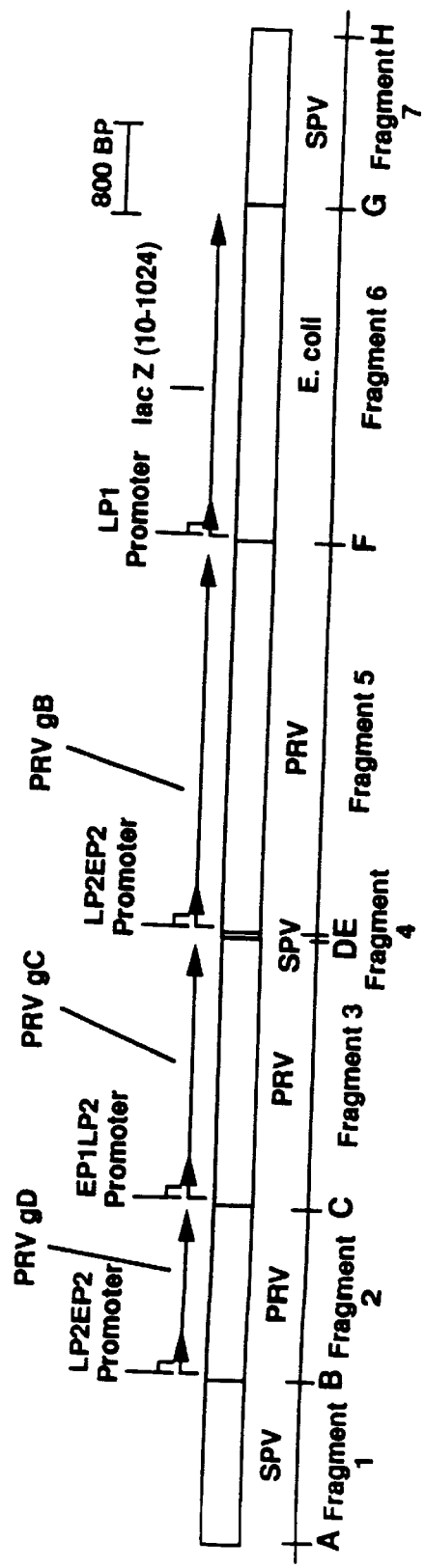
Figure 16C:
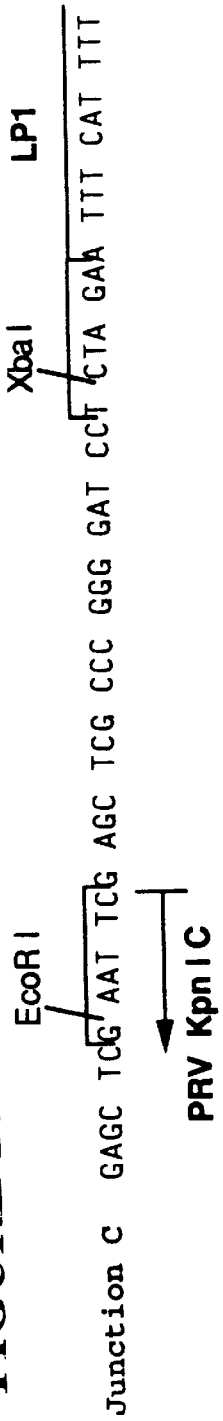
Figure 16C:
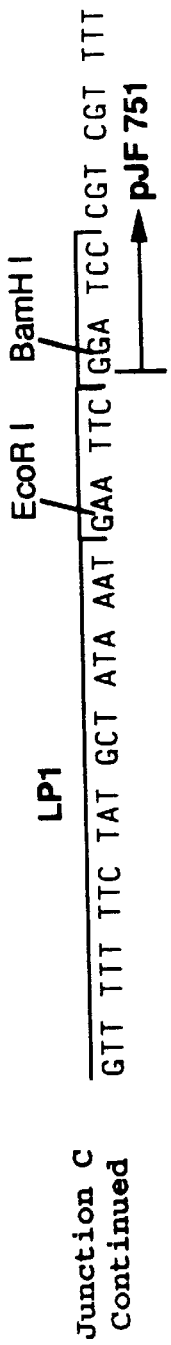
Figure 16C:
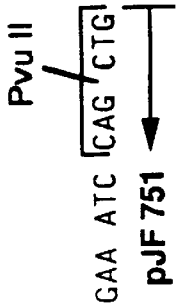
Figure 16C:
Figure 16D:
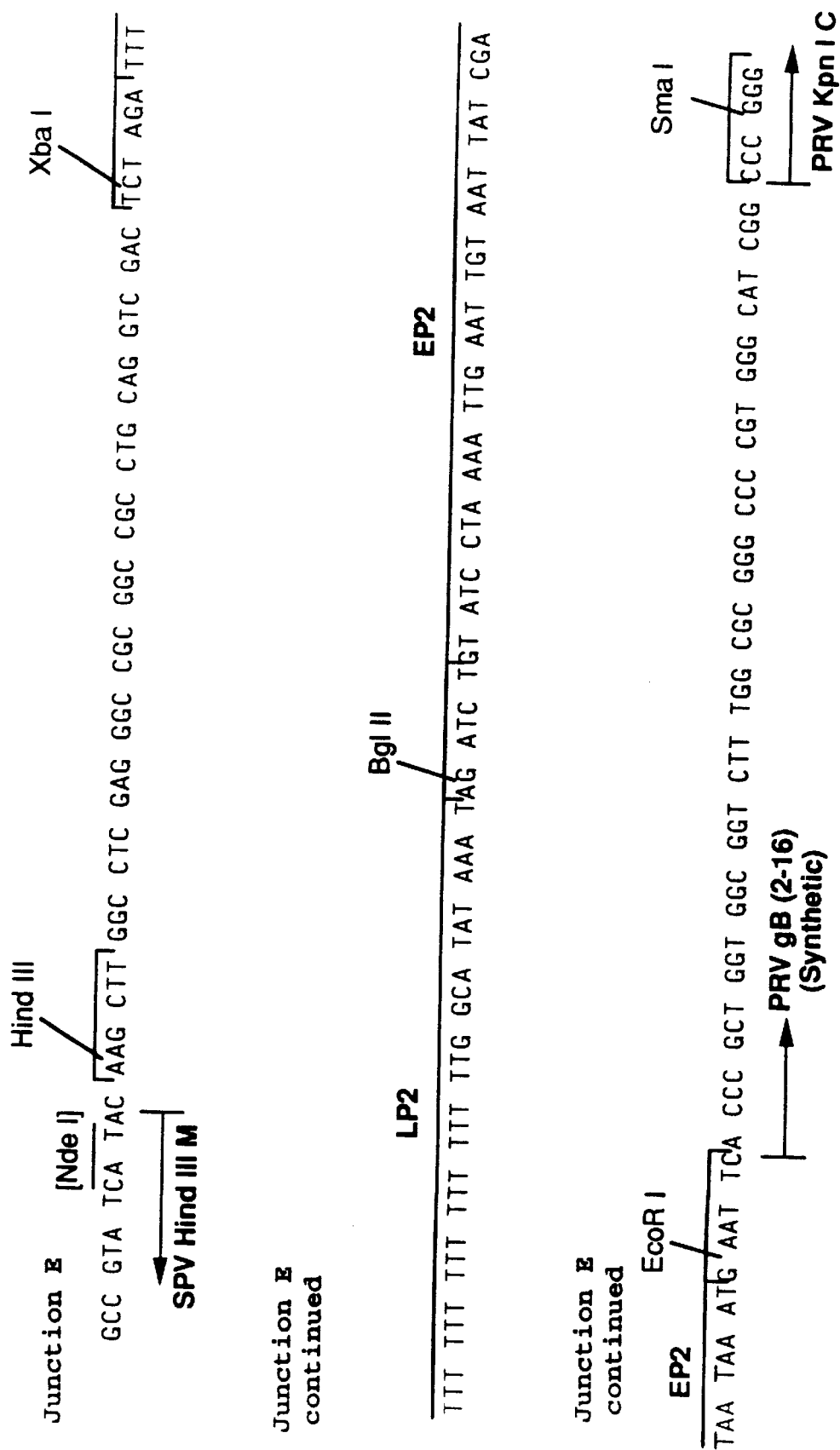
Figure 16E:
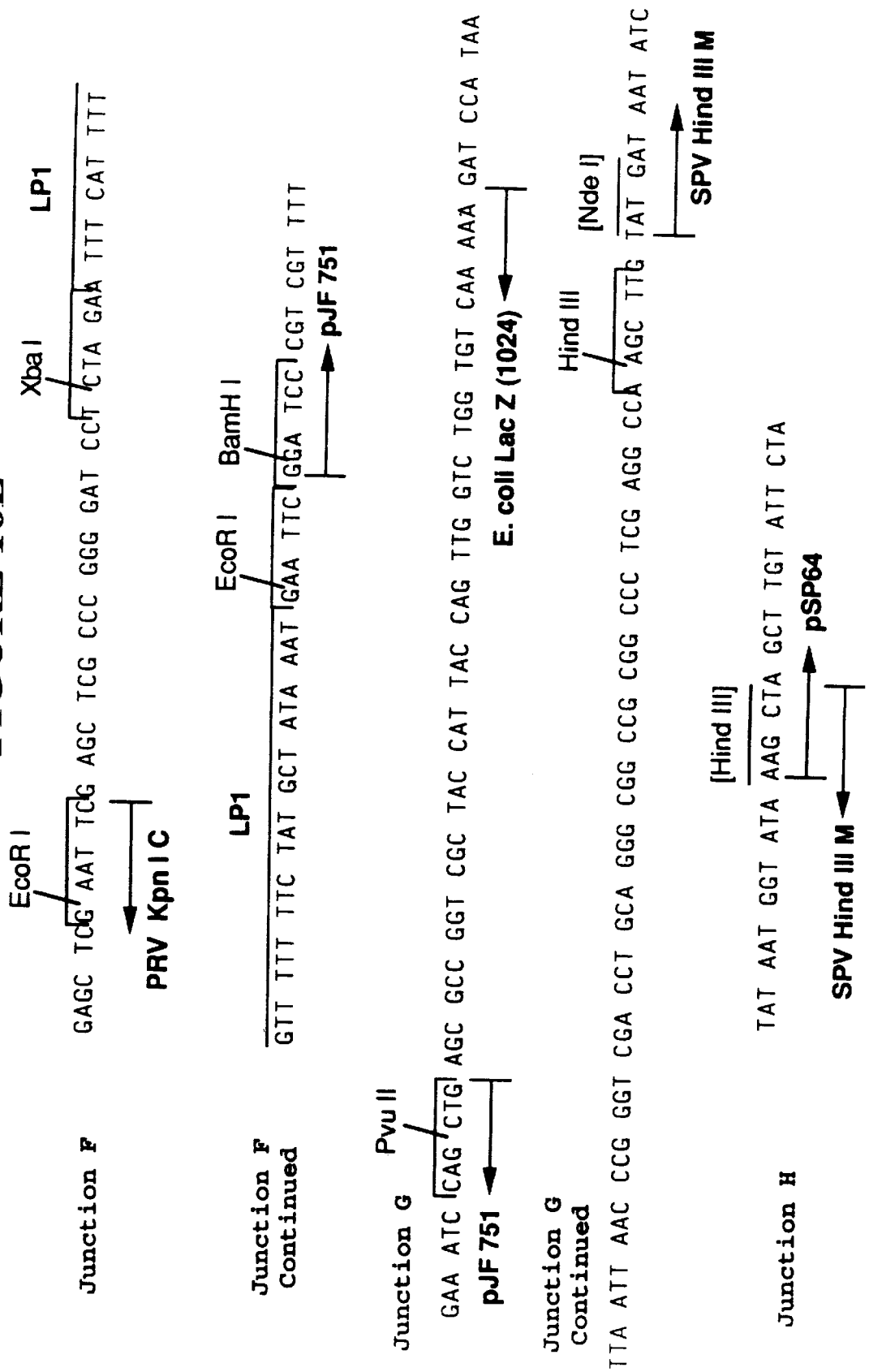

FIGS. 12A–12C: Detailed description of Swinepox Virus S-SPV-047 and the DNA insertion in Homology Vector 779-94.31. Diagram showing the orientation of DNA fragments assembled in plasmid 779-94.31. The origin of each fragment is indicated in the table. The sequences located at each of the junctions between fragments is also shown. FIGS. 12A–12C show the sequences located at Junction A (SEQ ID NO: 124), B (SEQ ID NO: 125), C (SEQ ID NO: 126), D (SEQ ID NO: 127), and E (SEQ ID NO: 128) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 2 early promoter 2 (LP2EP2), pox synthetic late promoter 1 (LP1), base pairs (BP).

FIGS. 13A–13D: Detailed description of Swinepox Virus S-SPV-052 and the DNA insertion in Homology Vector 789-41.7. Diagram showing the orientation of DNA fragments. assembled in plasmid 789-41.7. The origin of each fragment is indicated in the table. The sequences located at each of the junctions between fragments is also shown. FIGS. 13A–13D show the sequences located at Junction A (SEQ ID NO: 129), B (SEQ ID NO: 130), C (SEQ ID NO: 131), D (SEQ ID NO: 132), E (SEQ ID NO: 133), F (SEQ ID NO: 134) and G (SEQ ID NO: 135) fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 2 early promoter 2 (LP2EP2), pox synthetic early promoter 1 late promoter 2 (EP1LP2), pox synthetic late promoter 1 (LP1), base pairs (BP).

FIGS. 14A–14D: Detailed description of Swinepox Virus S-SPV-053 and the DNA insertion in Homology Vector 789-41.27. Diagram showing the orientation of DNA fragments assembled in plasmid 789-41.27. The origin of each fragment is indicated in the table. The sequences located at each of the junctions between fragments is also shown. FIGS. 14A–14D show the sequences located at Junction A (SEQ ID NO: 136), B (SEQ ID NO: 137), C (SEQ ID NO: 138), D (SEQ ID NO: 139), E (SEQ ID NO: 140), F (SEQ ID NO: 141) and G (SEQ ID NO: 142) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 2 early promoter 2 (LP2EP2), pox synthetic early promoter 1 late promoter 2 (EP1LP2), pox synthetic late promoter 1 (LP1), base pairs (BP).

FIGS. 15A–15D: Detailed description of Swinepox Virus S-SPV-054 and the DNA insertion in Homology Vector 789-41.47. Diagram showing the orientation of DNA fragments assembled in plasmid 789-41.47. The origin of each fragment is indicated in the table. The sequences located at each of the junctions between fragments is also shown. FIGS. 15A–15D show the sequences located at Junction A (SEQ ID NO: 143), B (SEQ ID NO: 144), C (SEQ ID NO: 145), D (SEQ ID NO: 146), E (SEQ ID NO: 147), F (SEQ ID NO: 148) and G (SEQ ID NO: 149) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: swinepox virus (SPV), pseudorabies virus (PRV), *Escherichia coli* (*E. coli*), pox synthetic early promoter 1 late promoter 2 (EP1LP2), pox synthetic late promoter 1 (LP1), base pairs (BP).

FIGS. 16A–16E: Detailed description of Swinepox Virus S-SPV-055 and the DNA insertion in Homology Vector 789-41.73. Diagram showing the orientation of DNA fragments assembled in plasmid 789-41.73. The origin of each fragment is indicated in the table. The sequences located at each of the junctions between fragments is also shown. FIGS. 16A–16E show the sequences located at Junction A (SEQ ID NO: 150), B (SEQ ID NO: 151), C (SEQ ID NO: 152), D (SEQ ID NO: 153), E (SEQ ID NO: 154), F (SEQ ID NO: 155), G (SEQ ID NO: 156), and H (SEQ ID NO: 157) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 2 early promoter 2 (LP2EP2), pox synthetic early promoter 1 late promoter 2 (EP1LP2), pox synthetic late promoter 1 (LP1), base pairs (BP).

DETAILED DESCRIPTION OF THE INVENTION

The present invention provides a recombinant swinepox virus comprising a foreign DNA sequence inserted into the swinepox virus genomic DNA, wherein the foreign DNA sequence is inserted within a HindIII K fragment of the swinepox virus genomic DNA and is capable of being expressed in a swinepox virus infected host cell.

In one embodiment the recombinant swinepox virus contains the foreign DNA sequence is inserted into an approximately 2 kB HindIII to BamHI subfragment of the HindIII N fragment of the swinepox virus genomic DNA. In another embodiment the foreign DNA sequence is inserted into an open reading frame within an approximately 2 kB HindIII to BamHI subfragment of the HindIII N fragment of the swinepox virus genomic DNA. In another embodiment: the open reading frame encodes a I7L gene.

In another embodiment the foreign DNA sequence is inserted within a EcoRV restriction endonuclease site within the approximately 2 kB HindIII to BamHI subfragment of the swinepox virus genomic DNA. In another embodiment the foreign DNA sequence is inserted within a SnaBI restriction endonuclease site within the approximately 2.0 kB HindIII to BamHI subfragment of the swinepox virus genomic DNA.

In another embodiment the foreign DNA sequence is inserted within an approximately 1.2 kB BamHI to HindIII subfragment of the HindIII N fragment of the swinepcx virus genomic DNA. In another embodiment the foreign DNA sequence is inserted into an open reading frame within an approximately 1.2 kB BamHI to HindIII subfragment of the HindIII N fragment of the swinepox virus genomic DNA. In another embodiment the foreign DNA sequence is inserted into an open reading frame which encodes a I4L gene. In another embodiment the foreign DNA sequence is inserted within a BglII restriction endonuclease site within the approximately 1.2 kB BamHI to HindIII subfragment of the swinepox virus genomic DNA.

The present invention provides a recombinant swinepox virus comprising a foreign DNA sequence inserted into the swinepox virus genomic DNA, wherein the foreign DNA sequence is inserted within a HindIII M fragment of the swinepox virus genomic DNA and is capable of being expressed in a swinepox virus infected host cell.

In one embodiment the recombinant swinepox virus contains the foreign DNA sequence inserted into an approximately 2 kB BglII to HindIII subfragment of the HindIII M fragment of the swinepox virus genomic DNA. In another embodiment the foreign DNA sequence is inserted into an open reading frame within an approximately 2 kB BglII to HindIII subfragment of the HindIII M fragment of the swinepox virus genomic DNA. In another embodiment the open reading frame encodes a 01L gene. In the preferred embodiment the foreign DNA sequence is inserted within a BglII restriction endonuclease site within the approximately 2 kB BglII to HindIII subfragment of the swinepox virus genomic DNA.

In another embodiment the recombinant swinepox virus contains the foreign DNA sequence inserted within an approximately 3.6 kB larger HindIII to BglII subfragment of the HindIII M fragment of the swinepox virus genomic DNA. In another embodiment the foreign DNA sequence is inserted into an open reading frame within an approximately 3.6 kB larger HindIII to BglII subfragment of the HindIII M fragment of the swinepox virus genomic: DNA. In another embodiment the open reading frame encodes a I4L gene.

In one embodiment the foreign DNA sequence of the recombinant swinepox virus is inserted within a non-essential Open Reading Frame (ORF) of the HindIII M fragment. Example of ORF's include, but are not limited to: I4L, I2L, 01L, and E10L.

In another embodiment the foreign DNA sequence of the recombinant swinepox virus is inserted within an approximately 2 Kb HindIII to BglII subfragment of the HindIII M fragment of the swinepox virus genomic DNA. In a preferred embodiment the foreign DNA sequence is inserted within a BglII site located within the approximately 2 Kb HindIII to BglII subfragment of the swinepox virus genomic DNA.

In another embodiment the foreign DNA sequence is inserted within a larger HindIII to BglII subfragment of the HindIII M fragment of the swinepox virus genomic DNA. In a preferred embodiment the foreign DNA sequence is inserted within an AccI site located within the larger HindIII to BglII subfragment of the swinepox virus genomic DNA.

In another embodiment the recombinant swinepox virus further comprises a foreign DNA sequence inserted into an open reading frame encoding swinepox virus thymidine kinase. In one embodiment the foreign DNA sequence is inserted into a NdeI site located within the open reading frame encoding the swinepox virus thymidine kinase.

This invention provides a recombinant swinepox virus comprising a foreign DNA sequence inserted into the swinepox virus genomic DNA, wherein the foreign DNA sequence is inserted within a HindIII K fragment of the swinepox virus genomic DNA and is capable of being expressed in a swinepox virus infected host cell.

In one embodiment the foreign DNA sequence is inserted into an approximately 3.2 kB subfragment of the HindIII K fragment of the swinepox virus genomic DNA. In another embodiment the foreign DNA sequence is inserted into an open reading frame within an approximately 3.2 kB subfragment of the HindIII K fragment of the swinepox virus genomic DNA. In another embodiment the open reading frame encodes a B18R gene. In another embodiment the open reading frame encodes a B4R gene. In another embodiment the open reading frame encodes swinepox homologue of the 77.2 kD protein gene. In another embodiment the open reading frame encodes swinepox homologue of the T5 protein gene.

For purposes of this invention, "a recombinant swinepox virus capable of replication" is a live swinepox virus which has been generated by the recombinant methods well known to those of skill in the art, e.g., the methods set forth in HOMOLOGOUS RECOMBINATION PROCEDURE FOR GENERATING RECOMBINANT SPV in *Materials and Methods* and has not had genetic material essential for the replication of the recombinant swinepox virus deleted.

For purposes of this invention, "an insertion site which is not essential for replication of the swinepox virus" is a location in the swinepox viral genome where a sequence of DNA is not necessary for viral replication, for example, complex protein binding sequences, sequences which code for reverse transcriptase or an essential glycoprotein, DNA sequences necessary for packaging, etc. For purposes of this invention, a "promoter" is a specific DNA sequence on the DNA molecule to which the foreign RNA polymerase attaches and at which transcription of the foreign RNA is initiated.

For purposes of this invention, an "open reading frame" is a segment of DNA which contains codons that can be transcribed into RNA which can be translated into an amino acid sequence and which does not contain a termination codon.

In addition, the present invention provides a recombinant swinepox virus (SPV) capable of replication in an animal into which the recombinant swinepox virus is introduced which comprises swinepox viral DNA and foreign DNA encoding RNA which does not naturally occur in the animal into which the recombinant swinepox virus is introduced, the foreign DNA being inserted into the swinepox viral DNA at an insertion site which is not essential for replication of the swinepox virus and being under the control of a promoter.

The invention further provides a foreign DNA sequence or foreign RNA which encodes a polypeptide. Preferably, the polypeptide is antigenic in the animal. Preferably, this antigenic polypeptide is a linear polymer of more than 10 amino acids linked by peptide bonds which stimulates the animal to produce antibodies.

The invention further provides a recombinant swinepox virus capable of replication which contains a foreign DNA encoding a polypeptide which is a detectable marker. Preferably the detectable marker is the polypeptide *E. coli* β-galactosidase or *E. coli* beta-glucuronidase. Preferably, the insertion site for the foreign DNA encoding *E. coli* β-galactosidase is the AccI restriction endonuclease site located within the HindIII M fragment of the swinepox viral DNA. Preferably, this recombinant swinepox virus is designated S-SPV-003 (ATCC Accession No. VR 2335). The S-SPV-003 swinepox virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2335.

For purposes of this invention, a "polypeptide which is a detectable marker" includes the bimer, trimer and tetramer form of the polypeptide. *E. coli* β-galactosidase is a tetramer composed of four polypeptides or monomer sub-units.

The present invention further provides a recombinant swinepox virus in which the foreign DNA encodes an antigenic polypeptide is: Swine Influenza Virus hemagglutin, Swine Influenza Virus neurominidase, Swine Influenza Virus matrix, Swine Influenza Virus nuceloprotein, African Swine Fever Virus or Mycoplasma hyopneumoniae. Preferred embodiments of such virus are designated S-SPV-121, and S-SPV-122.

The present invention further provides a recombinant swinepox virus in which the foreign DNA encodes an antigenic polypeptide is: cytokine is chicken macrophage migration inhibitory factor (cMIF), chicken myelomonocytic growth factor (cMGF) or chicken interferon (cIFN). Preferred embodiments of such virus are designated S-SPV-068, and S-SPV-105.

The present invention further provides a recombinant swinepox virus in which the foreign DNA encodes an antigenic polypeptide is: porcine reproductive and respiratory syndrome virus (PRRS) ORF2, ORF3, ORF4, ORF5, ORF6 and ORF7, pseudorabies gB, gD, gI. Preferred embodiments of such virus are designated S-SPV-076, S-SPV-079, S-SPV-090, S-SPV-084, S-SPV-091, S-SPV-092, S-SPV-093, S-SPV-094, S-SPV-095.

The present invention further provides a recombinant swinepox virus in which the foreign DNA encodes an antigenic polypeptide is: Infectious bovine rhinotracheitis virus glycoprotein B, glycoprotein D and glycoprotein I, bovine respiratory syncytial virus attachment protein (BRSV G), bovine respiratory syncytial virus fusion protein (BRSV F), bovine respiratory syncytial virus nucleocapsid protein (BRSV N). Preferred embodiments of such virus are designated S-SPV-109, S-SPV-110, S-SPV-111, S-SPV-113, S-SPV-115, S-SPV-119, S-SPV-112.

The present invention further provides a recombinant swinepox virus in which the foreign DNA encodes an antigenic polypeptide is: bovine viral diarrhea virus (BVDV) glycoprotein 48 or glycoprotein 53. A Preferred embodiment of such a virus is designated S-SPV-099.

The present invention further provides a recombinant swinepox virus in which the foreign DNA encodes an antigenic polypeptide is: feline immunodeficiency virus gag/protease and envelope, feline leukemia virus gag/protease and envelope. Preferred embodiments of such viruses are designated: S-SPV-106, S-SPV-089, S-SPV-100, S-SPV-107, S-SPV-108.

The present invention further provides a recombinant swinepox virus in which the foreign DNA encodes an antigenic polypeptide is: canine parvovirus VP2 and VP1/2. Preferred embodiments of such viruses are designated: S-SPV-114, S-SPV-116, S-SPV-117, S-SPV-118.

The present invention provides a recombinant swinepox virus comprising a foreign DNA inserted into the swinepox virus genomic DNA, wherein the one or more foreign DNAs are inserted within each of the HindIII K fragment of the swinepox virus genomic DNA and within the HindIII M fragment of the swinepox virus genomic DNA and is capable of being expressed in a swinepox virus infected host cell. Preferred embodiments of such viruses are designated: S-SPV-127, S-SPV-128, S-SPV-131, and S-SPV-132.

The present invention provides a recombinant swinepox virus comprising a foreign DNA inserted into the swinepox virus genomic DNA, wherein the one or more foreign DNAs which encode a fusion protein are inserted within each of the HindIII K fragment of the swinepox virus genomic DNA and within the HindIII M fragment of the swinepox virus genomic. DNA and is capable of being expressed in a swinepox virus infected host cell. Preferred embodiments of such viruses are designated: S-SPV-130.

The invention further provides a recombinant swinepox virus capable of replication which contains foreign DNA encoding an antigenic polypeptide which is or is from pseudorabies virus (PRV) g50 (gD), pseudorabies virus (PRV) gII (gB), Pseudorabies virus (PRV) gIII (gC), pseudorabies virus (PRV) glycoprotein H, pseudorabies virus (PRV) glycoprotein E, Transmissible gastroenteritis (TGE) glycoprotein 195, Transmissible gastroenteritis (TGE) matrix protein, swine rotavirus glycoprotein 38, swine parvovirus capsid protein, *Serpulina hydodysenteriae* protective antigen, Bovine Viral Diarrhea (BVD) glycoprotein 55, Newcastle Disease Virus (NDV) hemagglutinin-neuraminidase, swine flu hemagglutinin or swine flu neuraminidase. Preferably, the antigenic polypeptide is Pseudorabies Virus (PRV) g50 (gD). Preferably, the antigenic protein is Newcastle Disease Virus (NDV) hemagglutinin-neuraminidase.

The invention further provides a recombinant swinepox virus capable of replication which contains foreign DNA encoding an antigenic polypeptide which is or is from *Serpulina hyodysenteriae*, Foot and Mouth Disease Virus, Hog Cholera Virus, African Swine Fever Virus or *Mycoplasma hyopneumoniae*.

The invention further provides for a recombinant swinepox virus capable of replication which contains foreign DNA encoding pseudorabies virus (PRV) g50 (gD) and foreign DNA encoding pseudorabies virus (PRV) gIII (gC). This recombinant swinepox virus can also be further engineered to contain foreign DNA encoding a detectable marker, such as *E. coli* β-galactosidase. A preferred site within the swinepox viral DNA for insertion of the foreign DNA encoding PRV g50 (gD), PRV gIII (gC) and *E. coli* β-galactosidase is the AccI site within the HindIII M fragment of the swinepox viral DNA.

The invention further provides for a recombinant swinepox virus capable of replication which contains foreign DNA encoding pseudorabies virus (PRV) g50 (gD) and foreign DNA encoding pseudorabies virus (PRV) gII (gB). This recombinant swinepox virus can also be further engineered to contain foreign DNA encoding a detectable marker, such as *E. coli* β-galactosidase. A preferred site within the swinepox viral genome for insertion of foreign DNA encoding PRV g50 (gD), PRV gII (gB) and *E. coli* β-galactosidase is the AccI site within the HindIII M fragment of the swinepox viral DNA.

The invention further provides for a recombinant swinepox virus capable of replication which contains foreign DNA encoding pseudorabies virus (PRV) gIII (gC) and foreign DNA encoding pseudorabies virus (PRV) gII (gB). This recombinant swinepox virus can also be further engineered to contain foreign DNA encoding a detectable marker, such as *E. coli* β-galactosidase. A preferred site within the swinepox viral genome for insertion of foreign DNA encoding PRV gIII (gC), PRV gII (gB) and *E. coli* β-galactosidase is the AccI site within the HindIII M fragment of the swinepox viral DNA.

The invention further provides for a recombinant swinepox virus capable of replication which contains foreign DNA encoding pseudorabies virus (PRV) g50 (gD), foreign DNA encoding pseudorabies virus (PRV) gIII (gC), and foreign DNA encoding pseudorabies virus (PRV) gII (gB). This recombinant swinepox virus can also be further engineered to contain foreign DNA encoding a detectable marker, such as *E. coli* β-galactosidase.

A preferred site within the swinepox viral genome for insertion of foreign DNA encoding PRV g50 (gD), PRV gIII (gC), PRV gII (gB) and *E. coli* β-galactosidase is the AccI site within the HindIII M fragment of the swinepox viral DNA.

The invention further provides for a recombinant swinepox virus capable of replication which contains foreign DNA encoding RNA encoding the antigenic polypeptide Newcastle Disease Virus (NDV) hemagglutinin-neuraminidase further comprising foreign DNA encoding a polypeptide which is a detectable marker.

The present invention further provides a recombinant swinepox virus which comprises a foreign DNA sequence inserted into a non-essential site of the swinepox genome, wherein the foreign DNA sequence encodes an antigenic polypeptide derived from infectious bovine rhinotracheitis virus and is capable of being expressed in a host infected by the recombinant swinepox virus. Examples of such antigenic polypeptide are infectious bovine rhinotracheitis virus glycoprotein E and glycoprotein G. The present invention further provides a recombinant swinepox virus which comprises a foreign DNA sequence inserted into a non-essential site of the swinepox genome, wherein the foreign DNA sequence encodes an antigenic polypeptide derived from infectious laryngotracheitis virus and is capable of being expressed in a host infected by the recombinant swinepox virus. Examples of such antigenic polypeptide are infectious laryngotracheitis virus glycoprotein G and glycoprotein I.

In one embodiment of the recombinant swinepox virus the foreign DNA sequence encodes a cytokine. In another embodiment the cytokine is chicken myelomonocytic growth factor (cMGF) or chicken interferon (cIFN). Cytokines include, but are not limited to: transforming growth factor beta, epidermal growth factor family, fibroblast growth factors, hepatocyte growth factor, insulin-like growth factor, vascular endothelial growth factor, interleukin 1, IL-1 receptor antagonist, interleukin-2, interleukin-3, interleukin-4, interleukin-5, interleukin-6, IL-6 soluble receptor, interleukin-7, interleukin-8, interleukin-9, interleukin-10, interleukin-11, interleukin-12, interleukin-13, angiogenin, chemokines, colony stimulating factors, granulocyte-macrophage colony stimulating factors, erythropoietin, interferon, interferon gamma, Stem cell factor (or known as mast cell growth factor, or c-kit ligand protein), leukemia inhibitory factor, oncostatin M, pleiotrophin, secretory leukocyte protease inhibitor, stem cell factor, tumor necrosis factors, and soluble TNF receptors. These cytokines are from humans, bovine, equine, feline, canine, porcine or avian.

The present invention further provides a recombinant swinepox virus which comprises a foreign DNA sequence inserted into a non-essential site of the swinepox genome, wherein the foreign DNA sequence encodes an antigenic polypeptide derived from a human pathogen and is capable of being expressed in a host infected by the recombinant swinepox virus.

Recombinant SPV expressing cytokines is used to enhance the immune response either alone or when combined with vaccines containing cytokines or antigen genes of disease causing microorganisms.

Antigenic polypeptide of a human pathogen which are derived from human herpesvirus include, but are not limited to: hepatitis B virus and hepatitis C virus hepatitis B virus surface and core antigens, hepatitis C virus, human immunodeficiency virus, herpes simplex virus-1, herpes simplex virus-2, human cytomegalovirus, Epstein-Barr virus, Varicella-Zoster virus, human herpesvirus-6, human herpesvirus-7, human influenza, measles virus, hantaan virus, pneumonia virus, rhinovirus, poliovirus, human respiratory syncytial virus, retrovirus, human T-cell leukemia virus, rabies virus, mumps virus, malaria (*Plasmodium falciparum*), Bordetella pertussis, Diptheria, *Rickettsia prowazekii, Borrelia berfdorferi*, Tetanus toxoid, malignant tumor antigens.

In one embodiment of the invention, a recombinant swinepox virus contains the foreign DNA sequence encoding hepatitis B virus core protein.

The present invention further provides a recombinant swinepox virus which comprises a foreign DNA sequence inserted into a non-essential site of the swinepox genome, wherein the foreign DNA sequence encodes a cytokine capable of stimulating an immune in a host infected by the recombinant swinepox virus and is capable of being expressed in the host infected.

The present invention further provides a recombinant swinepox virus which comprises a foreign DNA sequence inserted into a non-essential site of the swinepox genome, wherein the foreign DNA sequence encodes an antigenic polypeptide derived from an equine pathogen and is capable of being expressed in a host infected by the recombinant swinepox virus.

The antigenic polypep tide of an equine pathogen can derived from equine influenza virus, or equine herpesvirus. In one embodiment the antigenic polypeptide is equine influenza neuraminidase or hemagglutinin. Examples of such antigenic polypeptide are equine influenza virus type A/Alaska 91 neuraminidase, equine influenza virus type A/Prague 56 neuraminidase, equine influenza virus type A/Miami 63 neuraminidase, equine influenza virus type A/Kentucky 81 neuraminidase, equine influenza virus type A/Kentucky 92 neuraminidase equine herpesvirus type 1 glycoprotein B, equine herpesvirus type 1 glycoprotein D, *Streptococcus equi*, equine infectious anemia virus, equine encephalitis virus, equine rhinovirus and equine rotavirus.

The present invention further provides an antigenic polypeptide which includes, but is not limited to: hog cholera virus gE1, hog cholera virus gE2, swine influenza virus hemagglutinin, neurominidase, matrix and nucleoprotein, pseudorabies virus gB, gC and gD, and PRRS virus ORF7.

The present invention further provides a recombinant swinepox virus which comprises a foreign DNA sequence inserted into a non-essential site of the swinepox genome, wherein the foreign DNA sequence encodes an antigenic polypeptide derived from bovine respiratory syncytial virus or bovine parainfluenza virus, and is capable of being expressed in a host infected by the recombinant swinepox virus.

For example, the antigenic polypeptide of derived from infectious bovine rhinotracheitis virus gE, bovine respiratory syncytial virus equine pathogen can derived from equine influenza virus is bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

The present invention further provides a recombinant swinepox virus which comprises a foreign DNA sequence inserted into a non-essential site of the swinepox genome, wherein the foreign DNA sequence encodes bovine viral diarrhea virus (BVDV) glycoprotein 48 or glycoprotein 53, and wherein the foreign DNA sequence is capable of being expressed in a host infected by the recombinant swinepox virus.

The present invention further provides a recombinant swinepox virus which comprises a foreign DNA sequence inserted into a non-essential site of the swinepox genome, wherein the foreign DNA sequence encodes an antigenic polypeptide derived from infectious bursal disease virus and wherein the foreign DNA sequence is capable of being expressed in a host infected by the recombinant swinepox virus. Examples of such antigenic polypeptide are infectious bursal disease virus polyprotein and VP2.

The present invention further provides a recombinant swinepox virus in which the foreign DNA sequence encodes an antigenic polypeptide which includes, but is not limited to: MDV gA, MDV gB, MDV gD, NDV HN, NDV F, ILT gB, ILT gI, ILT gD, IBDV VP2, IBDV VP3, IBDV VP4, IBDV polyprotein, IBV spike, IBV matrix, avian encephalomyelitis virus, avian reovirus, avian paramyxovirus, avian influenza virus, avian adenovirus, fowl pox virus, avian coronavirus, avian rotavirus, chick anemia virus, Salmonella spp. *E. coli*, Pasteurella spp., Bordetella spp., Eimeria spp., Histomonas spp., Trichomonas spp., Poultry nematodes, cestodes, trematodes, poultry mites/lice, and poultry protozoa.

The invention further provides that the inserted foreign DNA sequence is under the control of a promoter. In one embodiment the is a swinepox viral promoter. In another embodiment the foreign DNA sequence is under control of an endogenous upstream poxvirus promoter. In another embodiment the foreign DNA sequence is under control of a heterologous upstream promoter.

For purposes of this invention, promoters include but is not limited to: synthetic pox viral promoter, pox synthetic late promoter 1, pox synthetic late promoter 2 early promoter 2, pox O1L promoter, pox I4L promoter, pox I3L promoter, pox I2L promoter, pox I1L promoter, pox ELOR promoter, PRV gX, HSV-1 alpha 4, HCMV immediate early, MDV gA, MDV gB, MDV gD, ILT gB, BHV-1.1 VP8 and ILT gD. Alternate promoters are generated by methods well known to those of skill in the art, for example, as set forth in the STRATEGY FOR THE CONSTRUCTION OF SYNTHETIC POX VIRAL PROMOTERS in *Materials and Methods*.

The invention provides for a homology vector for producing a recombinant swinepox virus by inserting foreign DNA into the genomic DNA of a swinepox virus. The homology vector comprises a double-stranded DNA molecule consisting essentially of a double-stranded foreign DNA sequence or (RNA) which does not naturally occur in an animal into which the recombinant swinepox virus is introduced, with at one end of the foreign DNA, double-stranded swinepox viral DNA homologous to genomic DNA located at one side of a site on the genomic DNA which is not essential for replication of the swinepox virus, and at the other end of the foreign DNA, double-stranded swinepox viral DNA homologous to genomic DNA located at the other side of the same site on the genomic DNA. Preferably, the RNA encodes a polypeptide.

In another embodiment of the present invention, the double-stranded swinepox viral DNA of the homology vectors described above is homologous to genomic DNA present within the HindIII M fragment. In another embodiment the double-stranded swinepox viral DNA of the homology vectors described above is homologous to genomic DNA present within an approximately 2 Kb HindIII to BglII sub-fragment. In a preferred embodiment the double-stranded swinepox viral DNA is homologous to genomic DNA present within the BglII site located in this HindIII to BglII subfragment.

In another embodiment the double-stranded swinepox viral DNA is homologous to genomic DNA present within the open reading frame contained in the larger HindIII to BglII subfragment. Preferably, the double-stranded swinepox viral DNA is homologous to genomic DNA present within the AccI restriction endonuclease site located in the larger HindIII to BglII subfragment.

In one embodiment, the polypeptide is a detectable marker. Preferably, the polypeptide which is a detectable marker is *E. coli* β-galactosidase.

In one embodiment, the polypeptide is antigenic in the animal. Preferably, the antigenic polypeptide is or is from pseudorabies virus (PRV) g50 (gD), pseudorabies virus (PRV) gII (gB), Pseudorabies virus (PRV) gIII (gC), Pseudorabies virus (PRV) glycoprotein H, Transmissible gastroenteritis (TGE) glycoprotein 195, Transmissible gastroenteritis (TGE) matrix protein, swine rotavirus glycoprotein 38, swine parvovirus capsid protein, *Serpulina hydodysenteriae* protective antigen, Bovine Viral Diarrhea (BVD) glycoprotein 53 and g48, Newcastle Disease Virus (NDV) hemagglutinin-neuraminidase, swine flu hemagglutinin or swine flu neuraminidase. Preferably, the antigenic polypeptide is or is from *Serpulina hyodysenteriae*, Foot and Mouth Disease Virus, Hog Cholera Virus gE1 and gE2, Swine Influenza Virus, African Swine Fever Virus or *Mycoplasma hyopneumoniae*, swine influenza virus hemagglutinin, neuraminidase and matrix and nucleoprotein, PRRS virus ORF7, and hepatitis B virus core protein.

In an embodiment of the present invention, the double stranded foreign DNA sequence in the homology vector encodes an antigenic polypeptide derived from a human pathogen.

For example, the antigenic polypeptide of a human pathogen is derived from human herpesvirus, herpes simplex virus-1, herpes simplex virus-2, human cytomegalovirus, Epstein-Barr virus, Varicell-Zoster virus, human herpesvirus-6, human herpesvirus-7, human influenza, human immunodeficiency virus, rabies virus, measles virus, hepatitis B virus and hepatitis C virus. Furthermore, the antigenic polypeptide of a human pathogen may be associated with malaria or malignant tumor from the group conisting of *Plasmodium falciparum*, Bordetella pertusis, and malignant tumor.

In an embodiment of the present invention, the double stranded foreign DNA sequence in the homology vector encodes a cytokine capable of stimulating human immune response. In one embodiment the cytokine is a chicken myelomonocytic growth factor (cMGF) or chicken interferon (cIFN). For example, the cytokine can be, but not limited to, interleukin-2, interleukin-6, interleukin-12, interferons, granulocyte-macrophage colony stimulating factors, and interleukin receptors.

In an embodiment of the present invention, the double stranded foreign DNA sequence in the homology vector encodes an antigenic polypeptide derived from an equine pathogen.

The antigenic polypeptide of an equine pathogen can derived from equine influenza virus or equine herpesvirus. Examples of such antigenic polypeptide are equine influenza virus type A/Alaska 91 neuraminidase, equine influenza virus type A/Prague 56 neuraminidase, equine influenza virus type A/Miami 63 neuraminidase, equine influenza virus type A/Kentucky 81 neuraminidase equine herpesvirus type 1 glycoprotein B, and equine herpesvirus type 1 glycoprotein D.

In an embodiment of the present invention, the double stranded foreign DNA sequence of the homology vector encodes an antigenic polypeptide derived from bovine respiratory syncytial virus or bovine parainfluenza virus.

For example, the antigenic polypeptide is derived from infectious bovine rhinotracheitis gE, bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

In an embodiment of the present invention, the double stranded foreign DNA sequence of the homology vector encodes an antigenic polypeptide derived from infectious bursal disease virus. Examples of such antigenic polypeptide are infectious bursal disease virus polyprotein and infectious bursal disease virus VP2, VP3, or VP4.

For purposes of this invention, a "homology vector" is a plasmid constructed to insert foreign DNA in a specific site on the genome of a swinepox virus.

In one embodiment of the invention, the double-stranded swinepox viral DNA of the homology vectors described above is homologous to genomic DNA present within the open reading frame encoding swinepox thymidine kinase. Preferably, the double-stranded swinepox viral DNA is homologous to genomic DNA present within the NdeI restriction endonuclease site located in the open reading frame encoding swinepox thymidine kinase.

The invention further provides a homology vectors described above, the foreign DNA sequence of which is under control of a promoter located upstream of the foreign DNA sequence. The promoter can be an endogenous swinepox viral promoter or an exogenous promoter. Promoters include, but are not limited to: synthetic pox viral promoter, pox synthetic late promoter 1, pox synthetic late promoter 2 early promoter 2, pox O1L promoter, pox I4L promoter, pox I3L promoter, pox I2L promoter, pox I1L promoter, pox E10R promoter, PRV gX, HSV-1 alpha 4, HCMV immediate early, BHV-1.1 VP8, infectious laryngotracheitis virus glycoprotein B, infectious laryngotracheitis virus gD, marek's disease virus glycoprotein A, marek's disease virus glycoprotein B, and marek's disease virus glycoprotein D.

The invention further provides a vaccine which comprises an effective immunizing amount of a recombinant swinepox virus of the present invention and a suitable carrier.

Suitable carriers for the swinepox virus are well known in the art and include proteins, sugars, etc. One example of such a suitable carrier is a physiologically balanced culture medium containing one or more stabilizing agents such as stabilized, hydrolyzed proteins, lactose, etc.

For purposes of this invention, an "effective immunizing amount" of the recombinant swinepox virus of the present invention is within the range of $10^3$ to $10^9$ PFU/dose.

The present invention also provides a method of immunizing an animal, wherein the animal is a human, swine, bovine, equine, caprine or ovine. For purposes of this invention, this includes immunizing the animal against the virus or viruses which cause the disease or diseases pseudorabies, transmissible gastroenteritis, swine rotavirus, swine parvovirus, *Serpulina hyodysenteriae*, bovine viral diarrhea, Newcastle disease, swine influenza, PRRS, bovine respiratory synctial virus, bovine parainfluenza virus type 3, foot and mouth disease, hog cholera, African swine fever or *Mycoplasma hyopneumoniae*. For purposes of this invention, the method of immunizing also includes immunizing the animal against human pathogens, bovine pathogens, equine pathogens, avian pathogens described in the preceding part of this section.

The method comprises administering to the animal an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally or orally.

The present invention also provides a method for testing a swine to determine whether the swine has been vaccinated with the vaccine of the present invention, particularly the embodiment which contains the recombinant swinepox virus S-SPV-008 (ATCC Accession No. VR 2339), or is infected with a naturally-occurring, wild-type pseudorabies virus. This method comprises obtaining from the swine to be tested a sample of a suitable body fluid, detecting in the sample the presence of antibodies to pseudorabies virus, the absence of such antibodies indicating that the swine has been neither vaccinated nor infected, and for the swine in which antibodies to pseudorabies virus are present, detecting in the sample the absence of antibodies to pseudorabies virus antigens which are normally present in the body fluid of a swine infected by the naturally-occurring pseudorabies virus but which are not present in a vaccinated swine indicating that the swine was vaccinated and is not infected.

The present invention provides a recombinant SPV which when inserted with a foreign DNA sequence or gene may be employed as a diagnostic assay. In one embodiment FIV env and gag genes and *D. immitis* p39 and 22 kd are employed in a diagnostic assay to detect feline immunodeficiency caused by FIV and to detect heartworm caused by *D. immits*, respectively.

The present invention also provides a host cell infected with a recombinant swinepox virus capable of replication. In one embodiment, the host cell is a mammalian cell. Preferably, the mammalian cell is a Vero cell. Preferably, the mammalian cell is an ESK-4 cell, PK-15 cell or EMSK cell.

For purposes of this invention a "host cell" is a cell used to propagate a vector and its insert. Infecting the cells was accomplished by methods well known to those of skill in the art, for example, as set forth in INFECTION—TRANSFECTION PROCEDURE in *Material and Methods*.

Methods for constructing, selecting and purifying recombinant swinepox viruses described above are detailed below in *Materials and Methods*.

EXPERIMENTAL DETAILS

Materials and Methods

PREPARATION OF SWINEPOX VIRUS STOCK SAMPLES.

Swinepox virus (SPV) samples were prepared by infecting embryonic swine kidney (EMSK) cells, ESK-4 cells, PK-15 cells or Vero cells at a multiplicity of infection of 0.01 PFU/cell in a 1:1 mixture of Iscove's Modified Dulbecco's Medium (IMDM) and RPMI 1640 medium containing 2 mM glutamine, 100 units/ml penicillin, 100 units/ml streptomycin (these components were obtained from Sigma or equivalent supplier, and hereafter are referred to as EMSK negative medium). Prior to infection, the cell monolayers were washed once with EMSK negative medium to remove traces of fetal bovine serum. The SPV contained in the initial inoculum (0.5 ml for 10 cm plate; 10 ml for T175 cm flask) was then allowed to absorb onto the cell monolayer for two hours, being redistributed every half hour. After this period, the original inoculum was brought up to the recommended volume with the addition of complete EMSK medium (EMSK negative medium plus 5% fetal bovine serum). The plates were incubated at 37° C., in 5% $CO_2$ until cytopathic effect was complete. The medium and cells were harvested and frozen in a 50 ml conical screw cap tube at −70° C. Upon thawing at 37° C., the virus stock was aliquoted into 1.0 ml vials and refrozen at −70° C. The titers were usually about $10^6$ PFU/ml.

PREPARATION OF SPV DNA.

For swinepox virus DNA isolation, a confluent monolayer of EMSK cells in a T175 $cm^2$ flask was infected at a multiplicity of 0.1 and incubated 4–6 days until the cells were showing 100% cytopathic effect. The infected cells were then harvested by scraping the cells into the medium and centrifuging at 3000 rpm for 5 minutes in a clinical centrifuge. The medium was decanted, and the cell pellet was gently resuspended in 1.0 ml Phogphate Buffer Saline (PBS: 1.5 g $Na_2HPO_4$, 0.2 g $KH_2PO_4$, 0.8 g NaCL and 0.2 g KCl per liter $H_2O$) (per T175) and subjected to two successive freeze-thaws (−70° C. to 37° C.). Upon the last thaw, the cells (on ice) were sonicated two times for 30 seconds each with 45 seconds cooling time in between. Cellular debris was then removed by centrifuging (Sorvall RC-5B superspeed centrifuge) at 3000 rpm for 5 minutes in a HB4 rotor at 4° C. SPV virions, present in the supernatant, were then pelleted by centrifugation at 15,000 rpm for 20 minutes at 4° C. in a SS34 rotor (Sorvall) and resuspended in 10 mM Tris (pH 7.5). This fraction was then layered onto a 36% sucrose gradient (w/v in 10 mM tris pH 7.5) and centrifuged (Beckman L8-70M Ultracentrifuge) at 18,000 rpm for 60 minutes in a SW41 rotor (Beckman) at 4° C. The virion pellet was resuspended in 1.0 ml of 10 mM tris pH 7.5 and sonicated on ice for 30 seconds. This fraction was layered onto a 20% to 50% continuous sucrose gradient and centrifuged 16,000 rpm for 60 minutes in a SW41 rotor at 4° C. The SPV virion band located about three quarters down the gradient was harvested, diluted with 20% sucrose and pelleted by centrifugation at 18,000 rpm for 60 minutes in a SW41 rotor at 4° C. The resultant pellet was then washed once with 10 mM Tris pH 7.5 to remove traces of sucrose and finally resuspended in 10 mM Tris pH 7.5. SPV DNA was then extracted from the purified virions by lysis (4 hours at 60° C.) induced by the addition of EDTA, SDS, and proteinase K to final concentrations of 20 mM, 0.5% and 0.5 mg/ml, respectively. After digestion, three phenol:chloroform (1:1) extractions were conducted and the sample precipitated by the addition of two volumes of absolute ethanol and incubation at −20° C. for 30 minutes. The sample was then centrifuged in an Eppendorf minifuge for 5 minutes at full speed. The supernatant was decanted, and the pellet air dried and rehydrated in 0.01 M Tris pH 7.5, 1 mM EDTA at 4° C.

PREPARATION OF INFECTED CELL LYSATES.

For cell lysate preparation, serum free medium was used. A confluent monolayer of cells (EMSK, ESK-4, PK-15 or Vero for SPV or VERO for PRV) in a 25 $cm^2$ flask or a 60 mm petri dish was infected with 100 μl of virus sample. After cytopathic effect was complete, the medium and cells were harvested and the cells were pelleted at 3000 rpm for 5 minutes in a clinical centrifuge. The cell pellet was resuspended in 250 μl of disruption buffer (2% sodium dodecyl sulfate, 2% β-mercapto-ethanol). The samples were sonicated for 30 seconds on ice and stored at −20° C.

WESTERN BLOTTING PROCEDURE.

Samples of lysates and protein standards were run on a polyacrylamide gel according to the procedure of Laemnli (1970). After gel electrophoresis the proteins were transferred and processed according to Sambrook et al. (1982). The primary antibody was a swine anti-PRV serum (Shope strain; lot370, PDVB201, NVSL, Ames, Iwoa) diluted 1:100 with 5% non-fat dry milk in Tris-sodium chloride, and sodium Azide (TSA: 6.61 g Tris-HCl, 0.97 g Tris-base, 9.0 g NaCl and 2.0 g Sodium Azide per liter $H_2O$). The secondary antibody was a goat anti-swine alkaline phosphatase conjugate diluted 1:1000 with TSA.

MOLECULAR BIOLOGICAL TECHNIQUES.

Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al. (1982) and Sambrook et al. (1989). Except as noted, these were used with minor variation.

DNA SEQUENCING.

Sequencing was performed using the USB Sequenase Kit and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone™ and Supersee™ programs from Coral Software.

CLONING WITH THE POLYMERASE CHAIN REACTION.

The polymerase chain reaction (PCR) was used to introduce restriction sites convenient for the manipulation of various DNAs. The procedures used are described by Innis, et al. (1990). In general, amplified fragments were less than 500 base pairs in size and critical regions of amplified fragments were confirmed by DNA sequencing. The primers used in each case are detailed in the descriptions of the construction of homology vectors below.

HOMOLOGOUS RECOMBINATION PROCEDURE FOR GENERATING RECOMBINANT SPV.

This method relies upon the homologous recombination between the swinepox virus DNA and the plasmid homology vector DNA which occurs in the tissue culture cells containing both swinepox virus DNA and transfected plasmid homology vector. For homologous recombination to occur, the monolayers of EMSK cells are infected with S-SPV-001 (Kasza SPV strain, 17) at a multiplicity of infection of 0.01 PFU/cell to introduce replicating SPV (i.e. DNA synthesis) into the cells. The plasmid homology vector DNA is then transfected into these cells according to the INFECTION—TRANSFECTION PROCEDURE. The construction of homology vectors used in this procedure is described below

INFECTION—TRANSFECTION PROCEDURE.

6 cm plates of EMSK cells (about 80% confluent) were infected with S-SPV-001 at a multiplicity of infection of 0.01 PFU/cell in EMSK negative medium and incubated at 37° C. in a humidified 5% $CO_2$ environment for 5 hours. The transfection procedure used is essentially that recommended for Lipofectin™ Reagent (BRL). Briefly, for each 6 cm plate, 15 μg of plasmid DNA was diluted up to 100 μl with $H_2O$. Separately, 50 micrograms of Lipofectin Reagent was diluted to 100 μl with $H_2O$. The 100 μl of diluted Lipofectin Reagent was then added dropwise to the diluted plasmid DNA contained in a polystyrene 5 ml snap cap tube and mixed gently. The mixture was then incubated for 15–20 minutes at room temperature. During this time, the virus inoculum was removed from the 6 cm plates and the cell monolayers washed once with EMSK negative medium. Three ml of EMSK negative medium was then added to the plasmid DNA/lipofectin mixture and the contents pipetted onto the cell monolayer. The cells were incubated overnight (about 16 hours) at 37° C. in a humidified 5% $CO_2$ environment. The next day the 3 ml of EMSK negative medium was removed and replaced with 5 ml EMSK complete medium. The cells were incubated at 37° C. in 5% $CO_2$ for 3–7 days until cytopathic effect from the virus was 80–100%. Virus was harvested as described above for the preparation of virus stocks. This stock was referred to as a transfection stock and was subsequently screened for recombinant virus by the BLUOGAL SCREEN FOR RECOMBINANT SWINEPOX VIRUS OR CPRG SCREEN FOR RECOMBINANT SWINEPOX VIRUS.

SCREEN FOR RECOMBINANT SPV EXPRESSING β-galactosidase (BLUOGAL AND CPRG ASSAYS).

When the E. coli β-galactosidase (lacZ) marker gene was incorporated into a recombinant virus the plaques containing the recombinants were visualized by one of two simple methods. In the first method, the chemical Bluogal™ (Bethesda Research Labs) was incorporated (200 μg/ml) into the agarose overlay during the plaque assay, and plaques expressing active β-galactosidase turned blue. The blue plaques were then picked onto fresh cells (EMSK) and purified by further blue plaque isolation. In the second method, CPRG (Boehringer Mannheim) was incorporated (400 μg/ml) into the agarose overlay during the plaque assay, and plaques expressing active β-galactosidase turned red. The red plaques were then picked onto fresh cells (EMSK) and purified by further red plaque isolation. In both cases viruses were typically purified with three rounds of plaque purification.

SCREEN FOR FOREIGN GENE EXPRESSION IN RECOMBINANT SPV USING BLACK PLAQUE ASSAYS.

To analyze expression of foreign antigens expressed by recombinant swinepox viruses, monolayers of EMSK cells were infected with recombinant SPV, overlayed with nutrient agarose media and incubated for 6–7 days at 37° C. for plaque development to occur. The agarose overlay was then removed from the dish, the cells fixed with 100% methanol for 10 minutes at room temperature and the cells air dried. Fixation of the cells results in cytoplasmic antigen as well as surface antigen detection whereas specific surface antigen expression can be detected using non-fixed cells. The primary antibody was then diluted to the appropriate dilution with PBS and incubated on the cell monolayer for 2 hours at room temperature. To detect PRV g50 (gD) expression from S-SPV-008, swine anti-PRV serum (Shope strain; lot370, PDV8201, NVSL, Ames, Iowa) was used (diluted 1:100). To detect NDV HN expression from S-SPV-009, a rabbit antiserum specific for the HN protein (rabbit anti-NDV#2) was used (diluted 1:1000). Unbound antibody was then removed by washing the cells three times with PBS at room temperature. The secondary antibody, either a goat anti-swine (PRV g50 (gD); S-SPV-008) or goat anti-rabbit (NDV HN; S-SPV-009), horseradish peroxidase conjugate was diluted 1:250 with PBS and incubated with the cells for 2 hours at room temperature. Unbound secondary antibody was then removed by washing the cells three times with PBS at room temperature. The cells were then incubated 15–30 minutes at room temperature with freshly prepared substrate solution (100 μg/ml 4-chloro-1-naphthol, 0.003% $H_2O_2$ in PBS). Plaques expressing the correct antigen stain black.

PROCEDURE FOR PURIFICATION OF VIRAL GLYCOPROTEINS FOR USE AS DIAGNOSTICS.

Viral glycoproteins are purified using antibody affinity columns. To produce monoclonal antibodies, 8 to 10 week old BALB/c female mice are vaccinated intraperitoneally seven times at two to four week intervals with 107 PFU of S-SPV-009, –014, –016, –017, –018, or –019. Three weeks after the last vaccination, mice are injected intraperitoneally with 40 mg of the corresponding viral glycoprotein. Spleens are removed from the mice three days after the last antigen dose.

Splenocytes are fused with mouse NS1/Ag4 plasmacytoma cells by the procedure modified from Oi and Herzenberg, (41). Splenocytes and plasmacytoma cells are pelleted together by centrifugation at 300×g for 10 minutes. One ml of a 50% solution of polyethylene glycol (m.w. 1300–1600) is added to the cell pellet with stirring over one minute. Dulbecco's modified Eagles's medium (5 ml) is added to the cells over three minutes. Cells are pelleted by centrifugation at 300×g for 10 minutes and resuspended in medium with 10% fetal bovine serum and containing 100 mM hypoxanthine, 0.4 mM aminopterin and 16 mM thymidine (HAT). Cells (100 ml) are added to the wells of eight to ten 96-well tissue culture plates containing 100 ml of normal spleen feeder layer cells and incubated at 37° C. Cells are fed with fresh HAT medium every three to four days.

Hybridoma culture supernatants are tested by the ELISA ASSAY in 96-well microtiter plates coated with 100 ng of viral glycoprotein. Supernatants from reactive hybridomas are further analyzed by black-plaque assay and by Western Blot. Selected hybridomas are cloned twice by limiting dilution. Ascetic fluid is produced by intraperitoneal injection of $5 \times 10^6$ hybridoma cells into pristane-treated BALB/c mice.

Cell lysates from S-SPV-009, –014, –016, –017, –018, or –019 are obtained as described in PREPARATION OF INFECTED CELL LYSATES. The glycoprotein-containing cell lysates (100 mls) are passed through a 2-ml agarose affinity resin to which 20 mg of glycoprotein monoclonal antibody has been immobilized according to manufacturer's instructions (AFC Medium, New Brunswick Scientific, Edison, N.J.). The column is washed with 100 ml of 0.1% Nonidet P-40 in phosphate-buffered saline (PBS) to remove nonspecifically bound material. Bound glycoprotein is eluted with 100 mM carbonate buffer, pH 10.6 (40). Pre- and posteluted fractions are monitored for purity by reactivity to the SPV monoclonal antibodies in an ELISA system.

ELISA ASSAY.

A standard enzyme-linked immunosorbent assay (ELISA) protocol is used to determine the immune status of cattle following vaccination and challenge.

A glycoprotein antigen solution (100 ml at ng/ml in PBS) is allowed to absorb to the wells of microtiter dishes for 18 hours at 4° C. The coated wells are rinsed one time with PBS. Wells are blocked by adding 250 ml of PBS containing 1% BSA (Sigma) and incubating 1 hour at 37° C. The blocked wells are rinsed one time with PBS containing 0.02% Tween 20. 50 ml of test serum (previously diluted 1:2 in PBS containing 1% BSA) are added to the wells and incubated 1 hour at 37° C. The antiserum is removed and the wells are washed 3 times with PBS containing 0.02% Tween 20. 50 ml of a solution containing anti-bovine IgG coupled to horseradish peroxidase (diluted 1:500 in PBS containing 1% BSA, Kirkegaard and Perry Laboratories, Inc.) is added to visualize the wells containing antibody against the specific antigen. The solution is incubated 1 hour at 37° C., then removed and the wells are washed 3 times with PBS containing 0.02% Tween 20. 100 ml of substrate solution (ATBS, Kirkegaard and Perry Laboratories, Inc.) are added to each well and color is allowed to develop for 15 minutes. The reaction is terminated by addition of 0.1M oxalic acid. The color is read at absorbance 410 nm on an automatic plate reader.

STRATEGY FOR THE CONSTRUCTION OF SYNTHETIC POX VIRAL PROMOTERS.

For recombinant swinepox vectors synthetic pox promoters offer several advantages including the ability to control the strength and timing of foreign gene expression. Three promoter cassettes LP1, EP1 and LP2 based on promoters that have been defined in the vaccinia virus (1, 7 and 8) were designed. Each cassette was designed to contain the DNA sequences defined in vaccinia flanked by restriction sites which could be used to combine the cassettes in any order or combination. Initiator methionines were also designed into each cassette such that inframe fusions could be made at either EcoRI or BamHI sites. A set of translational stop codons in all three reading frames and an early transcriptional termination signal (9) were also engineered downstream of the inframe fusion site. DNA encoding each cassette was synthesized according to standard techniques and cloned into the appropriate homology vectors (see FIGS. 3 and 4).

VACCINATION STUDIES IN SWINE USING RECOMBINANT SWINEPOX VIRUS CONTAINING PSEUDORABIES VIRUS GLYCOPROTEIN GENES:

Young weaned pigs from pseudorabies-free herd are used to test the efficacy of the recombinant swinepox virus containing one or more of the pseudorabies virus glycoprotein genes (SPV/PRV). The piglets are inoculated intramuscularly, intradermally or orally about $10^3$ to $10^7$ plaque forming units (PFU) of the recombinant SPV/PRV viruses.

Immunity is determined by measuring PRV serum antibody levels and by challenging the vaccinated pigs with virulent strain of pseudorabies virus. Three to four weeks post-vaccination, both vaccinated and non-vaccinated groups of pigs are challenged with virulent strain of pseudorabies virus (VDL4892). Post challenge, the pigs are observed daily for 14 days for clinical signs of pseudorabies.

Serum samples are obtained at the time of vaccination, challenge, and at weekly intervals for two to three weeks post-vaccination and assayed for serum neutralizing antibody.

CLONING OF BOVINE VIRAL DIARREEA VIRUS g48 and g53 GENES.

The bovine viral diarrhea g48 and g53 genes were cloned by a PCR CLONING procedure essentially as described by Katz et al. (42) for the HA gene of human influenza. Viral RNA prepared from BVD virus Singer strain grown in Madin-Darby bovine kidney (MDBK) cells was first converted to cDNA utilizing an oligonucleotide primer specific for the target gene. The cDNA was then used as a template for polymerase chain reaction (PCR) cloning (15) of the targeted region. The PCR primers were designed to incorporate restriction sites which permit the cloning of the amplified coding regions into vectors containing the appropriate signals for expression in SPV. One pair of oligonucleotides were required for each coding region. The g48 gene coding region from the BVDV Singer strain (49) was cloned using the following primers: 5'-ACGTCGGATCCC TTACCAAACCACGTCTTACTCTTGTTTTCC-3' (SEQ ID NO: 61) for cDNA priming and combined with 5'-ACATAGGATCCCATGGGAGAAAACATAACACAG TGGAACC-3' (SEQ ID NO:62) for PCR. The g53 gene coding region from the BVDV Singer strain (49) was cloned using the following primers: 5'-CGTGGATCCTCAATT ACAAGAGGTATCGTCTAC-3' (SEQ ID NO: 63) for cDNA priming and combined with 5'-CATAGATCTTGT GGTGCTGTCCGACTTCGCA-3' (SEQ ID NO: 64) for PCR. Note that this general strategy is used to clone the coding region of g48 and g53 genes from other strains of BVDV. The DNA fragment for BVDV g 48 was digested with BamHI to yield an 678 bp fragment. The DNA fragment for BVDV g53 was digested with BglII and BamHI to yield an 1187 bp fragment. The BVDV g48 or g53 DNA fragments were cloned into the Ba HI site next to the LP2EP2 promoter of the SPV homology vector to yield homology vectors, 727-78.1 and 738-96, respectively.

CLONING OF BOVINE RESPIRATORY SYNCYTIAL VIRUS FUSION, NUCLEOCAPSID AND GLYCOPROTEIN GENES.

The bovine respiratory syncytial virus fusion (F), nucleocapsid (N), and glycoprotein (G) genes were cloned by a PCR CLONING procedure essentially as described by Katz et al. (42) for the HA gene of human influenza. Viral RNA prepared from BRSV virus grown in bovine nasal turbinate (BT) cells was first converted to cDNA utilizing an oligonucleotide primer specific for the target gene. The cDNA was then used as a template for polymerase chain reaction (PCR) cloning (15) of the targeted region. The PCR primers were designed to incorporate restriction sites which permit the cloning of the amplified coding regions into vectors containing the appropriate signals for expression in SPV. One pair of oligonucleotides were required for each coding region. The F gene coding region from the BRSV strain 375 (VR-1339) was cloned using the following primers: 5'-TGCAGGATCCTCATTTACTAAAGGAAAGATTGT TGAT-3' (SEQ ID NO: 65) for cDNA priming and combined with 5'-CTCTGGATCCTACAGCCATGAGGATGATCA TCAGC-3' (SEQ ID NO: 66) for PCR. The N gene coding region from BRSV strain 375 (VR-1339) was cloned utilizing the following primers: 5'-CGTCGGATCCCTCACAGT TCCACATCATTGTCTTTGGGAT-3' (SEQ ID NO: 67) for cDNA priming and combined with 5'-CTTAGGATC CCATGGCTCTTAGCAAGGTCAAACTAAATGAC-3' (SEQ ID NO: 68) for PCR. The G gene coding region from BRSV strain 375 (VR-1339) was cloned utilizing the following primers: 5'-CGTTGGATCCCTAGATCT GTGTAGTTGATTGATTTGTGTGA-3' (SEQ ID NO: 69) for cDNA priming and combined with 5'-CTCTGGATC CTCATACCCATCATCTTAAATTCAAGACATTA-3' (SEQ ID NO: 70) for PCR. Note that this general strategy is used to clone the coding region of F, N and G genes from other strains of BRSV. The DNA fragments for BRSV F, N, or G were digested with BamHI to yield 1722 bp, 1173 bp, or 771 bp fragments, respectively. The BRSV F, N, and G DNA fragments were cloned into the BamHI site next to the LP2EP2 promoter of the SPV homology vector to yield homology vectors, 727-20.10, 713-55.37 and 727-20.5, respectively.

RNA ISOLATED FROM CONCANAVALIN A STIMULATED CHICKEN SPLEEN CELLS.

Chicken spleens were dissected from 3 week old SPAFAS hatched chicks, washed, and disrupted through a syringe/needle to release cells. After allowing stroma and debri to settle out, the cells were pelleted and washed twice with PBS. The cell pellet was treated with a hypotonic lysis buffer to lyse red blood cells, and splenocytes were recovered and washed twice with PBS. Splenocytes were resuspended at $5 \times 10^6$ cells/ml in RPMI containing 5% FBS and 5 µg/ml Concanavalin A and incubated at 39° for 48 hours. Total RNA was isolated from the cells using guanidine isothionate lysis reagents and protocols from the Promega RNA isolation kit (Promega Corporation, Madison Wis.). 4 µg of total RNA was. used in each 1st strand reaction containing the appropriate antisense primers and AMV reverse transcriptase (Promega Corporation, Madison Wis.). cDNA synthesis was performed in the same tube following the reverse transcriptase reaction, using the appropriate sense primers and Vent® DNA polymerase (Life Technologies, Inc. Bethesda, Md.).

SCREEN FOR RECOMBINANT HERPESVIRUS EXPRESSING ENZYMATIC MARKER GENES.

When the E. coli β-glucuronidase (uidA) marker gene was incorporated into a recombinant virus the plaques containing recombinants were visualized by a simple assay. The enzymatic substrate was incorporated (300 μg/ml) into the agarose overlay during the plaque assay. For the uidA marker gene the substrate X-Glucuro Chx (5-bromo-4-chloro-3-indolyl-β-D-glucuronic acid Cyclohexylammonium salt, Biosynth AG) was used. Plaques that expressed active marker enzyme turned blue. The blue plaques were then picked onto fresh ESK-4 cells and purified by further blue plaque isolation. In recombinant virus strategies in which the enzymatic marker gene is removed the assay involves plaque purifying white plaques from a background of parental blue plaques. In both cases viruses were typically purified with three rounds of plaque purification.

HOMOLOGY VECTOR 515-85.1.

The plasmid 515-85.1 was constructed for the purpose of inserting foreign DNA into SPV. It contains a unique AccI restriction enzyme site into which foreign DNA may be inserted. When a plasmid, containing a foreign DNA insert at the AccI site, is used according to the HOMOLOGOUS RECOMBINATION PROCEDURE FOR GENERATING RECOMBINANT SPV a virus containing the foreign DNA will result. A restriction map of the DNA insert in homology vector 515-85.1 is given in FIGS. 3A–3C. It may be constructed utilizing standard recombinant DNA techniques (22 and 29), by joining two restriction fragments from the following sources. The first fragment is an approximately 2972 base pair HindIII to BamHI restriction fragment of pSP64 (Promega). The second fragment is an approximately 3628 base pair HindIII to BglII restriction sub-fragment of the SPV HindIII restriction fragment M (23).

HOMOLOGY VECTOR 520-17.5.

The plasmid 520-17.5 was constructed for the purpose of inserting foreign DNA into SPV. It incorporates an E. coli β-galactosidase (lacZ) marker gene flanked by SPV DNA. Upstream of the marker gene is an approximately 2149 base pair fragment of SPV DNA. Downstream of the marker gene is an approximately 1484 base pair fragment of SPV DNA. When this plasmid is used according to the HOMOLOGOUS RECOMBINATION PROCEDURE FOR GENERATING RECOMBINANT SPV a virus containing DNA coding for the marker gene will result. Note that the β-galactosidase (lacZ) marker gene is under the control of a synthetic early/late pox promoter. A detailed description of the plasmid is given in FIGS. 3A–3C. It may be constructed utilizing standard recombinant DNA techniques (22 and 30), by joining restriction fragments from the following sources with the synthetic DNA sequences indicated in FIGS. 3A–3C. The plasmid vector was derived from an approximately 2972 base pair HindIII to BamHI restriction fragment of pSP64 (Promega). Fragment 1 is an approximately 2149 base pair HindIII to AccI restriction sub-fragment of the SPV HindIII restriction fragment M (23). Fragment 2 is an approximately 3006 base pair BamHI to PvuII restriction fragment of plasmid pJF751 (11). Fragment 3 is an approximately 1484 base pair AccI to BglII restriction sub-fragment of the SPV HindIII fragment M (23).

HOMOLOGY VECTOR 538-46.16.

The plasmid 538-46.16 was constructed for the purpose of inserting foreign DNA into SPV. It incorporates an E. coli β-galactosidase (lacZ) marker gene and the PRV g50 (gD) gene flanked by SPV DNA. Upstream of the foreign genes is an approximately 2149 base pair fragment of SPV DNA. Downstream of the foreign genes is an approximately 1484 base pair fragment of SPV DNA. When this plasmid is used according to the HOMOLOGOUS RECOMBINATION PROCEDURE FOR GENERATING RECOMBINANT SPV a virus containing DNA coding for the foreign genes will result. Note that the β-galactosidase (lacZ) marker gene is under the control of a synthetic late pox promoter (LPl) and the g50 (gD) gene is under the control of a synthetic early/late pox promoter (EP1P2). A detailed description of the plasmid is given in 3A–3C. It may be constructed utilizing standard recombinant DNA techniques (22 and 30), by joining restriction fragments from the following sources with the synthetic DNA sequences indicated in FIGS. 3A–3C. The plasmid vector was derived from an approximately 2972 base pair HindIII to BamHI restriction fragment of pSP64 (Promega). Fragment 1 is an approximately 2149 base pair HindIII to AccI restriction sub-fragment of the SPV HindIII restriction fragment M (23). Fragment 2 is an approximately 3006 base pair BamHI to PvuII restriction fragment of plasmid pJF751 (11). Fragment 3 is an approximately 1571 base pair EcoRI to StuI restriction sub-fragment of the PRV BamHI fragment 7 (21). Note that the EcoRI site was introduced in to this fragment by PCR cloning. In this procedure the primers described below were used along with a template consisting of a PRV BamHI #7 fragment subcloned into pSP64. The first primer 87.03 (5'-CGCGAATTCGCTCG CAGCGCTATTGGC-3') (SEQ ID NO: 71) sits down on the PRV g50 (gD) sequence (26) at approximately amino acid 3 priming toward the 3' end of the gene. The second primer 87.06 (5'-GTAGGAGTGGCTGCTGAAG-3') (SEQ ID NO: 72) sits down on the opposite strand at approximately amino acid 174 priming toward the 5' end of the gene. The PCR product may be digested with EcoRI and SalI to produce an approximately 509 base pair fragment. The approximately 1049 base pair SalI to StuI sub-fragment of PRV BamHI #7 may then be ligated to the approximately 509 base pair EcoRI to SalI fragment to generate the approximately 1558 base pair EcoRI to StuI fragment 3. Fragment 4 is an approximately 1484 base pair AccI to BglII restriction sub-fragment of the SPV HindIII fragment M (23).

HOMOLOGY VECTOR 570-91.41.

The plasmid 570-91.41 was constructed for the purpose of inserting foreign DNA into SPV. It incorporates an E. coli β-galactosidase (lacZ) marker gene and the PRV gIII (gC) gene flanked by SPV DNA. Upstream of the foreign DNA genes is an approximately 2149 base pair fragment of SPV DNA. Downstream of the foreign genes is an approximately 1484 base pair fragment of SPV DNA. When this plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the gIII (gC) gene is under the control of a synthetic early late pox promoter (EP1LP2). A detailed description of the plasmid is given in FIGS. 5A–5D. It may be constructed utilizing standard recombinant DNA techniques (22 and 30), by joining restriction fragments from the following sources with the synthetic DNA sequences indicated in 5A–5D. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 2378 base pair NcoI to NcoI fragment of plasmid 251-41.A, a subfragment of PRV BamHI #2 and #9. EcoRI linkers have replaced the NcoI and NcoI sites at the ends of this fragment. Fragment 4 is an approximately 2149 base pair AccI to HindIII restriction sub-fragment of the SPV HindIII fragment M (23). The AccI sites in fragments 1 and 4 have been converted to PstI sites using synthetic DNA linkers.

HOMOLOGY VECTOR 570-91.64.

The plasmid 570-91.64 was constructed for the purpose of inserting foreign DNA into SPV. It incorporates an *E. coli* β-galactosidase (lacZ) marker gene and the PRV gIII (gC) gene flanked by SPV DNA. Upstream of the foreign DNA genes is an approximately 1484 base pair fragment of SPV DNA. Downstream of the foreign genes is an approximately 2149 base pair fragment of SPV DNA. When this plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the gIII (gC) gene is under the control of a synthetic late early pox promoter (LP2EP2). A detailed description of the plasmid is given in FIGS. 7A–7D. It may be constructed utilizing standard recombinant DNA techniques (22 and 30), by joining restriction fragments from the following sources with the synthetic DNA sequences indicated in 5 A-5D. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 2378 base pair NcoI to NcoI fragment of plasmid 251-41.A, a subfragment of PRV BamHI #2 and #9. EcoRI linkers have replaced the NcoI and NcoI sites at the ends of this fragment. Fragment 4 is an approximately 2149 base pair AccI to HindIII restriction sub-fragment of the SPV HindIII fragment M (23). The AccI sites in fragments 1 and 4 have been converted to PstI sites using synthetic DNA linkers.

HOMOLOGY VECTOR 727-54.60.

The plasmid 727-54.60 was constructed for the purpose of inserting foreign DNA into SPV. It incorporates an *E. coli* β-galactosidase (lacZ) marker gene and the pseudorabies virus (PRV) gII (gB) gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the PRV gB gene is under the control of a synthetic late/early pox promoter (LP2EP2). A detailed description of the plasmid is given in FIGS. 7A–7D. It may be constructed utilizing standard recombinant DNA techniques (22, 30), by joining restriction fragments from the following sources with the synthetic DNA sequences indicated in FIGS. 7A–7D. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3500 base pair fragment which contains the coding sequence for the PRV gB gene within the KpnI C fragment of genomic PRV DNA (21). Fragment 2 contains an approximately 53 base pair synthetic fragment containing the amino terminus of the PRV gB gene, an approximately 78 base pair SmaI to Nhe I fragment from the PRV KpnI C genomic fragment, and an approximately 3370 base pair NheI to EcoRI fragment from the PRV KpnI C genomic fragment (21). Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 751-07.A1.

The plasmid 751-07.A1 was used to insert foreign DNA into SPV. It incorporates an *E. coli* β-galactosidase (lacZ) marker gene and the chicken interferon (cIFN) gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the β-galactosidase (lacZ) marker gene is under the control of a synthetic late pox promoter (LP1) and the cIFN gene is under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 2972 base pair HindIII to BamHI restriction fragment of pSP64 (Promega). Fragment 1 is an approximately 1146 base pair BglII to AccI restriction sub-fragment of the SPV HindIII fragment M (23). Fragment 2 is an approximately 577 base pair EcoRI to BglII fragment coding for the cIFN gene (54) derived by reverse transcription and polymerase chain reaction (PCR) (Sambrook, et al., 1989) of RNA ISOLATED FROM CONCANAVALIN A STIMULATED CHICKEN SPLEEN CELLS. The antisense primer (6/94.13) used for reverse transcription and PCR was 5'-CGAC <u>GGATCC</u>GAGGTGCGTTTGGGGCTAAGTGC-3' (SEQ ID NO: 211). The sense primer (6/94.12) used for PCR was 5'-CCAC <u>GGATCC</u>AGCACAACGCGAGTCCCACCATGGCT-3' (SEQ ID NO: 212). The BamHI fragment resulting from reverse transcription and PCR was gel purified and used as a template for a second PCR reaction to introduce a unique EcoRI site at the 5' end and a unique BglII site at the 3' end. The second PCR reaction used primer 6/94.22 (5'-CCAC <u>GAATTC</u>GATGGCTGTGCCTGCAAGCCCACAG-3'; SEQ ID NO: 213) at the 5' end and primer 6/94.34 (5'-CGA <u>AGATCT</u>GAGGTGCGTTTGGGGCTAAGTGC-3'; SEQ ID NO: 214) at the 3' end to yield an approximately 577 base pair fragment. The DNA fragment contains the coding sequence from amino acid 1 to amino acid 193 of the chicken interferon protein (54) which includes a 31 amino acid signal sequence at the amino terminus and 162 amino acids of the mature protein encoding chicken interferon. Fragment 3 is an approximately 3002 base pair BamHI to PvuII restriction fragment of plasmid pJF751 (11). Fragment 4 is an approximately 2156 base pair AccI to HindIII restriction sub-fragment of the SPV HindIII restriction fragment M (23). The AccI site in the SPV homology vector was converted to a unique NotI site.

HOMOLOGY VECTOR 751-56.A1.

The plasmid 751-56.A1 was used to insert foreign DNA into SPV. It incorporates an *E. coli* β-galactosidase (lacZ) marker gene and the chicken myelomonocytic growth factor (cMGF) gene flanked by SPV DNA. When this plasmid was used according to the HOMOLOGOUS RECOMBINATION PROCEDURE FOR GENERATING. RECOMBINANT SPV a virus containing DNA coding for the foreign genes results. Note that the β-galactosidase (lacZ) marker gene is under the control of a synthetic late pox promoter (LP1) and the cMGF gene is under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 2972 base pair HindIII to BamHI restriction fragment of pSP64 (Promega). Fragment 1 is an approximately 1146 base pair BglII to AccI restriction sub-fragment of the SPV HindIII fragment M (23). Fragment 2 is an approximately 640 base pair EcoRI to BamHI fragment coding for the cMGF gene(55) derived by reverse transcription and polymerase chain reaction (PCR) (Sambrook, et al., 1989) of RNA ISOLATED FROM CONCANAVALIN A STIMULATED CHICKEN SPLEEN CELLS. The antisense primer (6/94.20) used for reverse transcription and PCR was 5'-CGCAGGATCCGGGGCGTCAGAGGCGGGCGA GGTG-3' (SEQ ID NO: 215). The sense primer (5/94.5) used for PCR was 5'-GAGCGGATCCTGCAGGAGGAGA CACAGAGCTG-3' (SEQ ID NO: 216). The BamHI fragment derived from PCR was subcloned into a plasmid and used as a template for a second PCR reaction using primer 6/94.16 (5'-GCGCGAATTCCATGTGCTGCCTCACCC CTGTG-3'; SEQ ID NO: 217) at the 5' end and primer 6/94.20 (5'-CGCAGGATCCGGGGCGTCAGAGGCGGG CGAGGTG-3'; SEQ ID NO: 218) at the 3' end to yield an approximately 640 base pair fragment. The DNA fragment contains the coding sequence from amino acid 1 to amino acid 201 of the cMGF protein (55) which includes a 23 amino acid signal sequence at the amino terminus and 178 amino acids of the mature protein encoding cMGF. Fragment 3 is an approximately 3002 base pair BamHI to PvuII restriction fragment of plasmid pJF751 (11). Fragment 4 is an approximately 2156 base pair AccI to HindIII restriction sub-fragment of the SPV HindIII restriction fragment M (23). The AccI site in the SPV homology vector was converted to a unique NotI site.

HOMOLOGY VECTOR 752-22.1.

The plasmid 752-22.1 was constructed for the purpose of inserting foreign DNA into SPV. It incorporates an *E. coli* β-galactosidase (lacZ) marker gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a swinepox virus 01L gene promoter. The homology vector also contains the synthetic late/early promoter (LP2EP2) into which a second foreign gene is inserted into a unique BamHI or EcoRI site. A detailed description of the plasmid is given in FIGS. 10A–10D. It was constructed utilizing standard recombinant DNA techniques (22, 30), by joining restriction fragments from the following sources with the synthetic DNA sequences indicated in FIGS. 10A–10D. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5'-GAAGCATGCCCGTTCTTATCAATAGTT TAGTCGAAAATA-3' (SEQ ID NO: 73) and 5'-CATAAGATCTGGCATTGTGTTATTATACTAACAAA AATAAG-3' (SEQ ID NO: 74) to produce an 855 base pair fragment with SphI and BglII ends. Fragment 2 is a 3002 base pair BamHI to PvuII fragment derived from plasmid pJF751 (49) containing the *E. coli* lacZ gene. Fragment 3 is an approximately 1113 base pair subfragment of the SPV HindIII fragment M synthesized by polymerase chain reaction using DNA primers 5'-CCGTAGTCGACA AAGATCGACTTATTAATATGTATGGGATT-3' (SEQ ID NO: 75) and 5'-GCCTGAAGCTTCTAGTACAGTATTTAC GACTTTTGAAAT-3' (SEQ ID NO: 76) to produce an 1113 base pair fragment with SalI and HindIII ends.

HOMOLOGY VECTOR 752-29.33.

The plasmid 759.33 was constructed for the purpose of inserting foreign DNA into SPV. It incorporates an *E. coli* β-galactosidase (lac Z) marker gene and an equine herpesvirus type 1 gB gene flanked by SPV DNA. Upstream of the foreign gene is an approximately 855 base pair fragment of SPV DNA. Downstream of the foreign genes is an approximately 113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a swinepox virus 01L gene promoter and the EHV-1 gB gene is under the control of the late/early promoter (LP2EP2). The LP2EP2 promoter-EHV-1 gB gene cassette was inserted into a NotI site of homology vector 738-94.4. Homology vector 752-29.33 was constructed utilizing standard recombinant DNA techniques (22, 30), by joining restriction fragments from the following sources with the synthetic DNA sequences. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5'-GAAGCATGCCCGTTCTTATCAATAGTT TAGTCGAAAATA-3' (SEQ ID NO: 73) and 5'-CATAAGATCTGGCATTGTGTTATTATACTAACA AAAATAAG-3' (SEQ ID NO: 74) to produce an 855 base pair fragment with SphI and BglII ends. Fragment 2 is a 3002 base pair BamHI to PvuII fragment derived from plasmid pJF751 (49) containing the *E. coli* lacZ gene. Fragment 3 is the product of a PCR reaction (EcoRI to BamHI) and a restriction fragment (BamHI to PmeI) ligated together to yield an EHV-1 gB gene which is an EcoRI to PmeI fragment approximately 2941 base pairs (979 amino acids) in length. The PCR fragment is an approximately 429 base pair fragment having a synthetic EcoRI site at the 5' end of the gene and a natural BamHI site at the 3' end within the BamHI "a" fragment of EHV-1 genomic DNA. The restriction fragment is an approximately 2512 base pair fragment from BamHI to PmeI within the BamHI "I" fragment of EHV-1 genomic DNA. In the procedure to produce the 5' end PCR fragment, the primers described below were used with a template consisting of the EHV-1 BamHI "a" and "i" fragments.

The first primer 5/94.3 (5'-CGGAATTCCTCTGGT TCGCCGT-3') (SEQ ID NO: 77) sits down on the EHV-1 gB sequence at amino acid number 2 and introduces an EcoRI site at the 5' end of the EHV-1 gB gene and an ATG start codon. The second primer 5/94.4 (5'-GACGGTGGATCCGGTAGGCGGT-3') (SEQ ID NO: 78) sits down on the EHV-1 gB sequence at approximately amino acid 144 on the opposite strand to primer 5/94.3 and primes toward the 5' end of the gene. The PCR product was digested with EcoRI and BamHI to yield a fragment 429 base pairs in length corresponding to the 5' end of the EHV-1 gB gene. Fragment 3 consists of the products of the PCR reaction (EcoRI to BamHI) and the restriction fragment (BamHI to PmeI) ligated together to yield an EHV-1 gB gene which is an EcoRI to PmeI fragment approximately 2941 base pairs (979 amino acids) in length. Fragment 4 is an approximately 1113 base pair subfragment of the SPV HindIII fragment M synthesized by polymerase chain reaction using DNA primers 5'-CCGTAGTCGACAAAGATCGACTTATTAATATGTATGGGATT-3' (SEQ ID NO: 75) and 5'-GCCTGAAGCTTCTAGTACAGTATTTACGACTTTTGAAAT-3' (SEQ ID NO: 76) to produce an 1113 base pair fragment with SalI and HindIII ends.

HOMOLOGY VECTOR 746-94.1.

The plasmid 746-94.1 was constructed for the purpose of inserting foreign DNA into SPV. It incorporates an *E. coli* β-galactosidase (lacZ) marker gene and an infectious bovine rhinotracheitis virus glycoprotein E (gE) gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a swinepox virus 01L gene promoter and the IBRV gE gene is under the control of the late/early promoter (LP2EP2). It was constructed utilizing standard recombinant DNA techniques (22, 30), by joining restriction fragments from the following sources with the synthetic DNA sequences. A 1250 base pair EcoRI to BamHI fragment coding for amino acids 1 to 417 of the IBRV gE gene (missing 158 amino acids of the carboxy terminal transmembrane region) was inserted into unique EcoRI and BamHI sites of homology vector 752-22.1 (FIGS. 10A–10D). The 1250 base pair EcoRI to BamHI fragment was synthesized by polymerase chain reaction (15) using IBRV (Cooper) genomic DNA as a template and primer 10/94.23 (5'-GGGGAATTCAATGCAACCCACCGC GCCGCCCC-3'; SEQ ID NO: 219) at the 5' end of the IBRV gE gene (amino acid 1) and primer 10/94.22 (5'-GGGGGATCCTAGGGCGCGCCCGCCGGCTCGCT-3'; SEQ ID NO: 220) at amino acid 417 of the IBRV gE gene.

HOMOLOGY VECTOR 767-67.3.

The plasmid 767-67.3 was constructed for the purpose of inserting foreign DNA into SPV. It incorporates an *E. coli* β-galactosidase (lacZ) marker gene and an bovine viral diarrhea virus glycoprotein 53 (BVDV gp53) gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a swinepox virus 01L gene promoter and the BVDV gp53 gene is under the control of the late/early promoter (LP2EP2). It was constructed utilizing standard recombinant DNA techniques (22, 30), by joining restriction fragments from the following sources with the synthetic DNA sequences. A 1187 base pair BamHI fragment coding for the BVDV gp53 was inserted into the unique BamHI sites of homology vector 752-22.1 (FIGS. 10A–10D). The 1187 base pair BamHI fragment was synthesized by polymerase chain reaction (15) as described in CLONING OF BOVINE VIRAL DIARRHEA VIRUS gp48 AND gp53 GENES.

HOMOLOGY VECTOR 771-55.11.

The plasmid 771-55.11 was constructed for the purpose of inserting foreign DNA into SPV. It incorporates an *E. coli* β-galactosidase (lacZ) marker gene and an bovine viral diarrhea virus glycoprotein 48 (BVDV gp48) gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a swinepox virus 01L gene promoter and the BVDV gp48 gene is under the control of the late/early promoter (LP2EP2). It was constructed utilizing standard recombinant DNA techniques (22, 30), by joining restriction fragments from the following sources with the synthetic DNA sequences. A 678 base pair BamHI fragment coding for the BVDV gp48 was inserted into the unique BamHI sites of homology vector 752-22.1 (FIGS. 10A–10D). The 678 base pair BamHI fragment was synthesized by polymerase chain reaction (15) as described in CLONING OF BOVINE VIRAL DIARRHEA VIRUS gp48 AND gp53 GENES.

PLASMID 551-47.23.

The plasmid 551-47.23 was constructed for the purpose of inserting foreign DNA into SPV. It incorporates the *E. coli* β-glucuronidase (β-glu) marker gene under the control of a late/early pox promoter (LP2EP2). It is useful to insert the marker gene into sites in the SPV genome to produce a recombinant swinepox virus. It was constructed utilizing standard recombinant DNA techniques (22, 30), by joining restriction fragments from the following sources. The plastid vector was derived from an approximately 3005 base pair HindIII restriction fragment of pSP65 (Promega). Fragment 1 is an approximately 1823 base pair EcoRI to SmaI fragment of the plasmid pRAJ260 (Clonetech). Note that the EcoRI and SmaI sites were introduced by PCR cloning. Plasmid 551-47.23 was used to make recombinant swinepox viruses S-SPV-059, S-SPV-060, S-SPV-061, and S-SPV-062.

HOMOLOGY VECTOR 779-94.31.

The plasmid 779-94.31 was constructed for the purpose of inserting foreign DNA into SPV. It incorporates an *E. coli* β-galactosidase (lacZ) marker gene and the pseudorabies virus (PRV) gB (gII) gene flanked by SPV DNA. Upstream of the foreign genes is an approximately 538 base pair fragment of SPV DNA. Downstream of the foreign genes is an approximately 1180 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1) and the PRV gB gene is under the control of a synthetic late/early pox promoter (LP2EP2). A detailed description of the plasmid is given in FIGS. 12A–12E. It was constructed utilizing standard recombinant DNA techniques (22, and 30), by joining restriction fragments from the following sources with the synthetic DNA sequences. The plasmid vector was derived from an approximately 2986 base pair HindIII to PstI restriction fragment of pSP64 (Promega). Fragment 1 is an approximately 542 base pair HindIII to BglII restriction sub-fragment of the SPV HindIII restriction fragment M (23). Fragment 2 is an approximately 3500 base pair fragment which contains the coding sequence for the PRV gB gene within the KpnI C fragment of genomic PRV DNA (21). Fragment 2 contains an approximately 53 base pair synthetic fragment containing the amino terminus of the PRV gB gene, an approximately 78 base pair SmaI to Nhe I fragment from the PRV KpnI C genomic fragment, and an approximately 3370 base pair NheI to EcoRI fragment from the PRV KpnI C genomic fragment (21). Fragment 3 is an approximately 3010 base pair BamHI to PvuII restriction fragment of plasmid pJF751 (11). Fragment 4 is an approximately 1180 base pair BglII to PstI subfragment of the SPV HindIII fragment M. The BglII sites in fragments 1 and 4 were converted to unique HindIII sites using HindIII linkers.

HOMOLOGY VECTOR 789-41.7.

The plasmid 789-41.7 was constructed for the purpose of inserting foreign DNA into SPV. It incorporates an *E. coli* β-galactosidase (lacZ) marker gene, the pseudorabies virus (PRV) gB (gII) gene and the PRV gD (g50) gene flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LPl), the PRV gB gene is under the control of a synthetic late/early pox promoter (LP2EP2), and the PRV gD gene is under the control of a synthetic early/late pox promoter (EP1LP2). A detailed description of the plasmid is given in FIGS. 13A–13D. It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1552 base pair subfragment of the PRV BamHI #7 fragment which contains the coding sequence of the PRV gD gene from amino acid 3 to amino acid 279. The EcoRI site and the ATG translation start codon are derived from a polymerase chain reaction using a 5' primer with an EcoRI site. The StuI site at the 3' end is normally within the PRV gI gene 3' to the PRV gD gene. The entire open reading frame beginning at the EcoRI site codes for 405 amino acids. Fragment 3 is an approximately 48 base pair AccI to NdeI subfragment of the SPV HindIII M fragment. Fragment 4 is an approximately 3500 base pair fragment which contains the coding sequence for the PRV gB gene within the KpnI C fragment of genomic PRV DNA(21). Fragment 4 contains an approximately 53 base pair synthetic fragment containing the amino terminus of the PRV gB gene, an approximately 78 base pair SmaI to Nhe I fragment from the PRV KpnI C genomic fragment, and an approximately 3370 base pair NheI to EcoRI fragment from the PRV KpnI C genomic fragment (21). Fragment 5 is an approximately 3010 base pair BamHI to PvuII restriction fragment of plasmid pJF751 (11). Fragment 6 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 6 were converted to unique HindIII sites using HindIII linkers. An approximately 545 base pair NdeI to NdeI subfragment (Nucleotides 1560 to 2104;) of the SPV HindIII M fragment has been deleted which would span SPV fragments 3 and 6.

HOMOLOGY VECTOR 789-41.27.

The plasmid 789-41.27 was constructed for the purpose of inserting foreign DNA into SPV. It incorporates an *E. coli* β-galactosidase (lacZ) marker gene, the pseudorabies virus (PRV) gB (gII) gene and the PRV gC (gIII) gene flanked by SPV DNA. Upstream of the foreign genes is an approximately 1560 ' base pair fragment of SPV DNA. Downstream of the foreign genes is an approximately 1484 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the PRV gB gene is under the control of a synthetic late/early pox promoter (LP2EP2), and the PRV gC gene is under the control of a synthetic early/late pox promoter (EP1LP2). A detailed description of the plasmid is given in FIGS. 14A–14D. It was constructed utilizing standard recombinant DNA techniques (22, 30), by joining restriction fragments from the following sources with the synthetic DNA sequences indicated. The plasmid vector was derived from an approximately 2972 base pair HindIII to BamHI restriction fragment of pSP64 (Promega). Fragment 1 is an approximately 1560 base pair HindIII to NdeI subfragment of the SPV HindIII fragment M. Fragment 2 is an approximately 3500 base pair fragment which contains the coding sequence for the. PRV gB gene within the KpnI C fragment of genomic PRV DNA(21). Fragment 2 contains an approximately 53 base pair synthetic fragment containing the amino terminus of the PRV gB gene, an approximately 78 base pair SmaI to Nhe I fragment from the PRV KpnI C genomic fragment, and an approximately 3370 base pair NheI to EcoRI fragment from the PRV KpnI C genomic fragment (21). Fragment 3 is an approximately 3010 base pair BamHI to PvuII restriction fragment of plasmid pJF751 (11). Fragment 4 is an approximately 48 base pair AccI to NdeI subfragment of the SPV HindIII M fragment. Fragment 5 is an approximately 2378 base pair NcoI to NcoI fragment of plasmid 251-41.A, a subfragment of PRV BamHI #2 and #9. EcoRI linkers have replaced the NcoI sites at the ends of the fragment. Fragment 6 is an approximately 1484 base pair AccI to BglII restriction sub-fragment of the SPV HindIII restriction fragment M (23). The NdeI sites in fragments 1 and 4 were converted to unique HindIII sites using HindIII linkers. The AccI site in fragments 4 and 6 were converted to unique PstI sites using PstI linkers. An approximately 545 base pair NdeI to NdeI (Nucleotides 1560 to 2104;) subfragment of the SPV HindIII M fragment has been deleted which would span SPV fragments 4 and 6.

HOMOLOGY VECTOR 789-41.47.

The plasmid 789-41.47 was constructed for the purpose of inserting foreign DNA into SPV. It incorporates an *E. coli* β-galactosidase (lacZ) marker gene, the pseudorabies virus (PRV) gC (gIII) gene and the PRV gD (g50) gene flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the PRV gC gene is under the control of a synthetic early/late pox promoter (EP1LP2), and the PRV gD gene is under the control of a synthetic early/late pox promoter (EP1LP2). A detailed description of the plasmid is given in FIGS. 15A–15D. It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1552 base pair subfragment of the PRV BamHI #7 fragment. which contains the coding sequence of the PRV gD gene from amino acid 3 to amino acid 279. The EcoRI site and the ATG translation start codon are derived from a polymerase chain reaction using a 5' primer with an EcoRI site. The StuI site at the 3' end is normally within the PRV gI gene 3' to the PRV gD gene. The entire open reading frame beginning at the EcoRI site codes for 405 amino acids. Fragment 3 is an approximately 48 base pair AccI to NdeI subfragment of the SPV HindIII M fragment. Fragment 4 is an approximately 3010 base pair BamHI to PvuII restriction fragment of plasmid pJF751 (11). Fragment 5 is an approximately 2378 base pair NcoI to NcoI fragment of plasmid 251-41.A, a subfragment of PRV BamHI #2 and #9. EcoRI linkers have replaced the NcoI sites at the ends of the fragment. Fragment 6 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 6 were converted to unique HindIII sites using HindIII linkers. An approximately 545 base pair NdeI to NdeI subfragment (Nucleotides 1560 to 2104;) of the SPV HindIII M fragment has been deleted which would span SPV fragments 3 and 6.

HOMOLOGY VECTOR 789-41.73.

The plasmid 789-41.73 was constructed for the purpose of inserting foreign DNA into SPV. It incorporates an *E. coli* β-galactosidase (lacZ) marker gene, the pseudorabies virus (PRV) gB (gII) gene, the PRV gC (gIII) gene and the PRV gD (g50) gene flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the PRV gB gene is under the control of a synthetic late/early pox promoter (LP2EP2), the PRV gC gene is under the control of a synthetic early/late promoter (EP1LP2), and the PRV gD gene is under the control of a synthetic late/early pox promoter (LP2EP2). A detailed description of the plasmid is given in FIGS. 16A–16E. It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1552 base pair subfragment of the PRV BamHI #7 fragment which contains the coding sequence of the PRV gD gene from amino acid 3 to amino acid 279. The EcoRI site and the ATG translation start codon are derived from a polymerase chain reaction using a 5' primer with an EcoRI site. The StuI site at the 3' end is normally within the PRV gI gene 3' to the PRV gD gene. The entire open reading frame beginning at the EcoRI site codes for 405 amino acids. Fragment 3 is an approximately 2378 base pair NcoI to NcoI fragment of plasmid 251-41.A, a subfragment of PRV BamHI #2 and #9. EcoRI linkers have replaced the NcoI sites at the ends of the fragment. Fragment 4 is an approximately 48 base pair AccI to NdeI subfragment of the SPV HindIII M fragment. Fragment 5 is an approximately 3500 base pair fragment which contains the coding sequence for the PRV gB gene within the KpnI C fragment of genomic PRV DNA(21). Fragment 5 contains an approximately 53 base pair synthetic fragment containing the amino terminus of the PRV gB gene, an approximately 78 base pair SmaI to Nhe I fragment from the PRV KpnI C genomic fragment, and an approximately 3370 base pair NheI to EcoRI fragment from the PRV KpnI C genomic fragment (21). Fragment 6 is an approximately 3010 base pair BamHI to PvuII restriction fragment of plasmid pJF751 (11). Fragment 7 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 6 were converted to unique HindIII sites using HindIII linkers. An approximately 545 base pair NdeI to NdeI subfragment (Nucleotides 1560 to 2104;) of the SPV HindIII M fragment has been deleted which would span SPV fragments 3 and 6.

HOMOLOGY VECTOR 791-63.19.

The plasmid 791-63.19 was constructed for the purpose of inserting foreign DNA into SPV. It incorporates an *E. coli* β-galactosidase (lacZ) marker gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1). It was constructed utilizing standard recombinant DNA techniques (22, 30), by joining restriction fragments from the following sources with the synthetic DNA sequence. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 2149 base pair AccI to HindIII subfragment of the SPV HindIII fragment M. The AccI sites in fragments 1 and 3 were converted to unique NotI sites using NotI linkers.

HOMOLOGY VECTOR 791-63.41.

The plasmid 791-63.41 was constructed for the purpose of inserting foreign DNA into SPV. It incorporates an *E. coli* β-galactosidase (lacZ) marker gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 2149 base pair AccI to HindIII subfragment of the SPV HindIII fragment M. The AccI sites in fragments 1 and 3 were converted to unique NotI sites using NotI linkers.

HOMOLOGY VECTOR 796-18.9.

The plasmid 796-18.9 was constructed for the purpose of inserting foreign DNA into SPV. It incorporates an *E. coli* β-galactosidase (lacZ) marker gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic early pox promoter (EP1). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 2149 base pair AccI to HindIII subfragment of the SPV HindIII fragment M. The AccI sites in fragments 1 and 3 were converted to unique NotI sites using NotI linkers.

HOMOLOGY VECTOR 783-39.2.

The plasmid 783-39.2 was constructed for the purpose of inserting foreign DNA into SPV. It incorporates an *E. coli* β-galactosidase (lacZ) marker gene and an bovine viral diarrhea virus glycoprotein 53 (BVDV gp53) gene flanked by SPV DNA. Upstream of the foreign gene is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a late promoter (LP1) and the BVDV gp53 gene is under the control of the late/early promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1187 base pair BamHI fragment coding for the BVDV gp53. The 1187 base pair BamHI fragment was synthesized by polymerase chain reaction (15) as described in CLONING OF BOVINE VIRAL DIARRHEA VIRUS gp48 AND gp53 GENES. Fragment 3 is an approximately 3010 base pair BamHI to PvuII restriction fragment of plasmid pJF751 (11). Fragment 4. is an approximately 2149 base pair AccI to HindIII subfragment of the SPV HindIII fragment M. The AccI sites in fragments 1 and 4 were converted to unique NotI sites using NotI linkers.

HOMOLOGY VECTOR 749-75.78.

The plasmid 749-75.78 was constructed for the purpose of inserting foreign DNA into SPV. It incorporates an *E. coli* β-galactosidase (lacZ) marker gene and the infectious bursal disease virus (IBDV) polymerase gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1) and the IBDV polymerase gene is under the control of a synthetic late/early promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 2700 EcoRI to AscI restriction fragment synthesized by cDNA cloning and polymerase chain reaction (PCR) from an IBDV RNA template. cDNA and PCR primers (5'-CAC<u>GAATTC</u>TGACATTTTCAACAGTCC ACAGGCGC-3' (SEQ ID NO: 79); 12/93.4) and 5'-GCTGTTGGACATCACGGGCCAGG-3' (SEQ ID NO: 80); 9/93.28) were used to synthesize an approximately 1400 base pair EcoRI to BclI fragment at the 5' end of the IBDV polymerase gene. cDNA and PCR primers (5'-ACCCGGAACATATGGTCAGCTCCAT-3' (SEQ ID NO: 81); 12/93.2) and 5'-<u>GGCGCGCC</u>AGGCGAAGGC CGGGGATACGG-3' (SEQ ID NO: 82); 12/93.3) were used to synthesize an approximately 1800 base pair BclI to AscI fragment at the 3' end of the IBDV polymerase gene. The two fragments were ligated at the BclI site to form the approximately 2700 base pair EcoRI to BclI fragment. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

HOMOLOGY VECTOR 761-75.B18.

The plasmid 761-75.B18 was constructed for the purpose of inserting foreign DNA into SPV. It incorporates an *E. coli* β-galactosidase (lac Z) marker gene and a feline immunodeficiency virus (FIV) protease (gag) gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a swinepox virus 01L gene promoter and the FIV gag gene is under the control of the late/early promoter (LP2EP2). The homology vector was constructed utilizing standard recombinant DNA techniques (22, 30), by joining restriction fragments from the following sources with the synthetic DNA sequences. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5' GAAGCATGCCCGTTCTTATCAATAGTTTAGTCGAAA ATA-3' (SEQ ID NO: 73) and 5'-CATAAGATCTGGCATTGTGTTATTATACTAACAAAAATAAG-3' (SEQ ID NO: 74) to produce an 855 base pair fragment with SphI and BglII ends. Fragment 2 is a 3002 base pair BamHI to PvuII fragment derived from plasmid pJF751 (49) containing the *E. coli* lacZ gene. Fragment 3 is an approximately 1878 base pair EcoRI to BglII restriction fragment synthesized by polymerase chain reaction (PCR) using cDNA from the FIV (PPR strain) (61). The primer (5' GCGTGAATTCGGGGAATGGACAGGGGCGAGAT-3' (SEQ ID NO: 83); 11/94.9) synthesizes from the 5' end of the FIV gag gene, introduces an EcoRI site at the 5' end of the gene and an ATG start codon. The primer (5'-GAGCCAGATCTGCTCTTTTTACTTTCCC-3' (SEQ ID NO: 84); 11/94.10) synthesizes from the 3' end of the FIV gag gene. The PCR product was digested with EcoRI and BglII to yield a fragment 1878 base pairs in length corresponding to the FIV gag gene. Fragment 4 is an approximately 1113 base pair subfragment of the SPV HindIII fragment M synthesized by polymerase chain reaction using DNA primers 5'-CCGTAGTCGACAAAGATCGACTTATTAATATGTATGGGATT-3' (SEQ ID NO: 75) and 5' GCCTGAAGCTTCTAGTACAGTATTTACGACTTTTGAAAT-3' (SEQ ID NO: 76) to produce an 1113 base pair fragment with SalI and HindIII ends.

HOMOLOGY VECTOR 781-84.C11.

The plasmid 781-84.C11 was used to insert foreign DNA into SPV. It incorporates an *E. coli* β-galactosidase (lacZ) marker gene and the feline immunodeficiency virus (FIV) envelope (env) gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the β galactosidase (lacZ) marker gene is under the control of a synthetic late pox promoter (LP1) and the FIV env gene is under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII fragment M (23). Fragment 3 is an approximately 2564 base pair BamHI to BamHI fragment of the FIV env gene (61) synthesized by CLONING WITH THE POLYMERASE CHAIN REACTION. The template for the PCR reaction was FIV strain PPR genomic cDNA (61). The upstream primer 10/93.21 (5'-GCCCGGATCCTATGGCAGAAGGGTTTGCAGC-3'; (SEQ ID NO: 85)) was synthesized corresponding to the 5' end of the FIV env gene starting at nucleotide 6263 of FIV strain PPR genomic cDNA, and the procedure introduced a BamHI site at the 5' end. The BamHI site was destroyed during the cloning of the PCR fragment. The downstream primer 10/93.20 (5'-CCGTGGATCCGGCACTCCATCATTCCTCCTC-3'; (SEQ ID NO: 86)) was synthesized corresponding to the 3' end of the FIV env gene starting at nucleotide 8827 of FIV PPR genomic cDNA, and the procedure introduced a BamHI site at the 3' end. Fragment 3 is an approximately 3010 base pair BamHI to PvuII restriction fragment of plasmid pJF751 (11). Fragment 4 is an approximately 2149 base pair AccI to HindIII restriction sub-fragment of the SPV HindIII restriction fragment M (23). The AccI site in the SPV homology vector was converted to a unique NotI site.

EXAMPLES

Example 1

Homology Vector 515-85.1.

The homology vector 515-85.1 is a plasmid useful for the insertion of foreign DNA into SPV. Plasmid 515-85.1 contains a unique AccI restriction site into which foreign DNA may be cloned. A plasmid containing such a foreign DNA insert may be used according to the HOMOLOGOUS RECOMBINATION PROCEDURE FOR GENERATING RECOMBINANT SPV to generate a SPV containing the foreign DNA. For this procedure to be successful it is important that the insertion site (AccI) be in a region non-essential to the replication of the SPV and that the site be flanked with swinepox virus DNA appropriate for mediating homologous recombination between virus and plasmid DNAs. AccI site in homology vector 515-85.1 is used to insert foreign DNA into at least three recombinant SPV (see examples 2–4).

In order to define an appropriate insertion site, a library of SPV HindIII restriction fragments was generated. Several of these restriction fragments (HindIII fragments G, J, and M see FIGS. 1A–1B) were subjected to restriction mapping analysis. Two restriction sites were identified in each fragment as potential insertion sites. These sites included HpaI and NruI in fragment G, BalI and XbaI in fragment J, and AccI and PstI in fragment M. A β-galactosidase (lacZ) marker gene was inserted in each of the potential sites. The resulting plasmids were utilized in the HOMOLOGOUS RECOMBINATION PROCEDURE FOR GENERATING RECOMBINANT SPV. The generation of recombinant virus was determined by the SCREEN FOR RECOMBINANT SPV EXPRESSING β-GALACTOSIDASE ASSAYS. Four of the six sites were found to generate recombinant virus, however the ability of each of these viruses to be purified away from the parental SPV varied greatly. In one case virus could not be purified above the level of 1%, in another case virus could not be purified above the level of 50%, and in a third case virus could not be purified above the level of 90%. The inability to purify these viruses indicates instability at the insertion site. This makes the corresponding sites inappropriate for insertion of foreign DNA. However the insertion at one site, the AccI site of Homology vector 515-85.1, resulted in a virus which was easily purified to 100% (see example 2), clearly defining an appropriate site for the insertion of foreign DNA.

The homology vector 515-85.1 was further characterized by DNA sequence analysis. Two regions of the homology vector were sequenced. The first region covers a 599 base pair sequence which flanks the unique AccI site. The second region covers the 899 base pairs upstream of the unique HindIII site. The sequence of the first region codes for an open reading frame (ORF) which shows homology to amino acids 1 to 115 of the vaccinia virus (VV) 01L open reading frame identified by Goebel et al, 1990 (see FIGS. 2A–2C). The sequence of the second region codes for an open reading frame which shows homology to amino acids 568 to 666 of the same vaccinia virus 01L open reading frame (see FIGS. 2A–2C). These data suggest that the AccI site interrupts the presumptive VV 01L-like ORF at approximately amino acid 41, suggesting that this ORF codes for a gene non-essential for SPV replication. Goebel et al. suggest that the VV 01L ORF contains a leucine zipper motif characteristic of certain eukaryotic transcriptional regulatory proteins, however they indicate that it is not known whether this gene is essential for virus replication.

The DNA sequence located upstream of the VV 01L-like ORF would be expected to contain a swinepox viral promoter. This swinepox viral promoter will be useful as the control element of foreign DNA introduced into the swinepox genome.

Example 2

S-SPV-003

S-SPV-003 is a swinepox virus that expresses a foreign gene. The gene for E. coli β-galactosidase (lacZ gene) was inserted into the SPV 515-85.1 ORF. The foreign gene (lacZ) is under the control of a synthetic early/late promoter (EP1LP2).

S-SPV-003 was derived from S-SPV-001 (Kasza strain). This was accomplished utilizing the homology vector 520-17.5 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-003. This virus was assayed for β-galactosidase expression, purity, and insert stability by multiple passages monitored by the blue plaque assay as described in *Materials and Methods*. After the initial three rounds of purification, all plaques observed were blue indicating that the virus was pure, stable and expressing the foreign gene. The assays described here were carried out in VERO cells as well as EMSK cells, indicating that VERO cells would be a suitable substrate for the production of SPV recombinant vaccines. S-SPV-003 has been deposited with the ATCC under Accession No. VR 2335.

Example 3

S-SPV-008

S-SPV-008 is a swinepox virus that expresses at least two foreign genes. The gene for *E. coli* β-galactosidase (lacZ gene) and the gene for pseudorabies virus (PRV) g50 (gD) (26) were inserted into the SPV 515-85.1 ORF. The lacZ gene is under the control of a synthetic late promoter (LP1) and the g50 (gD) gene is under the control of a synthetic early/late promoter (EP1LP2).

S-SPV-008 was derived from S-SPV-001 (Kasza strain). This was accomplished utilizing the homology vector 538-46.16 (see *Materials and Methods*) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-008. This virus was assayed for β-galactosidase expression, purity, and insert stability by multiple passages monitored by the blue plaque assay as described in *Materials and Methods*. After the initial three rounds of purification, all plaques observed were blue indicating that the virus was pure, stable and expressing the marker gene.

S-SPV-008 was assayed for expression of PRV specific antigens using the BLACK PLAQUE SCREEN FOR FOREIGN GENE EXPRESSION IN RECOMBINANT SPV. Swine anti-PRV serum was shown to react specifically with S-SPV-008 plaques and not with S-SPV-009 negative control plaques. All S-SPV-008 observed plaques reacted with the swine antiserum indicating that the virus was stably expressing the PRV foreign gene. The black plaque assay was also performed on unfixed monolayers. The SPV plaques on the unfixed monolayers also exhibited specific reactivity with swine anti-PRV serum indicating that the PRV antigen is expressed on the infected cell surface.

To confirm the expression of the PRV g50 (gD) gene product, cells were infected with SPV and samples of infected cell lysates were subjected to SDS-polyacrylamide gel electrophoresis. The gel was blotted and analyzed using the WESTERN BLOTTING PROCEDURE. The swine anti-PRV serum was used to detect expression of PRV specific proteins. The lysate from S-SPV-008 infected cells exhibits a specific band of approximately 48 kd, the reported size of PRV g50 (gD) (35).

PRV g50 (gD) is the g50 (gD) homologue of HSV-1 (26). Several investigators have shown that VV expressing HSV-1 g50 (gD) will protect mice against challenge with HSV-1 (6 and 34). Therefore the S-SPV-008 should be valuable as a vaccine to protect swine against PRV disease.

It is anticipated that several other PRV glycoproteins will be useful in the creation of recombinant swinepox vaccines to protect against PRV disease. These PRV glycoproteins include gII (28), gIII (27), and gH (19). The PRV gIII coding region has been engineered behind several synthetic pox promoters. The techniques utilized for the creation of S-SPV-008 will be used to create recombinant swinepox viruses expressing all four of these PRV glycoprotein genes. Such recombinant swinepox viruses will be useful as vaccines against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals. S-SPV-008 has been deposited with the ATCC under Accession No. VR 2339.

Example 6

S-SPV-013

S-SPV-013 is a swinepox virus that expresses at least two foreign genes. The gene for *E. coli* β-galactosidase (lacZ) and the gene for pseudorabies virus gIII (gC) were inserted into the unique PstI restriction site (PstI linkers inserted into a unique AccI site) of the homology vector 570-33.32. The lacZ gene is under the control of the synthetic late promoter (LP1) and the PRV gIII (gC) gene is under the control of the synthetic late early promoter (LP2EP2).

S-SPV-013 was derived from S-SPV-001 (Kasza Strain). This was accomplished utilizing the homology vector 570-91.64 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-013. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-013 was assayed for expression of PRV specific antigens using the BLACK PLAQUE SCREEN FOR FOREIGN GENE EXPRESSION IN RECOMBINANT SPV. Polyclonal goat anti-PRV gIII (gC) antibody was shown to react specifically with S-SPV-013 plaques and not with S-SPV-001 negative control plaques. All S-SPV-013 observed plaques reacted with the swine anti-PRV serum indicating that the virus was stably expressing the PRV foreign gene. The assays described here were carried out in EMSK and VERO cells, indicating that EMSK cells would be a suitable substrate for the production of SPV recombinant vaccines.

To confirm the expression of the PRV gIII (gC) gene product, cells were infected with SPV and samples of infected cell lysates were subjected to SDS-polyacrylamide gel electrophoresis. The gel was blotted and analyzed using the WESTERN BLOTTING PROCEDURE. Polyclonal goat anti-PRV gIII (gC) antibody was used to detect expression of PRV specific proteins. The lysate from S-SPV-013 infected cells exhibits two specific bands which are the reported size of PRV gIII (gC) (37)—a 92 kd mature form and a 74 kd pre-Golgi form.

Recombinant-expressed PRV gIII (gC) has been shown to elicit a significant immune response in mice and swine (37, 38). Furthermore, when gIII (gC) is coexpressed with gII (gB) or g50 (gD), significant protection from challenge with virulent PRV is obtained. (39) Therefore S-SPV-013 is valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals. S-SPV-013 has been deposited with the ATCC under Accession No. 2418.

Protection against Aujeszky's disease using recombinant swinepox virus vaccines S-SPV-008 and S-SPV-013.

A vaccine containing S-SPV-008 and S-SPV-013 (1×10⁶PFU/ml) (2 ml of a 1:1 mixture of the two viruses) was given to two groups of pigs (5 pigs per group) by intradermal inoculation or by oral/pharyngeal spray. A control group of 5 pigs received S-SPV-001 by both intradermal and oral/pharyngeal inoculation. Pigs were challenged three weeks post-vaccination with virulent PRV, strain 4892, by intranasal inoculation. The table presents a summary of clinical responses. The data support an increase in protection against Aujeszky's disease in the S-SPV-008/S-SPV-013 vaccinates compared to the S-SPV-001 vaccinate controls.

| Vaccine | Route of inoculation | Post-challenge Respiratory Signs: (# with signs/ total number) | Post-challenge CNS signs: (# with signs/ total number) | Post-challenge Group average: (Days of clinical signs) |
|---|---|---|---|---|
| S-SPV-008 + S-SPV-013 | Intradermal | 3/5 | 0/5 | 2.6 |
| S-SPV-008 + S-SPV-013 | Oral/ pharyngeal | 3/5 | 0/5 | 2.2 |
| S-SPV-001 (Control) | Intradermal + Oral/ Pharyngeal | 5/5 | 2/5 | 7.8 |

Example 7

S-SPV-015

S-SPV-015 is a swinepox virus that expresses at least two foreign genes. The gene for *E. coli* β-galactosidase (lacZ) and the gene for pseudorabies virus (PRV) gII (gB) were inserted into the SPV 617-48.1 ORF (a unique NotI restriction site has replaced a unique AccI restriction site). The lacZ gene is under the control of the synthetic late promoter (LP1), and the PRV gB gene is under the control of the synthetic late/early promoter (LP2EP2).

S-SPV-015 was derived from S-SPV-001 (Kasza Strain). This was accomplished utilizing the homology vector 727-54.60 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-015. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-015 was assayed for expression of PRV-specific antigens using the BLACK PLAQUE SCREEN FOR FOREIGN GENE EXPRESSION IN RECOMBINANT SPV. Polyclonal swine anti-PRV serum was shown to react specifically with S-SPV-015 plaques and not with S-SPV-001 negative control plaques. All S-SPV-015 observed plaques reacted with the antiserum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gII gene product, cells were infected with SPV-015 and samples of infected cell lysates were subjected to SDS-polyacrylamide gel electrophoresis. The gel was blotted and analyzed using the WESTERN BLOTTING PROCEDURE. Polyclonal swine anti-PRV serum was used to detect expression of PRV specific proteins. The lysate from S-SPV-015 infected cells exhibited bands corresponding to 120 kd, 67 kd and 58 kd, which are the expected size of the PRV gII glycoprotein.

S-SPV-015 is useful as a vaccine in swine against pseudorabies virus. A superior vaccine is formulated by combining S-SPV-008 (PRV g50), S-SPV-013 (PRV gIII), and S-SPV-015 for protection against pseudorabies in swine.

Therefore S-SPV-015 should be valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals. S-SPV-015 has been deposited with the ATCC under Accession No. 2466.

Example 8

Recombinant swinepox virus expressing more than one pseudorabies virus (PRV) glycoproteins, which can elicit production of neutralizing antibodies against pseudorabies virus, is constructed in order to obtain a recombinant swinepox virus with enhanced ability to protect against PRV infection than that which can be obtained by using a recombinant swinepox virus expressing only one of those PRV glycoproteins.

There are several examples of such recombinant swinepox virus expressing more than one PRV glycoproteins: a recombinant swinepox virus expressing PRV g50 (gD) and gIII (gC), a recombinant swinepox virus expressing PRV g50 (gD) and gII (gB); a recombinant swinepox virus expressing PRV gII (gB) and gIII (gC); and a recombinant swinepox virus expressing PRV g50 (gD), gIII (gC) and gII (gB). Each of the viruses cited above is also engineered to contain and express E. coli β-galactosidase (lac Z) gene, which will facilitate the cloning of the recombinant swinepox virus.

Listed below are three examples of a recombinant swinepox virus expressing PRV g50 (gD), PRV gIII (gC), PRV gII (gB) and E. coli β-galactosidase (lacZ):

a) Recombinant swinepox virus containing and expressing PRV g50 (gD) gene, PRV gIII (gC) gene, PRV gII (gB) gene and lacZ gene. All four genes are inserted into the unique AccI restriction endonuclease site within the HindIII M fragment of the swinepox virus genome. PRV g50 (gD) gene is under the control of a synthetic early/late promoter (EP1LP2), PRV gIII (gC) gene is under the control of a synthetic early promoter (EP2), PRV gII (gB) gene is under the control of a synthetic late/early promoter (LP2EP2) and lacZ gene is under the control of a synthetic late promoter (LP1).

b) Recombinant swinepox virus containing and expressing PRV g50 (gD) gene, PRV gIII (gC) gene, PRV gII (gB) gene and lacZ gene. All four genes are inserted into the unique AccI restriction endonuclease site within the HindIII M fragment of the swinepox virus genome. PRV g50 (gD) gene is under the control of a synthetic early/late promoter (EP1LP2), PRV gIII (gC) gene is under the control of a synthetic early/late promoter (EP1LP2), PRV gII (gB) gene is under the control of a synthetic late/early promoter (LP2EP2) and lacZ gene is under the control of a synthetic late promoter (LP1).

c) Recombinant swinepox virus containing and expressing PRV g50 (gD) gene, PRV gIII (gC) gene, PRV gII (gB) gene and lacZ gene. All four genes are inserted into the unique AccI restriction endonuclease site within the HindIII M fragment of the swinepox virus genome. PRV g50 (gD) gene is under the control of a synthetic early/late promoter (EP1LP2), PRV gIII (gC) gene is under the control of a synthetic late/early promoter (LP2EP2), PRV gII (gB) gene is under the control of a synthetic late/early promoter (LP2EP2) and lacZ gene is under the control of a synthetic late promoter (LP1).

Protection against Aujeszky's disease using recombinant swinepox virus vaccines S-SPV-008, S-SPV-013 and S-SPV-015.

A vaccine containing S-SPV-008, S-SPV-013, or S-SPV-015 (2 ml of 1×10$^7$ PFU/ml of the virus) or a mixture of S-SPV-008, S-SPV-013, and S-SPV-015 (2 ml of a 1:1:1 mixture of the three viruses; 1×10$^7$ PFU/ml) was given to four groups of pigs (5 pigs per group) by intramuscular inoculation. A control group of 5 pigs received S-SPV-001 by intramuscular inoculation. Pigs were challenged four weeks post-vaccination with virulent PRV, strain 4892, by intranasal inoculation. The pigs were observed daily for 14 days for clinical signs of pseudorabies, and the table presents a summary of clinical responses. The data show that pigs vaccinated with S-SPV-008, S-SPV-013, or S-SPV-015 had partial protection and pigs vacinated with the combination vaccine S-SPV-008/S-SPV-013/S-SPV-015 had complete protection against Aujeszky's disease caused by pseudorabies virus compared to the S-SPV-001 vaccinate controls.

| Vaccine | Route of inoculation | Post-challenge Respiratory Signs: (# with signs/ total number) | Post-challenge CNS signs: (# with signs/ total number) | Post-challenge Group average: (Days of clinical signs) |
|---|---|---|---|---|
| S-SPV-008 + | Intramuscular | 2/5 | 2/5 | 2.0 |
| S-SPV-013 | Intramuscular | 1/5 | 0/5 | 0.4 |
| S-SPV-015 | Intramuscular | 3/5 | 0/5 | 1.0 |
| S-SPV-008 + S-SPV-013 + S-SPV-015 | Intramuscular | 0/5 | 0/5 | 0.0 |
| S-SPV-001 (Control) | Intramuscular | 5/5 | 2/5 | 3.6 |

Example 17

The development of vaccines utilizing the swinepox virus to express antigens from various disease causing microorganisms can be engineered.

TRANSMISSIBLE GASTROENTERITIS VIRUS

The major neutralizing antigen of the transmissible gastroenteritis virus (TGE), glycoprotein 195, for use in the swinepox virus vector has been cloned. The clone of the neutralizing antigen is disclosed in U.S. Ser. No. 078,519, filed Jul. 27, 1987. It is contemplated that the procedures that have been used to express PRV g50 (gD) in SPV and are disclosed herein are applicable to TGE.

PORCINE PARVOVIRUS

The major capsid protein of the porcine (swine) parvovirus (PPV) was cloned for use in the swinepox virus vector. The clone of the capsid protein is disclosed in U.S. Pat. No. 5,068,192 issued Nov. 26, 1991. It is contemplated that the procedures that have been used to express PRV g50 (gD) in SPV and are disclosed herein are applicable to PPV.

SWINE ROTAVIRUS

The major neutralizing antigen of the swine rotavirus, glycoprotein 38, was cloned for use in the swinepox virus vector. The clone of glycoprotein 38 is disclosed in U.S. Pat. No. 5,068,192 issued Nov. 26, 1991. It is contemplated that the procedures that have been used to express PRV g50 (gD) in SPV and are disclosed herein are applicable to SRV.

HOG CHOLERA VIRUS

The major neutralizing antigen of the bovine viral diarrhea (BVD) virus was cloned as disclosed in U.S. Ser. No. 225,032, filed Jul. 27, 1988. Since the BVD and hog cholera viruses are cross protective (31), the BVD virus antigen has been targeted for use in the swinepox virus vector. It is contemplated that the procedures that have been used to express PRV g50 (gD) in SPV and are disclosed herein are applicable to BVD virus.

SERPULINA HYODYSENTERIAE

A protective antigen of Serpulina hyodysenteriae (3), for use in the swinepox virus vector has been cloned. It is contemplated that the procedures that have been used to express PRV g50 in SPV and are disclosed herein are also applicable to Serpulina hyodysenteriae.

Antigens from the following microorganisms may also be utilized to develop animal vaccines: swine influenza virus, foot and mouth disease virus, African swine fever virus, hog cholera virus, Mycoplasma hyopneumoniae, porcine reproductive and respiratory syndrome/swine infertility and respiratory syndrome (PRRS/SIRS).

Antigens from the following microorganisms may also be utilized for animal vaccines: 1) canine—herpesvirus, canine distemper, canine adenovirus type 1 (hepatitis), adenovirus type 2 (respiratory disease), parainfluenza, *Leptospira canicola*, icterohemorragia, parvovirus, coronavirus, *Borrelia burgdorferi*, canine herpesvirus, *Bordetella bronchiseptica, Dirofilaria immitis* (heartworm) and rabies virus. 2) Feline—Fiv gag and env, feline leukemia virus, feline immunodeficiency virus, feline herpesvirus, feline infectious peritonitis virus, canine herpesvirus, canine coronavirus, canine parvovirus, parasitic diseases in. animals (including *Dirofilaria iminitis* in dogs and cats), equine infectious anemia, *Streptococcus equi*, coccidia, emeria, chicken anemia virus, *Borrelia bergdorferi*, bovine coronavirus, *Pasteurella haemolytica*.

Example 24

Homology Vector 738-94.4

Homology Vector 738-94.4 is a swinepox virus vector that expresses one foreign gene. The gene for *E. coli* β-galactosidase (lacZ) was inserted into the the 01L open reading frame. The lacZ gene is under the control of the 01L promoter. The homology vector 738-94.4 contains a deletion of SPV DNA from nucleotides 1679 to 2452 (SEQ ID NO: 189) which deletes part of the 01L ORF.

The upstream SPV sequences were synthesized by polymerase chain reaction using DNA primers 5'-GAAGCATGCCCGTTCTTATCAATAGTTTAGTCG AAAATA-3' (SEQ ID NO: 73) and 5'-CATAAGATCTGG CATTGTGTTATTATACTAACAAAAATAAG-3' (SEQ ID NO: 74) to produce an 855 base pair fragment with BglII and SphI ends. The 01L promoter is present on this fragment. The downstream SPV sequences were synthesized by polymerase chain reaction using DNA primers 5'-CCGTAGTCGACAAAGATCGACTTATTAATATGT ATGGGATT-3' (SEQ ID NO: 75) and 5'-GCCTGA AGCTTCTAGTACAGTATTTACGACTTTTGAAAT-3' (SEQ ID NO: 74) to produce an 1113 base pair fragment with SalI and HindIII ends. A recombinant swinepox virus was derived utilizing homology vector 738-94.4 and S-SPV-001 (Kasza strain) in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification is the recombinant virus. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene. Recombinant swinepox viruses. derived from homology vector 738-94.4 are utilized as an expression vector to express foreign antigens and as a vaccine to raise a protective immune response in animals to foreign genes expressed by the recombinant swinepox virus. Other promoters in addition to the 01L promoter are inserted into the deleted region including LP1, EP1LP2, LP2EP2, HCMV immediate early, and one or more foreign genes are expressed from these promoters.

Example 24B

Homology Vector 752-22.1 is a swinepox virus vector that is utilized to express two foreign genes. The gene for *E. coli* β-galactosidase (lacZ) was inserted into the the 01L open reading frame. The lacZ gene is under the control of the 01L promoter. A second foreign gene is expressed from the LP2EP2 promoter inserted into an EcoRI or BamHI site following the LP2EP2 promoter sequence. The homology vector 752-22.1 contains a deletion of SPV DNA from nucleotides 1679 to 2452 (SEQ ID NO: 189) which deletes part of the 01L ORF. The homology vector 752-22.1 was derived from homology vector 738-94.4 by insertion of the LP2EP2 promoter fragment (see Materials and Methods). The homology vector 752-22.1 is further improved by placing the lacZ gene under the control of the synthetic LP1 promoter. The LP1 promoter results in higher levels of lacZ expression compared to the SPV 01L promoter Example 25

S-SPV-041:

S-SPV-041 is a swinepox virus that expresses at least two foreign genes. The gene for *E. coli* β-galactosidase (lacZ) and the gene for equine herpesvirus type 1 glycoprotein B (gB) were inserted into the 738-94.4 ORF (a 773 base pair deletion of the SPV 01L ORF; Deletion of nucleotides 1679 to 2452, SEQ ID NO: 189). The lacZ gene is under the control of the swinepox 01L promoter, and the EHV-1 gB gene is under the control of the synthetic late/early promoter (LP2EP2).

S-SPV-041 was derived from S-SPV-001 (Kasza Strain). This was accomplished utilizing the homology vector 752-29.33 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-041. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-041 is useful as a vaccine in horses against EHV-1 infection and is useful for expression of EHV-1 glycoprotein B.

S-SPV-045:

S-SPV-045 is a swinepox virus that expresses at least two foreign genes. The gene for *E. coli* β-galactosidase (lacZ) and the gene for infectious bovine rhinotracheitis virus glycoprotein E (gE) were inserted into the 738-94.4 ORF (a 773 base pair deletion of the SPV 01L ORF; Deletion of nucleotides 1679 to 2452, SEQ ID NO: 189). The lacZ gene is under the control of the swinepox 01L promoter, and the IBRV gE gene is under the control of the synthetic late/early promoter (LP2EP2).

S-SPV-045 was derived from S-SPV-001 (Kasza Strain) This was accomplished utilizing the homology vector 746-94.1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-045. This virus was assayed for β-galactosidase expression, purity, and insert stability by multiple passages monitored by the blue plaque assay as described in Materials and Methods. After the initial three rounds of purification, all plaques observed were blue indicating that the. virus was pure, stable, and expressing the foreign gene.

S-SPV-045 is useful for expression of IBRV glycoprotein E.

S-SPV-049:

S-SPV-049 is a swinepox virus that expresses at least two foreign genes. The gene for *E. coli* β-galactosidase (lacZ)

and the gene for bovine viral diarrhea virus glycoprotein 48 (gp48) were inserted into the 738-94.4 ORF (a 773 base pair deletion of the SPV 01L ORF; Deletion of nucleotides 1679 to 2452, SEQ ID NO: 189). The lacZ gene is under the control of the swinepox 01L promoter, and the BVDV gp48 gene is under the control of the synthetic late/early promoter (LP2EP2).

S-SPV-049 was derived from S-SPV-001 (Kasza Strain). This was accomplished utilizing the homology vector 771-55.11 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-049. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-049 is useful as a vaccine in cattle against BVDV infection and is useful for expression of BVDV glycoprotein 48.

S-SPV-050:

S-SPV-050 is a swinepox virus that expresses at least two foreign genes. The gene for E. coli β-galactosidase (lacZ) and the gene for the bovine viral diarrhea virus glycoprotein 53 (gp53) were inserted into the 738-94.4 ORF (a 773 base pair deletion of the SPV 01L ORF; Deletion of nucleotides 1679 to 2452, SEQ ID NO: 189). The lacZ gene is under the control of the swinepox 01L promoter, and the IBRV gE gene is under the control of the synthetic late/early promoter (LP2EP2).

S-SPV-050 was derived from S-SPV-001 (Kasza Strain). This was accomplished utilizing the homology vector 767-67.3 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-050. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-050 is useful as a vaccine in cattle against BVDV infection and is useful for expression of BVDV glycoprotein 53.

Example 26

Recombinant swinepox virus, S-SPV-042 or S-SPV-043, expressing chicken interferon (cIFN) or chicken myelomonocytic growth factor (cMGF), respectively, are useful to enhance the immune response when added to vaccines against diseases of poultry. Chicken myelomonocytic growth factor (cMGF) is homologous to mammalian interleukin-6 protein, and chicken interferon (cIFN) is homologous to mammalian interferon. When used in combination with vaccines against specific avian diseases, S-SPV-042 and S-SPV-043 provide enhanced mucosal, humoral, or cell mediated immunity against avian disease-causing viruses including, but not limited to, Marek's disease virus, Newcastle disease virus, infectious laryngotracheitis virus, infectious bronchitis virus, infectious bursal disease virus.

Example 26A

S-SPV-042:

S-SPV-042 is a swinepox virus that expresses at least two foreign genes. The gene for E. coli β-galactosidase (lacZ) and the gene for chicken interferon (cIFN) were inserted into the SPV 617-48.1 ORF (a unique NotI restriction site has replaced a unique AccI restriction site). The lacZ gene is under the control of the synthetic late promoter (LP1), and the cIFN gene is under the control of the synthetic late/early promoter (LP2EP2).

S-SPV-042 was derived from S-SPV-001 (Kasza Strain). This was accomplished utilizing the homology vector 751-07.A1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-042. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene. S-SPV-042 has interferon activity in cell culture. Addition of S-SPV-042 conditioned media to chicken embryo fibroblast (CEF) cell culture inhibits infection of the CEF cells by vesicular stomatitis virus or by herpesvirus of turkeys. S-SPV-042 is useful to enhance the immune response when added to vaccines against diseases of poultry.

Example 26B

S-SPV-043:

S-SPV-043 is a swinepox virus that expresses at least two foreign genes. The gene for E. coli β-galactosidase (lacZ) and the gene for chicken myelomonocytic growth factor (cMGF) were inserted into the SPV 617-48.1 ORF (a unique NotI restriction site has replaced a unique AccI restriction site). The lacZ gene is under the control of the synthetic late promoter (LP1), and the cMGF gene is under the control of the synthetic late/early promoter (LP2EP2).

S-SPV-043 was derived from S-SPV-001 (Kasza Strain). This was accomplished utilizing the homology vector 751-56.A1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-043. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene. S-SPV-043 is useful to enhance the immune response when added to vaccines against diseases of poultry.

Example 27

Insertion into a Non-essential site in the 2.0 kb HindIII to BglII Region of the Swinepox Virus HindIII M Fragment.

A 2.0 kb HindIII to BglII region of the swinepox virus HindIII M fragment is useful for the insertion of foreign DNA into SPV. The foreign DNA is inserted into a unique BglII restriction site in the region Nucleotide 540 of SEQ ID NOs: 195). A plasmid containing a foreign DNA insert is used according to the HOMOLOGOUS RECOMBINATION PROCEDURE FOR GENERATING RECOMBINANT SPV to generate an SPV containing the foreign DNA. For this procedure to be successful, it is important that the insertion site be in a region non-essential to the replication of the SPV and that the site be flanked with swinepox virus DNA appropriate for mediating homologous recombination between virus and plasmid DNAs. The unique BglII restriction site in the 2.0 kb HindIII to BglII region of the swinepox virus HindIII M fragment is located within the coding region of the SPV I4L open reading frame. The I4L ORF has sequence similarity to the vaccinia virus and smallpox virus ribonucleotide reductase (large subunit) gene (56-58). The ribonucleotide reductase (large subunit) gene is non-essential for DNA replication of vaccinia virus and is an appropriate insertion site in swinepox virus.

Example 28

S-SPV-047

S-SPV-047 is a swinepox virus that expresses two foreign genes. The gene for *E. coli* β-galactosidase (lacZ) and the gene for pseudorabies virus gB (gII) were inserted into a unique HindIII site (HindIII linker inserted into the BglII restriction endonuclease site within the 2.0 kb BglII to HindIII subfragment of the HindIII M fragment.) The BglII insertion site is within the SPV I4L open reading frame which has significant homology to the vaccinia virus ribonucleoside-diphosphate reductase gene. The lacZ gene is under the control of the synthetic late promoter (LP1), and the PRV gB (gII) gene is under the control of the synthetic late/early promoter (LP2EP2).

S-SPV-047 was derived from S-SPV-001 (Kasza Strain). This was accomplished utilizing the homology vector 779-94.31 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-047. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-047 was assayed for expression of PRV specific antigens using the BLACK PLAQUE SCREEN FOR FOREIGN GENE EXPRESSION IN RECOMBINANT SPV. Polyclonal swine anti-PRV serum was shown to react specifically with S-SPV-047 plaques and not with S-SPV-001 negative control plaques. All S-SPV-047 observed plaques reacted with the swine anti-PRV serum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gB gene product, cells were infected with S-SPV-047 and samples of infected cell lysates and culture supernatants were subjected to SDS polyacrylamide gel electrophoresis. The gel was blotted and analyzed using the WESTERN BLOTTING PROCEDURE. A polyclonal swine anti-PRV serum was used to detect expression of PRV specific proteins. The cell lysate and supernatants from S-SPV-047 infected cells exhibited bands corresponding to 120 kD, 67 kD and 58 kD, which are the expected size of the PRV glycoprotein B.

SPV recombinant-expressed PRV gB has been shown to elicit a significant immune response in swine (37, 38; See example 8). Furthermore, PRV gB is expressed in recombinant SPV, significant protection from challenge with virulent PRV is obtained. (See Examples 6 and 8) Therefore S-SPV-047 is valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals.

S-SPV-052

S-SPV-052 is a swinepox virus that expresses three foreign genes. The gene for *E. coli* β-galactosidase (lacZ) and the gene for pseudorabies virus gB (gII) were inserted into the unique HindIII restriction site (HindIII linkers inserted into a unique NdeI site in the SPV 01L open reading frame; An approximately 545 base pair NdeI to NdeI subfragment (Nucleotides 1560 to 2104;) of the SPV HindIII M fragment has been deleted). The gene for PRV gD (g50) was inserted into the unique PstI restriction site (PstI linkers inserted into a unique AccI site in the SPV 01L open reading frame). The lacZ gene is under the control of the synthetic late promoter (LP1), the PRV gB (gII) gene is under the control of the synthetic late/early promoter (LP2EP2), and the PRV gD (g50) gene is under the control of the synthetic early/late promoter (EP1LP2).

S-SPV-052 was derived from S-SPV-001 (Kasza Strain). This was accomplished utilizing the homology vector 789-41.7 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 052. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-052 was assayed for expression of PRV specific antigens using the BLACK PLAQUE SCREEN FOR FOREIGN GENE EXPRESSION IN RECOMBINANT SPV. Polyclonal swine anti-PRV serum was shown to react specifically with S-SPV- 052 plaques and not with S-SPV-001 negative control plaques. All S-SPV-052 observed plaques reacted with the swine anti-PRV serum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gB and gD gene products, cells were infected with S-SPV-052 and samples of infected cell lysates and culture supernatants were subjected to SDS polyacrylamide gel electrophoresis. The gel was blotted and analyzed using the WESTERN BLOTTING PROCEDURE. A polyclonal swine anti-PRV serum was used to detect expression of PRV specific proteins. The cell lysate and supernatants from S-SPV-052 infected cells exhibited bands corresponding to 120 kD, 67 kD and 58 kD, which are the expected size of the PRV glycoprotein B; and a 48 kD which is the expected size of the PRV glycoprotein D.

SPV recombinant-expressed PRV gB and gD has been shown to elicit a significant immune response in swine (37, 38; See example 8). Furthermore, PRV gB and gD are expressed in recombinant SPV, significant protection from challenge with virulent PRV is obtained. (See Examples 6 and 8) Therefore S-SPV-052 is valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals.

S-SPV-053

S-SPV-053 is a swinepox virus that expresses three foreign genes. The gene for E. coli β-galactosidase (lacZ) and the gene for pseudorabies virus gB (gII) were inserted into the unique HindIII restriction site (HindIII linkers inserted into a unique NdeI site in the SPV 01L open reading frame; An approximately 545 base pair NdeI to NdeI subfragment (Nucleotides 1560 to 2104;) of the SPV HindIII M fragment has been deleted). The gene for PRV gC (gIII) was inserted into the unique PstI restriction site (PstI linkers inserted into a unique AccI site in the SPV 01L open reading frame). The lacZ gene is under the control of the synthetic late promoter (LP1), the PRV gB (gII) gene is under the control of the synthetic late/early promoter (LP2EP2), and the PRV gC (gIII) gene is under the control of the synthetic early/late promoter (EP1LP2).

S-SPV-053 was derived from S-SPV-001 (Kasza Strain). This was accomplished utilizing the homology vector 789-41.27 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 053. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-053 was assayed for expression of PRV specific antigens using the BLACK PLAQUE SCREEN FOR FOREIGN GENE EXPRESSION IN RECOMBINANT SPV. Polyclonal swine anti-PRV serum was shown to react specifically with S-SPV- 053 plaques and not with S-SPV-001 negative control plaques. All S-SPV-053 observed plaques reacted with the swine anti-PRV serum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gB and gC gene products, cells were infected with S-SPV-053 and samples of infected cell lysates and culture supernatants were subjected to SDS polyacrylamide gel electrophoresis. The gel was blotted and analyzed using the WESTERN BLOTTING PROCEDURE. A polyclonal swine anti-PRV serum was used to detect expression of PRV specific proteins. The cell lysate and supernatants from S-SPV-053 infected cells exhibited bands corresponding to 120 kD, 67 kD and 58 kD, which are the expected size of the PRV glycoprotein B; and a 92 kD which is the expected size of the PRV glycoprotein C.

SPV recombinant-expressed PRV gB and gC has been shown to elicit a significant immune response in swine (37, 38; See example 8). Furthermore, PRV gB and gC are expressed in recombinant SPV, significant protection from challenge with virulent PRV is obtained. (See Examples 6 and 8) Therefore S-SPV-053 is valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals.

S-SPV-054

S-SPV-054 is a swinepox virus that expresses three foreign genes. The gene for E. coli β-galactosidase (lacZ) and the gene for pseudorabies virus gC (gIII) were inserted into the unique HindIII restriction site (HindIII linkers inserted into a unique NdeI site in the SPV 01L open reading frame; An approximately 545 base pair NdeI to NdeI subfragment (Nucleotides 1560 to 2104;) of the SPV HindIII M fragment has been deleted). The gene for PRV gD (g50) was inserted into the unique PstI restriction site (PstI linkers inserted into a unique AccI site in the SPV 01L open reading frame). The lacZ gene is under the control of the synthetic late promoter (LP1), the PRV gC (gIII) gene is under the control of the synthetic early/late promoter (EP1LP2), and the PRV gD (g50) gene is under the control of the synthetic early/late promoter (EP1LP2).

S-SPV-054 was derived from S-SPV-001 (Kasza Strain) This was accomplished utilizing the homology vector 789-41.47 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 054. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-054 was assayed for expression of PRV specific antigens using the BLACK PLAQUE SCREEN FOR FOREIGN GENE EXPRESSION IN RECOMBINANT SPV. Polyclonal swine anti-PRV serum was shown to react specifically with S-SPV-054 plaques and not with S-SPV-001 negative control plaques. All S-SPV-054 observed plaques reacted with the swine anti-PRV serum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gC and gD gene products, cells were infected with S-SPV-054 and samples of infected cell lysates and culture supernatants were subjected to SDS polyacrylamide gel electrophoresis. The gel was blotted and analyzed using the WESTERN BLOTTING PROCEDURE. A polyclonal swine anti-PRV serum was used to detect expression of PRV specific proteins. The cell lysate and supernatants from S-SPV-054 infected cells exhibited a band corresponding to 92 kD which is the expected size of the PRV glycoprotein C and a 48 kD which is the expected size of the PRV glycoprotein D.

SPV recombinant-expressed PRV gC and gD has been shown to elicit a significant immune response in swine (37, 38; See example 8). Furthermore, PRV gC and gD are expressed in recombinant SPV, significant protection from challenge with virulent PRV is obtained. (See Examples 6 and 8) Therefore S-SPV-054 is valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals.

S-SPV-055

S-SPV-055 is a swinepox virus that expresses four foreign genes. The gene for *E. coli* β-galactosidase (lacZ) and the gene for pseudorabies virus gB (gII) were inserted into the unique HindIII restriction site (HindIII linkers inserted into a unique NdeI site in the SPV 01L open reading frame; An approximately 545 base pair NdeI to NdeI subfragment (Nucleotides 1560 to 2104;) of the SPV HindIII M fragment has been deleted). The gene for PRV gD (g50) and PRV gC (gIII) were inserted into the unique PstI restriction site (PstI linkers inserted into a unique AccI site in the SPV 01L open reading frame). The lacZ gene is under the control of the synthetic late promoter (LP1), the PRV gB (gII) gene is under the control of the synthetic late/early promoter (LP2EP2), the PRV gD (g50) gene is under the control of the synthetic late/early promoter (LP2EP2), and the PRV gC (gIII) gene is under the control of the synthetic early/late promoter (EP1LP2).

S-SPV-055 was derived from S-SPV-001 (Kasza Strain). This was accomplished utilizing the homology vector 789-41.73 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 055. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-055 was assayed for expression of PRV specific antigens using the BLACK PLAQUE SCREEN FOR FOREIGN GENE EXPRESSION IN RECOMBINANT SPV. Polyclonal swine anti-PRV serum was shown to react specifically with S-SPV-055 plaques and not with S-SPV-001 negative control plaques. All S-SPV-055 observed plaques reacted with the swine anti-PRV serum indicating that the virus was stably expressing the PRV foreign gene. The assays described here were carried out in ESK-4 cells, indicating that ESK-4 cells would be a suitable substrate for the production of SPV recombinant vaccines.

To confirm the expression of the PRV gB, gC and gD gene products, cells were infected with S-SPV-055 and samples of infected cell lysates and culture supernatants were subjected to SDS polyacrylamide gel electrophoresis. The gel was blotted and analyzed using the WESTERN BLOTTING PROCEDURE. A polyclonal swine anti-PRV serum was used to detect expression of PRV specific proteins. The cell lysate and supernatants from S-SPV-055 infected cells exhibited a bands corresponding to 120 kD, 67 kD, and 58 kD which is the expected size of the PRV glycoprotein B; a 92 kD which is the expected size of the PRV glycoprotein C; and a 48 kD which is the expected size of the PRV glycoprotein D SPV recombinant-expressed PRV gB, gC and gD has been shown to elicit a significant immune response in swine (37, 38; See example 8). Furthermore, PRV gB, gC and gD are expressed in recombinant SPV, significant protection from challenge with virulent PRV is obtained. (See Examples 6 and 8) Therefore S-SPV-055 is valuable as a vaccine to protect swine against PRV disease. Since the PRV vaccines described here do not express PRV gX or gI, they would be compatible with current PRV diagnostic tests (gX HerdChek®, gI HerdChek® and ClinEase®) which are utilized to distinguish vaccinated animals from infected animals.

Example 29

S-SPV-059

S-SPV-059 is a swinepox virus that expresses one foreign gene. The gene for *E. coli* B-glucuronidase (uidA) was inserted into the unique EcoRI restriction site in the SPV B18R open reading frame within the SPV HindIII K genomic fragment. The uidA gene is under the control of the synthetic late/early promoter (LP2EP2). Partial sequence of the SPV 3.2 kb region of the SPV 6.5 kb HindIII K fragment indicates three potential open reading frames. The SPV B18R ORF shows sequences homology to the vaccinia virus B18R gene, 77.2K protein from rabbit fibroma virus, vaccinia virus C19L/B25R ORF and an ankyrin repeat region from a human brain variant. The B18R gene codes for a soluble interferon receptor with high affinity and broad specificity. The SPV B4R open reading frame shows sequence homology to the T5 protein of rabbit firbroma virus.

S-SPV-059 was derived from S-SPV-001 (Kasza Strain) This was accomplished utilizing the homology vector 796-50.31 and virus S-SPV-001 in the HOMOLOGOUS RECOMBINATION PROCEDURE FOR GENERATING RECOMBINANT SPV. Homology vector 796-50.31 was generated by insertion of a blunt ended NotI fragment containing the LP2EP2 promoter uidA cassette from plasmid 551-47.23 (see Materials and Methods) into a unique EcoRI site (blunt ended) in the SPV 6.5 kb HindIII K fragment, (FIG. 29B). The transfection stock was screened by the SCREEN FOR RECOMBINANT HERPESVIRUS EXPRESSING ENZYMATIC MARKER GENES. The final result of blue plaque purification was the recombinant virus designated S-SPV-059. This virus was assayed for B-glucuronidase expression, purity, and insert stability by multiple passages monitored by the blue plaque assay as described in Materials and Methods. After the initial three rounds of purification, plaques observed were blue indicating that the virus was pure, stable, and expressing the foreign gene.

S-SPV-059 has been purified and expresses the foreign gene, *E. coli* uidA, indicating that the EcoRI site within the 6.5 kb HindIII K fragment is a stable insertion site for foreign genes. Recombinant swinepox virus utilizing this insertion site is useful for expression of foreign antigen genes, as a vaccine against disease or as an expression vector to raise antibodies to the expressed foreign gene.

S-SPV-060

S-SPV-060 is a swinepox virus that expresses one foreign gene. The gene for *E. coli* B-glucuronidase (uidA) was inserted into the unique EcoRV restriction site within the SPV HindIII N genomic fragment. The uidA gene is under the control of the synthetic late/early promoter (LP2EP2). Partial sequence of the SPV 3.2 kb HindIII N fragment (SEQ ID NO.) indicates two potential open reading frames. The SPV I7l ORF shows sequences homology to protein I7 of vaccinia virus. The SPV I4L open reading frame shows sequence homology to the ribonucleoside diphosphate reductase gene of vaccinia virus. Two potential open reading frames I5L and I6L, between I4L adn I7L ORF are of unknown function.

S-SPV-060 was derived from S-SPV-001 (Kasza Strain). This was accomplished utilizing the homology vector 796-71.31 and virus S-SPV-001 in the HOMOLOGOUS RECOMBINATION PROCEDURE FOR GENERATING RECOMBINANT SPV. Homology vector 796-71.31 was generated by insertion of a blunt ended NotI fragment containing the LP2IP2 promoter uidA cassette from plasmid 551-47.23 (see Materials and Methods) into a unique EcoRV site in the SPV 3.2 kb HindIII N fragment (FIG. 11A). The transfection stock was screened by the SCREEN FOR RECOMBINANT HERPESVIRUS EXPRESSING ENZYMATIC MARKER GENES. The final result of blue plaque purification is teh recombinant virus designated S-SPV-060. This virus is assayed for β-glucuronidase expression, purity, and insert stability by multiple passages monitored by the blue plaque assay las described in Materials and Methods. After the initial three rounds of purification, plaques observed are blue indicating that the virus is pure, stable, and expressing the foreign gene.

S-SPV-060 is purified and expresses the foreign gene, *E. coli* uidA, indicating that the EcoRI site within the 3.2 kb HindIII N fragment is a stable insertion site for foreign genes. Recombinant swinepox virus utilizing this insertion site is useful for expression of foreign antigen genes, as a vaccine against disease or as an expression vector to raise antibodies to the expressed foreign gene.

S-SPV-061 s-SPV-061 is a swinepox virus that expressed one foreign gene. The gene for *E. coli* β-*glucuronidase (uidA) was inserted into the unique SnaBI restriction site within the SPV HindIII N genomic fragment. The uidA gene is under the control of the synthetic late/early promoter (LP*2EP2). Partial sequence of the SPV 3.2 kb HindIII N fragment indicates two potential open reading frames. The SPV I7L ORF shows sequence homology to protein 17 of vaccinia virus. The SPV I4L open reading frame shows sequence homology to the ribonucleoside diphosphate reductase gene of vaccinia virus. Two potential open reading frames I5L and I6L, between I4L ORF and I7L ORF are of unknown function.

S-SPV-061 was derived from S-SPV-001 (Kasza Strain). This was accomplished utilizing the homology vector 796-71.41 and virus S-SPV-001 in the HOMOLOGOUS RECOMBINATION PROCEDURE FOR GENERATING RECOMBINANT SPV. Homology vector 796-71.41 was generated by insertion of a blunt ended NotI fragment containing the LP2EP2 promoter uidA cassette from plasmid 551-47.23 (see Materials and Methods) into a unique SnaBI site in the SPV 3.2 kb HindIII N fragment. The transfection stock was screened by the SCREEN FOR RECOMBINANT HERPESVIRUS EXPRESSING ENZYMATIC MARKER GENES. The final result of blue plaque purification is the recombinant virus designated S-SPV-061. This virus is assayed for β-glucuronidase expression, purity, and insert stability by multiple passages monitored by the blue plaque assay as described in Materials and Methods. After the initial three rounds of purification, plaques observed are blue indicating that the virus is pure, stable, and expressing the foreign gene.

S-SPV-061 is purified and expresses the foreign gene, *E. coli* uidA, indicating that the SnaBI site within the 3.2 kb HindIII N fragment is a stable insertion site for foreign genes. Recombinant swinepox virus utilizing this insertion site is useful for expression of foreign antigen genes, as a vaccine against disease or as an expression vector to raise antibodies to the expressed foreign gene.

S-SPV-062

S-SPV-062 is a swinepox virus that expresses one foreign gene. The gene for *E. coli* β-glucuronidase (uidA) was inserted into the unique BglII restriction site within the SPV HindIII N genomic fragment (FIG. 11A). The uidA gene is under the control of the synthetic late/early promoter (LP2EP2). Partial sequence of the SPV 3.2 kb HindIII N fragment indicates two potential open reading frames. The SPV I7L ORF shows sequence homology to protein 17 of vaccinia virus. The SPV I4L open reading frame shows sequence homology to the ribonucleoside diphosphate reductase gene of vaccinia virus. Two potential open reading frames I5L and I6L, between I4L ORF and I7L ORF are of unknown function.

S-SPV-062 was derived from S-SPV-001 (Kasza Strain). This was accomplished utilizing the homology vector 796-71.51 and virus S-SPV-001 in the HOMOLOGOUS RECOMBINATION PROCEDURE FOR GENERATING RECOMBINANT SPV. Homology vector 796-71.51 was generated by insertion of a blunt ended NotI fragment containing the LP2EP2 promoter uidA cassette from plasmid 551-47.23 (see Materials and Methods) into a unique BglII site in the SPV 3.2 kb HindIII N fragment. The transfection stock was screened by the SCREEN FOR RECOMBINANT HERPESVIRUS EXPRESSING ENZYMATIC MARKER GENES. The final result of blue plaque purification is the recombinant virus designated S-SPV-062. This virus is assayed for β-glucuronidase expression, purity, and insert stability by multiple passages monitored by the blue plaque assay as described in Materials and Methods. After the initial three rounds of purification, plaques observed are blue indicating that the virus is pure, stable, and expressing the foreign gene.

S-SPV-062 is purified and expresses the foreign gene, *E. coli* uidA, indicating that the BglII site within the 3.2 kb HindIII N fragment is a stable insertion site for foreign genes. Recombinant swinepox virus utilizing this insertion site is useful for expression of foreign antigen genes, as a vaccine against disease or as an expression vector to raise antibodies to the expressed foreign gene.

Example 30

Recombinant swinepox virus expressing *E. coli* β-galactosidase (lacZ) under the control of a synthetic early or synthetic late pox promoter.

Three recombinant swinepox viruses, S-SPV-056, S-SPV-057, and S-SPV-058 expressing *E. coli* β-galactosidase (lacZ) under the control of a synthetic pox promoter, LP1, LP2, and EP1, respectively, have been constructed.

S-SPV-056 was derived from S-SPV-001 (Kasza Strain) This was accomplished utilizing the homology vector 791-63.19 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). S-SPV-057 was derived from S-SPV-001 (Kasza Strain). This was accomplished utilizing the homology vector 791-63.41 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). S-SPV-058 was derived from S-SPV-001 (Kasza Strain). This was accomplished utilizing the homology vector 796-18.9 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBI- NANT SPV EXPRESSING β-galactosidase (BLUOGAL AND CPRG ASSAYS). The final result of red plaque purification were the recombinant viruses designated S-SPV-056, S-SPV-057 and S-SPV-058. The viruses were assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

Recombinant swinepox virus expresses a foreign gene such as *E. coli* β-galactosidase in a human cell line but does not replicate in the human cell line. To optimize expression of the foreign gene, S-SPV-056, S-SPV-057 and S-SPV-058 are used to compare optimal expression levels of *E. coli* β-galactosidase under the control of early or late synthetic pox viral promoters. The human cell lines in which expression of recombinant swinepox virus has been detected include, but are not limited to 143B (osteosarcoma), A431 (epidermoid carcinoma), A549 (lung carcinoma), Capan-1 (liver carcinoma), CF500 (foreskin fibroblasts), Chang Liver (liver), Detroit (down's foreskin fibroblasts), HEL-199 (embryonic lung), HeLa (cervical carcinoma), HEp-2 (epidermal larynx carcinoma), HISM (intestinal smooth muscle), HNK (neonatal kidney), MRC-5 (embryonic lung), NCI-H292 (pulmonary mucoepidermoid carcinoma), OVCAR-3 (ovarian carcinoma), RD (rhabdosarcoma), THP (monocyte leukemia), WIL2-NS (B lymphocyte line, non-secreting), WISH (amnion).

Example 31

S-SPV-051

S-SPV-051 is a swinepox virus that expresses at least two foreign genes. The gene for *E. coli* β-galactosidase (lacZ) and the gene for the bovine viral diarrhea virus glycoprotein 53 (g53) were inserted into the SPV 617-48.1 ORF (a unique NotI restriction site has replaced a unique AccI restriction site). The lacZ gene is under the control of the synthetic late promoter (LP1), and the BVDV g53 gene is under the control of the synthetic late/early promoter (LP2EP2).

S-SPV-051 was derived from S-SPV-001 (Kasza Strain). This was accomplished utilizing the homology vector 783-39.2 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 051. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-051 was assayed for expression of BVDV specific antigens using the BLACK PLAQUE SCREEN FOR FOREIGN GENE EXPRESSION IN RECOMBINANT SPV. A mouse monoclonal antibody to BVDV g53 was shown to react specifically with S-SPV-051 plaques and not with S-SPV-001 negative control plaques. All S-SPV-051 observed plaques reacted with the monoclonal antibody to BVDV g53 indicating that the virus was stably expressing the BVDV foreign gene. The assays described here were carried out in ESK-4 cells, indicating that ESK-4 cells would be a suitable substrate for the production of SPV recombinant vaccines.

To confirm the expression of the BVDV g53 gene product, cells were infected with S-SPV-051 and samples of infected cell lysates and culture supern atants were subjected to SDS polyacrylamide gel electrophoresis. The gel was blotted and analyzed using the WESTERN BLOTTING PROCEDURE. A mouse monoclonal antibody to BVDV g53 was used to detect expression of BVDV specific proteins. The cell lysate and supernatant from S-SPV-051 infected cells exhibited bands at 53 kd and higher indicating glycosylated and unglycosylated forms of the BVDV g53 protein.

S-SPV-051 is useful as a vaccine in cattle against BVDV infection and is useful for expression of BVDV glycoprotein 53.

Example 32

S-SPV-044:

S-SPV-044 is a swinepox virus that expresses at least two foreign genes. The gene for *E. coli* β-galactosidase (lacZ) and the gene for the infectious bursal disease virus (IBDV) polymerase protein were inserted into the 617-48.1 ORF (a unique NotI site has replaced a unique AccI restriction site). The lacZ gene is under the control of the synthetic late promoter (LP1), and the IBDV polymerase gene is under the control of the synthetic late/early promoter (LP2EP2).

S-SPV-044 was derived from S-SPV-001 (Kasza Strain) This was accomplished utilizing the homology vector 749-75.78 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-044. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-044 is useful for expression of IBDV polymerase protein. S-SPV-044 is useful in an in vitro approach to a recombinant IBDV attenuated vaccine. RNA strands from the attenuated IBDV strain are synthesized in a bacterial expression system using T3 or T7 promoters (pBlueScript plasmid; Stratagene, Inc.) to synthesize double stranded short and long segments of the IBDV genome. The IBDV double stranded RNA segments and S-SPV-044 are transfected into CEF cells. The swinepox virus expresses the IBDV polymerase but does not replicate in CEF cells. The IBDV polymerase produced from S-SPV-044 synthesizes infectious attenuated IBDV virus from the double stranded RNA genomic templates. The resulting attenuated IBDV virus is useful as a vaccine against infectious bursal disease in chickens.

Example 33

S-SPV-046:

S-SPV-046 is a swinepox virus that expresses at least two foreign genes. The gene for *E. coli* β-galactosidase (lacZ) and the gene for the feline immunodeficiency virus (FIV) gag protease (gag) were inserted into the 738-94.4 ORF (a 773 base pair deletion of the SPV 01L ORF; Deletion of nucleotides 1669 to 2452, SEQ ID NO: 189). The lacZ gene is under the control of the swinepox 01L promoter, and the FIV gag gen e is under the control of the synthetic late/early promoter (LP2EP2).

S-SPV-046 was derived from S-SPV-001 (Kasza Strain) This was accomplished utilizing the homology vector 761-

75.B18 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 046. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

To confirm the expression of the FIV gag gene product, cells were infected with S-SPV-046 and samples of infected cell lysates and culture supernatants were subjected to SDS polyacrylamide gel electrophoresis. The gel was blotted and analyzed using the WESTERN BLOTTING PROCEDURE. Feline anti-FIV (PPR strain) sera was used to detect expression of FIV specific proteins. The cell lysate and supernatant from S-SPV-046 infected cells exhibited bands at 26 kd and 17 kd which are the expected sizes of the processed form of the FIV gag protein. The recombinant swinepox virus expressed FIV gag protein is processed properly and secreted into the culture media.

S-SPV-048

S-SPV-048 is a swinepox virus that expresses at least two foreign genes. The gene for *E. coli* β-galactosidase (lacZ) and the gene for feline immunodeficiency virus (FIV) envelope (env) were inserted into the SPV 617 48.1 ORF (a unique NotI restriction site has replaced a unique AccI restriction site). The lacZ gene is under the control of the synthetic late promoter (LP1), and the FIV env gene is under the control of the synthetic late/early promoter (LP2EP2).

S-SPV-048 was derived from S-SPV-001 (Kasza Strain). This was accomplished utilizing the homology vector 781-84.C11 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 048. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-046 and S-SPV-048 are useful alone or in combination as a vaccine in cats against FIV infection and are useful for expression of the FIV env and gag proteins. A recombinant swinepox virus expressing both the FIV env and gag proteins is useful as a vaccine in cats against FIV infection.

Recombinant swinepox virus expressing human respiratory synctial virus F and G proteins is useful as a vaccine against the human disease.

Example 34

In Vitro Properties of Chicken IFN Expressed in Recombinant Pox viruses.

Growth properties of recombinant viruses in cell culture. Growth properties of recombinant S-SPV-042 were not effected in embryonic swine kidney cells (ESK-4) compared to wild-type swinpox virus.

Western blot analysis was performed on supernatants from cells infected with SPV/cIFN recombinant virus. Rabbit and mouse antisera were raised against cIFN from concentrated SPV/cIFN infected supernatants and pre-cleared against ESK-4 cells infected with wild-type SPV in preparation for western analysis. Rabbit and mouse anti-cIFN antisera were reacted with denatured proteins on nitrocellulose from recombinant SPV/cIFN and SPV wild type virus infected supernatants. A reactive band with an estimated molecular weight size range of 17–20 kilodaltons was present in the SPV/cIFN lanes, and absent in the SPV wild type control lanes.

Effect of cIFN Expressed in Supernatants from SPV/cIFN (S-SPV-042), FPV/cIFN, and FPV/cIFN/NDV Infected Cells on the Growth of Vesicular Stomatis Virus.

Virion cleared supernatants from SPV/cIFN, FPV/cIFN and FPV/cIFN/NDV infected cells were tested for the presence of viral inhibitory activity, results shown in Table 1. Briefly, CEF cells were incubated with serially diluted viral supernatants. Subsequently, 40,000 plaque forming units (pfu)/well of vesicular stomatitis virus (VSV) were added and 48 hours later, wells were scored for the presence of VSV cytopathic effect (CPE). Recombinant viral supernatants containing cIFN were shown to inhibit VSV induced CPE, whereas, control viral supernatants did not. VSV induced cytopathic effect could be reversed in the presence of rabbit anti-cIFN sera.

TABLE 1

| Recombinant Viral Supernatants | cIFN Activity (units/ml)[a] |
|---|---|
| SPV/IFN | 2,500 000 |
| SPV | <100 |
| FPV/IFN | 250,000 |
| FPV/cIFN/NDV | 250,000 |
| FPV | <100 |

[a]One unit of cIFN activity is defined as the dilution of pox virus supernatant at which 100% VSV CPE was inhibited.

Effect of cIFN Expressed from Supernatants of SPV/cIFN Infected Cells on Herpes Virus of Turkeys.

Supernatant containing recombinant cIFN from ESK-4 cells infected with SPV/cIFN virus, was tested for its ability to inhibit the growth of herpes virus of turkeys (HVT) in CEF cells, results shown in Table 2. Briefly, serially diluted supernatants were incubated with CEF cells, and then subsequently infected with 100 pfu/well of wild-type HVT. Plaques were counted in all wells after 48 hours. It was shown that 10–100 units of cIFN activity inhibited plaque formation of HVT(100 pfu/well). Supernatants from wild type SPV did not inhibit HVT plaque formation.

TABLE 2

| SPV/cIFN Supernatant (units/ml[a]) | Number of HVT plaques |
|---|---|
| 0 | 99 |
| 1000 | 0 |
| 100 | 0 |
| 10 | 45 |

[a]One unit of cIFN activity is defined as the dilution of pox virus supernatant at which 100% VSV CPE was inhibited.

Induction of NO by Chicken Macrophages after Treatment with cIFN Expressed in Supernatants from SPV/cIFN Infected Cells.

HD 11 cells or bone marrow adherent cells were incubated with 1000 unit/ml of cIFN from SPV/cIFN supernatants, lipopolysaccharide (LPS) (6 ng/ml) or with both cIFN and LPS, results shown in Table 3. After 24 hours, supernatant fluids were collected and nitrite levels were measured. These data demonstrate that cIFN expressed from SPV/cIFN supernatants has the ability to activate chicken macrophages in the presence of LPS.

TABLE 3

| Cell source | Nitrite (micro/mol) levels following stimulation with: | | |
|---|---|---|---|
| | LPS | SPV/cIFN | LPS + SPV/cIFN |
| HD11 | 10.76 | 6.4 | 35.29 |
| BMAC | 13.1 | 5.8 | 35.10 |

Conclusions:

1. Recombinant swinepox viruses express biologically active chicken interferon into the supernatants of infected cells, as measured by protection of CEF cells from VSV infection.

2. Chicken interferon expressed in supernatants from recombinant SPV/cIFN infected cells has been shown to protect CEF cells against infection with HVT in a dose dependent manner.

3. Chicken interferon expressed from SPV/cIFN acted synergistically with LPS to activate chicken macrophages as detected by nitric oxide induction.

4. The foregoing data indicate that recombinant swinepox viruses expressing chicken IFN may have beneficial applications as immune modulating agents in vitro, in vivo and in ovo.

Example 35

As an alternative to the construction of a IBD vaccine using a viral vectored delivery system and/or subunit approaches, IBD virus RNA is directly manipulated re-constructing the virus using full length RNA derived from cDNA clones representing both the large (segment A) and small (segment B) double-stranded RNA subunits. Generation of IBD virus is this manner offers several advantages over the first two approaches. First, if IBD virus is re-generated using RNA templates, one is able to manipulate the cloned cDNA copies of the viral genome prior to transcription (generation of RNA). Using this approach, it is possible to either attenuate a virulent IBD strain or replace the VP2 variable region of the attenuated vaccine backbone with that of virulent strains. In doing so, the present invention provides protection against the virulent IBDV strain while providing the safety and efficacy of the vaccine strain. Furthermore, using this approach, the present invention constructs and tests temperature sensitive IBD viruses generated using the RNA polymerase derived from the related birnavirus infectious pancreatic necrosis virus (IPNV) and the polyprotein derived from IBDV. The IPNV polymerase has optimum activity at a temperature lower than that of IBDV. If the IPNV polymerase recognizes the regulatory signals present on IBDV, the hybrid virus is expected to be attenuated at the elevated temperature present in chickens. Alternatively, it is possible to construct and test IBD viruses generated using the RNA polymerase derived from IBDV serotype 2 viruse and the polyprotein derived from IBDV serotype 1 virus.

cDNA clones representing the complete genome of IBDV (double stranded RNA segments A and B) is constructed, initially using the BursaVac vaccine strain (Sterwin Labs). Once cDNA clones representing full length copies of segment A and B are constructed, template RNA is prepared. Since IBDV exists as a bisegmented double-stranded RNA virus, both the sense and anti-sense RNA strands of each segment are produced using the pBlueScript plasmid; Stratagene, Inc.). These vectors utilize the highly specific phage promoters SP6 or T7 to produce substrate amounts of RNA in vitro. A unique restriction endonuclease site is engineered into the 3' PCR primer to linearize the DNA for the generation of run-off transcripts during transcription.

The purified RNA transcripts (4 strands) are transfected into chick embryo fibroblasts (CEF) cells to determine whether the RNA is infectious. If IBD virus is generated, as determined by black plaque assays using IBDV specific Mabs, no further manipulations are required and engineering of the vaccine strain can commence. The advantage of this method is that engineered IBD viruses generated in this manner will be pure and require little/no purification, greatly decreasing the time required to generate new vaccines. If negative results are obtained using the purified RNA's, functional viral RNA polymerase is required by use of a helper virus. Birnaviruses replicate their nucleic acid by a strand displacement (semi-conservative) mechanism, with the RNA polymerase binding to the ends of the double-stranded RNA molecules forming circularized ring structures (Muller & Nitschke, Virology 159, 174–177, 1987). RNA polymerase open reading frame of about 878 amino acids in swinepox virus is expressed and this recombinant is virus (S-SPV-044) is used to provide functional IBDV RNA polymerase in trans. Swinpox virus expressed immunologically recognizable foreign antigens in avian cells (CEF cells), where there are no signs of productive replication of the viral vector. In the present invention the IBDV polymerase protein is expressed in the same cells as the transfected RNA using the swinepox vector without contaminating the cells with SPV replication.

With the demonstration that IBD virus is generated in vitro using genomic RNA, an improved live attenuated virus vaccines against infectious bursal disease is developed. Using recombinant DNA technology along with the newly defined system of generating IBD virus, specific deletions within the viral genome, facilitating the construction of attenuated viruses are made. Using this technology, the region of IBDV responsible for virulence and generate attenuated, immunogenic IBDV vaccines are identified. The present invention provides a virulent IBD strain or replacement of the VP2 variable region of the attenuated vaccine backbone with that of a virulent strain, thus protecting against the virulent strain while providing the safety and efficacy of the vaccine strain.

Example 36

Effects of Rabbit Anti-chicken Interferon (cIFN) Antibody on the Growth of Herpes Virus of Turkeys.

Supernatants from SPV/cIFN (SPV 042) infected ESK-4 cells were harvested 48 hours after infection and then concentrated 5–10 times, by Centricon 10 columns (Amicon). One ml of concentrated supernatant was injected into a rabbit 3 times, at 3 week intervals, and then bled. This rabbit antisera was then used in culture to study the effect of interferon on the growth of HVT. It was shown that anti-cIFN reverses the block to HVT (1:200) and VSV(1:80) growth induced by the addition of cIFN in plaque assays. Furthermore, it was shown that the addition of anti-cIFN (1:100) in the media of CEFs transiently transfected with sub-plaqueing levels of HVT viral DNA, enhances the formation of HVT plaques (200 plaques/well). CEFs transfected with HVT DNA in the absence of anti-cIFN did not yield plaques.

HVT is highly susceptible to interferon produced from CEFs and that when cIFN is blocked, HVT growth is enhanced.

Applications include: (1) Use antibody to cIFN as an additive to increase HVT titers in vaccine stocks; (2) Use antibody to cIFN as an additive to facilitate the formation of new recombinant HVT viruses via cosmid reconstructions.

S-SPV-063

S-SPV-063 is a swinepox virus that expresses at least two foreign genes. The gene for E. coli β-galactosidase (lacZ) and the gene for swine influenza virus (SIV) NP (H1N1) were inserted into the SPV 617 48.1 ORF (a unique NotI restriction site has replaced a unique AccI restriction site). The lacZ gene is under the control of the synthetic late promoter (LP1), and the SIV NP gene is under the control of the synthetic late/early promoter (LP2EP2).

S-SPV-063 was derived from S-SPV-001 (Kasza Strain). This was accomplished utilizing the homology vector 807-41.3, (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 063. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-063 was assayed for expression of SIV specific antigens using the BLACK PLAQUE SCREEN FOR FOREIGN GENE EXPRESSION IN RECOMBINANT SPV. Polyclonal swine anti-SIV serum or a polyclonal goat anti-NP serum was shown to react specifically with S-SPV-063 plaques and not with S-SPV-001 negative control plaques. All S-SPV-063 observed plaques reacted with the swine anti-SIV serum or goat anti-NP serum indicating that the virus was stably expressing the SIV foreign gene. The assays described here were carried out in ESK-4 cells, indicating that ESK-4 cells would be a suitable substrate for the production of SPV recombinant vaccines.

To confirm the expression of the SIV NP gene products, cells were infected with S-SPV-063 and samples of infected cell lysates and culture supernatants were subjected to SDS polyacrylamide gel electrophoresis, The gel was blotted and analyzed using the WESTERN BLOTTING PROCEDURE. A polyclonal swine anti-SIV serum or a polyclonal goat anti-NP serum was used to detect expression of SIV specific proteins. The cell lysate and supernatant from S-SPV-063 infected cells exhibited bands corresponding to 56 kd, which is the expected size of the SIV NP protein.

S-SPV-063 is useful as a vaccine in swine against SIV infection and is useful for expression of SIV NP. S-SPV-063 is useful as a vaccine in combination with S-SPV-066 which expresses NA and S-SPV-065 which expresses SIV HA.

S-SPV-064

S-SPV-064 is a swinepox virus that expresses one foreign gene. The gene for E. coli β-glucuronidase (uidA) was inserted into the unique XhoI restriction site within the 6.9 kb SPV HindIII J genomic fragment. The uidA gene is under the control of the synthetic late/early promoter (LP2EP2). The HindIII J genomic fragment contains part of the A50R ORF (aa 227 to 552). The unique XhoI site is not within the A50R ORF. The XhoI site is 25 kb from the 3' end of the swinepox virus genome (62).

S-SPV-064 was derived from S-SPV-001 (Kasza Strain). This was accomplished utilizing the homology vector 807-42.28 and virus S-SPV-001 in the HOMOLOGOUS RECOMBINATION PROCEDURE FOR GENERATING RECOMBINANT SPV. Homology vector 807-42.28 was generated by insertion of a NotI fragment containing the LP2EP2 promoter uidA gene cassette from plasmid 551-47.23 (see Materials and Methods) into a NotI site (unique XhoI site converted to NotI by a DNA linker) in the SPV 6.9 kb HindIII J fragment. The transfection stock was screened by the SCREEN FOR RECOMBINANT HERPESVIRUS EXPRESSING ENZYMATIC MARKER GENES. The final result of blue plaque purification is the recombinant virus designated S-SPV-064. This virus is assayed for β-glucuronidase expression, purity, and insert stability by multiple passages monitored by the blue plaque assay as described in Materials and Methods. After the initial three rounds of purification, plaques observed are blue indicating that the virus is pure, stable, and expressing the foreign gene.

S-SPV-064 is purified and expresses the foreign gene, E. coli uidA, indicating that the XhoI site within the 6.9 kb HindIII J fragment is a site non-essential for virus growth and a stable insertion site for foreign genes. Recombinant swinepox virus utilizing this insertion site is useful for expression of foreign antigen genes, as a vaccine against disease or as an expression vector to raise antibodies to the expressed foreign gene.

S-SPV-065

S-SPV-065 is a swinepox virus that expresses at least two foreign genes. The gene for E. coli β-galactosidase (lacZ) and the gene for swine influenza virus (SIV) HA (H1N1) were inserted into the SPV 617 48.1 ORF (a unique NotI restriction site has replaced a unique AccI restriction site). The lacZ gene is under the control of the synthetic late promoter (LP1), and the SIV HA gene is under the control of the synthetic late/early promoter (LP2EP2).

S-SPV-065 was derived from S-SPV-001 (Kasza Strain). This was accomplished utilizing the homology vector 807-84.8 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 065. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene. S-SPV-065 was assayed for expression of SIV specific antigens using the BLACK PLAQUE SCREEN FOR FOREIGN GENE EXPRESSION IN RECOMBINANT SPV. Polyclonal swine anti-SIV serum or a Polyclonal goat anti-HA serum was shown to react specifically with S-SPV-065 plaques and not with S-SPV-001 negative control plaques. All S-SPV-065 observed plaques reacted with the swine anti-SIV serum or the SIV foreign gene. The assays described here were carried out in ESK-4 cells, indicating that ESK-4 cells would be a suitable substrate for the production of SPV recombinant vaccines.

To confirm the expression of the SIV NP gene products, cells were infected with S-SPV-065 and samples of infected cell lysates and culture supernatants were subjected to SDS polyacrylamide gel electrophoresis. The gel was blotted and analyzed using the WESTERN BLOTTING PROCEDURE. A Polyclonal swine anti-SIV serum or a Polyclonal goat anti-HA serum was used to detect expression SIV specific proteins. The cell lysate and supernatant from S-SPV-065 infected cells exhibited bands corresponding to 64 kd, which is the expected size of the SIV-HA protein.

S-SPV-065 is useful as a vaccine in swine against SIV infection and is useful for expression of SIV HA. S-SPV-065 is useful as a vaccine in combination with S-SPV-066 which expresses NA and S-SPV-063 which expresses SIV NP.

S-SPV-066

S-SPV-066 is a swinepox virus that expresses at least two foreign genes. The gene for *E. coli* β-galactosidase (lacZ) and the gene for swine influenza virus (SIV) NA (H1N1) were inserted into the SPV 617 48.1 ORF (a unique NotI restriction site has replaced a unique AccI restriction site). The lacZ gene is under the control of the synthetic late promoter (LP1), and the SIV NA gene is under the control of the synthetic late/early promoter (LP2EP2).

S-SPV-066 was derived from S-SPV-001 (Kasza Strain). This was accomplished utilizing the homology vector 807-84.35 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 066. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

To confirm the expression of the SIV NA gene products, cells were infected with S-SPV-066 and samples of infected cell lysates and culture supernatants were subjected to SDS polyacrylamide gel electrophoresis. The gel was blotted and analyzed using the WESTERN BLOTTING PROCEDURE. A Polyclonal swine anti-SIV serum or a Polyclonal goat anti-NA serum was used to detect expression of SIV specific proteins. The cell lysate and supernatant from S-SPV-066 infected cells exhibited bands corresponding to 64 kd, which is the expected size of the SIV HA protein.

S-SPV-066 is useful as a vaccine in swine against SIV infection and is useful for expression of SIV-NA. S-SPV-066 is useful as a vaccine in combination with S-SPV-065 which expresses HA and S-SPV-063 which expresses SIV NP.

S-SPV-071

S-SPV-071 is a swinepox virus that expresses at least four foreign genes. The gene for *E. coli* β-galactosidase (lacZ) and the genes for swine influenza virus (SIV) HA (H1N1) and NA (H1N1) were inserted into the SPV 617 48.1 ORF (a unique NotI restriction site has replaced a unique AccI restriction site). The lacZ gene is under the control of the synthetic late promoter (LP1), and the SIV HA, and NA genes are under the control of the synthetic late/early promoter (LP2EP2).

S-SPV-071 was derived from S-SPV-001 (Kasza Strain). This was accomplished utilizing the homology vector 817-86.35 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 071. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-071 was assayed for expression of SIV specific antigens using the BLACK PLAQUE SCREEN FOR FOREIGN GENE EXPRESSION IN RECOMBINANT SPV. Polyclonal goat anti-HA serum was shown to react specifically with S-SPV-071 plaques and not with S-SPV-001 negative control plaques. All S-SPV-071 observed plaques reacted with the goat anti-HA serum indicating that the virus was stably expressing the SIV foreign gene. The assays described here were carried out in ESK-4 cells, indicating that ESK-4 cells would be a suitable substrate for the production of SPV recombinant vaccines.

To confirm the expression of the SIV HA and NA gene products, cells were infected with S-SPV-071 and samples of infected cell lysates and culture supernatants were subjected to SDS polyacrylamide gel electrophoresis. The gel was blotted and analyzed using the WESTERN BLOTTING PROCEDURE. A Polyclonal swine anti-SIV serum or a Polyclonal goat anti-HA serum was used to detect expression of SIV specific proteins. The cell lysate and supernatant from S-SPV-071 infected cells exhibited bands corresponding to 64 kd and 52 kd, which is the expected size of the SIV HA and NA protein.

S-SPV-071 is useful as a vaccine in swine against SIV infection and is useful for expression of SIV-HA and NA. S-SPV-071 is useful as a vaccine in combination with S-SPV-063 which expresses SIV NP.

S-SPV-074

S-SPV-074 is a swinepox virus that expresses at least four foreign genes. The gene for *E. coli* β-glucuronidase (uidA) and the genes for swine influenza virus (SIV) HA (H1N1) and NA (H1N1) were inserted into the SPV 617 48.1 ORF (a unique NotI restriction site has replaced a unique AccI restriction site). The uidA gene is under the control of the synthetic late/early promoter (LP2EP2), and the SIV HA and NA genes are under the control of the synthetic late/early promoter (LP2EP2).

S-SPV-074 was derived from S-SPV-001 (Kasza Strain) This was accomplished utilizing the homology vector 817.14.2 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 074. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-074 was assayed for expression of SIV specific antigens using the BLACK PLAQUE SCREEN FOR FOREIGN GENE EXPRESSION IN RECOMBINANT SPV. Polyclonal swine anti-SIV serum was shown to react specifically with S-SPV-074 plaques and not with S-SPV-001 negative control plaques. All S-SPV-074 observed plaques reacted with the goat anti-HA serum indicating that the virus was stably expressing the SIV foreign gene. The assays described here were carried out in ESK-4 cells, indicating that ESK-4 cells would be a suitable substrate for the production of SPV recombinant vaccines.

S-SPV-074 is useful as a vaccine in a swine against SIV infection and is useful for expression of SIV HA and NA. S-SPV-074 is useful as a vaccine in combination with S-SPV-063 which expresses SIV NP. S-SPV-063, −065, −066, −071, and −074, are useful alone or in combination as a vaccine in swine against swine influenza infection and are useful for expression of the SIV NP, HA, and NA proteins.

S-SPV-068:

S-SPV-068 is a swinepox virus that expresses at least two foreign genes. The gene for E. coli β-galactosidase (lacZ) and the gene for chicken macrophage migration inhibitory factor (cMIF) were inserted into the 738-94.4 ORF (a 773 base pair deletion of the SPV 01L ORF; Deletion of nucleotides 1679 to 2452, SEQ ID NO: 189). The lacZ gene is under the control of the swinepox 01L promoter, and the cMIF gene is under the control of the synthetic late/early promoter (LP2EP2).

S-SPV-068 was derived from S-SPV-001 (Kasza Strain) This was accomplished utilizing the homology vector 802-95.A1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-068. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

To confirm the expression of the cMIF gene product, cells were infected with S-SPV-068 and samples of infected cell lysates were subjected to SDS polyacrylamide gel electrophoresis. The gel was blotted and analyzed using the WESTERN BLOTTING PROCEDURE. A polyclonal goat anti-human cMIF antibody was used to detect expression of cMIF specific proteins. The cell lysate from S-SPV-068 infected cells exhibited a band corresponding to approximately 15 kd, which is the expected size of the cMIF protein.

S-SPV-068 is useful as a vaccine in chickens to inhibit migration of macrophages and to stimulate an immune response against infection by avian pathogens. S-SPV-068 is useful for expression of cMIF.

HOMOLOGY VECTOR 802-95.A1.

The plasmid 802-95.A1 was constructed for the purpose of inserting foreign DNA into SPV. It incorporates an E. coli β-galactosidase (lac Z) marker gene and an chicken macrophage migration inhibitory factor (cMIF) gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a swinepox virus 01L gene promoter and the cMIF gene is under the control of the late/early promoter (LP2EP2). The LP2EP2 cMIF gene cassette was inserted into a BamHI site of homology vector 752-22.1. Homology vector 802-95.A1 was constructed utilizing standard recombinant DNA techniques (22, 30), by joining restriction fragments from the following sources with the synthetic DNA sequences. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5' GAAGCATGC CCGTTCTTATCAATAGTTTAGTCGAAAATA-3' (SEQ ID NO: 73) and 5'-CATAAGATCTGGCATTGTGTT ATTATACTAACAAAAATAAG-3' (SEQ ID NO: 74) to produce an 855 base pair fragment with SphI and BglII ends. Fragment 2 is a 3002 base pair BamHI to PvuII fragment derived from plasmid pJF751 (49) containing the E. coli lacz gene. Fragment 3 is an approximately 363 base pair BglII fragment coding for the cMIF gene (63) derived by reverse transcription and polymerase chain reaction (PCR) (Sambrook, et al., 1989) of RNA ISOLATED FROM CONCANAVALIN A STIMULATED CHICKEN SPLEEN CELLS. The antisense primer used for reverse transcription and PCR was 5' TCGAAGATCTTCTCATGCAAAGGT GGAACCGTTC-3' (6/95.28; SEQ ID NO: 59). The sense primer used for PCR was 5' TCGAAGATCTCA TGCCTATGTTCACCATCCACAC-3' (6/95.27; SEQ ID NO: 60). The DNA fragment contains the open reading frame of 121 amino acids of the chicken macrophage migration inhibitory factor protein. The native methionine codon of cMIF is preceded by amino acid codons for met-asn-ser-asp-lys. Fragment 4 is an approximately 1113 base pair subfragment of the SPV HindIII fragment M synthesized by polymerase chain reaction using DNA primers 5'-CCGTAGTCGACAAAGATCGACTTATTAATA TGTATGGGATT-3' (SEQ ID NO: 75) (and 5' GCCT-GAAGCTTCTAGTACAGTATTTACGACTTTTGAAAT-3' (SEQ ID NO: 76) to produce an 1113 base pair fragment with SalI and HindIII ends.

S-SPV-069

S-SPV-069 is a swinepox virus that expresses at least two foreign genes. The gene for E. coli β-galactosidase (lacZ) and the gene for human respiratory syncytial virus (HRSV) fusion (F) protein were inserted into the SPV 738-94.4 ORF (a 773 base pair deletion of the SPV 01ORF; Deletion of nucleotides 1669 to 2452, SEQ ID NO: 189). The lacZ gene is under the control of the swinepox $P_{OIL}$ promoter and the HRSV F gene is under the control of the synthetic late/early promoter (LP2EP2). S-SPV-069 was derived from S-SPV-001 (Kasza Strain). This was accomplished utilizing the homology vector 810-29.A2 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 069. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-069 was assayed for expression of HRSV specific antigens using the BLACK PLAQUE SCREEN FOR FOREIGN GENE EXPRESSION IN RECOMBINANT SPV. Monoclonal antibody 621 (Biodesign, Inc.) against HRSV F was shown to react specifically with S-SPV-069 plaques and not with S-SPV-001 negative control plaques. All S-SPV-069 observed plaques reacted with the monoclonal antibody 621 indicating that the virus was stably expressing the PRV foreign gene. The assays described here were carried out in ESK-4 cells, indicating that ESK-4 cells would be a suitable substrate for the production of SPV recombinant vaccines.

S-SPV-078

S-SPV-078 is a swinepox virus that expresses at least two foreign genes. The gene for E. coli β-galactosidase (lacZ) and the gene for human respiratory syncytial virus (HRSV)

attachment (G) protein were inserted into the SPV 617 48.1 ORF (a unique NotI restriction site has replaced a unique AccI restriction site). The lacZ gene is under the control of the synthetic late/early promoter (LP2EP2), and the HRSV G gene is under the control of the synthetic late/early promoter (LP2EP2). S-SPV-078 was derived from S-SPV-001 (Kasza Strain) This was accomplished utilizing the homology vector 822-52G.7 (see Materials and Methods) and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING β-galactosidase (BLUOGAL AND CPRG ASSAYS). The final result of red plaque purification is the recombinant virus designated S-SPV-078. This virus is assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene.

S-SPV-069 and S-SPV-078 are useful individually or in combination as a vaccine in swine against human respiratory syncytial virus infection and are useful for expression of HRSV F and G genes.

HOMOLOGY VECTOR 810-29.A2.

The plasmid 810-29.A2 was constructed for the purpose of inserting foreign DNA into SPV. It incorporates an E. coli β-galactosidase (lac Z) marker gene and a human respiratory syncytial virus (HRSV) fusion (F) gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a swinepox virus 01L gene promoter and the HRSV F gene is under the control of the late/early promoter (LP2EP2). The homology vector was constructed utilizing standard recombinant DNA techniques (22, 30), by joining restriction fragments from the following sources with the synthetic DNA sequences. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5' GAAGCATGCCCGT TCTTATCAATAGTTTAGTCGAAAATA-3' (SEQ ID NO: 73) and 5'-CATAAGATCTGGCATTGTGTTATTATACTA ACAAAAATAAG-3' (SEQ ID NO: 74) to produce an 855 base pair fragment with SphI and BglII ends. Fragment 2 is a 3002 base pair BamHI to PvuII fragment derived from plasmid pJF751 (49) containing the E. coli lacZ gene. Fragment 3 is an approximately 1728 base pair EcoRI restriction fragment synthesized by reverse transcriptase and polymerase chain reaction (PCR) (15, 42) using RNA from the HRSV Strain A2 (ATCC VR-1302). The primer (5' GCC<u>GAATTC</u>GCTAATCCTCAAAAGCAAATGCAAT-3'; 4/95.23) (SEQ ID NO: 87) synthesizes from the 5' end of the HRSV F gene, introduces an EcoRI site at the 5' end of the gene and an ATG start codon. The primer (5'-GGT <u>GAATTC</u>TTTATTTAGTTACTAAATGCAATATTATTT-3'; 4/95.24) (SEQ ID NO: 88) synthesizes from the 3' end of the HRSV F gene and was used for reverse transcription and polymerase chain reaction. The PCR product was digested with EcoRI to yield a fragment 1728 base pairs in length corresponding to the HRSV F gene. Fragment 4 is an approximately 1113 base pair subfragment of the SPV HindIII fragment M synthesized by polymerase chain reaction using DNA primers 5'-CCGTAGTCGACAAAGATC GACTTATTAATATGTATGGGATT-3' (SEQ ID NO: 75) and 5' GCCTGAAGCTTCTAGTACAGTATTTACGAC TTTTGAAAT-3' (SEQ ID NO: 76) to produce an 1113 base pair fragment with SalI and HindIII ends.

HOMOLOGY VECTOR 822-52G.7.

The plasmid 822-52G.7 was constructed for the purpose of inserting foreign DNA into SPV. It incorporates an E. coli β-galactosidase (lacZ) marker gene and the human respiratory syncytial virus (HRSV) attachment (G) gene flanked by SPV DNA. Upstream of the foreign genes is an approximately 1484 base pair fragment of SPV DNA. Downstream of the foreign genes is an approximately 2149 base pair fragment of SPV DNA. When this plasmid is used according to the HOMOLOGOUS RECOMBINATION PROCEDURE FOR GENERATING RECOMBINANT SPV a virus containing DNA coding for the foreign genes will result. Note that the β-galactosidase (lacZ) marker gene is under the control of a synthetic late/early pox promoter (LP2EP2) and the HRSV G gene is under the control of a synthetic late/early pox promoter (LP2EP2). It was constructed utilizing standard recombinant DNA techniques (22 and 30), by joining restriction fragments from the following sources. The plasmid vector was derived from an approximately 2972 base pair HindIII to BamHI restriction fragment of pSP65 (Promega). Fragment 1 is an approximately 1484 base pair AccI to BglII restriction sub-fragment of the SPV HindIII fragment M (23). Fragment 2 is an approximately 3006 base pair BamHI to PvuII restriction fragment of plasmid pJF751 (11). Fragment 3 is an approximately 899 base pair EcoRI restriction fragment synthesized by reverse transcriptase and polymerase chain reaction (PCR) (15, 42) using RNA from the HRSV Strain A2 (ATCC VR-1302). The primer (5' GCC<u>GAATTC</u>CAAAAACAAGGACCA ACGCAC-3'; 4/95.25) (SEQ ID NO: 89) synthesizes from the 5' end of the HRSV F gene, introduces an EcoRI site at the 5' end of the gene and an ATG start codon. The primer (5'-GCCGAATTCACTACTGGCGTGGTGTGTTG-3'; 4/95.26) (SEQ ID NO: 90) synthesizes from the 3' end of the HRSV G gene and was used for reverse transcription and polymerase chain reaction. The PCR product was digested with EcoRI to yield a fragment 899 base pairs in length corresponding to the HRSV G gene. Fragment 4 is an approximately 2149 base pair HindIII to AccI restriction sub-fragment of the SPV HindIII restriction fragment M (23).

HOMOLOGY VECTOR 807-41.3.

The plasmid 807-41.3 was used to insert foreign DNA into SPV. It incorporates an E. coli β-galactosidase (lacZ) marker gene and the swine influenza virus (SIV) nucleoprotein (NP) gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the B galactosidase (lacZ) marker gene is under the control of a synthetic late pox promoter (LP1) and the SIV NP gene is under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 2972 base pair Hindiii to Bam HI restriction fragment of pSP64 (Promega). Fragment 1 is an approximately 1484 base Bglii to AccI restriction sub-fragment of the SPV HindIII fragment M(23). Fragment 2 is an approximately 1501 base pair EcoRI to EcoRI fragment of the SIV NP gene synthesized by reverse transcription (RT) and polymerase chain reaction (PCR) (15,42) using RNA from the SIV H1N1 strain (NVSL). The primer (5'CATGAATTC TCAAGGCACCAAACGATCATATGAAC-3'; 6/95.13) (SEQ ID NO: 91) synthesizes from the 5' end of the SIV NP gene and introduces an EcoRI site at the 5'-ATTTGAATTCAATTGTCATACTCCTCTCGCATTGT CT-3'; 6/95.14) (SEQ ID NO: 92) synthesizes from the 3' end of the SIV NP gene, introduces an EcoRI site st the 3' end of the gene, and was used for reverse transcription and polymerase chain reaction. The PCR product was digested with EcoRI to yield a fragment 1501 base pairs in length corresponding to the SIV NP gene. Fragment 3 is approximately 3010 base pair BamHI to PuvII restriction fragment of plasmid pJF751 (11). Fragment 4 is approximately 2149 base pair AccI to HindIII restriction sub-fragment of the SPV Hind III restriction fragment M (23).

HOMOLOGY VECTOR 807-84.8.

The plasmid 807-84.8 was used to insert foreign DNA into SPV. It incorporates an E. coli B-galactosidase (lacZ) marker gene and the swine influenza virus (SIV) hemmagglutinin (HA) gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the B-galactosidase (lacZ) marker gene is under the control of a synthetic late pox promoter (LP1) and the SIV HA gene is under the control of a synthetic late/early promoter (LP2EP2). The homology vector was constructed utilizing standard recombinant DNA techniques (22 and 30), by joining restricting fragments from the following sources with the appropriate synthetic DNA sequences. The plasmid vector was derived from an approximately 2972 base pair HindIII to BamHI resriction fragment of pSP64 (Promega). Fragment 1 is an approximately 1484 base pair BglII to AccI restriction sub-fragment fo the SPV HindIII fragment M(23). Fragment 2 is an approximately 1721 base pair BamHI to BamHI gragment of the SIV HA gene synthesized by reverse transcription (RT) and polymerase chain reaction (PCR) (15,42) using RNA from the SIV H1N1 strain (NVSL). The primer (5'CCGAGGATCCGGCAATACTATTAGTCTTGC TATGTACAT-3'; 6/95.5) (SEQ ID NO: 93) synthesizes from the 5' end of the SIV HA gene and introduces an BamHI site at the 5; end of the gene. The primer (5'-CTCTGGATCCTAATTTAAATACATATTCTGCACT GTS-3'; 6/95.6) (SEQ ID NO: 94) synthesizes from the 3' end of the SIV HA gene, introduces a Bam HI site at the 3' end of the gene, and was used for the reverse transcription and polymerase chain reaction. The PCR product was idgested with EcoRI to yield a fragment 1721 base pairs in length corresponding to the SIV HA gene. Fragment 3 is an approximately 3010 base pair BamHI to PvuII restriction fragment of plasmid pJF751 (11). Fragment 4 is an approximately 2149 base pair AccI to fragmeny M (23).

HOMOLOGY VECTOR 807-84.35.

The plasmid 807-84.35 was used to insert foreign DNA into SPV. It incorporates an E. coli B-galactosidase (lacZ) marker gene and. the swine influenza virus (SIV) neuraminidase (NA) gene flanked by SPV DNA. When this PROCEDURE FOR GENERATING RECOMBINANT SPV a virus containing DNA coding for the foreign genes results. Note that the B-galactosidase (lacZ) marker gene is under the control of a synthetic late pox promoter (LP1) and the SIV NA gene isunder the control of a synthetic late/early pox promoter (LP2EP2). The homology vector was constructed utilizing standard recombinant DNA techniques (22 and 30) by joining restricting fragments from the following sources with the appropriate synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII fragment M (23). Fragment 2 is an approximately 1414 base pair EcoRI to BglII fragment of the SIV NA gene synthesized by reverse transcription (RT) and polymerase chain reaction)(PCR) (15,42) using RNA from the SIV H1N1 strain (NVSL). The primer (5' AATGAATTCAAATCAAAAAATAATAACCAT TGGGTCAAT-3'; 6.95.12) (SEQ ID NO: 95) synthesizes from the 3' end of the SIV NA gene, introducer an EcoRI site at the 5' end of the gene. The primer (5'-GGAAGA TCTACTTGTCAATGGTGAATGGCAGATCAG-3'; 6/95.13) (SEQ ID NO: 96) synthesizes from the 3' end of the SIV NA gene, introduces an BglII site at the 3' end of the gene, and was used for reverse transcription and polymerase chain reaction. The PCR product was digested with EcoRI to yield a fragment 1414 base pairs in length corresponding to the SIV NA gene. Fragment 3 is an approximately 3010 base pair BamHI to PvuII restriction fragment of plasmid pJF751 (11). Fragment 4 is an approximately 2149 base pair AccI to HindIII restriction sub-fragment of the SPV HindIII restriction fragment M (23).

HOMOLOGY VECTOR 807-86.35.

The plasmid 807-86.35 was used to insert foreign DNA into SPV. It incorporates an *E. coli* B-galactosidase (lacZ) marker gene and the swine influenza virus (SIV) HEMAGGLUTININ (HA) and neuraminidae (NA) gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the B-galactosidase (lacZ) marker gene is under the control of a synthetic late pox promoter (LP1) and the SIV NA and HA genes are each under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 2972 base pair HindIII to BamHI restriction fragment of pSP64 (Promega). Fragment 1 is approximately 1484 base pair BglII to AccI restriction sub-fragment of the SPV HindIII fragment M (23). Fragment 2 is an approximately 1721 base pair BamHI to BamHI fragment fo the SIV HA gene synthesized by reverse transcription (RT) and polymerase chain reaction (PCR) (15,42) using RNA from the SIV H1N1 strain (NVSL). The primer (5'-CCGAGGATCCGGCAATAC TATTAGTCTTGCTATGTACAT-3'; 6/95.5 (SEQ ID NO: 93) synthesizes from the 5' end of the SIV HA gene and introduces an Bam HI site at the 5' end of the gene. The primer (5'-CTCTGGGATCCTAATTTTAAATACATA TTCTGCACTGTA-3'; 6/95.6) (SEQ ID NO: 97) synthesizes from the 3' end of the SIV HA gene, introduces an BamHI site at the 3' end of the gene, introduces an BamHI site at the 3' end of the gene, and was used for reverse transcription and polymerase chain reaction. The PCR product was digested with EcoRI to yield a fragment 1721 base pairs in length corresponding to the SIV HA gene. Fragment 3 is an approximately 1414 base pair EcoRI to BglII fragment of the SIV NA gene synthesized by reverse transcription (RT) and polymerase chain reaction (PCR) (15,42) using RNA from the SIV H1N1strain (NVSL). The primer (5' AATGAATTCAAATCAAAAAATAATAACCATTGG GTCAAT-3'; 6/95.12) (SEQ ID NO: 95) synthesizes from the 5' end of the SIV NA gene and introduces an EcoRI site at the 5' end of the gene. The primer (5'-GGAAGATCTACTTGTCAATGGTGAATGGCAGAT CAG-3'; 6/95.13) (SEQ ID NO: 96) synthesizes from the 3' end of the SIV NA gene, introduces an BglII site at the 3' end of the gene, and was used for reverse transcription and polymerase chain reaction. The PCR product was digested with EcoRI to yield a fragment 1414 base pairs in length corresponding to the SIV NA gene. Fragment 4 is an approximately 2149 base pair AccI to HindIII restriction sub-fragment of the SPV HindIII restriction fragment M (23).

HOMOLOGY VECTOR 817-14.2.

The plasmid 817-14.2 was used to insert foreign DNA into SPV. It incorporates an *E. coli* B-galactosidase (lacZ) marker gene and the swine influenza virus (SIV) HEMAG-GLUTININ (HA) and neuraminidae (NA) gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the B-galactosidase (uida) marker gene is under the control of a synthetic late/early pox promoter (LP2EP2) and the SIV NA and HA genes are each under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 2972 base pair HindIII to BamHI restriction fragment of pSP64 (Promega). Fragment 1 is an approximately 1484 base pair BglII to AccI restriction subfragment to the SPV HindIII fragment M (23). Fragment 2 is an approximately 1721 base pair BamHI to BamHI fragment of the SIV HA gene synthesized by reverse transcription (RT) and polymerase chain reaction (PCR) (15,42) using RNA from the SIV H1N1 strain (NVSL). The primer (5' CCG AGGATCCGGCAATACTATTAGTCTTGCTATGTACAT-3'; 6/95.5) (SEQ ID NO: 93) synthesizes from the 5' end of the SIV HA gene and introduces an BamHI site at the 5' end of the gene. The primer (5'-CTCTGGGATCCTAATTTTAA ATACATATTCTGCACTGTA-3'; 6/95.6) (SEQ ID NO: 97) synthesizes from the 3' end of the SIV HA gene, introduces an BamHI site at the 3' end of the gene, and was used for reverse transcription and polymerase chain reaction. The PCR product was digested with EcoRI to yield a fragment 1721 base pairs in length corresponding to the SIV HA gene. Fragment 3 is an approximately 1414 base pair EcoRI to BglII fragment of the SIV HA gene synthesized by reverse transcription (RT) and polymerase chain reaction (PCR) (15,42) using RNA for the SIV H1N1 strain (NVSL). The primer (5' AATGAATTCAAATCAAAAAATAATAAC ATTGGGTCAAT-3'; 6/95.12) (SEQ ID NO: 98) synthesizes from the 5' end of the SIV NA gene, introduces an EcoRI site at the 5' end of the gene. The primer (5'-GGAAGA TCTACTTGTCAATGGTGAATGGCAGATCAG-3'; 6/95.13) (SEQ ID NO: 96) synthesizes from the 3' end of the SIV NA gene, introduces an BglII site at the 3' end of the gene, and was used for reverse transcription and polymerase chain reaction. The PCR product was digested with EcoRI to yield a fragment 1414 base pairs in length corresponding to the SIV NA gene. Fragment 4 is an approximately 1823 base pair NotI restriction fragment of plasmid pRAJ260 (Clonetech). Fragment 5 is an approximately 2149 base pair AccI to HindIII restriction sub-fragment of the SPV HindIII restriction fragment M (23).

PRRS HOMOLOGY VECTORS CONTAINING SINGLE OR MULTIPLE

PRRS GENES (ORF2, ORF3, ORF4, ORF5, ORF6 or ORF7: The PRRS homology vector is constructed for the purpose of inserting foreign DNA into SPV. It incorporates an *E. coli* B-galactosidase (lacZ) marker gene and a porcine reproductive and respiratory syndrome virus (PRRS) ORF2, ORF3, ORF4, ORF5, ORF6 or ORF7 gene flanked by SPV DNA. Upstream of the foreign gene is an approximately 855 base pair fragment of SPV DNA. Downstream of the foreign genes is an approximately 1113 base pair frament of SPV DNA. When the plasmid is used according to the HOMOLOGOUS RECOMBINATION PROCEDURE FOR GENERATING RECOMBINANT SPV, a virus containing DNA coding for the foreign genes will result. Note that the B-galactosidase (lacZ) marker gene is under the control of a swinepox virus 01L gene promoter and the PRRS gene is under the control of the late/early promoter (LP2EP2). The homology vector was constructed utilizing standard recombinant DNA sequences. The plasmid vector was derived from an approximately 2519 base pair HINDIII to SphI restriction fragment of pSP65 (Promega). Fragment 1 is an approximately 855 base pair sub-fragment of the SPV polymerase chain reaction using DNA primers 5' GAA GCATGCCCGTTCTTATCAATAGTTTAGTCGAAAATA-3' (SEQ ID NO: 73) and 5'-CATAAGATCTGGCATTGTGT TAT TATACT AACAAAAATAAG-3' (SEQ ID NO: 74) to produce an 855 base pair fragment with SphI and BglII ends. Fragment 2 is a 3002 base pair BamHI to PvuII fragment derived from plasmid pJF751 (49) containing the *E. coli* lacZ gene. Fragment 3 is an EcoRI to BamHI restriction fragment synthesized by reverse transcription and polymerase chain reaction (PCR) using genomic RNA from a U.S. Isolate of PRRS obtained from the NVSL (Reference strain). Each homology vector contains one or multiple of the PRRS virus ORF2 through 7. To synthesize PRRS ORF2, the primer (5' AATGAATTCGAAATGGGTCC ATGCAAAGCCTTTTTG-3'; 1/96.15) (SEQ ID NO: 99) synthesizes from the 5' end of the PRRS ORF2 gene, introduces an EcoRI site at the 5' end of the gene. The primer (5'-CAAGGATCCCACACCGTGTAATTCACTGTGAGT TCG-3'; 1/96.16) (SEQ ID NO: 45) is used for reverse transcription and PCR and synthesizes from the 3' end of the PRRS ORF2 gene. The PCR product was digested with EcoRI and BamHI to yield a fragment 771 base pairs in length corresponding to the PRRS ORF2 gene. To synthesize PRRS ORF3, the primer (5' TTCGAATTCGGC TAATAGCTGTACATTCCTCCATATTT-3'; 1/96.7) (SEQ ID NO: 48) synthesizes from the 5' end of the PRRS ORF3 gene, introduces an EcoRI site at the 5' end fo the gene. The primer (5'-GGGGATCCTATCGCCGTACGGCAC TGAGGG-3'; 1/96.8) (SEQ ID NO: 49) is used for reverse transcription and PCR and synthesizes from the 3' end of the PRRS ORF3 gene. To synthesize PRRS ORF4, the primer (5' CCGAATTCGGCTGCGTCCCTTCTTTTCCTCATGG-3'; 1/96.11) (SEQ ID NO: 50) synthesizes from the 5' end of the PRRS ORF4 gene, introduces an EcoRI site at the 5'-CTGGATCCTTCAAATTGCCAACAGAATGGCAA AAAGAC-3'; 1/96.12) (SEQ ID NO: 51) is used for reverse transcription and PCR and synthesizes from the 3' end of the PRRS ORF4 gene. The PCR product was digested with EcoRI adn BamHI to yield a fragment 537 base pairs in length corresponding to the PRRS ORF4 gene. To synthesize PRRS ORF5, the primer (5' TTGAATTCGTTGGAG AAATGCTTGACCGCGGGC-3'; 1/96.13) (SEQ ID NO: 52) synthesizes from the 5' end of the PRRS ORF5 gene, introduces an EcoRI site at the 5' end of the gene. The primer (5'-GAAGGATCCTAAGGACGACCCCATTGTTCCG CTG-3'; 1/96.14) (SEQ ID NO: 53) is used for reverse transcription and PCR and synthesizes from the 3' end of the PRRS ORF5 gene. The PCR product was digested with EcoRI and BamHI to yield a fragment 603 base pairs in length corresponding to the PRRS ORF5 gene. To synthesize PRRS ORF6, the primer (5' CGGGAATTCGGG GTCGTCCTTAGATGACTTCTGC-3'; 1/96.17) (SEQ ID NO: 42) synthesizes from the 5' end of the PRRS ORF6 gene, introduces an EcoRI site at the 5' end of hte gene. The primer (5'GCGGATCCTTGTTATGTGGCATATTTGAC AAGGTTTAC-3'; 1/96.18) (SEQ ID NO: 43) is used for reverse transcription and PCR and synthesize from the 3' end of the PRRS ORF6 gene. The PCR product was digested with EcoRI and BamHI to yield a fragment 525 base pairs in length corresponding to the PRRS ORF6 gene. To synthesize PRRS ORF7, the primer (5' GTCGAATTC GCCAAATAACAACGGCAAGCAGCAGAAG-3'; 1/96.19) (SEQ ID NO: 46) synthesizes from the 3' end of the PRRS ORF7 gene. Fragment 4 is an approximately 1113 base pair subfragment of the SPV HindIII fragment M synthesized by polymerase chain reaction using DNA primers 5'-CCGTAGTCGACAAAGATCGACTTATTAATATG TATGGGATT-3' (SEQ ID NO: 75) and 5' GCCTGAAGCTTCTAGTACAGTATTTACGACTTTTGAAT-3' (SEQ ID NO: 100) to produce and 1113 base pair fragment with SalI and HindIII ends.

Recombinant Swinepox Virus Expressing Pseudorabies Genes

S-SPV-076 is a swinepox virus that expresses at least three foreign genes. The gene for *E. coli* B-galactosidase (lacZ) and the genes for pseudorabies virus (PRV) gD and gI were inserted into the SPV 617 48.1 ORF (a unique NotI restriction site has replaced a unique AccI restriction site). The lacZ gene is under the control of the synthetic late promoter (LP1), and the PRV gD and gI genes are under the control of the synthetic late/early promoter (LP2EP2).

S-SPV-077 is a swinepox virus that expresses at least two foreign genes. The gene for *E. coli* B-galactosidase (lacZ) and the gene for pseudorabies virus (PRV) gI were inserted into the SPV 617 48.1 ORF (a unique NotI restriction site has replaced a unique AccI restriction site). The lacZ gene is under the control of the synthetic late promoter (LP1), and the PRV gI gene is under the control of the synthetic late/early promoter (LP2EP2).

S-SPV-079 is a swinepox virus that expresses at least two foreign genes. The gene for *E. coli* B-galactosidase (lacZ) and the gene for pseudorabies virus (PRV) gI were inserted into the SPV 617 48.1 ORF (a unique NotI restriction site has replaced a unique AccI restriction site). The lacZ gene is under the control of the synthetic late promoter (LP1), and the PRV gB gene is under the control of the synthetic late/early promoter (LP2EP2).

S-SPV-076, S-SPV-077, S-SPV-079 have been tested by BLACK PLAQUE ASSAY and WESTERN BLOT for expression of the PRV glycoproteins. S-SPV-076, S-SPV-077, and S-SPV-079 were derived from S-SPV-001 (Kasza Strain). This was accomplished utilizing a homology vector and virus S-SPV-001 in the HOMOLOGOUS RECOMBINATION PROCEDURE FOR GENERATING RECOMBINANT SPV. The transfection stock were screened by the SCREEN FOR RECOMBINANT SPV EXPRESSING B-galactosidase (BLUOGAL AND CPRG ASSAYS). The final result of red plaque purification was the recombinant virus designated S-SPV-076, S-SPV-077, and S-SPV-079. The viruses were assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-076, S-SPV-077, and S-SPV-079 are useful as a vaccine in swine against PRV infection and is useful for expression of PRV gD, gI or gB. S-SPV-071 is useful as a vaccine in combination with a recombinant swinepox virus which expresses PRV gC, such as S-SPV-011, S-SPV-012 or S-SPV-013.

| | |
|---|---|
| 143B | carcinoma* osteosarcoma* |
| A431 | epidermoid carcinoma* |
| A549 | lung carcinoma* |
| Capan-1 | liver carcinoma* |
| CF500 | foreskin fibroblasts |
| Chang Liver | liver |
| Detroit | Downs' foreskin fibroblasts |
| HEL-199 | embryonic lung |
| HeLa | cervical carcinoma* |
| Hep-2 | epidermal larynx carcinoma |
| HISM | intestinal smooth muscle |
| HNK | neonatal kidney |
| MRC-5 | embryonic lung |
| NCI-H292 | pulmonary mucoepidermoid |
| OVCAR-3 | ovarian carcinoma* |
| RD | rhabdosarcoma* |
| THP | monocyte (leukemia)* |
| WIL2-NS | B lymphocyte line, non-secreting |
| WISH | amnion |
| PBL | peripheral blood lymphocytes |

Example 38

Recombinant Swinepox Virus Expressing PRRS Genes ORF2, ORF3, ORF4, ORF5 and ORF6

S-SPV-080 is a swinepox virus that expresses at least two foreign genes. The gene for *E. coli* B-galactosidase (lacZ) and the gene for porcine reproductive and respiratory syndrome virus (PRRS) ORF2 were inserted into the SPV 738-94.4 ORF (a 773 base pair deletion of the SPV 01L ORF; Deletion of nucleotides 1669 to 2452, (SEQ ID NO: 189). The lacZ gene is under the control of the swinepox $P_{OIL}$ promoter and the PRRS ORF2 gene is under the control of the synthetic late/early promoter (LP2EP2).

S-SPV-081 is a swinepox virus that expresses at least two foreign genes. The gene for *E. coli* B-galactosidase (lacZ) and the gene for porcine reproductive and respiratory syndrome virus (PRRS) ORF3 were inserted into the SPV 738-94.4 ORF (a 773 base pair deletion of the SPV 01L ORF; Deletion of nucleotides 1669 to 2452, (SEQ ID NO: 189). The lacZ gene is under the control of the swinepox $P_{OIL}$ promoter and the PRRS ORF3 gene is under the control of the synthetic late/early promoter (LP2EP2).

S-SPV-082 is a swinepox virus that expresses at least two foreign genes. The gene for *E. coli* B-galactosidase (lacZ) and the gene for porcine reproductive and respiratory syndrome virus (PRRS) ORF4 were inserted into the SPV 738-94.4 ORF (a 773 base pair deletion of the SPV 01L ORF; Deletion of nucleotides 1669 to 2452, (SEQ ID NO: 189). The lacZ gene is under the control of the swinepox $P_{OIL}$ promoter and the PRRS ORF4 gene is under the control of the synthetic late/early promoter (LP2EP2).

S-SPV-083 is a swinepox virus that expresses at least two foreign genes. The gene for *E. coli* B-galactosidase (lacZ) and the gene for porcine reproductive and respiratory syndrome virus (PRRS) ORF5 were inserted into the SPV 738-94.4 ORF (a 773 base pair deletion of the SPV 01L ORF; Deletion of nucleotides 1669 to 2452, (SEQ ID NO:

189). The lacZ gene is under the control of the swinepox $P_{OIL}$ promoter and the PRRS ORF5 gene is under the control of the synthetic late/early promoter (LP2EP2).

S-SPV-084 is a swinepox virus that expresses at least two foreign genes. The gene for *E. coli* B-galactosidase (lacZ) and the gene for porcine reproductive and respiratory syndrome virus (PRRS) ORF6 were inserted into the SPV 738-94.4 ORF (a 773 base pair deletion of the SPV 01L ORF; Deletion of nucleotides 1669 to 2452, (SEQ ID NO: 189). The lacZ gene is under the control of the swinepox $P_{OIL}$ promoter and the PRRS ORF6 gene is under the control of the synthetic late/early promoter (LP2EP2).

S-SPV-085 is a swinepox virus that expresses at least two foreign genes. The gene for *E. coli* B-galactosidase (lacZ) and the gene for porcine reproductive and respiratory syndrome virus (PRRS) ORF7 were inserted into the SPV 738-94.4 ORF (a 773 base pair deletion of the SPV 01ORF; Deletion of nucleotides 1669 to 2452, (SEQ ID NO: 189). The lacZ gene is under the control of the swinepox $P_{OIL}$ promoter and the PRRS ORF7 gene is under the control of the synthetic late/early promoter (LP2EP2).

S-SPV-080, S-SPV-081, S-SPV-082, S-SPV-083, S-SPV-084, S-SPV-085 were derived from S-SPV-001 (Kasza Strain). This was accomplished utilizing the homology vector Material and Methods (PRRS HOMOLOGY VECTORS) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-galactosidase (BLUOGAL AND CPRG ASSAYS). The final result of red plaque purification was the recombinant virus designated S-SPV-080, S-SPV-081, S-SPV-082, S-SPV-083, S-SPV-084, S-SPV-085. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene. S-SPV-080, S-SPV-081, S-SPV-082, S-SPV-083, S-SPV-084, S-SPV-085 are useful individually or in combination as vaccines in swine against PRRS infection and are useful for expression of PRRS ORF2, ORF3, ORF4, ORF5, ORF6 and ORF7.

Example 39

The following experiment was performed to determine the ability of swinepox virus to infect human cells in culture and express a foreign DNA as lacZ.

S-SPV-003 was absorbed to the human cell lines listed in the Table below at an MOI=0.1 for 2 to 3 hours. Cells were rinsed three times with PBS, growth media was added, and cells were incubated at 37° C. for four days. Cells were harvested and a lysate prepared in 200 microliters of PBS by freeze/thaw three times. Cell debris was pelleted, and 10 microliters of supernatant was assayed for -galactosidase activity by ONPG assay at 37° C. for 1½ hours. The table shows the results of infection of various human cell lines with S-SPV-003 and the relative levels of cytopathic effect and expression of lacZ.

The results show that various human cell lines vary in the ability to take up S-SPV-003 and express lacZ. CPE was minimal in all cases and did not result in viral replication. One exception A549 cells which did show some rounding of cells and lifting off the plate in one instance, and another instance of ten-fold increase in titer during passage suggesting limited viral replication. Several cell lines how significant lacZ activity with no cytopathetic effect.

Different pox promoters express lacZ from recombinant swinepox virus in a number of human cell lines. Six different swinepox viruses were constructed which expressed lacZ from EP1, LP1, LP2, EP1LP2, LP2EP2, or the SPV P01L promoter. Viruses were each used to infect A549, Chang liver, or 143B cells at 0.1 moi, and cells were rinsed between 2 and 3 hours later and then incubated for 4 days at 37° C. Each cell line maintained a different hierarchy of promoter activity, which was reproducible in following experiments.

For example, the EP1, LP2EP2, and P01L promoters gave the most expression in 143B cells, while the LP2 was strongest in Chang liver cells, and the EP1LP2 in A549. In the Chang liver and A549 cells, expression from the P01L promoter was poorest, whereas in 143B, espression from LP2 was poorest. Therefore, different human cell lines utilize pox promoters in dissimilar ways. This may reflect how far the swinepox virus can proceed along the replication pathway in different cell lines.

These early and late promoters exhibited lower or higher lacZ activity depending on the human cell type infected by the recombinant swinepox virus. By choosing different promoters for different target tissues, one is able to regulate the amounts of foreign gene product delivered by the swinepox virus to target tissues.

Recombinant swinepox virus is useful as a vaccine for human infectious disease and to deliver therapeutic agents to humans. Recombinant swinepox virus is useful as a vaccine against viral or bacterial infection in humans, and as a therapeutic for cancer or genetic disease to deliver antibodies, tumor antigens, cell surface ligands and receptors, immune modulating molecules such as cytokines.

Example 40

S-SPV-003 Expression of lacZ in human cell lines
Measurement of cytopathic effect and lacZ expression

| Cell Type | Cytopathetic Effect* | LacZ Expression** |
|---|---|---|
| A431 epidermoid carcinoma* | — | — |
| A549 lung carcinoma* | ++ | +++ |
| Capan-1 liver carcinoma* | — | — |
| CF500 foreskin fibroblasts | + | + |
| Chang Liver | + | +++ |
| Detroit Down's foreskin fibroblasts | +/− | — |
| HEL-199 embryonic lung | +/− | +++ |
| HEp-2 epidermal larynx carcinoma* | — | — |
| HISM intestinal smooth muscle | + | + |
| HNK neonatal kidney | — | ++ |
| MRC-5 embryonic lung | +/− | + |
| NCI-H292 pulmonary mucoepidermoid carcinoma* | — | +++ |
| OVCAR-3 ovarian carcinoma* | — | +++ |
| RD rhabdosarcoma* | — | + |
| THP monocyte (leukemia)* | — | + |
| WIL2-NS | — | — |

S-SPV-003 Expression of lacZ in human cell lines
Measurement of cytopathic effect and lacZ expression

| Cell Type | Cytopathetic Effect* | LacZ Expression** |
|---|---|---|
| B lymphocyte line, non-secreting WISH | +/– | ++ |
| amnion HeLa | — | +++ |
| PBL peripheral blood lymphocytes | — | — |

*When human cells are infected with SPV, a cytopathic effect is sometimes seen. In most cell lines, this cytopathic effec is evidenced by a chang in the appearance of the cells, with cells becoming thinner and more ragged along the edges; cells look stressed. This phenomenon was assessed as follows:
– indicates no difference between infected & uninfected cells;
+/– indicates that the monolayer is visibly different from uninfected, though most cells appear normal;
+ indicates that the monolayer is obviously affected, with most cells looking stressed. It should be noted that in certain cell lines (HeLa, CF500, 143B), in which titers were obtained after serial passage, there was no evidence for replication of SPV, with one exception. A549 was given a ++ for cytopathic effect in one instance, when cells appeared to round up and come off the plate during infection, though this observation was not repeated. A549 also showed evidence in another case of a ten-fold increase in titer during passage, suggesting that it might support limited viral replication.
**β-galactosidase activity in $A_{260}$ units per cell lysate from 1/20 of a 35 mm dish:
— No activity
+ 0.2–0.9 $A_{260}$ unit
++ 0.9–1,6 $A_{260}$ unit
+++ greater than 1.6 $A_{260}$ units.

Example 41
BOVINE CONSTRUCTS AND VACCINES
S-SPV-112

S-SPV-112 is a swinepox virus that expresses three foreign genes. The gene for E. coli β-galactosidase (lacZ) and the gene for bovine respiratory syncytial virus (BRSV) attachment (G) were inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The gene for BRSV fusion (F) was inserted into the unique PstI restriction site (PstI linkers inserted into a unique AccI site in the SPV 01L open reading frame). The lacZ gene is under the control of the synthetic late promoter (LP1), the BRSV G and F genes are each under the control of the synthetic late/early promoter (LP2EP2).

S-SPV-112 was derived from S-SPV-001 (Kasza Strain) This was accomplished utilizing the homology vector 848-02 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 112. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-112 is useful as a vaccine in bovine against disease caused by bovine respiratory syncytial virus. The BRSV antigens are key to raising a protective immune response in the animal. The recombinant viruses are useful alone or in combination as an effective vaccine. The swinepox virus is useful for cloning other subtypes of BRSV to protect against rapidly evolving variants in this disease. S-SPV-112 is also useful as an expression vector for expressing BRSV antigens. Such BRSV antigens are useful to identify antibodies directed against the wild-type BRSV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 848-02.

The plasmid 848-02 was constructed for the purpose of inserting foreign DNA into SPV. It incorporates an E. coli β-galactosidase (lacZ) marker gene, the bovine respiratory syncytial virus (BRSV) attachment (G) and fusion (F) genes flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the BRSV F and G genes are under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1722 base pair Bam HI fragment generated by PCR which contains the coding sequence of the BRSV F gene. Fragment 3 is an approximately 48 base pair AccI to NdeI subfragment of the SPV HindIII M fragment. Fragment 4 is an approximately 771 base pair Bam HI fragment generated by PCR which contains the coding sequence for the BRSV G gene. The BRSV F and G genes were synthesized by PCR as described in the CLONING OF BOVINE RESPIRATORY SYNCYTIAL VIRUS FUSION, NUCLEOCAPSID AND GLYCOPROTEIN GENES. Fragment 5 is an approximately 3010 base pair BamHI to PvuII restriction fragment of plasmid pJF751 (11). Fragment 6 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 6 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 6.

Recombinant Swinepox Virus Expressing BRSV F and G Fusion Protein
S-SPV-130:

S-SPV-130 is a swinepox virus that expresses three foreign genes. The gene E. coli β-galactosidase (lacZ) is inserted into the unique PstI restriction site (PstI linkers inserted into a unique AccI site in the SPV 01L open reading frame). The genes for bovine respiratory syncytial virus (BRSV) attachment (G) and BRSV fusion (F) are inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the BRSV F/G fusion gene is under the control of the synthetic late/early promoter (LP2EP2). The BRSV F/G fusion gene comprises approximately 1560 nucleotides of the F gene (520 amino acids including the amino terminus) fused in frame to approximately 580 nucleotides of the G gene (193 amino acids including the carboxy terminus).

S-SPV-130 is derived from S-SPV-001 (Kasza Strain). This is accomplished utilizing the HOMOLOGY VECTOR 807-75.41 (see Materials and Methods) and virus S-SPV-001 in the. HOMOLOGOUS RECOMBINATION PROCEDURE FOR GENERATING RECOMBINANT SPV. The transfection stock is screened by the SCREEN FOR RECOMBINANT SPV EXPRESSING β-galactosidase (BLUOGAL AND CPRG ASSAYS). The recombinant virus is isolated by red plaque purification. This virus is assayed for β-galactosidase expression, purity, and insert stability by multiple passages monitored by the blue plaque assay as described in Materials and Methods. After the initial three rounds of purification, all plaques observed are blue indicating that the virus was pure, stable, and expressing the foreign gene.

S-SPV-130 is useful as a vaccine in bovine against disease caused by bovine respiratory syncytial virus. The BRSV F/G fusion protein is particularly effective and key to raising a protective immune response in the animal. The BRSV F/G fusion protein contains the intact amino terminus of the F protein and the intact carboxy terminus of the G protein which includes the known immunogenic region of each protein. The BRSV F/G fusion protein provides an improved immune response compared to expressing the BRSV F and G proteins separately or expressing isolated epitopes of the BRSV F and G proteins. The swinepox virus is useful for cloning other subtypes of BRSV to protect against rapidly evolving variants in this disease. Recombinant swinepox virus is also useful as an expression vector for expressing BRSV antigens. Such BRSV antigens are useful to identify antibodies directed against the wild-type BRSV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 807-75.41.

The homology vector 807-75.41 was constructed for the purpose of inserting foreign DNA into SPV. It incorporates an *E. coli* β-galactosidase (lacZ) marker gene, a fusion protein of the bovine respiratory syncytial virus (BRSV) attachment (G) and fusion (F) genes flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the BRSV F/G fusion gene is under the control of a synthetic late/early pox promoter (LP2EP2). It was constructed utilizing standard recombinant DNA techniques (22, 30), by joining restriction fragments from the following sources with the synthetic DNA sequences. The plasmid vector is derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 1560 base pair Bam HI fragment generated by PCR which contains the coding sequence of the BRSV F gene. The F gene coding region from the BRSV strain 375 (VR-1339) was cloned using the following primers: 5'-GC GGATCCGGCGCGCCGGATTTTCCTACATCTACACT-3' (5/96.26; SEQ ID NO 12) for cDNA priming and combined with 5'-CTAAAATTGAATTGTAAT-3' (1/95.19; SEQ ID NO 13:) for PCR. The DNA encodes 520 amino acids at the amino terminus of the BRSV F protein. Fragment 5 is an approximately 580 base pair AscI fragment generated by PCR which contains the coding sequence for the BRSV G gene. The G gene coding region from the BRSV strain 375 (VR-1339) was cloned using the following primers: 5' TT GGCGCGCCCTAGATCTGTGTAGTTGATTGATTTG-3' (5/96.28; SEQ ID NO 14:) for cDNA priming and combined with 5' TACGGCGCGCCGGGAAATGCTAAAGCC CCACCCACA-3' (5/96.27; SEQ ID NO 15:) for PCR. The DNA product encodes 193 amino acids (including a translation stop codon) of the carboxy terminus of the BRSV G protein. The BRSV F and G coding sequences are fused in the correct translational reading frame. Fragment 6 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 6 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 6.

S-SPV-099

S-SPV-099 is a swinepox virus that expresses two foreign genes. The gene *E. coli* β-galactosidase (lacZ) is inserted into the unique PstI restriction site (PstI linkers inserted into a unique AccI site in the SPV 01L open reading frame). The gene for bovine viral diarrhea virus type 2 (BVDV-2) (strain 890) glycoprotein 53 (gp53) was inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the BVDV-2 gp53 gene is under the control of the synthetic late/early promoter (LP2EP2).

S-SPV-099 was derived from S-SPV-001 (Kasza Strain) This was accomplished utilizing the homology vector 815-73.16A (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 099. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-099 is useful as a vaccine in bovine against disease caused by bovine viral diarrhea virus. The BVDV-2 gp53 antigen is key to raising a protective immune response in the animal. The recombinant virus is useful alone or in combination as an effective vaccine. S-SPV-099 is also useful as an expression vector for expressing BVDV antigens. Such BVDV antigens are useful to identify antibodies directed against the wild-type BVDV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 815-73.16A.

The homology vector 815-73.16A was constructed for the purpose of inserting foreign DNA into SPV. It incorporates an E. coli β-galactosidase (lacZ) marker gene and bovine viral diarrhea virus type 2 (BVDV-2) glycoprotein 53 (gp53) gene flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), theBVDV gp53 gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 1113 base pair EcoRI/BamHI fragment generated by PCR which contains the coding sequence of the BVDV gp53 gene. BVDV gp53 gene coding region was cloned by reverse transcription and PCR using RNA from BVDV type 2 (Strain 890) as an RNA template for reverse transcription and the following PCR using primers: 5'-TTCGGATCCTGCTCAGACAGTATTGTGTATGTT ATCAAGAGC-3' (2/96.32; SEQ ID NO 16:) at the 3' end of the BVDV gp53 gene for reverse transcription and PCR combined with 5'-CCATGAATTCCTTCCCTGAATGC AAGGAGGGCTTC-3' (2/96.15; SEQ ID NO 17:) at the 5' end of the BVDV gp53 gene for PCR. The DNA encodes approximately 373 amino acids of the BVDV gp53 protein. Fragment 5 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 5 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 5.

S-SPV-109

S-SPV-109 is a swinepox virus that expresses two foreign genes. The gene E. coli β-galactosidase (lacZ) is inserted into the unique PstI restriction site (PstI linkers inserted into a unique AccI site in the SPV 01L open reading frame). The gene for infectious bovine rhinotracheitis virus (IBRV) glycoprotein D (gD) was inserted into the unique HindIII restriction site (HindIII linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the IBRV gD gene is under the control of the synthetic late/early promoter (LP2EP2).

S-SPV-109 was derived from S-SPV-001 (Kasza Strain) This was accomplished utilizing the homology vector 835-57.5 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 109. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-109 is useful as a vaccine in bovine against disease caused for infectious bovine rhinotracheitis virus. The IBRV gD antigen is key to raising a protective immune response in the animal. The recombinant viruses are useful alone or in combination as an effective vaccine. S-SPV-109 is also useful as an expression vector for expressing IBRV antigens. Such IBRV antigens are useful to identify antibodies directed against the wild-type IBRV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 835-57.5.

The homology vector 835-57.5 was constructed for the purpose of inserting foreign DNA into SPV. It incorporates an E. coli β-galactosidase (lacZ) marker gene and the infectious bovine rhinotracheitis virus (IBRV) glycoprotein D (gD) gene flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the IBRV gD gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 1320 base pair EcoRI/BamHI fragment generated by PCR which contains the coding sequence of the IBRV gD gene. The IBRV gD gene coding region was cloned by PCR using the HindIII K fragment of the IBRV Cooper strain (pSY 524) as DNA template and the following PCR primers: 5'-CGGGATCCTCACCCGGGCAGCGC GCTGTA-3' (4/96.12; SEQ ID NO 18:) at the 3' end of the IBRV gD gene and combined with 5'-CGGAATTCA CAAGGGCCGACATTGGCC-3' (4/96.11; SEQ ID NO 19:) at the 5' end of the IBRV gD gene. The DNA encodes approximately 440 amino acids of the IBRV gD protein. Fragment 5 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 5 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 5.

S-SPV-110

S-SPV-110 is a swinepox virus that expresses two foreign genes. The gene *E. coli* β-galactosidase (lacZ) is inserted into the unique PstI restriction site (PstI linkers inserted into a unique AccI site in the SPV 01L open reading frame). The gene for infectious bovine rhinotracheitis virus (IBRV) glycoprotein I (gI) was inserted into the unique HindIII restriction site (HindIII linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the IBRV gI gene is under the control of the synthetic late/early promoter (LP2EP2).

S-SPV-110 was derived from S-SPV-001 (Kasza Strain) This was accomplished utilizing the homology vector 835-58.5 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 110. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-110 is useful as a vaccine in bovine against disease caused for infectious bovine rhinotracheitis virus. The IBRV gI antigen is key to raising a protective immune response in the animal. The recombinant viruses are useful alone or in combination as an effective vaccine. S-SPV-110 is also useful as an expression vector for expressing IBRV antigens. Such IBRV antigens are useful to identify antibodies directed against the wild-type IBRV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 835-58.5.

The homology vector 835-58.5 was constructed for the purpose of inserting foreign DNA into SPV. It incorporates an *E. coli* β-galactosidase (lacZ) marker gene and the infectious bovine rhinotracheitis virus (IBRV) glycoprotein I (gI) gene flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the IBRV gI gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 1140 base pair EcoRI/BamHI fragment generated by PCR which contains the coding sequence of the IBRV gI gene. The IBRV gI gene coding region was cloned by PCR using the HindIII K fragment of the IBRV Cooper strain (pSY 524) as DNA template and the following PCR primers: 5'-ATCGGGATCCCGTTATTCTTCGCTGA TGGTGG-3' (4/96.18; SEQ ID NO 20) at the 3' end of the IBRV gI gene and combined with 5'-ATCG GAATTCGCGGTGCCTG TTGCTCTGGATG-3' (4/96.17; SEQ ID NO 21) at the 5' end of the IBRV gI gene. The DNA encodes approximately 380 amino acids of the IBRV gI protein. Fragment 5 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 5 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 5.

S-SPV-111

S-SPV-111 is a swinepox virus that expresses two foreign genes. The gene *E. coli* β-galactosidase (lacZ) is inserted into the unique PstI restriction site (PstI linkers inserted into a unique AccI site in the SPV 01L open reading frame). The gene for infectious bovine rhinotracheitis virus (IBRV) glycoprotein B (gB) was inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the IBRV gB gene is under the control of the synthetic late/early promoter (LP2EP2). The direction of transcription of the IBRV gB gene is opposite the direction of transcription of the lacZ gene and the SPV 01L gene.

S-SPV-111 was derived from S-SPV-001 (Kasza Strain). This was accomplished utilizing the homology vector 847-15.1C (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 111. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-111 is useful as a vaccine in bovine against disease caused for infectious bovine rhinotracheitis virus. The IBRV gB antigen is key to raising a protective immune response in the animal. The recombinant viruses are useful alone or in combination as an effective vaccine. S-SPV-111 is also useful as an expression vector for expressing IBRV antigens. Such IBRV antigens are useful to identify antibodies directed against the wild-type IBRV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 847-15.1C.

The homology vector 847-15.1C was constructed for the purpose of inserting foreign DNA into SPV. It incorporates an *E. coli* β-galactosidase (lacZ) marker gene and the infectious bovine rhinotracheitis virus (IBRV) glycoprotein B (gB) gene flanked by SPV DNA. The direction of transcription of the IBRV gB gene is opposite the direction of transcription of the lacZ gene and the SPV 01L gene. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the IBRV gB gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 2800 base pair EcoRI/BamHI fragment generated by PCR which contains the coding sequence of the IBRV gB gene. The IBRV gB gene coding region was cloned by PCR using the HindIII A fragment of the IBRV Cooper strain (pSY 830-71) as DNA template and the following PCR primers: 5'-CTTCGGATCCTCATGCCCCCCCGACGTCG GCC ATC-3' (4/96.15; SEQ ID NO 22) at the 3' end of the IBRV gB gene and combined with 5'-TCATGAATTCGGCCGCTCGCGGCGGTG C T G A A CGC-3' (4/96.10; SEQ ID NO 23) at the 5' end of the IBRV gB gene. The DNA encodes approximately 932 amino acids of the IBRV gB protein. Fragment 5 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 5 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 5.

S-SPV-113

S-SPV-113 is a swinepox virus that expresses two foreign genes. The gene *E. coli* β-galactosidase (lacZ) is inserted into the unique PstI restriction site (PstI linkers inserted into a unique AccI site in the SPV 01L open reading frame). The gene for infectious bovine rhinotracheitis virus (IBRV) glycoprotein C (gC) was inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the IBRV gC gene is under the control of the synthetic late/early promoter (LP2EP2).

S-SPV-113 was derived from S-SPV-001 (Kasza Strain) This was accomplished utilizing the homology vector 848-08 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 113. This virus was assayed for β-galactosidase expression, purity, and insert stability. by multiple passages monitored by the blue plaque assay as described in Materials and Methods. After the initial three rounds of purification, all plaques observed were blue indicating that the virus was pure, stable, and expressing the foreign gene.

S-SPV-113 is useful as a vaccine in bovine against disease caused by infectious bovine rhinotracheitis virus. The IBRV gC antigen is key to raising a protective immune response in the animal. The recombinant viruses are useful alone or in combination as an effective vaccine. S-SPV-113 is also useful as an expression vector for expressing IBRV antigens. Such IBRV antigens are useful to identify antibodies directed against the wild-type IBRV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 848-08.

The homology vector 848-08 was constructed for the purpose of inserting foreign DNA into SPV. It incorporates an *E. coli* β-galactosidase (lacZ) marker gene and the infectious bovine rhinotracheitis virus (IBRV) glycoprotein C (gC) gene flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the IBRV gC gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 1563 base pair EcoRI/BamHI fragment generated by PCR which contains the coding sequence of the IBRV gC gene. The IBRV gC gene coding region was cloned by PCR using the HindIII I fragment of the IBRV Cooper strain (pSY 830-71) as DNA template and the following PCR primers: 5'-CGGGATCCC TAGGGCGCG GAGCCGAGGGC-3' (4/96.14; SEQ ID NO 24) at the 3' end of the IBRV gC gene and combined with 5'-CGGAATTCAGGCCCGCTGGGGCGAGC G T G G-3' (4/96.13; SEQ ID NO 25) at the 5' end of the IBRV gC gene. The DNA encodes approximately 521 amino acids of the IBRV gC protein. Fragment 5 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 5 were converted to unique NotI sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 5.

S-SPV-115

S-SPV-115 is a swinepox virus that expresses two foreign genes. The gene E. coli β-galactosidase (lacZ) is inserted into the unique PstI restriction site (PstI linkers inserted into a unique AccI site in the SPV 01L open reading frame). The gene for infectious bovine rhinotracheitis virus (IBRV) glycoprotein B (gB) was inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the IBRV gB gene is under the control of the synthetic late/early promoter (LP2EP2). The direction of transcription of the IBRV gB gene is the same as the direction of transcription of the lacZ gene and the SPV 01L gene.

S-SPV-115 was derived from S-SPV-001 (Kasza Strain). This was accomplished utilizing the homology vector 847-19.59 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 115. This virus was assayed for β-galactosidase expression, purity, and insert stability by multiple passages monitored by the blue laque assay as described in Materials and Methods. fter the initial three rounds of purification, all plaques observed were blue indicating that the virus was pure, stable, and expressing the foreign gene.

S-SPV-115 is useful as a vaccine in bovine against disease caused for infectious bovine rhinotracheitis virus. The IBRV gB antigen is key to raising a protective immune response in the animal. The recombinant viruses are useful alone or in combination as an effective vaccine. S-SPV-115 is also useful as an expression vector for expressing IBRV antigens. Such IBRV antigens are useful to identify antibodies directed against the wild-type IBRV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 847-19.59.

The homology vector 847-19.59 was constructed for the purpose of inserting foreign DNA into SPV. It incorporates an E. coli β-galactosidase (lacZ) marker gene and the infectious bovine rhinotracheitis virus (IBRV) glycoprotein B (gB) gene flanked by SPV DNA. The direction of transcription of the IBRV gB gene is the same as the direction of transcription of the lacZ gene and the SPV 01L gene. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the IBRV gB gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII- restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 2800 base pair EcoRI/BamHI fragment generated by PCR which contains the coding sequence of the IBRV gB gene. The IBRV gB gene coding region was cloned by PCR using the HindIII A fragment of the IBRV Cooper strain (pSY 830-71) as DNA template and the following PCR primers: 5'-CTTC GGATCCTCATGCCCCCCCGA C G T C G G C C ATC-3' (4/96.15; SEQ ID NO 26) at the 3' end of the IBRV gB gene and combined with 5'-TCATGAATTCGGCCGCTC GCGGCGGTGCTGAACGC-3' (4/96.10; SEQ ID NO 27) at the 5' end of the IBRV gB gene. The DNA encodes approximately 932 amino acids of the IBRV gB protein. Fragment 5 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 5 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 5.

S-SPV-119

S-SPV-119 is a swinepox virus that expresses three foreign genes. The gene E. coli β-galactosidase (lacZ) is inserted into the unique PstI restriction site (PstI linkers inserted into a unique AccI site in the SPV 01L open reading frame). The genes for infectious bovine rhinotracheitis virus (IBRV) glycoprotein D (gD) and glycoprotein I (gI) were inserted into the unique HindIII restriction site (HindIII linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the IBRV gD and gI genes are each under the control of the synthetic late/early promoter (LP2EP2).

S-SPV-119 was derived from S-SPV-001 (Kasza Strain). This was accomplished utilizing the homology vector 835-83 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 119. This virus was assayed for β-galactosidase expression, purity, and insert stability by multiple passages monitored by the blue plaque assay as described in Materials and Methods. After the initial three rounds of purification, all plaques observed are blue indicating that the virus was pure, stable, and expressing the foreign gene.

S-SPV-119 is useful as a vaccine in bovine against disease caused for infectious bovine rhinotracheitis virus. The IBRV gD and gI antigens are key to raising a protective immune response in the animal. The recombinant viruses are useful alone or in combination as an effective vaccine. S-SPV-119 is also useful as an expression vector for expressing IBRV antigens. Such IBRV antigens are useful to identify antibodies directed against the wild-type IBRV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 835-83.

The homology vector 835-83 was constructed for the purpose of inserting foreign DNA into SPV. It incorporates an E. coli β-galactosidase (lacZ) marker gene and the infectious bovine rhinotracheitis virus (IBRV) glycoprotein D (gD) and glycoprotein I (gI) genes flanked by SPV DNA. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the IBRV gI gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 1320 base pair EcoRI/BamHI fragment generated by PCR which contains the coding sequence of the IBRV gD gene. The IBRV gD gene coding region was cloned by PCR using the HindIII K fragment of the IBRV Cooper strain (pSY 524) as DNA template and the following PCR primers: 5'-CG GGATCCTCACCCGGGCAGCGCGCTGTA-3' (4/96.12; SEQ ID NO 18) at the 3' end of the IBRV gD gene and combined with 5'-CGGAATTCACAAGGGCCGACA TTGGCC-3' (4/96.11; SEQ ID NO 19) at the 5' end of the IBRV gD gene. The DNA encodes approximately 440 amino acids of the IBRV gD protein. Fragment 5 is an approximately 1140 base pair EcoRI/BamHI fragment generated by PCR which contains the coding sequence of the IBRV gI gene. The IBRV gI gene coding region was cloned by PCR using the HindIII K fragment of the IBRV Cooper strain (pSY 524) as DNA template and the following PCR primers: 5'-ATCGGGATCCCGTTATTCTTCGCTGATG G T G G-3' (4/96.18; SEQ ID NO 20) at the 3' end of the IBRV gI gene and combined with 5'-ATCGGAATTCGCGGTGCCTG TTGCTCTGGATG-3' (4/96.17; SEQ ID NO 21) at the 5' end of the IBRV gI gene. The DNA encodes approximately 380 amino acids of the IBRV gI protein. Fragment 6 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 6 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 6.

Example 42

CANINE CONSTRUCTS AND VACCINES

S-SPV-114

S-SPV-114 is a swinepox virus that expresses two foreign genes. The gene E. coli β-galactosidase (lacZ) is inserted into the unique PstI restriction site (PstI linkers inserted into a unique AccI site in the SPV 01L open reading frame). The gene for canine parvovirus (CPV) VP2 protein was inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the CPV VP2 gene is under the control of the synthetic late/early promoter (LP2EP2). The direction of transcription of the CPV VP2 gene is the same as the direction of transcription of the lacZ gene and the SPV 01L gene.

S-SPV-114 was derived from S-SPV-001 (Kasza Strain) This was accomplished utilizing the homology vector 848-15.14 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 114. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-114 was assayed for expression of CPV-specific antigens using the BLACK PLAQUE SCREEN FOR FOREIGN GENE EXPRESSION IN RECOMBINANT SPV. Canine antiserum to CPV (from NVSL) was shown to react specifically with S-SPV-114 plaques and not with S-SPV-003 negative control plaques. All S-SPV-114 observed plaques reacted with the antiserum indicating that the virus was stably expressing the CPV foreign gene.

To confirm the expression of the CPV VP2 gene product, cells were infected with S-SPV-114 and samples of infected cell lysates were subjected to SDS polyacrylamide gel electrophoresis. The gel was blotted and analyzed using the WESTERN BLOTTING PROCEDURE. A canine antiserum to CPV (from NVSL) was used to detect expression of CPV specific proteins. The cell lysate from S-SPV-114 infected cells exhibited bands corresponding to 60 kd, which are the expected size of the CPV VP2 protein.

S-SPV-114 is useful as a vaccine in canine against disease caused by canine parvovirus. The CPV VP2 antigen is key to raising a protective immune response in the animal. The recombinant viruses are useful alone or in combination as an effective vaccine. S-SPV-114 is also useful as an expression vector for expressing CPV antigens. Such CPV antigens are useful to identify antibodies directed against the wild-type CPV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 848-15.14.

The homology vector 848-15.14 was constructed for the purpose of inserting foreign DNA into SPV. It incorporates an E. coli β-galactosidase (lacZ) marker gene and for canine parvovirus (CPV) VP2 protein gene flanked by SPV DNA. The direction of transcription of the CPV VP2 gene is the same as the direction of transcription of the lacZ gene and the SPV 01L gene. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the CPV VP2 gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 1758 base pair EcoRI/BamHI fragment generated by PCR which contains the coding sequence of the CPV VP2 gene. The CPV VP2 gene coding region was cloned by PCR using DNA from CPV 2B field isolate (NVSL) as DNA template and the following PCR primers: 5'-CGGGATCCTTAATATAATTTTC T A G GT G C T AG TTG-3' (4/96.26; SEQ ID NO 28) at the 3' end of the CPV VP2 gene and combined with 5'-CGGAATTCG ATGAGTGATGGAGCAGTTCAA-3' (4/96.25; SEQ ID NO 29) at the 5' end of the CPV VP2 gene. The DNA encodes approximately 586 amino acids of the CPV VP2 protein. Fragment 5 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 5. were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 5.

S-SPV-116

S-SPV-116 is a swinepox virus that expresses two foreign genes. The gene E. coli β-galactosidase (lacZ) is inserted into the unique PstI restriction site (PstI linkers inserted into a unique AccI site in the SPV 01L open reading frame). The gene for canine parvovirus (CPV) VP2 protein was inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the CPV VP2 gene is under the control of the synthetic late/early promoter (LP2EP2). The direction of transcription of the CPV VP2 gene is opposite the direction of transcription of the lacZ gene and the SPV 01L gene.

S-SPV-116 was derived from S-SPV-001 (Kasza Strain) This was accomplished utilizing the homology vector 848-15.13 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 116. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-116 was assayed for expression of CPV-specific antigens using the BLACK PLAQUE SCREEN FOR FOREIGN GENE EXPRESSION IN RECOMBINANT SPV. Canine antiserum to CPV (from NVSL) was shown to react specifically with S-SPV-116 plaques and not with S-SPV-003 negative control plaques. All S-SPV-116 observed plaques reacted with the antiserum indicating that the virus was stably expressing the CPV foreign gene.

To confirm the expression of the CPV VP2 gene product, cells were infected with S-SPV-116 and samples of infected cell lysates were subjected to SDS polyacrylamide gel electrophoresis. The gel was blotted and analyzed using the WESTERN BLOTTING PROCEDURE. A canine antiserum to CPV (from NVSL) was used to detect expression of CPV specific proteins. The cell lysate from S-SPV-116 infected cells exhibited bands corresponding to 60 kd, which are the expected size of the CPV VP2 protein.

S-SPV-116 is useful as a vaccine in canine against disease caused by canine parvovirus. The CPV VP2 antigen is key to raising a protective immune response in the animal. The recombinant viruses are useful alone or in combination as an effective vaccine. S-SPV-116 is also useful as an expression vector for expressing CPV antigens. Such CPV antigens are useful to identify antibodies directed against the wild-type CPV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 848-15.13.

The homology vector 848-15.13 was constructed for the purpose of inserting foreign DNA into SPV. It incorporates an E. coli β-galactosidase (lacZ) marker gene and for canine parvovirus (CPV) VP2 protein gene flanked by SPV DNA. The direction of transcription of the CPV VP2 gene is opposite the direction of transcription of the lacZ gene and the SPV 01L gene. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the CPV VP2 gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 1758 base pair EcoRI/BamHI fragment generated by PCR which contains the coding sequence of the CPV VP2 gene. The CPV VP2 gene coding region was cloned by PCR using DNA from CPV 2B field isolate (NVSL) as DNA template and t h e following PCR primers: 5'-CGGGATCCTTAATATAATTTTCTAGGTGC TAGTTG- 3' (4/96.26; SEQ ID NO 30) at the 3' end of the CPV VP2 gene and combined with 5'-CGGAATTCG ATGAGTGATGGAGCAGTTCAA-3' (4/96.25; SEQ ID NO 31) at the 5' end of the CPV VP2 gene. The DNA encodes approximately 586 amino acids of the CPV VP2 protein. Fragment 5 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 5 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 5.

S-SPV-117

S-SPV-117 is a swinepox virus that expresses two foreign genes. The gene E. coli β-galactosidase (lacZ) is inserted into the unique PstI restriction site (PstI linkers inserted into a unique AccI site in the SPV 01L open reading frame). The gene for canine parvovirus (CPV) VP1/2 protein was inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted. The lacZ gene is under the control of the synthetic late promoter (LP1), the CPV VP1/2 gene is under the control of the synthetic late/early promoter (LP2EP2). The direction of transcription of the CPV VP1/2 gene is opposite the direction of transcription of the lacZ gene and the SPV 01L gene.

S-SPV-117 was derived from S-SPV-001 (Kasza Strain) This was accomplished utilizing the homology vector 848-52A31 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 117. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-117 is useful as a vaccine in canine against disease caused by canine parvovirus. The CPV VP1/2 antigen is key to raising a protective immune response in the animal. The recombinant viruses are useful alone or in combination as an effective vaccine. S-SPV-117 is also useful as an expression vector for expressing CPV antigens. Such CPV antigens are useful to identify antibodies directed against the wild-type CPV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 848-52A31.

The homology vector 848-52A31 was constructed for the purpose of inserting foreign DNA into SPV. It incorporates an E. coli β-galactosidase (lacZ) marker gene and for canine parvovirus (CPV) VP1/2 protein gene flanked by SPV DNA. The direction of transcription of the CPV VP1/2 gene is opposite the direction of transcription of the lacZ gene and the SPV 01L gene. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the CPV VP1/2 gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 2172 base pair EcoRI/BamHI fragment generated by PCR which contains the coding sequence of the CPV VP1/2 gene. The CPV VP1/2 gene coding region was cloned by PCR using DNA from CPV 2B field isolate (NVSL) as DNA template and the following PCR primers: 5'-CGGGATCCTTAATATAATTTTCTAGGTGCTAGTTG-3' (4/96.26; SEQ ID NO 32) at the 3' end of the CPV VP1/2 gene and combined with 5'-CGGAATTCTATGTGT TTTTTTATAGGACTT-3' (5/96.25; SEQ ID NO 33) at the 5' end of the CPV VP1/2 gene. The DNA encodes approximately 724 amino acids of the CPV VP1/2 protein. Fragment 5 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 5 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 5.

S-SPV-118

S-SPV-118 is a swinepox virus that expresses two foreign genes. The gene E. coli β-galactosidase (lacZ) is inserted into the unique PstI restriction site (PstI linkers inserted into a unique AccI site in the SPV 01L open reading frame). The gene for canine parvovirus (CPV) VP1/2 protein was inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the CPV VP1/2 gene is under the control of the synthetic late/early promoter (LP2EP2). The direction of transcription of the CPV VP1/2 gene is the same as the direction of transcription of the lacZ gene and the SPV 01L gene.

S-SPV-118 was derived from S-SPV-001 (Kasza Strain) This was accomplished utilizing the homology vector 848-52C8 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 118. This virus was assayed for β-galactosidase expression, purity, and insert stability by multiple passages monitored by the blue plaque assay as described in Materials and Methods. After the initial three rounds of purification, all plaques observed are blue indicating that the virus is pure, stable, and expressing the foreign gene.

S-SPV-118 is useful as a vaccine in canine against disease caused by canine parvovirus. The CPV VP1/2 antigen is key to raising a protective immune response in the animal. The recombinant viruses are useful alone or in combination as an effective vaccine. S-SPV-118 is also useful as an expression vector for expressing CPV antigens. Such CPV antigens are useful to identify antibodies directed against the wild-type CPV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 848-52C8.

The homology vector 848-52C8 was constructed for the purpose of inserting foreign DNA into SPV. It incorporates an E. coli β-galactosidase (lacZ) marker gene and for canine parvovirus (CPV) VP1/2 protein gene flanked by SPV DNA. The direction of transcription of the CPV VP1/2 gene is the same as the direction of transcription of the lacZ gene and the SPV 01L gene. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the CPV VP1/2 gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 2172 base pair EcoRI/BamHI fragment generated by PCR which contains the coding sequence of the CPV VP1/2 gene. The CPV VP1/2 gene coding region was cloned by PCR using DNA from CPV 2B field isolate (NVSL) as DNA template and the following PCR primers: 5'-CGGGATCCTTAATATAATTTTCTAGG T G C T A G TTG-3' (4/96.26; SEQ ID NO 34) at the 3' end of the CPV VP1/2 gene and combined with 5'-CGGAATTCT ATGTGTTTTTTTATAGGACTT-3' (5/96.25; SEQ ID NO 35) at the 5' end of the CPV VP1/2 gene. The DNA encodes approximately 724 amino acids of the CPV VP1/2 protein. Fragment 5 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 5 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 5.

Example 43

AVIAN CONSTRUCTS AND VACCINES

S-SPV-105:

S-SPV-105 is a swinepox virus that expresses at least two foreign genes. The gene for E. coli β-galactosidase (lacZ) and the gene for chicken interferon gamma (cIFNγ) were inserted into the 738-94.4 ORF (a 773 base pair deletion of the SPV 01L ORF; Deletion of nucleotides 1679 to 2452, SEQ ID NO: 189). The lacZ gene is under the control of the swinepox 01L promoter, and the cIFNγ gene is under the control of the synthetic late/early promoter (LP2EP2).

S-SPV-105 was derived from S-SPV-001 (Kasza Strain) This was accomplished utilizing the homology vector 840-72.A1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-105. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-105 is confirmed to have cIFNγ activity by measuring the inhibition of vesicular stomatitis virus growth in permissive cells by cocultivation with S-SPV-105 compared to cocultivation of VSV with S-SPV-003. S-SPV-105 is useful as a vaccine in chickens to stimulate a humoral and cell mediated immune response against infection by avian pathogens. S-SPV-105 is useful for expression of cIFNγ.

HOMOLOGY VECTOR 840-72.A1.

The plasmid 840-72.A1 was constructed for the purpose of inserting foreign DNA into SPV. It incorporates an *E. coli* β-galactosidase (lac Z) marker gene and an chicken interferon gamma (cIFNγ) gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a swinepox virus 01L gene promoter and the cIFNγ gene is under the control of the late/early promoter (LP2EP2). The LP2EP2 cIFNγ gene cassette was inserted into a EcoRI and BamHI site of homology vector 752-22.1. Homology vector 840-72.A1 was constructed utilizing standard recombinant DNA techniques (22, 30), by joining restriction fragments from the following sources with the synthetic DNA sequences. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5' GAAGCATGCCCGTTCTTATCAATAGTTTA GTCGAAAATA-3 (SEQ ID NO: 73) and 5'-CATAAGATCTGGCATTGTGTTATTATACTAACAAA AATAAG-3' (SEQ ID NO: 74) to produce an 855 base pair fragment with SphI and BglII ends. Fragment 2 is a 3002 base pair BamHI to PvuII fragment derived from plasmid pJF751 (49) containing the *E. coli* lacz gene. Fragment 3 is an approximately 522 base pair EcoRI to BglII fragment coding for the cIFNγ gene (62) derived by reverse transcription and polymerase chain reaction (PCR) (Sambrook, et al., 1989) of RNA ISOLATED FROM CONCANAVALIN A STIMULATED CHICKEN SPLEEN CELLS. The antisense primer used for reverse transcription and PCR was 5' CGT CAGATCTCAGGAGGTCATAAGATGCCATTAGC-3' (1/96.38; SEQ ID NO 36). The sense primer used for PCR was 5' CGTTGAATTCGATGACTTGCCAGACTTACAAC TTG-3' (1/96.37; SEQ ID NO 37). The DNA fragment contains the open reading frame of 168 amino acids of the chicken interferon gamma protein. The native methionine codon of cIFNγ is preceded by DNA codons for methionine-asparagine-serine. Fragment 4 is an approximately 1113 base pair subfragment of the SPV HindIII fragment M synthesized by polymerase chain reaction using DNA primers 5'-CCGTAGTCGACAAAGATCGACTTATTAATATG TATGGGATT-3' (SEQ ID NO: 75) and 5' GCCTGA AGCTTCTAGTACAGTATTTACGACTTTTGAAAT-3' (SEQ ID NO: 76) to produce an 1113 base pair fragment with SalI and HindIII ends.

S-SPV-086

S-SPV-086 is a swinepox virus that expresses at least two foreign genes. The gene for *E. coli* β-galactosidase (lacZ) and antisense of the gene for chicken interferon gamma (cIFNγ) were inserted into the 738-94.4 ORF (a 773 base pair deletion of the SPV 01L ORF; Deletion of nucleotides 1679 to 2452, SEQ ID NO: 189), The lacZ gene is under the control of the swinepox 01L promoter, and the antisense-cIFNγ gene is under the control of the synthetic late/early promoter (LP2EP2).

S-SPV-086 was derived from S-SPV-001 (Kasza Strain) This was accomplished utilizing the homology vector 836-62.B1 and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-galactosidase (BLUOGAL AND CPRG ASSAYS). The final result of red plaque purification was the recombinant virus designated S-SPV-086. This virus was assayed. for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene. Homology vector 836-62.B1 is constructed in the same manner as homology vector 840-72.A1 except that in 836-62.B1, the approximately 522 base pair EcoRI to BglII fragment coding for he cIFNγ gene is in the opposite orientation relative to the LP2EP2 promoter compared to 840-72.A1.

S-SPV-086 was assayed for expression of B-galactosidase antigens using the BLACK PLAQUE SCREEN FOR FOREIGN GENE EXPRESSION IN RECOMBINANT SPV. Anti-B-galactosidase antiserum was shown to react specifically with S-SPV-086 plaques and not with S-SPV-003 negative control plaques. All S-SPV-086 observed plaques reacted with the antiserum indicating that the virus was stably expressing the B-galactosidase foreign gene.

S-SPV-086 is useful for expression of antisense RNA to the cIFNγ mRNA. When S-SPV-986 is transfected into duck embryo fibroblasts (DEF) or chicken embryo fibroblast (CEF) cells, it will not lyse the cells, but will express antisense cIFNγ RNA in CEF cells and inhibit expression of cIFNγ protein from DEF or CEF cells. Recombinant viruses, such as herpesvirus of turkeys (HVT) or Marek's disease virus, grow to higher titers ($10^8$ to $10^{10}$ pfu/ml) in S-SPV-086 transfected into DEF or CEF cells, and transfected cells are selected for puromycin resistance by growth in the presence of puromycin. These transfected cells will grow continuously, express antisense to cIFNγ gene and permit high titer growth of herpesvirus to turkeys or Marek's disease virus ($10^8$ to $10^{10}$ pfu/ml)

Example 44
FELINE CONSTRUCTS AND VACCINES
S-SPV-106

S-SPV-106 is a swinepox virus that expresses at least two foreign genes. The gene for *E. coli* β-galactosidase (lacZ)

and the genes for feline immunodeficiency virus (FIV) envelope (env) and gag-protease were inserted into the SPV 617 48.1 ORF (a unique NotI restriction site has replaced a unique AccI restriction site). The lacZ gene is under the control of the synthetic late promoter (LP1), and the FIV env and gag-protease genes are each under the control of the synthetic late/early promoter (LP2EP2).

S-SPV-106 was derived from S-SPV-001 (Kasza Strain) This was accomplished utilizing the homology vector 836-22.A1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 106. This virus was assayed for β-galactosidase expression, purity, and insert stability by multiple passages monitored by the blue plaque assay as described in Materials and Methods. After the initial five rounds of purification, all plaques observed were blue indicating that the virus was pure, stable, and expressing the foreign gene.

S-SPV-106 was assayed for expression of FIV-specific antigens using the BLACK PLAQUE SCREEN FOR FOREIGN GENE EXPRESSION IN RECOMBINANT SPV. Monoclonal antibodies to FIV gag-protease were shown to react specifically with S-SPV-106 plaques and not with S-SPV-003 negative control plaques. A1 1 S-SPV-106 observed plaques reacted with the antiserum indicating that the virus was stably expressing the FIV gag foreign gene.

S-SPV-106 is a recombinant swinepox virus expressing both the FIV env and gag-protease proteins and is useful as a vaccine in cats against FIV infection S-SPV-106 is also useful for expression of the FIV env and gag-protease proteins.

HOMOLOGY VECTOR 836-22.A1.

The plasmid 836-22.A1 was used to insert foreign DNA into SPV. It incorporates an *E. coli* β-galactosidase (lacZ) marker gene and the feline immunodeficiency virus (FIV) envelope (env) and gag/protease genes flanked by SPV DNA. When this plasmid was used according to the HOMOLOGOUS RECOMBINATION PROCEDURE FOR GENERATING RECOMBINANT SPV a virus containing DNA coding for the foreign genes results. Note that the β galactosidase (lacZ) marker gene is under the control of a synthetic late pox promoter (LP1) and the FIV env and gag/protease genes are under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII fragment M (23). Fragment 2 is an approximately 2564 base pair BamHI to BamHI fragment of the FIV env gene (61) (approximately 860 amino acids which includes the full length SU and TM coding regions of FIV env) synthesized by CLONING WITH THE POLYMERASE CHAIN REACTION. The template for the PCR reaction was FIV strain PPR genomic cDNA (61). The upstream primer 10/93.21 (5'-GCCCGGATCCTA TGGCAGAAGGGTTTGCAGC-3'; (SEQ ID NO: 85)) was synthesized corresponding to the 5' end of the FIV env gene starting at nucleotide 6263 of FIV strain PPR genomic cDNA, and the procedure introduced a BamHI site at the 5' end. The downstream primer 10/93.20 (5'-CCGTGGATCCGGCACTCCATCATTCCTCCTC-3'; (SEQ ID NO: 86)) was synthesized corresponding to the 3' end of the FIV env gene starting at nucleotide 8827 of FIV PPR genomic cDNA. Fragment 3 is an approximately 1878 base pair EcoRI to BglII restriction fragment of the FIV gag/protease (gag ORF is approximately 452 amino acids; protease ORF is approximately 209 amino acids) synthesized by polymerase chain reaction (PCR) using cDNA from the FIV (PPR strain) (61). The primer (5' GCGT <u>GAATTC</u>GGGGAATGGACAGGGGCGAGAT-3'; 11/94.9) (SEQ ID NO: 83) synthesizes from the 5' end of the FIV gag-protease gene, introduces an EcoRI site at the 5' end of the gene. The primer (5'-GAGCC<u>AGATCT</u>G CTCTTTTTACTTTCCC-3'; 11/94.10) (SEQ ID NO: 84) synthesizes from the 3' end of the FIV gag-protease gene and introduces a BglII site at the 3' end of the gene. The PCR product was digested with EcoRI and BglII to yield a fragment 1878 base pairs in length corresponding to the FIV gag-protease gene. Fragment 4 is an approximately 3010 base pair BamHI to PvuII restriction fragment of plasmid pJF751 (11). Fragment 5 is an approximately 2149 base pair AccI to HindIII restriction sub-fragment of the SPV HindIII restriction fragment M (23). The AccI site in the SPV homology vector was converted to a unique NotI site.

S-SPV-127

S-SPV-127 is a swinepox virus that expresses four foreign genes. The gene for *E. coli* β-galactosidase (lacZ) and the gene for the feline immunodeficiency virus (FIV) gag/protease (gag) were inserted into the 738-94.4 ORF (a 773 base pair deletion of the SPV 01L ORF; Deletion of nucleotides 1669 to 2452, SEQ ID NO: 189). The gene for *E. coli* β-glucuronidase (uidA) and the gene for the feline immunodeficiency virus (FIV) envelope (env) were inserted into a unique NotI site (NotI linkers inserted into a unique EcoRI restriction site within an approximately 3.2 kb region (SEQ ID NO 1) of the 6.7 kb SPV HindIII K fragment). The lacZ gene is under the control of the swinepox 01L promoter, the uidA gene is under the control of the synthetic early promoter (EP2) and the FIV gag/protease and envelope genes are each under the control of the synthetic late/early promoter (LP2EP2).

S-SPV-127 was derived from S-SPV-046 (Kasza Strain) This was accomplished utilizing the homology vector 849-61.A14 (see Materials and Methods) and virus S-SPV-046 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase and β-glucuronidase (BLUOGAL AND CPRG ASSAYS and SCREEN FOR RECOMBINANT HERPESVIRUS EXPRESSING ENZYMATIC MARKER GENES). The final result of red plaque and blue plaque purification was the recombinant virus designated S-SPV-127. This virus was assayed for β-galactosidase and β-glucuronidase expression, purity, and insert stability by multiple passages monitored by the blue plaque assay as described in Materials and Methods. After the initial three rounds of purification, all plaques observed are blue indicating that the virus is pure, stable, and expressing the foreign genes.

S-SPV-127 is useful as a vaccine in cats against FIV infection S-SPV-127 is also useful for expression of the FIV env and gag proteins.

HOMOLOGY VECTOR 849-61.A14.

The plasmid 849-61.A14 was used to insert foreign DNA into SPV. It incorporates an *E. coli* β-glucuronidase (uidA) marker gene and the feline immunodeficiency virus (FIV)

envelope (env) gene flanked by SPV DNA. When this plasmid was used according to the HOMOLOGOUS RECOMBINATION PROCEDURE FOR GENERATING RECOMBINANT SPV a virus containing DNA coding for the foreign genes results. Note that the β-glucuronidase (uidA) gene is under the control of a synthetic early pox promoter (EP2) and the FIV env gene is under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 3005 base pair HindIII restriction fragment of pSP65 (Promega). Fragment 1 is an approximately 1652 base pair HindIII to EcoRI restriction sub-fragment of the SPV HindIII restriction fragment K. Fragment 2 is an approximately 2564 base pair BamHI to BamHI fragment of the FIV env gene (61) (approximately 860 amino acids which includes the full length SU and TM coding regions of FIV env) synthesized by CLONING WITH THE POLYMERASE CHAIN REACTION. The template for the PCR reaction was FIV strain PPR genomic cDNA (61). The upstream primer 10/93.21 (5'-GCCCGGATCCTATGGCAGAAGGGTTTGCAGC-3'; (SEQ ID NO: 85) was synthesized corresponding to the 5' end of the FIV env gene starting at nucleotide 6263 of FIV strain PPR genomic cDNA, and the procedure introduced a BamHI site at the 5' end. The downstream primer 10/93.20 (5'-CCGTGGATCCGGCACTCCATCATTCCTCCTC-3'; (SEQ ID NO: 86)) was synthesized corresponding to the 3' end of the FIV env gene starting at nucleotide 8827 of FIV PPR genomic cDNA, and the procedure introduced a BamHI site at the 3' end. Fragment 3 is an approximately 1800 base pair EcoRI to XmaI restriction fragment containing the E. coli uidA gene. Fragment 4 is an approximately 3010 base pair BamHI to PvuII restriction fragment of plasmid pJF751 (11). Fragment 5 is an approximately 5053 base pair EcoRI to HindIII restriction sub-fragment of the SPV HindIII restriction fragment K. The EcoRI site in fragments 1 and 5 of the SPV homology vector was converted to a unique NotI site.

S-SPV-089

S-SPV-089 is a swinepox virus that expresses three foreign genes. The gene for E. coli β-galactosidase (lacZ) and the gene for feline leukemia virus (FeLV) gag/protease were inserted into the 738-94.4 ORF (a 773 base pair deletion of the SPV 01L ORF; Deletion of nucleotides 1679 to 2452, SEQ ID NO: 189). The lacZ gene is under the control of the swinepox 01L promoter, and the FeLV gag/protease gene is under the control of the synthetic late/early promoter (LP2EP2).

S-SPV-089 is derived from S-SPV-001 (Kasza Strain) This was accomplished utilizing the HOMOLOGY VECTOR 832-26.A1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 089. This virus was assayed for β-galactosidase expression, purity, and insert stability by multiple passages monitored by the blue plaque assay as described in Materials and Methods. After the initial three rounds of purification, all plaques observed were blue indicating that the virus is pure, stable, and expressing the foreign gene.

S-SPV-089 was assayed for expression of FeLV-specific antigens using the BLACK PLAQUE SCREEN FOR FOREIGN GENE EXPRESSION IN RECOMBINANT SPV. Polyclonal mouse anti-p27 serum, rabbit anti-p27 serum and rabbit anti-β-galactosidase were shown to react specifically with S-SPV-089 plaques and not with S-SPV-003 negative control plaques. All S-SPV-089 observed plaques reacted with the antiserum indicating that the virus was stably expressing the FeLV gag protease and E. coli β-galactosidase proteins.

S-SPV-089 is useful as a vaccine in cats against disease caused by feline leukemia virus. The FeLV gag/protease antigen is key to raising a protective immune response in the animal. The recombinant viruses are useful alone or in combination as an effective vaccine. S-SPV-089 is also useful as an expression vector for expressing FeLV antigens. Such FeLV antigens are useful to identify antibodies directed against the wild-type FeLV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 832-26.A1.

The plasmid 832-26.A1 was constructed for the purpose of inserting foreign DNA into SPV. It incorporates an E. coli β-galactosidase (lac Z) marker gene and the feline leukemia virus (FeLV) gag/protease gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a swinepox virus 01L gene promoter and the FeLV gag/protease gene is under the control of the late/early promoter (LP2EP2). The LP2EP2 FeLV gag/protease gene cassette was inserted into a EcoRI and BamHI site of homology vector 752-22.1. Homology vector 832-26.A1 was constructed utilizing standard recombinant DNA techniques (22, 30), by joining restriction fragments from the following sources with the synthetic DNA sequences. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5' GAA GCATGCCCGTTCTTATCAATAGTTTAGTCGAAAATA-3' (SEQ ID NO: 73) and 5'-CATAAGATCTGGCATTGTGT TATTATACTAACAAAAATAAG-3' (SEQ ID NO: 74) to produce an 855 base pair fragment with SphI and BglII ends. Fragment 2 is a 3002 base pair BamHI to PvuII fragment derived from plasmid pJF751 (49) containing the E. coli lacZ gene. Fragment 3 is an approximately 2160 base pair EcoRI to BamHI restriction fragment of the FeLV gag/protease (gag ORF is approximately 584 amino acids; protease ORF is approximately 136 amino acids) synthesized by polymerase chain reaction (PCR) using cDNA from FeLV/FAIDS strain, Type A (cDNA clone p61E; Dr. Mullens, NIAIDS repository). The primer (5' CGTCGAATTCGATGTCTGGAGCCTCTAGTG GGA-3'; 1/96.32) (SEQ ID NO 38) synthesizes from the 5' end of the FeLV gag/protease gene, introduces an EcoRI site at the 5' end of the gene and an ATG start codon. The primer (5'-CGTCGGATCCGGCTCAAATAGCCGATA C T C T T CTT-3'; 1/96.33) (SEQ ID NO 39) synthesizes from the 3' end of the FeLV gag/protease gene. The PCR product was digested with EcoRI and BglII to yield a fragment 2160 base pairs in length corresponding to the FeLV gag/protease gene. Fragment 4 is an approximately 1113 base pair subfragment of the SPV HindIII fragment M synthesized by polymerase chain reaction using DNA primers 5'-CCGTAGTCGACA AAGATCGACTTATTAATATGTAT GGGATT-3' (SEQ ID NO: 75) and 5' GCCTGAAGCTTCTAGTACAGTATT-TACGAC TTTTGAAAT-3' (SEQ ID NO: 76) to produce an 1113 base pair fragment with SalI and HindIII ends.

S-SPV-100

S-SPV-100 is a swinepox virus that expresses two foreign genes. The gene for *E. coli* β-galactosidase (lacZ) and the gene for feline leukemia virus (FeLV) envelope (env) gp70+p15E were inserted into the SPV 617-48.1 ORF (a unique NotI restriction site has replaced a unique AccI restriction site). The lacZ gene is under the control of the synthetic late promoter (LP1), and the FeLV env gene is under the control of the synthetic late/early promoter (LP2EP2).

S-SPV-100 is derived from S-SPV-001 (Kasza Strain) This was accomplished utilizing the HOMOLOGY VECTOR 843-9.322 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-100. This virus was assayed for β-galactosidase expression, purity, and insert stability by multiple passages monitored by the blue plaque assay as described in Materials and Methods. After the initial three rounds of purification, all plaques observed were blue indicating that the virus is pure, stable, and expressing the foreign gene.

S-SPV-100 was assayed for expression of FeLV-specific antigens using the BLACK PLAQUE SCREEN FOR FOREIGN GENE EXPRESSION IN RECOMBINANT SPV. Polyclonal mouse anti-p70 serum and rabbit anti-β-galactosidase were shown to react specifically with S-SPV-100 plaques and not with S-SPV-003 negative control plaques. All S-SPV-100 observed plaques reacted with the antiserum indicating that the virus was stably expressing the FeLV env and *E. coli* β-galactosidase proteins.

S-SPV-100 is useful as a vaccine in cats against disease caused by feline leukemia virus. The FeLV env antigen is key to raising a protective immune response in the animal. The recombinant viruses are useful alone or in combination as an effective vaccine. S-SPV-100 is also useful as an expression vector for expressing FeLV antigens. Such FeLV antigens are useful to identify antibodies directed against the wild-type FeLV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTOR 843-9.322.

The plasmid 843-9.322 was constructed for the purpose of inserting foreign DNA into SPV. It incorporates an *E. coli* β-galactosidase (lacZ) marker gene and a feline leukemia virus (FeLV) envelope (env) gp70+p15E gene flanked by SPV DNA. Upstream of the foreign gene is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a late promoter (LP1) and the FeLV env gene is under the control of the late/early promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 1973 base pair EcoRI to BamHI restriction fragment of the FeLV env (gp70+p15E) (env ORF is approximately 658 amino acids) synthesized by polymerase chain reaction (PCR) using cDNA from FeLV/FAIDS strain, Type A (cDNA clone p61E; Dr. Mullens, NIAIDS repository) The primer (5-'CGTC GAATTCAATGGAAAGTCCAACGCAC C C A A A A-3'; 1/96.31) (SEQ ID NO 40) synthesizes from the 5' end of the FeLV env gene, introduces an EcoRI site at the 5' end of the gene and an ATG start codon. The primer (5'-CGTC GGATCCGGGGACTAAATGGAATCATACA-3'; 1/96.28) (SEQ ID NO 41) synthesizes from the 3' end of the FeLV env gene. The PCR product was digested with EcoRI and BglII to yield a fragment 1973 base pairs in length corresponding to the FeLV env gene. Fragment 3 is an approximately 3010 base pair BamHI to PvuII restriction fragment of plasmid pJF751 (11). Fragment 3 is an approximately 2149 base pair AccI to HindIII subfragment of the SPV HindIII fragment M. The AccI sites in fragments 1 and 3 were converted to unique NotI sites using NotI linkers.

S-SPV-107 and S-SPV-108

S-SPV-107 is a swinepox virus that expresses three foreign genes. The gene *E. coli* β-galactosidase (lacZ) is inserted into the unique PstI restriction site (PstI linkers inserted into a unique AccI site in the SPV 01L open reading frame). The gene for feline leukemia virus (FeLV) gag/protease and envelope (env) gp70+p15E was inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the FeLV gag/protease and env genes are under the control of the synthetic late/early promoter (LP2EP2). The direction of transcription of the FeLV gag/protease and env gene are the same as direction of transcription of the lacZ gene and the SPV 01L gene.

S-SPV-107 is derived from S-SPV-001 (Kasza Strain). This is accomplished utilizing the HOMOLOGY VECTOR 840-68.A1 and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING β-galactosidase (BLUOGAL AND CPRG ASSAYS). The final result of red plaque purification is the recombinant virus designated S-SPV 107. This virus is assayed for β-galactosidase expression, purity, and insert stability by multiple passages monitored by the blue plaque assay as described in Materials and Methods. After the initial three rounds of purification, all plaques observed were blue indicating that the virus is pure, stable, and expressing the foreign gene.

S-SPV-108 is a swinepox virus that expresses three foreign genes. The gene E. coli β-galactosidase (lacZ) is inserted into the unique PstI restriction site (PstI linkers inserted into a unique AccI site in the SPV 01L open reading frame). The gene for feline leukemia virus (FeLV) gag/protease and envelope (env) gp70+p15E was inserted into the unique NotI restriction site (NotI linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the FeLV gag/protease and env gene is under the control of the synthetic late/early promoter (LP2EP2). The direction of transcription of the FeLV gag/protease and env gene are opposite the direction of transcription of the lacZ gene and the SPV 01L gene.

S-SPV-108 is derived from S-SPV-001 (Kasza Strain). This is accomplished utilizing the HOMOLOGY VECTOR VECTOR 840-68.A6 and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING β-galactosidase (BLUOGAL AND CPRG ASSAYS). The final result of red plaque purification is the recombinant virus designated S-SPV-108. This virus is assayed for β-galactosidase expression, purity, and insert stability by multiple passages monitored by the blue plaque assay as described in Materials and Methods. After the initial three rounds of purification, all plaques observed were blue indicating that the virus is pure, stable, and expressing the foreign gene.

S-SPV-107 or S-SPV-108 are useful as a vaccine in cats against disease caused by feline leukemia virus. The FeLV gag/protease and env antigens are key to raising a protective immune response in the animal. The recombinant viruses are useful alone or in combination as an effective vaccine. S-SPV-107 or S-SPV-108 are also useful as an expression vector for expressing FeLV antigens. Such FeLV antigens are useful to identify antibodies directed against the wild-type FeLV. The virus is also useful as a source of antigens for the production of monospecific polyclonal or monoclonal antibodies. Such antibodies are useful in the development of diagnostic tests specific for the viral proteins. Monoclonal or polyclonal antibodies are generated in mice utilizing these viruses according to the PROCEDURE FOR PURIFICATION OF VIRAL GLYCOPROTEINS FOR USE AS DIAGNOSTICS (Materials and Methods).

HOMOLOGY VECTORS 840-68.A1 AND 840-68.A6.

The homology vector are constructed for the purpose of inserting foreign DNA into SPV. It incorporates an E. coli β-galactosidase (lacZ) marker gene and for feline leukemia virus (FeLV) protease (gag) and envelope (env) gp70+p15E genes flanked by SPV DNA. The direction of transcription of the FeLV gag/protease and env gene is the same as direction of transcription of the LacZ gene and the SPV 01L gene in homology vector 840-68.A1. The direction of transcription of the FeLV gag/protease and env gene is opposite the direction of transcription of the lacZ gene and the SPV 01L gene in 840-68.A6. Upstream of the foreign genes is an approximately 1484 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the FeLV gag/protease and env gene are each under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 3010 base pair BamHI to PvuII restriction fragment of plasmid pJF751 (11). Fragment 3 is an approximately 48 base pair AccI to NdeI subfragment of the SPV HindIII M fragment. Fragment 4 is an approximately 2160 base pair EcoRI to BamHI restriction fragment of the FeLV gag/protease (gag ORF is approximately 584 amino acids; protease ORF is approximately 136 amino acids) synthesized by polymerase chain reaction (PCR) using cDNA from FeLV/FAIDS strain, Type A (cDNA clone p61E; Dr. Mullens, NIAIDS repository) The primer (5' CGTCGAATTCGATGTCTGGAGCCTCTAGTG GGA-3'; 1/96.32) (SEQ ID NO 38) synthesizes from the 5' end of. the FeLV gag/protease gene, introduces an EcoRI site at the 5' end of the gene. One in frame start codon (ATG) is in the LP2EP2 promoter, and a second in frame start codon is in the gene coded by the PCR primer. The primer (5'-CGTC GGATCCGGCTCAAATAGCCGAT A C T C T T C T T-3'; 1/96.33) (SEQ ID NO 39) synthesizes from the 3' end of the FeLV gag/protease gene. The PCR product was digested with EcoRI and BglII to yield a fragment 2160 base pairs in length corresponding to the FeLV gag/protease gene. Fragment 5 is an approximately 1973 base pair EcoRI to BamHI restriction fragment of the FeLV env (gp70+p15E) (env ORF is approximately 658 amino acids) synthesized by polymerase chain reaction (PCR) using cDNA from FeLV/FAIDS strain, Type A (cDNA clone p61E; Dr. Mullens, NIAIDS repository) The primer (5-'CGTC GAATTCAATGGAAAGTCCAACGCAC C C A A A A-3'; 1/96.31) (SEQ ID NO 40) synthesizes from the 5' end of the FeLV env gene, introduces an EcoRI site at the 5' end of the gene. One in frame start codon (ATG) is in the LP2EP2 promoter, and a second in frame start codon is in the gene coded by the PCR primer The primer (5'-CGTC GGATCCGGGGACTAAATGGAATCATACA-3'; 1/96.28) (SEQ ID NO 41) synthesizes from the 3' end of the FeLV env gene. The PCR product was digested with EcoRI and BglII to yield a fragment 1973 base pairs in length corresponding to the FeLV env gene. Fragment 6 is an approximately 1560 base pair NdeI to HindIII subfragment of the SPV HindIII fragment M. The AccI sites in fragments 1 and 3 were converted to unique PstI sites using PstI linkers. The NdeI sites in fragments 3 and 6 were converted to unique Not I sites using NotI linkers. An approximately 545 base pair NdeI to NdeI subfragment (Nucleotides 1560 to 2104; SEQ ID NO. 189) of the SPV HindIII M fragment has been deleted which would span SPV fragments 3 and 6.

S-SPV-128:

S-SPV-128 is a swinepox virus that expresses four foreign genes. The gene for E. coli β-galactosidase (lacZ) and the gene for for feline leukemia virus (FeLV) gag/protease and were inserted into the 738-94.4 ORF (a 773 base pair deletion of the SPV 01L ORF; Deletion of nucleotides 1669 to 2452, SEQ ID NO: 189). The gene for E. coli β-glucuronidase (uidA) and the gene for the feline leukemia virus (FeLV) envelope (env) gp70+p15E were inserted into a unique NotI site (NotI linkers inserted into a unique EcoRI restriction site within an approximately 3.2 kb region (SEQ ID NO 1) of the 6.7 kb SPV HindIII K fragment). The lacZ gene is under the control of the synthetic late promoter (LP1), the uidA gene is under the control of the synthetic early promoter (EP2) and the FeLV gag/protease and envelope genes are each under the control of the synthetic late/early promoter (LP2EP2).

S-SPV-128 was derived from S-SPV-089 (Kasza Strain) This was accomplished utilizing the homology vector 860-2 (see Materials and Methods) and virus S-SPV-089 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase and β-glucuronidase (BLUOGAL AND CPRG ASSAYS and SCREEN FOR RECOMBINANT HERPESVIRUS EXPRESSING ENZYMATIC MARKER GENES). The final result of red plaque and blue plaque purification was the recombinant virus designated S-SPV-128. This virus was assayed for β-galactosidase and β-glucuronidase expression, purity, and insert stability by multiple passages monitored by the blue plaque assay as described in Materials and Methods. After the initial three rounds of purification, all plaques observed are blue indicating that the virus is pure, stable, and expressing the foreign genes.

S-SPV-128 is useful as a vaccine in cats against FIV infection S-SPV-128 is also useful for expression of the FIV env and gag proteins.

HOMOLOGY VECTOR 860-2.

The plasmid 860-2 was used to insert foreign DNA into SPV. It incorporates a gene for *E. coli* β-glucuronidase (uidA) and the gene for the feline leukemia virus (FeLV) envelope (env) gp70+p15E flanked by SPV DNA. When this plasmid was used according to the HOMOLOGOUS RECOMBINATION PROCEDURE FOR GENERATING RECOMBINANT SPV a virus containing DNA coding for the foreign genes results. Note that the β-glucuronidase (uidA) gene is under the control of a synthetic early pox promoter (EP2) and the FeLV env gene is under the control of a synthetic late/early pox promoter (LP2EP2). The homology vector was constructed utilizing standard recombinant DNA techniques (22 and 30), by joining restriction fragments from the following sources with the appropriate synthetic DNA sequences. The plasmid vector was derived from an approximately 3005 base pair HindIII restriction fragment of pSP65 (Promega). Fragment 1 is an approximately 1652 base pair HindIII to EcoRI restriction subfragment of the SPV HindIII restriction fragment K. Fragment 2 is an approximately 1973 base pair EcoRI to BamHI restriction fragment of the FeLV env (gp70+p15E) (approximately 860 amino acids which includes the full length SU and TM coding regions of FIV env) synthesized by polymerase chain reaction (PCR) using cDNA from FeLV/FAIDS strain, Type A (cDNA clone p61E; Dr. Mullens, NIAIDS repository) The primer (5'-CGTC GAATTCAATGGAAAGTCCAACGCACC C A A A A-3'; 1/96.31) (SEQ ID NO 40) synthesizes from the 5' end of the FeLV env gene, introduces an EcoRI site at the 5' end of the gene and an ATG start codon. The primer (5'-CGTC GGATCCGGGGACTAAATGGAATCATACA-3'; 1/96.28) (SEQ ID NO 41) synthesizes from the 3' end of the FeLV env gene. The PCR product was digested with EcoRI and BglII to yield a fragment 1973 base pairs in length corresponding to the FeLV env gene. Fragment 3 is an approximately 1800 base pair EcoRI to XmaI restriction fragment containing the *E. coli* uidA gene. Fragment 4 is an approximately 5053 base pair EcoRI to HindIII restriction subfragment of the SPV HindIII restriction fragment K. The EcoRI sites in fragments 1 and 4 of the SPV homology vector were converted to a unique NotI site.

PORCINE CONSTRUCTS AND VACCINES

S-SPV-084

S-SPV-084 is a swinepox virus that expresses at least two foreign genes. The gene for *E. coli* β-galactosidase (lacZ) and the gene for porcine reproductive and respiratory syndrome virus (PRRS) ORF6 were inserted into the SPV 738-94.4 ORF (a 773 base pair deletion of the SPV 01L ORF; Deletion of nucleotides 1669 to 2452, SEQ ID NO: 189). The lacZ gene is under the control of the swinepox $P_{OIL}$ promoter and the PRRS ORF6 gene is under the control of the synthetic late/early promoter (LP2EP2).

S-SPV-084 was derived from S-SPV-001 (Kasza Strain). This was accomplished utilizing the homology vector 831-38.22 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 084. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

To confirm the expression of the PRRS ORF6 matrix protein gene product, cells were infected with S-SPV-084 and samples of infected cell lysates were subjected to SDS polyacrylamide gel electrophoresis. The gel was blotted and analyzed using the WESTERN BLOTTING PROCEDURE. A polyclonal swine anti-PRRS (NVSL) serum was used to detect expression of PRRS specific proteins. The cell lysate from S-SPV-084 infected cells exhibited a band corresponding to 18 kd, which is the expected size of the PRRS ORF6 matrix protein.

S-SPV-084 is useful as a vaccine in swine against PRRS infection S-SPV-084 is also useful for expression of the PRRS ORF6 matrix protein.

HOMOLOGY VECTOR 831-38.22.

The homology vector 831-38.22 was constructed for the purpose of inserting foreign DNA into SPV. It incorporates an *E. coli* β-galactosidase (lacZ) marker gene and the porcine reproductive and respiratory syndrome virus (PRRS) ORF6 matrix gene flanked by SPV DNA. Upstream of the foreign genes is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of the swinepox virus 01L promoter and the PRRS ORF6 matrix gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5' GAAGCATGCCCGTTCTTATCAATA GTTTAGTCGAAAATA-3' (SEQ ID NO: 73), and 5'-CATAAGATCTGGCATTGTGTTATTATACTAAC AAAAATAAG-3' (SEQ ID NO: 74) to produce an 855 base pair fragment with SphI and BglII ends. Fragment 2 is an approximately 3002 base pair BamHI to PvuII restriction fragment of plasmid pJF751 (11). Fragment 3 is an EcoRI to BamHI restriction fragment synthesized by reverse transcription and polymerase chain reaction (PCR) using genomic RNA from a U.S. Isolate of PRRS obtained from the NVSL (Reference strain, IA-2). To synthesize PRRS ORF6 matrix gene, the primer (5° CGGGAATTC GGGGTCGTCCTTAGATGACTTCTGCC-3'; 1/96.17) (SEQ ID NO 42) synthesizes from the 5' end of the PRRS ORF6 gene, introduces an EcoRI site at the 5' end of the gene. The primer (5' GCGGATCCTTGTTATGTGGCA TATTTGACAAGGTTTAC-3'; 1/96.18) (SEQ ID NO 43) is used for reverse transcription and PCR and synthesizes from the 3' end of the PRRS ORF6 gene. The PCR product was digested with EcoRI and BamHI to yield a fragment 532 base pairs in length corresponding to the PRRS ORF6 gene. Fragment 4 is an approximately 1113 base pair subfragment of the SPV HindIII fragment M synthesized by polymerase chain reaction using DNA primers 5'-CCGTAGTCG ACAAAGATCGACTTATTAATATGTATGGGATT-3' (SEQ ID NO: 75) and 5' GCCTGAAGCTTCTAGTACAG-TATTTACGAC TTTTGAAAT-3' (SEQ ID NO: 76) to produce an 1113 base pair fragment with SalI and HindIII ends.

S-SPV-091

S-SPV-091 is a swinepox virus that expresses at least two foreign genes. The gene for $E.$ $coli$ β-galactosidase (lacZ) and the gene for porcine reproductive and respiratory syndrome virus (PRRS) ORF2 were inserted into the SPV 617-48.1 ORF (a unique NotI restriction site has replaced a unique AccI restriction site). The lacZ gene is under the control of the synthetic late promoter (LP1), and the PRRS ORF2 gene is under the control of the synthetic late/early promoter (LP2EP2). S-SPV-091 was derived from S-SPV-001 (Kasza Strain). This was accomplished utilizing the homology vector 844-15.110 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 091. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-091 is useful as a vaccine in swine against PRRS infection. S-SPV-091 is also useful for expression of the PRRS ORF2 protein.

HOMOLOGY VECTOR 844-15.110.

The plasmid 844-15.110 was constructed for the purpose of inserting foreign DNA into SPV. It incorporates an $E.$ $coli$ β-galactosidase (lacZ) marker gene and a porcine reproductive and respiratory syndrome virus (PRRS) ORF2 gene flanked by SPV DNA. Upstream of the foreign gene is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a late promoter (LP1) and the PRRS ORF2 gene is under the control of the late/early promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an EcoRI to BamHI restriction fragment synthesized by reverse transcription and polymerase chain reaction (PCR) using genomic RNA from a U.S. Isolate of PRRS obtained from the NVSL (Reference strain, IA-2). To synthesize PRRS ORF2, the primer (5' AATGAATTCGAAATGGGGTCC ATGCAAAGCCTTTTTG-3'; 1/96.15) (SEQ ID NO 44) synthesized from the 5' end of the PRRS ORF2 gene, introduced an EcoRI site at the 5' end of the gene. The primer (5'-CAAGGATCCCACACCGTGTAATTCACT GTGAGTTCG-3'; 1/96.16) (SEQ ID NO 45) was used for reverse transcription and PCR and synthesized from the 3' end of the PRRS ORF2 gene. The PCR product was digested with EcoRI and BamHI to yield a fragment approximately 788 base pairs in length corresponding to the PRRS ORF2 gene. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

S-SPV-092

S-SPV-092 is a swinepox virus that expresses at least two foreign genes. The gene for $E.$ $coli$ β-galactosidase (lacZ) and the gene for porcine reproductive and respiratory syndrome virus (PRRS) ORF7 nucleocapsid were inserted into the SPV 617-48.1 ORF (a unique NotI restriction site has replaced a unique AccI restriction site). The lacZ gene is under the control of the synthetic late promoter (LP1), and the PRRS ORF7 nucleocapsid gene is under the control of the synthetic late/early promoter (LP2EP2).

S-SPV-092 was derived from S-SPV-001 (Kasza Strain). This was accomplished utilizing the homology vector 844-19.94 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 092. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-092 was assayed for expression of PRRS-specific antigens using the BLACK PLAQUE SCREEN FOR FOREIGN GENE EXPRESSION IN RECOMBINANT SPV. Polyclonal swine anti-PRRS (NVSL) serum and a monoclonal antibody to PRRS ORF7 nucleocapsid protein were each shown to react specifically with S-SPV-092 plaques and not with S-SPV-003 negative control plaques. All S-SPV-092 observed plaques reacted with the antiserum indicating that the virus was stably expressing the PRRS ORF7 nucleocapsid protein.

S-SPV-092 is useful as a vaccine in swine against PRRS infection. S-SPV-092 is also useful for expression of the PRRS ORF7 nucleocapsid protein.
HOMOLOGY VECTOR 844-19.94.

The plasmid 844-19.94 was constructed for the purpose of inserting foreign DNA into SPV. It incorporates an *E. coli* β-galactosidase (lacZ) marker gene and a porcine reproductive and respiratory syndrome virus (PRRS) ORF7 gene flanked by SPV DNA. Upstream of the foreign gene is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a late promoter (LP1) and the PRRS ORF7 gene is under the control of the late/early promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an EcoRI to BamHI restriction fragment synthesized by reverse transcription and polymerase chain reaction (PCR) using genomic RNA from a U.S. Isolate of PRRS obtained from the NVSL (Reference strain, IA-2). To synthesize PRRS ORF7, the primer (5' GTCGAATTCGCCAAATAACAA CGGCAAGCAGCAGAAG 3'; 1/96.19) (SEQ ID NO 46) synthesized from the 5' end of the PRRS ORF7 gene, introduced an EcoRI site at the 5' end of the gene. The primer (5'-CAAGGATCCCAGCCCATCATGCTGAGG GTGATG-3'; 1/96.20) (SEQ ID NO 47) was used for reverse transcription and PCR and synthesized from the 3' end of the PRRS ORF7 gene. The PCR product was digested with EcoRI and BamHI to yield a fragment approximately 383 base pairs in length corresponding to the PRRS ORF7 gene. Fragment 3 is an approximately 3010 base pair BamHI to PvuII restriction fragment of plasmid PJF751 (11). Fragment 4 is an approximately 2149 base pair AccI to HindIII subfragment of the SPV HindIII fragment M. The AccI sites in fragments 1 and 4 were converted to unique NotI sites using NotI linkers.
S-SPV-093

S-SPV-093 is a swinepox virus that expresses at least two foreign genes. The gene for *E. coli* β-galactosidase (lacZ) and the gene for porcine reproductive and respiratory syndrome virus (PRRS) ORF3 were inserted into the SPV 617-48.1 ORF (a unique NotI restriction site has replaced a unique AccI restriction site). The lacZ gene is under the control of the synthetic late promoter (LP1), and the PRRS ORF3 gene is under the control of the synthetic late/early promoter (LP2EP2).

S-SPV-093 was derived from S-SPV-001 (Kasza Strain). This was accomplished utilizing the homology vector 839-58.9 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 093. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-093 was assayed for expression of PRRS-specific antigens using the BLACK PLAQUE SCREEN FOR FOREIGN GENE EXPRESSION IN RECOMBINANT SPV. Polyclonal swine anti-PRRS (NVSL) serum was shown to react specifically with S-SPV-093 plaques and not with S-SPV-003 negative control plaques. All S-SPV-093 observed plaques reacted with the antiserum indicating that the virus was stably expressing the PRRS ORF3 protein.

To confirm the expression of the PRRS ORF3 protein gene product, cells were infected with S-SPV-093 and samples of infected cell lysates and culture supernatants were subjected to SDS polyacrylamide gel electrophoresis. The gel was blotted and analyzed using the WESTERN BLOTTING PROCEDURE. A polyclonal swine anti-PRRS (NVSL) serum was used to detect expression of PRRS specific proteins. The cell lysate a nd culture supernatant from S-SPV-093 infected cells exhibited a band corresponding to 45 kd, which is the expected size of the PRRS ORF3 protein. ORF3 protein was shown to be secreted from infected cells into the culture media.

S-SPV-093 is useful as a vaccine in swine against PRRS infection. S-SPV-093 is also useful for expression of the PRRS ORF3 protein.
HOMOLOGY VECTOR 839-58.9.

The plasmid 839-58.9 was constructed for the purpose of inserting foreign DNA into SPV. It incorporates an *E. coli* β-galactosidase (lacZ) marker gene and a porcine reproductive and respiratory syndrome virus (PRRS) ORF3 gene flanked by SPV DNA. Upstream of the foreign gene is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a late promoter (LP1) and the PRRS ORF3 gene is under the control of the late/early promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an EcoRI to BamHI restriction fragment synthesized by reverse transcription and polymerase chain reaction (PCR) using genomic RNA from a U.S. Isolate of PRRS obtained from the NVSL (Reference strain, IA-2). To synthesize PRRS ORF3, the primer 5'-TTCGAATTCGGCTAATAGCTGTA CATTCCTCCATATTT-3'; 1/96.7) (SEQ ID NO 48) synthesized from the 5' end of the PRRS ORF3 gene, introduced an EcoRI site at the 5' end of the gene. The primer (5'-GG GGATCCTATCGCCGTACGGCACTGAGGG-3'; 1/96.8) (SEQ ID NO 49) was used for reverse transcription and PCR and synthesized from the 3' end of the PRRS ORF3 gene. The PCR product was digested with EcoRI and BamHI to yield a fragment approximately 768 base pairs in length corresponding to the PRRS ORF3 gene. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.
S-SPV-094

S-SPV-094 is a swinepox virus that expresses at least two foreign genes. The gene for E. coli β-galactosidase (lacZ) and the gene for porcine reproductive and respiratory syndrome virus (PRRS) ORF4 were inserted into the SPV 617-48.1 ORF (a unique NotI restriction site has replaced a unique AccI restriction site). The lacZ gene is under the control of the synthetic late promoter (LP1), and the PRRS ORF4 gene is under the control of the synthetic late/early promoter (LP2EP2).

S-SPV-094 was derived from S-SPV-001 (Kasza Strain) This was accomplished utilizing the homology vector 839-58.36 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 094. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-094 was assayed for expression of PRRS-specific antigens using the BLACK PLAQUE SCREEN FOR FOREIGN GENE EXPRESSION IN RECOMBINANT SPV. Polyclonal swine anti-PRRS (NVSL) serum was shown to react specifically with S-SPV-094 plaques and not with S-SPV-003 negative control plaques. All S-SPV-094 observed plaques reacted with the antiserum indicating that the virus was stably expressing the PRRS ORF4 protein.

To confirm the expression of the PRRS ORF4 protein gene product, cells were infected with S-SPV-094 and samples of infected cell lysates were subjected to SDS polyacrylamide gel electrophoresis. The gel was blotted and analyzed using the WESTERN BLOTTING PROCEDURE. A polyclonal swine anti-PRRS (NVSL) serum was used to detect expression of PRRS specific proteins. The cell lysate from S-SPV-094 infected cells exhibited a band corresponding to 31 kd, which is the expected size of the PRRS ORF4 protein (202 amino acids).

S-SPV-094 is useful as a vaccine in swine against PRRS infection. S-SPV-094 is also useful for expression of the PRRS ORF4 protein.
HOMOLOGY VECTOR 839-58.36.

The plasmid 839-58.36 was constructed for the purpose of inserting foreign DNA into SPV. It incorporates an E. coli β-galactosidase (lacZ) marker gene and a porcine reproductive and respiratory syndrome virus (PRRS) ORF4 gene flanked by SPV DNA. Upstream of the foreign gene is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a late promoter (LP1) and the PRRS ORF4 gene is under the control of the late/early promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an EcoRI to BamHI restriction fragment synthesized by reverse transcription and polymerase chain reaction (PCR) using genomic RNA from a U.S. Isolate of PRRS obtained from the NVSL (Reference strain, IA-2). To synthesize PRRS ORF4, the primer (5'-CC<u>GAATTC</u>GGCTGCGTCC CTT CTTTTCCTCATGG-3'; 1/96.11) (SEQ ID NO 50) synthesized from the 5' end of the PRRS ORF4 gene, introduced an EcoRI site at the 5' end of the gene. The primer (5' CT <u>GGATCC</u>TTCAAATTGCCAACAGAATTGGC A A AAA GAC-3'; 1/96.12) (SEQ ID NO 51) was used for reverse transcription and PCR and synthesized from the 3' end of the PRRS ORF4 gene. The PCR product was digested with EcoRI and BamHI to yield a fragment approximately 542 base pairs in length corresponding to the PRRS ORF4 gene. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.
S-SPV-095

S-SPV-095 is a swinepox virus that expresses at least two foreign genes. The gene for E. coli β-galactosidase (lacZ) and the gene for porcine reproductive and respiratory syndrome virus (PRRS) ORF5 were inserted into the SPV 617-48.1 ORF (a unique NotI restriction site has replaced a unique AccI restriction site). The lacZ gene is under the control of the synthetic late promoter (LP1), and the PRRS ORF5 gene is under the control of the synthetic late/early promoter (LP2EP2).

S-SPV-095 was derived from S-SPV-001 (Kasza Strain). This was accomplished utilizing the homology vector 839-58.43 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 095. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

To confirm the expression of the PRRS ORF5 protein gene product, cells were infected with S-SPV-095 and samples of infected cell lysates were subjected to SDS polyacrylamide gel electrophoresis. The gel was blotted and analyzed using the WESTERN BLOTTING PROCEDURE. A polyclonal swine anti-PRRS (NVSL) serum was used to detect expression of PRRS specific proteins. The cell lysate from S-SPV-095 infected cells exhibited a band corresponding to 26 kd, which is the expected size of the PRRS ORF5 protein.

S-SPV-095 is useful as a vaccine in swine against PRRS infection. S-SPV-095 is also useful for expression of the PRRS ORF5 protein.
HOMOLOGY VECTOR 839-58.43.

The plasmid 839-58.43 was constructed for the purpose of inserting foreign DNA into SPV. It incorporates an E. coli β-galactosidase (lacZ) marker gene and a porcine reproductive and respiratory syndrome virus (PRRS) ORF5 gene flanked by SPV DNA. Upstream of the foreign gene is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a late promoter (LP1) and the PRRS ORF5 gene is under the control of the late/early promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an EcoRI to BamHI restriction fragment synthesized by reverse transcription and polymerase chain reaction (PCR) using genomic RNA from a U.S. Isolate of PRRS obtained from the NVSL (Reference strain, IA-2). To synthesize PRRS ORF5, the primer (5'-TTGAATTCGTTGGAGAAATGC TTGACCGCGGGC-3'; 1/96.13) (SEQ ID NO 52 (synthesized from the 5' end of the PRRS ORF5 gene, introduced an EcoRI site at the 5' end of the gene. The primer (5'-GAAGGATCCTAAGGACGACCCCATTGTT CCGCTG-3'; 1/96.14) (SEQ ID NO 53) was used for reverse transcription and PCR and synthesized from the 3' end of the PRRS ORF5 gene. The PCR product was digested with EcoRI and BamHI to yield a fragment approximately 606 base pairs in length corresponding to the PRRS ORF5 gene. Fragment 3 is an approximately 3010 base pair BamHI to PvuII restriction fragment of plasmid pJF751 (11). Fragment 4 is an approximately 2149 base pair AccI to HindIII subfragment of the SPV HindIII fragment M. The AccI sites in fragments 1 and 4 were converted to unique NotI sites using NotI linkers.

S-SPV-076

S-SPV-076 is a swinepox virus that expresses at least two foreign genes. The gene for *E. coli* β-galactosidase (lacZ) and the gene for pseudorabies virus (PRV) glycoprotein D (gD) and glycoprotein I (gI) were inserted into the SPV 617-48.1 ORF (a unique NotI restriction site has replaced a unique AccI restriction site). The lacZ gene is under the control of the synthetic late promoter (LP1), and the PRV gD and gI gene is under the control of the synthetic late/early promoter (LP2EP2).

S-SPV-076 was derived from S-SPV-001 (Kasza Strain). This was accomplished utilizing the homology vector 829-55.16 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-076. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-076 was assayed for expression of PRV-specific antigens using the BLACK PLAQUE SCREEN FOR FOREIGN GENE EXPRESSION IN RECOMBINANT SPV. Polyclonal swine anti-PRV serum was shown to react specifically with S-SPV-076 plaques and not with S-SPV-003 negative control plaques. All S-SPV-076 observed plaques reacted with the antiserum indicating that the virus was stably expressing the PRV gD protein.

S-SPV-076 is useful as a vaccine in swine against PRV infection. S-SPV-076 is also useful for expression of the PRV gD and gI proteins.

HOMOLOGY VECTOR 829-55.16.

The plasmid 829-55.16 was constructed for the purpose of inserting foreign DNA into SPV. It incorporates an *E. coli* β-galactosidase (lacZ) marker gene and a pseudorabies virus (PRV) glycoprotein D (gD) and glycoprotein I (gI) gene flanked by SPV DNA. Upstream of the foreign gene is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a late promoter (LP1) and the PRV gD and gI genes are under the control of the late/early promoter (LP2EP2). The homology vector was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII restriction fragment M (23). Fragment 2 is an approximately 500 base pair EcoRI to SalI restriction fragment derived from plasmid 538-46.16 (See WO95/03070). Fragment 3 is an approximately 1900 base pair SalI to BamHI restriction subfragment of PRV BamHI#7 genomic DNA fragment. Fragment 4 is an approximately 3010 base pair BamHI to PvuII restriction fragment of plasmid pJF751 (11). Fragment 5 is an approximately 2149 base pair AccI to HindIII subfragment of the SPV HindIII fragment M. The AccI sites in fragments 1 and 5 were converted to unique NotI sites using NotI linkers.

S-SPV-079

S-SPV-079 is a swinepox virus that expresses two foreign genes. The gene for *E. coli* β-galactosidase (lacZ) and the gene for pseudorabies virus (PRV) glycoprotein B (gB) were inserted into the unique HindIII restriction site (HindIII linkers inserted into a unique NdeI site in the SPV 01L open reading frame; An approximately 545 base pair NdeI to NdeI subfragment (Nucleotides 1560 to 2104; SEQ ID NO. 189) of the SPV HindIII M fragment has been deleted). The lacZ gene is under the control of the synthetic late promoter (LP1), the PRV gB gene is under the control of the synthetic late/early promoter (LP2EP2). S-SPV-079 contains a PRV gB gene which codes for a protein of 913 amino acids, including 69 amino acids at the carboxy terminus which are missing in the PRV gB gene of S-SPV-015.

S-SPV-079 was derived from S-SPV-001 (Kasza Strain). This was accomplished utilizing the homology vector 825-84.3 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV 079. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-079 was assayed for expression of PRV-specific antigens using the BLACK PLAQUE SCREEN FOR FOREIGN GENE EXPRESSION IN RECOMBINANT SPV. Polyclonal swine anti-PRV serum was shown to react specifically with S-SPV-079 plaques and not with S-SPV-003 negative control plaques. A1 1 S-SPV-079 observed plaques reacted with the antiserum indicating that the virus was stably expressing the PRV gB protein.

To confirm the expression of the PRV gB gene product, cells were infected with S-SPV-079 and samples of infected cell lysates were subjected to SDS polyacrylamide gel electrophoresis. The gel was blotted and analyzed using the WESTERN BLOTTING PROCEDURE. A polyclonal swine anti-PRV serum was used to detect expression of PRV specific proteins. The cell lysate from S-SPV-079 infected cells exhibited bands corresponding to 120 kd gB precursor and the 67 kd and 58 kd processed forms, which are the expected size of the PRV gB protein. PRV gB exists as a disulfide linked complex of these three forms.

S-SPV-079 is useful as a vaccine in swine against PRV infection. S-SPV-079 is also useful for expression of the PRV gB protein.

HOMOLOGY VECTOR 825-84.3.

The plasmid 825-84.3 was constructed for the purpose of inserting foreign DNA into SPV. It incorporates an *E. coli* β-galactosidase (lacZ) marker gene and the pseudorabies virus (PRV) glycoprotein B (gB) gene flanked by SPV DNA. Upstream of the foreign genes is an approximately 1532 base pair fragment of SPV DNA. Downstream of the foreign genes is an approximately 1560 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a synthetic late pox promoter (LP1), the PRV gB gene is under the control of a synthetic late/early pox promoter (LP2EP2). It was constructed utilizing standard recombinant DNA techniques (22, 30), by joining restriction fragments from the following sources with the synthetic DNA sequences. The plasmid vector was derived from an approximately 2972 base pair HindIII to BamHI restriction fragment of pSP64 (Promega). Fragment 1 is an approximately 1532 base pair BglII to NdeI restriction sub-fragment of the SPV HindIII restriction fragment M (23). Fragment 2 is an approximately 2600 base pair EcoRI to SalI fragment derived from plasmid 727-54.60. Fragment 2 contains approximately 43 base pairs of synthetic DNA coding for PRV gB amino acids 1 to 16 and an approximately 2600 base pair SmaI to SalI fragment of PRV KpnI C genomic DNA. Fragment 3 is an approximately 210 base pair SalI to BamHI fragment generated by PCR which contains the coding sequence of the PRV gB gene. Fragment 3 contains the carboxy terminal 69 amino acids of PRV gB which are missing from S-SPV-015. Fragment 3 is an approximately SalI to BamHI restriction fragment synthesized by polymerase chain reaction (PCR) using template DNA from PRV KpnI C genomic DNA. The primer (5' ATGAAGGCCCTGTACC CCGTCACGA-3'; 11/95.3) (SEQ ID NO 54) synthesized across the SalI of the PRV gB gene and reproduced a SalI site internal to the gB gene. The primer (5'-CGGGATCCG GCTACAGGGCGTCGGGGTCCTC3'-3'; 11/95.4) (SEQ ID NO 55) was used for PCR and synthesized from the 3' end of the PRV gB gene and introduced a BamHI site at the 3' end of the PRV gB gene. The PCR product was digested with SalI and BamHI to yield a fragment approximately 210 base pairs in length corresponding to the carboxy terminus of the PRV gB gene. Fragment 4 is an approximately 3010 base pair BamHI to PvuII restriction fragment of plasmid pJF751 (11). Fragment 5 is an approximately 1560 base pair NdeI to HindIII subfragment of the SPV HindIII fragment M. The NdeI sites in fragments 1 and 5 were converted to unique HindIII sites using HindIII linkers. An approximately 545 base pair NdeI to NdeI subfragment (Nucleotides 1560 to 2104; SEQ ID NO. 189) of the SPV HindIII M fragment has been deleted which would span SPV fragments 1 and 5.

S-SPV-090:

S-SPV-090 is a swinepox virus that expresses at least two foreign genes. The gene for *E. coli* β-galactosidase (lacZ) and the gene for pseudorabies virus (PRV) glycoprotein I (gI) were inserted into the 738-94.4 ORF (a 773 base pair deletion of the SPV 01L ORF; Deletion of nucleotides 1679 to 2452, SEQ ID NO: 189). The lacZ gene is under the control of the swinepox 01L promoter, and the PRV gI gene is under the control of the synthetic late/early promoter (LP2EP2).

S-SPV-090 was derived from S-SPV-001 (Kasza Strain) This was accomplished utilizing the homology vector 837-58.14 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-090. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-090 is useful as a vaccine in swine against PRV infection. S-SPV-090 is also useful for expression of the PRV gI protein.

HOMOLOGY VECTOR 837-58.14.

The plasmid 837-58.14 was constructed for the purpose of inserting foreign DNA into SPV. It incorporates an *E. coli* β-galactosidase (lac Z) marker gene and an pseudorabies virus (PRV) glycoprotein I (gI) gene flanked by SPV DNA. Upstream of the foreign gene is an approximately 855 base pair fragment of SPV DNA. Downstream of the foreign genes is an approximately 1113 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β galactosidase (lacZ) marker gene is under the control of a swinepox virus 01L gene promoter and the PRV gI gene is under the control of the late/early promoter (LP2EP2). The LP2EP2 PRV gI gene cassette was inserted into a NotI site of homology vector 752-22.1. Homology vector 840-72.A1 was constructed utilizing standard recombinant DNA techniques (22, 30), by joining restriction fragments from the following sources with the synthetic DNA sequences. The plasmid vector was derived from an approximately 2519 base pair HindIII to SphI restriction fragment of pSP65 (Promega). Fragment 1 is an approximately 855 base pair sub-fragment of the SPV HindIII restriction fragment M (23) synthesized by polymerase chain reaction using DNA primers 5' GAAGCATGCCCGTTCTTATCAATAGTTTAG TCGAAAATA-3' (SEQ ID NO: 73) and 5'-CATAAG ATCTGGCATTGTGTTATTATACTAACAAAAATAAG-3' (SEQ ID NO: 74) to produce an 855 base pair fragment with SphI and BglII ends. Fragment 2 is a 3002 base pair BamHI to PvuII fragment derived from plasmid pJF751 (49) containing the E. coli lacZ gene. Fragment 3 is an approximately 1150 base pair BamHI fragment coding for the PRV gI gene derived by polymerase chain reaction (PCR) (Sambrook, et al., 1989) using the PRV BamHI#7 DNA fragment (pSY 138.-09.W) as template for the PCR reaction. To synthesize PRV gI, the primer (5'-CCGGATCCGGCGCGCGAC GTGACCCGGCTC-3'; 11/95.1) (SEQ ID NO 56) synthesized from the 5' end of the PRV gI gene and introduced a BamHI site at the 5' end of the gene. The primer (5'-CC GGATCCGCGGACGGAGATAAAACGCCACCC A C-3'; 11/95.2) (SEQ ID NO 57) synthesized from the 3' end of the PRV gI gene and introduced a BamHI site at the 3' end of the gene. The PCR product was digested with BamHI to yield a fragment approximately 1150 base pairs in length corresponding to the PRV gI gene. Fragment 4 is an approximately 1113 base pair subfragment of the SPV HindIII fragment M synthesized by polymerase chain reaction using DNA primers 5'-CCGTAGTCGACAAAGATCGACTTA TTAATATGTATGGGATT-3' (SEQ ID NO: 75) and 5' GCCTGAAGCTTCTAGTACAGTATTTACGACTTTT GAAAT-3' (SEQ ID NO: 76) to produce an 1113 base pair fragment with SalI and HindIII ends.

Example 44

Homology Vectors Useful for Inserting Foreign DNA into the SPV HindIII K Genomic Region of a Recombinant Swinepox Virus Plasmid 854-90.1 was constructed for insertion of foreign DNA into a recombinant swinepox virus. Plasmid 854-90.1 was constructed by changing the unique Eco RI site within the SPV Hind III K genomic fragment (Nucleotides: SEQ ID NO: 1) to a unique Not I restriction site through use of a DNA linker. The homology vector 854-90.1 contains an 1652 base pair region of SPV DNA upstream of the Not I insertion site and 5058 base pair region of SPV DNA downstream of the Not I insertion site. A homology vector containing foreign DNA inserted into plasmid 854-90.1 is useful when combined with swinepox virus DNA by HOMOLOGOUS RECOMBINATION for the construction of recombinant swinepox viruses.

Plasmid 855-37.5 was constructed for insertion of foreign DNA into a recombinant swinepox virus. Plasmid 855-37.5 was constructed by inserting an approximately 1875 base pair Dra I restriction fragment within swinepox virus HindIII K genome fragment from plasmid 854-90.1 containing the unique Not I insertion site, into plasmid PNEB193. The homology vector 855-37.5 contains an approximately 881 base pair region of SPV DNA upstream of the Not I insertion site and an approximately 994 base pair region of SPV DNA downstream of the Not I insertion site. The total size of homology vector 855-37.5 is approximately 3.9 kb making it ideal for the insertion of two or more foreign genes into the homology vector and by homologous recombination into a recombinant swinepox virus.

Plasmid 847-42.2C was constructed for insertion of foreign DNA into a recombinant swinepox virus. Plasmid 847-42.2C was constructed by inserting the uidA gene into the unique EcoRI site within the SPV HindIII K genomic fragment. The uidA gene is under the control of the synthetic pox promoter, EP2. Additional foreign DNA is inserted upstream of the uidA gene into unique restriction sites NotI, SfiI and XhoI.

Plasmid 847-42.7B was constructed for insertion of foreign DNA into a recombinant swinepox virus. Plasmid 847-42.2C was constructed by inserting the uidA gene into the unique EcoRI site within the SPV HindIII K genomic fragment. The uidA gene is under the control of the synthetic early promoter, EP2. Additional foreign DNA is inserted downstream of the uidA gene into unique restriction sites NotI, SfiI and XhoI.

S-SPV-120:

S-SPV-120 is a swinepox virus that expresses two foreign genes. The gene for E. coli β-galactosidase (lacZ) was inserted a unique AccI restriction site in the 01L ORF of the SPV HindIII M fragment. The gene for E. coli β-glucuronidase (uidA) was inserted into a unique NotI site (NotI linkers inserted into a unique EcoRI restriction site within an approximately 3.2 kb region (SEQ ID NO: 1) of the 6.7 kb SPV HindIII K fragment). The lacZ gene is under the control of the synthetic late promoter (LP1), the uidA gene is under the control of the synthetic early promoter (EP2).

S-SPV-120 was derived from S-SPV-003 (Kasza Strain). This was accomplished utilizing the homology vector 847-42.2C (see above) and virus S-SPV-003 in the HOMOLOGOUS RECOMBINATION PROCEDURE FOR GENERATING RECOMBINANT SPV. The transfection stock was screened by, the SCREEN FOR RECOMBINANT SPV EXPRESSING β-galactosidase or β-glucuronidase (BLUOGAL AND CPRG ASSAYS and SCREEN FOR RECOMBINANT HERPESVIRUS EXPRESSING ENZYMATIC MARKER GENES). The final result of red plaque purification was the recombinant virus designated S-SPV 120. This virus was assayed for β-galactosidase and β-glucuronidase expression, purity, and insert stability by multiple passages monitored by the blue plaque assay as described in Materials and Methods. After the initial three rounds of purification, all plaques observed are blue indicating that the virus is pure, stable, and expressing the foreign genes.

S-SPV-120 is useful for inserting additional foreign DNA sequences into recombinant swinepox virus using white plaque selection in the presence of BLUOGAL or X-GLUC to selection for foreign DNA insertion into the unique AccI restriction site in the 01L ORF of the SPV HindIII M fragment and the unique EcoRI restriction site within an approximately 3.2 kb region of the 6.7 kb SPV HindIII K fragment.

Some examples of recombinant swinepox viruses expressing foreign DNA in the unique AccI restriction site in the 01L ORF of the HindIII M fragment and the unique EcoRI restriction site within an approximately 3.2 kb region of the 6.7 kb SPV HindIII K fragment are: Recombinant SPV expressing swine influenza virus hemagglutinin, neuraminidase, and nucleoprotein; Recombinant SPV expressing porcine reproductive and respiratory disease virus ORF 5 and ORF6; Recombinant SPV expressing porcine reproductive and respiratory disease virus ORF2, ORF3, ORF4, ORF 5 and ORF6; Recombinant SPV expressing feline immunodeficiency virus gag/protease and envelope; Recombinant SPV expressing feline leukemia virus gag/protease and envelope; Recombinant SPV expressing feline immunodeficiency virus gag/protease and envelope and feline leukemia virus gag/protease and envelope; Recombinant SPV expressing infectious bovine rhinotracheitis glycoprotein B, glycoprotein D, and glycoprotein I.

Additional examples of foreign DNA insertion sites in recombinant swinepox virus are exemplified by, but not limited to, one or more of the following: the unique AccI restriction site in the 01L ORF of the SPV HindIII M fragment; the unique NdeI restriction site in the 01L ORF of the SPV HindIII M fragment (See Example S-SPV-052); the unique BglII restriction site within the 2.0 kb BglII to HindIII subfragment of the SPV HindIII M fragment (See Example S-SPV-047); the unique EcoRI restriction site within an approximately 3.2 kb region of the 6.7 kb SPV HindIII K fragment (See Example S-SPV-059); the unique XhoI restriction site within the SPV HindIII J fragment (See Example S-SPV-064); the unique BglII restriction site within the SPV HindIII N fragment (See Example S-SPV-062); the unique EcoRV restriction site within the SPV HindIII N fragment (See Example S-SPV-060); the unique SnaBI restriction site within the SPV HindIII N fragment (See Example S-SPV-061).

Example 45

Recombinant Swinepox Virus Expressing Swine Influenza Virus Genes in the SPV HindIII M and SPV HindIll K Insertion Sites A recombinant swinepox virus expresses four foreign genes. The gene for swine influenza virus (SIV) hemaglutinin (HA) (H1N1) and the gene for E. coli β-galactosidase (lacZ) were inserted into the SPV 617-48.1 ORF (a unique NotI restriction site has replaced a unique AccI restriction site). The gene for swine influenza virus (SIV) neuraminidase (NA) and the gene for E. coli β-glucuronidase (uidA) were inserted into a unique NotI site (NotI linkers inserted into a unique EcoRI restriction site within an approximately 3.2 kb region (SEQ ID NO: 1) of the 6.7 kb SPV HindIII K fragment). The SIV HA (H1N1) gene is under the control of the synthetic late/early promoter (LP2EP2), the SIV NA gene is under the control of the synthetic late/early promoter (LP2EP2), the lacZ gene is under the control of the synthetic late promoter (LP1), and the uidA gene is under the control of the synthetic early promoter (EP2).

The recombinant swinepox virus expressing swine influenza virus genes in the SPV HindIII M and SPV HindIII K insertion sites is derived from S-SPV-065 (Kasza Strain). This is accomplished utilizing the homology vector (with the SIV NA and E. coli uidA genes inserted into a unique NotI site in plasmid 855-37.5 (see above)) and virus S-SPV-065 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase or β-glucuronidase (BLUOGAL AND CPRG ASSAYS and SCREEN FOR RECOMBINANT HERPESVIRUS EXPRESSING ENZYMATIC MARKER GENES). The final result of red plaque and blue plaque purification is the recombinant swinepox virus. This virus was assayed for β-galactosidase and β-glucuronidase expression, purity, and insert stability by multiple passages monitored by the blue plaque assay as described in Materials and Methods. After the initial three rounds of purification, all plaques observed are blue indicating that the virus is pure, stable, and expressing the foreign genes.

Recombinant swinepox virus expressing swine influenza virus genes in the SPV HindIII M and SPV HindIII K insertion sites is useful as a vaccine in swine against SIV infection and is also useful for expression of the SIV HA and NA proteins.

S-SPV-121:

S-SPV-121 is a swinepox virus that expresses at least one foreign gene. The gene for swine influenza virus (SIV) hemagluttinin (HA) (H1N1) was inserted into a a unique NotI site (NotI linkers inserted into a unique EcoRI restriction site within an approximately 3.2 kb region (SEQ ID NO: 1) of the 6.7 kb SPV HindIII K fragment). The SIV HA gene is under the control of the synthetic late/early promoter (LP2EP2).

S-SPV-121 is derived from S-SPV-059 (Kasza Strain) This is accomplished utilizing the homology vector with the SIV HA gene into a unique NotI site in plasmid 855-37.5 (see above) and virus S-SPV-059 in the HOMOLOGOUS RECOMBINATION PROCEDURE FOR GENERATING RECOMBINANT SPV. The transfection stock was screened by the SCREEN FOR RECOMBINANT SPV EXPRESSING ENZYMATIC MARKER GENES (X-GLUC ASSAY). The final result of white plaque purification is the recombinant virus designated S-SPV-121. This virus is assayed for the absence of β-glucuronidase expression, purity, and insert stability by multiple passages monitored by the blue plaque assay as described in Materials and Methods. After the initial three rounds of purification, all plaques observed are white indicating that the virus is pure, stable, and expressing the foreign genes.

S-SPV-121 is useful as a vaccine in swine against SIV infection S-SPV-121 is also useful for expression of the SIV HA protein.

S-SPV-122:

S-SPV-122 is a swinepox virus that expresses two foreign genes. The gene for swine influenza virus (SIV) hemagluttinin (HA) (H1N1) and neuraminidase (NA) were inserted into a unique NotI site (NotI linkers inserted into a unique EcoRI restriction site within an approximately 3.2 kb region (SEQ ID NO: 1) of the 6.7 kb SPV HindIII K fragment). The SIV HA gene is under the control of the synthetic late/early promoter (LP2EP2) and the SIV NA gene is under the control of the synthetic early late promoter (EP2LP2).

S-SPV-122 is derived from S-SPV-059 (Kasza Strain) This is accomplished utilizing the homology vector with the SIV HA and NA genes inserted into a unique NotI site in plasmid 855-37.5 (see above) and virus S-SPV-059 in the HOMOLOGOUS RECOMBINATION PROCEDURE FOR GENERATING RECOMBINANT SPV. The transfection stock was screened by the SCREEN FOR RECOMBINANT HERPESVIRUS EXPRESSING ENZYMATIC MARKER GENES. The final result of white plaque purification is the recombinant virus designated S-SPV-122. This virus is assayed for the absence of β-glucuronidase expression, purity, and insert stability by multiple passages monitored by the blue plaque assay as described in Materials and Methods. After the initial three rounds of purification, all plaques observed are white indicating that the virus is pure, stable, and expressing the foreign genes.

S-SPV-122 is useful as a vaccine in swine against SIV infection S-SPV-122 is also useful for expression of the SIV HA and NA proteins.

Example 46

Recombinant Swinepox Virus Expressing Porcine Reproductive and Respiratory Syndrome Virus Genes in the SPV HindIII M and SPV HindIII K Insertion Sites A recombinant swinepox virus expresses four foreign genes. The gene for porcine reproductive and respiratory syndrome virus (PRRS) ORF5 and the gene for E. coli β-galactosidase (lacZ) were inserted into the SPV 617-48.1 ORF (a unique NotI restriction site has replaced a unique AccI restriction site). The gene for porcine reproductive and respiratory syndrome virus (PRRS) ORF6 and the gene for E. coli β-glucuronidase (uidA) were inserted into a unique NotI site (NotI linkers inserted into a unique EcoRI restriction site within an approximately 3.2 kb region (SEQ ID NO: 1) of the 6.7 kb SPV HindIII K fragment). The PRRS ORF5 gene is under the control of the synthetic late/early promoter (LP2EP2), the PRRS ORF6 gene is under the control of the synthetic late/early promoter (LP2EP2), the lacZ gene is under the control of the synthetic late promoter (LP1), and the uidA gene is under the control of the synthetic early promoter (EP1), The recombinant swinepox virus expressing porcine reproductive and respiratory syndrome virus virus genes in the SPV HindIII M and SPV HindIII K insertion sites is derived from S-SPV-095 (Kasza Strain). This is accomplished utilizing the homology vector (with the PRRS ORF6 and E. coli uidA genes inserted into a unique NotI site in plasmid 855-37.5 (see above)) and virus S-SPV-095 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase or β-glucuronidase (BLUOGAL AND CPRG ASSAYS and SCREEN FOR RECOMBINANT HERPESVIRUS EXPRESSING ENZYMATIC MARKER GENES). The final result of red plaque and blue plaque purification is the recombinant swinepox virus. This virus was assayed for β-galactosidase and β-glucuronidase expression, purity, and insert stability by multiple passages monitored by the blue plaque assay as described in Materials and Methods. After the initial three rounds of purification, all plaques observed are blue indicating that the virus is pure, stable, and expressing the foreign genes.

A recombinant swinepox virus expresses four foreign genes. The gene for porcine reproductive and respiratory syndrome virus (PRRS) ORF6 and the gene for E. coli B-galactosidase (lacZ) are inserted into the SPV 617-48.1 ORF (a unique NotI restriction site has replaced. a uniques AccI restriction site.) The gene for porcine reproductive and respiratory system virus (PRRS) ORF5 and the gene for E. coli B-glucuronidase (uidA) are inserted into a unique NotI site (NotI linkers inserted into a unique EcoRI restriction site within an approximately 3.2 kb region (SEQ ID NO 1) of the 6.7 kb SPV HindIII k fragment). The PRRS ORF6 gene is under the control of the synthetic late/early promoter (LP2EP2), the PRRS ORF5 gene is under the control of the synthetic late/early promoter (LP2EP2), the lacZ gene is under the control of the synthetic late promoter (LP1), and the uidA gene is under the control of the synthetic early promoter (EP2).

The recombinant swinepox virus expressing porcine reproductive and respiratory syndrome virus virus genes in the SPV HindIII M and SPV HindIII K insertion sites is derived from S-SPV-084 (Kasza Strain). This is accomplished utilizing the homology vector (with the PRRS ORF5 and E. coli uidA genes inserted into a unique NotI site in plasmid 855-37.5 (see above) and virus S-SPV-084 in the HOMOLOGOUS RECOMBINATION PROCEDURE FOR GENERATING RECOMBINANT SPV. The transfection stock in screened by the SCREEN FOR RECOMBINANT SPV EXPRESSING B-galactosidase or B-glucuronidase (BLUOGAL AND CPRG ASSAYS and SCREEN FOR RECOMBINANT HERPESVIRUS EXPRESSING ENZYMATIC MARKER GENES). The final result of red plaque and blue plaque purification is the recombinant swinepox virus. This virus is assayed for B-galactosidase and B-glucuronidase expression, purity, and insert stability by multiple passages monitored by the blue plaque assay as described in Materials and Methods. After the initial three rounds of purification, all plaques observed are blue indicating that the virus is pure, stable, and expressing the foreign genes.

The recombinant swinepox virus expressing porcine reproductive and respiratory syndrome virus genes in the SPV HindIII M and SPV HindIII K insertion sites is useful as a vaccine in swine against PRRS infection and is also useful for expression of the PRRS ORF5 and ORF6 protein.

Example 47
Recombinant Swinepox Virus Expressing Bovine Viral Diarrhea Virus Type 1 and Type 2 Genes in the SPV HindIII M and SPV HindIII K Insertion Sites
S-SPV-132

S-SPV-132 is a recombinant swinepox virus which expresses four foreign genes. The gene for bovine viral diarrhea virus type 1 (BVDV-1) glycoprotein 53 (gp53) and the gene for E. coli B-galactosidase (lacZ) are inserted into the SPV 617-48.1 ORF (a unique NotI restriction site has replaced a unique AccI restriction site.) The gene for bovine viral diarrhea virus type 2 (BVDV-2) glycoprotein 53 (gp53) and the gene for E. coli B-glucuronidase (uidA) are inserted into a unique NotI site (NotI linkers are inserted into a unique EcoRI restriction site within an approximately 3.2 kb region (SEQ ID NO 1) OF THE 6.7 KB SPV HindIII K fragment). Teh BVDV-1 gp53 gene and the BVDV-2 gp53 gene are under the control of the synthetic late/early promoter (LP2EP2), the lacZ gene is under the control of the synthetic late promoter (LP1), and the uidA gene is under the control of the synthetic early promoter (EP2).

S-SPV-132 is derived from S-SPV-051 (Kasza Strain) This is accomplished utilizing the homology vector (with the BVDV-2 gp53 and E. coli uidA genes inserted into a unique NotI site in plasmid 855-37.5 (see above)) and virus S-SPV-051 in the HOMOLOGOUS RECOMBINATION PROCEDURE FOR GENERATING RECOMBINANT SPV. The transfection stock is screened by the SCREEN FOR RECOMBINANT SPV EXPRESSING B-galactosidase or B-glucuronidase (BLUOGAL AND CPRG ASSAYS and SCREEN FOR RECOMBINANT HERPESVIRUS EXPRESSING ENZYMATIC MARKER GENES). The final result of red plaque and blue plaque purification is the recombinant swinepox virus. This virus is assayed for B-galactosidase and B-glucuronidase expression, purity, and insert stability by multiple passages monitored by the blue plaque assay as described in Materials and Methods. After the initial three rounds of purification, all plaques observed are blue indicating that the virus is pure, stable, and expressing the foreign genes.

S-SPV-132 is useful as a vaccine in swine against BVDV infection and is also useful for expression of the BVDV-1 gp53 and BVDV-2 gp53.

REFERENCES

1. C. Bertholet, et al., *EMBO Journal* 5, 1951–1957 (1986).
2. R. A. Bhat, et al., *Nucleic Acids Research* 17, 1159–1176 (1989).
3. D. A. Boyden, et al., *Infection and Immunity* 57, 3808–3815 (1989).
4. D. B. Boyle and B. E. H. Coupar, *Virus Research* 10, 343–356 (1988).
5. R. M. Buller, et al., *Nature* 317, 813–815 (1985).
6. K. J. Cremer, et al., *Science* 228, 737–739 (1985).
7. A. J. Davidson and B. Moss, *J. Mol. Biol.* 210, 749–769 (1989).
8. A. J. Davidson and B. Moss, *J. Mol. Biol.* 210, 771–784 (1989).
9. P. L. Earl, et al., *Journal of Virology* 64, 2448–2451 (1990).
10. J. J. Esposito, et al., *Virology* 165, 313 (1988).

11. F. A. Ferrari, et al., *J. of Bacteriology* 161, 556–562 (1985).
12. C. Flexner, et al., *Vaccine* 8, 17–21 (1990).
13. S. J. Goebel, et al., *Virology* 179, 247–266 (1990).
14. U. Gubler and B. J. Hoffman, *Gene* 25, 263–269 (1983).
15. M. A. Innis, et al., *PCR Protocols A Guide to Methods and Applications*, 84–91, Academic Press, Inc., San Diego (1990).
16. S. Joshi, et al., *Journal of Virology.* 65, 5524–5530 (1991).
17. L. Kasza, et al., *Am. J. Vet. Res.* 21, 269–273 (1960).
18. L. Kasza, Diseases of Swine, 254–260, Ed. A. D. Leman, et al., The Iowa State University Press, Ames, Iowa (1981).
19. B. G. Klupp and T. C. Mettenleiter, *Virology* 182, 732–741 (1991).
20. U. K. Laemnli, *Nature* 227, 680–685 (1970).
21. B. Lominiczi, et al., *Journal of Virology* 49, 970–979 (1984).
22. T. Maniatis, et al., *Molecular Cloning: A Laboratory Manual*, Cold Spring Harbor Press, Cold Spring Harbor, N.Y. (1982).
23. R. F. Massung, and R. W. Moyer, *Virology* 180, 347–354 (1991).
24. R. F. Massung, and R. W. Moyer, *Virology* 180, 355–364 (1991).
25. B. Moss, *Science* 252, 1662–1667 (1991).
26. E. A. Petrovskis, et al., *Journal of Virology* 59, 216–223 (1986).
27. A. K. Robbins et al., *Journal of Virology* 58, 339–347 (1986).
28. A. K. Robbins et al., *Journal of Virology* 61, 2691–2701 (1987).
29. A. C. R. Samson, *Journal of Virology* 67, 1199–1203 (1986).
30. J. Sambrook, et al., *Molecular Cloning A Laboratory Manual Second Edition*, Cold Spring Harbor Press, Cold Spring Harbor, N.Y. (1989).
31. Sheffy, et al., *Proceedings 65th Annual Meeting of the United States Livestock Association* 65, 347–353 (1961).
32. W. M. Schnitzlein and D. N. Tripathy, *Virology* 181, 727–732, (1991).
33. J. Taylor, et al., *Vaccine* 9, 190–193, (1991).
34. M. Wachsman, et al., *Journal of General Virology* 70, 2513–2520 (1989).
35. M. W. Wathen, et al., *Journal of Virology* 51, 57–62 (1984).
36. M. Weerasinge, *Journal of Virology* 65, 5531–5534 (1991).
37. T. Ben-Porat, et al., *Journal of Virology*, volume 154, 325–334 (1986).
38. F. Zuckerman, et al., *Vaccination and Control of Adjesky's Disease*, J. T. Van Oirchot (ed.). Kluwer Academic Publishers, London, pp. 107–117 (1989).
39. Paolette, et al., *Journal of Virology*, volume 66, pp. 3424–3434 (June, 1992).
40. M. W. Mellencamp, et al., *Journal of Clinical Microbiology*, volume 27, pp. 2208–2213 (1989).
41. L. A. Herzenberg, et al., *Selected Methods in Cellular Immunology*, Freeman Publ. Co., San Francisco, 351–372 (1980).
42. Katz et al., *Journal of Virology* 64, 1808–1811 (1990).
43. Taniguchi, T., et al., *Biochem. Biophys. Res. Commun.* 115 1040–1047 (1983).
44. Cochran, M. D. and Macdonald, R. D., WO 93/02104, published Feb. 4, 1993.
45. Galibert, F., et al., *Nature* 281, 646–650 (1979).
46. Thomsen, D. R., et al., *Proc. Natl. Acad. Sci. USA* 81, 659–663 (1984).
47. Catalog Number 267402, Beckman Instruments, Inc., Fullerton Calif.
48. Whalley, J. M., et al., *Journal of General Virology* 57 307–323 (1981).
49. Collett, M. S., et al., *Virology* 1.65 200–208 (1988).
50. Schodel, F. et al., *Journal of Virology* 66, 106–114 (1992).
51. Cochran, M. D., WO 93/25665, published Dec. 23, 1993.
52. C. A. Hjerpe, *The bovine Respiratory Disease Complex.* Ed. by J. L. Howard, Philadelphia, W. B. Saunders Co., 670–680 (1986).
53. F. Fenner, et al., *Veterinary Virology.* Academic Press, Inc., Orlando Fla., 183–202 (1987).
54. A. Leutz, et al., EMBO Journal 8: 175–182 (1989).
55. M. J. Sekellick, et al., Journal of Interferon Research 14: 71–79 (1994).
56. S. J. Child, et al., Virology 174: 625–629 (1990).
57. G. P. Johnson, et al. Virology 196: 381–401 (1993).
58. R. F Massung, et al. Virology 201: 215–240 (1994).
60. Child, S. J. et al., Virology 174, 625–629 (1990).
61. T. R. Phillips, et al., J. Virology 64, 4605–4613 (1990).
62. Digby, M. R., and Lowenthal, J. W., Journal of Interferon and Cytokine Research 15: 939 (1996).
63. G. J. Winston et al., Proc. Natl. Acad. Sci. USA 90: 1272 (1993).

SEQUENCE LISTING

<160> NUMBER OF SEQ ID NOS: 231

<210> SEQ ID NO 1
<211> LENGTH: 3164
<212> TYPE: DNA
<213> ORGANISM: Swinepox virus
<220> FEATURE:
<221> NAME/KEY: CDS
<222> LOCATION: (1)..(231)
<221> NAME/KEY: CDS
<222> LOCATION: (339)..(1628)
<221> NAME/KEY: CDS
<222> LOCATION: (1683)..(3161)

<400> SEQUENCE: 1

```
aag ctt ctc aat tat gat aat ttt tta aga tta aaa aat tta gta atg        48
Lys Leu Leu Asn Tyr Asp Asn Phe Leu Arg Leu Lys Asn Leu Val Met
  1               5                  10                  15 tat gga tca cat ata gaa aat att atc aaa aat aca tat atg tat tat        96
Tyr Gly Ser His Ile Glu Asn Ile Ile Lys Asn Thr Tyr Met Tyr Tyr
                 20                  25                  30 tct aac att gat aaa gcg att tat gta att atg aag cac tgc aag aaa       144
Ser Asn Ile Asp Lys Ala Ile Tyr Val Ile Met Lys His Cys Lys Lys
             35                  40                  45 cat agt tac tgg atg agg att cct ata gaa ata caa cga tat ata tta       192
His Ser Tyr Trp Met Arg Ile Pro Ile Glu Ile Gln Arg Tyr Ile Leu
         50                  55                  60 tta cat tta aca atg aag gac tta tca ata ata ctt aag taataatgtc        241
Leu His Leu Thr Met Lys Asp Leu Ser Ile Ile Leu Lys
 65                  70                  75 ataatattga aaaaaattt tttttctagt aatgtggcta ttattagtag cccatgaata      301
cattttggtt atcgtttaaa tagtttgtaa gaaggaa atg gat aat ata aga aga      356
                                         Met Asp Asn Ile Arg Arg
                                                          80 ata ata tca aat ata aaa cag gat gat aat ata gcc act gat atg tta       404
Ile Ile Ser Asn Ile Lys Gln Asp Asp Asn Ile Ala Thr Asp Met Leu
             85                  90                  95 gct aca ttt tta agt tca tcg ttg cac gta ttt aaa tta aaa gag ttg       452
Ala Thr Phe Leu Ser Ser Ser Leu His Val Phe Lys Leu Lys Glu Leu
100             105                 110                 115 aaa gaa att gta tta tta ctg ctt aat aaa ggt gct aat tta aat ggg       500
Lys Glu Ile Val Leu Leu Leu Leu Asn Lys Gly Ala Asn Leu Asn Gly
                120                 125                 130 ata tct ata tat gat aaa aca cca ttt cat tgt tat ttt aca ttt aat       548
Ile Ser Ile Tyr Asp Lys Thr Pro Phe His Cys Tyr Phe Thr Phe Asn
            135                 140                 145 acg aat gtt aca att aaa gta ata aag ttt ctt att tat cat ggt ggt       596
Thr Asn Val Thr Ile Lys Val Ile Lys Phe Leu Ile Tyr His Gly Gly
        150                 155                 160 gac att aac agt gta cat aga tgt gga gac acc ata ttg cat aaa tac       644
Asp Ile Asn Ser Val His Arg Cys Gly Asp Thr Ile Leu His Lys Tyr
165                 170                 175 ctt ggt aat gag aat ata gat tat aaa gtt gtt gag ttt tta ata aga       692
Leu Gly Asn Glu Asn Ile Asp Tyr Lys Val Val Glu Phe Leu Ile Arg
180                 185                 190                 195 aaa gga ttt gat gta tgt aaa cta aat aat agt ctg aag aat cct att       740
Lys Gly Phe Asp Val Cys Lys Leu Asn Asn Ser Leu Lys Asn Pro Ile
                200                 205                 210 cat ata ttt aca att aga cac atc aat aac act aat tta aat ata ttg       788
His Ile Phe Thr Ile Arg His Ile Asn Asn Thr Asn Leu Asn Ile Leu
            215                 220                 225 aat ttg ctt tgt tcg cat ata aaa cat gaa tat aat aaa aat gat gaa       836
Asn Leu Leu Cys Ser His Ile Lys His Glu Tyr Asn Lys Asn Asp Glu
        230                 235                 240 atg atg tcg ata tta aac acg atg tta aac tat tgt cac gac gat tat       884
Met Met Ser Ile Leu Asn Thr Met Leu Asn Tyr Cys His Asp Asp Tyr
245                 250                 255 aca tgt ttt tcg gcg gtc cca tat act ata gat atc aca acc ata aac       932
Thr Cys Phe Ser Ala Val Pro Tyr Thr Ile Asp Ile Thr Thr Ile Asn
260                 265                 270                 275 tat aga gat aaa tta gga tat tct cct gtt gtg tat gca tct acc acg       980
Tyr Arg Asp Lys Leu Gly Tyr Ser Pro Val Val Tyr Ala Ser Thr Thr
                280                 285                 290 gat aaa act atc ttg gtg gat tat ctt att aaa tta gga gca aac atg      1028
```

-continued

```
Asp Lys Thr Ile Leu Val Asp Tyr Leu Ile Lys Leu Gly Ala Asn Met
        295                 300                 305 aac ata aca acg aac gat ggt aat aca tgt ggt tcg ttt gct gta atg      1076
Asn Ile Thr Thr Asn Asp Gly Asn Thr Cys Gly Ser Phe Ala Val Met
        310                 315                 320 aat tgt aac agg gat att aat aga cta ttt ctt aat caa aat cca aat      1124
Asn Cys Asn Arg Asp Ile Asn Arg Leu Phe Leu Asn Gln Asn Pro Asn
325                 330                 335 ata gaa act ata tat aat aca ttg aag ata tta tcg gag aat ata gta      1172
Ile Glu Thr Ile Tyr Asn Thr Leu Lys Ile Leu Ser Glu Asn Ile Val
340                 345                 350                 355 ttc ata gac gga tgt gat gta cgt acg aat atg gtt aaa aaa ata cta      1220
Phe Ile Asp Gly Cys Asp Val Arg Thr Asn Met Val Lys Lys Ile Leu
                360                 365                 370 atg tac gga ttt act tta gat cca cta ttt tac aag aac cac gat atc      1268
Met Tyr Gly Phe Thr Leu Asp Pro Leu Phe Tyr Lys Asn His Asp Ile
                375                 380                 385 att gtt gaa tat ttt tca agt agt att aaa aag tat aat aag att att      1316
Ile Val Glu Tyr Phe Ser Ser Ser Ile Lys Lys Tyr Asn Lys Ile Ile
                390                 395                 400 tta caa atg atc gat gag aaa att ggg aat aga tcc gta tac gat att      1364
Leu Gln Met Ile Asp Glu Lys Ile Gly Asn Arg Ser Val Tyr Asp Ile
        405                 410                 415 ata ttt act aaa tca aat aca ggt atg gat gtt aga tat gta tgt aat      1412
Ile Phe Thr Lys Ser Asn Thr Gly Met Asp Val Arg Tyr Val Cys Asn
420                 425                 430                 435 gat atc att ata aaa tat gca agt gtt aaa tat tat gga tct tta ata      1460
Asp Ile Ile Ile Lys Tyr Ala Ser Val Lys Tyr Tyr Gly Ser Leu Ile
                440                 445                 450 aaa cgt ttg ata tat cat tct aag aaa agg aag cga aat ata tta aaa      1508
Lys Arg Leu Ile Tyr His Ser Lys Lys Arg Lys Arg Asn Ile Leu Lys
                455                 460                 465 gct ata cat gcg atg gag aat aac aca acc ttg tgg aat tac cta cca      1556
Ala Ile His Ala Met Glu Asn Asn Thr Thr Leu Trp Asn Tyr Leu Pro
                470                 475                 480 ttg gaa gta aaa atg tat att atg gat ttc tta ccc gat act gat ata      1604
Leu Glu Val Lys Met Tyr Ile Met Asp Phe Leu Pro Asp Thr Asp Ile
        485                 490                 495 act aac att ctt ttt atg aaa aaa tgaaaatata tacataagac agggaattcc     1658
Thr Asn Ile Leu Phe Met Lys Lys
500                 505 tattgttttt ttatataggg gaaa atg gat aat cta tac cga tat att act       1709
                         Met Asp Asn Leu Tyr Arg Tyr Ile Thr
                                     510                 515 gta tcc gat aca gtg gac gta gat aat gta aga aaa tta tta tct tcg      1757
Val Ser Asp Thr Val Asp Val Asp Asn Val Arg Lys Leu Leu Ser Ser
                520                 525                 530 tgt aat atc gac gta gtc tct aca ata ttt caa aaa tat ctt cat aga      1805
Cys Asn Ile Asp Val Val Ser Thr Ile Phe Gln Lys Tyr Leu His Arg
                535                 540                 545 aac gat att aaa tta gat atc gtt gaa gag ttt gtg aat aac gga gct      1853
Asn Asp Ile Lys Leu Asp Ile Val Glu Glu Phe Val Asn Asn Gly Ala
        550                 555                 560 aaa ctg aat ggg aaa gat ttt aac gat aaa aat ata cca ttg tgt aca      1901
Lys Leu Asn Gly Lys Asp Phe Asn Asp Lys Asn Ile Pro Leu Cys Thr
565                 570                 575                 580 tta tta tct aat aaa ttc ata gat tat aat agt gcc atc gat ata aca      1949
Leu Leu Ser Asn Lys Phe Ile Asp Tyr Asn Ser Ala Ile Asp Ile Thr
                585                 590                 595
```

```
agt ttt atg att aca cat gga gcg gat ata aat aag aga aat aag gat        1997
Ser Phe Met Ile Thr His Gly Ala Asp Ile Asn Lys Arg Asn Lys Asp
            600                 605                 610 ggg cgt act cct ata ttt tgt tta cta cat aat tct aca tta aat aat        2045
Gly Arg Thr Pro Ile Phe Cys Leu Leu His Asn Ser Thr Leu Asn Asn
        615                 620                 625 tta gaa ttt gta tct ttt atg ata gac cat ggt gca gat att aca ata        2093
Leu Glu Phe Val Ser Phe Met Ile Asp His Gly Ala Asp Ile Thr Ile
    630                 635                 640 gtt gat gga ttc ggg ttc aca tca tta caa ata tat tta caa tca tca        2141
Val Asp Gly Phe Gly Phe Thr Ser Leu Gln Ile Tyr Leu Gln Ser Ser
645                 650                 655                 660 aat gta caa tta gat ttg gtt gag tta ttg ata caa aag ggg gtc gat        2189
Asn Val Gln Leu Asp Leu Val Glu Leu Leu Ile Gln Lys Gly Val Asp
                665                 670                 675 gta aat ata cat aat aat tgg ttc tat tac aat aca tta cat tgt tat        2237
Val Asn Ile His Asn Asn Trp Phe Tyr Tyr Asn Thr Leu His Cys Tyr
            680                 685                 690 ata aag aaa aat tat aac cgt att aat atg gat att ata aaa tat ata        2285
Ile Lys Lys Asn Tyr Asn Arg Ile Asn Met Asp Ile Ile Lys Tyr Ile
        695                 700                 705 atg gac aat gga ttt aca att aat gag aat aaa ttt acc aaa tca aca        2333
Met Asp Asn Gly Phe Thr Ile Asn Glu Asn Lys Phe Thr Lys Ser Thr
    710                 715                 720 ttt tta gat ata ttg gta tca att att gat agt aaa aac ttt gac tca        2381
Phe Leu Asp Ile Leu Val Ser Ile Ile Asp Ser Lys Asn Phe Asp Ser
725                 730                 735                 740 aac gtt gtt gat ttt ata tta aaa tat att gat att aat gaa aag aat        2429
Asn Val Val Asp Phe Ile Leu Lys Tyr Ile Asp Ile Asn Glu Lys Asn
                745                 750                 755 att ttt gat ttt acg cca tta tac tgt tct gta gat gca aat aat gaa        2477
Ile Phe Asp Phe Thr Pro Leu Tyr Cys Ser Val Asp Ala Asn Asn Glu
            760                 765                 770 aag atg tgt tct tat tta cta aaa aag aat gca gac cct aat att atc        2525
Lys Met Cys Ser Tyr Leu Leu Lys Lys Asn Ala Asp Pro Asn Ile Ile
        775                 780                 785 aca gta ttt ggt gaa acg tgt ata cta aca gct atc aat aat cat aat        2573
Thr Val Phe Gly Glu Thr Cys Ile Leu Thr Ala Ile Asn Asn His Asn
    790                 795                 800 aaa aat ata tta tat aaa cta tta aat tat gat ata gat ata aat act        2621
Lys Asn Ile Leu Tyr Lys Leu Leu Asn Tyr Asp Ile Asp Ile Asn Thr
805                 810                 815                 820 atc caa aat aca tta ttt aaa ctg gaa caa gat att att aac tct acc        2669
Ile Gln Asn Thr Leu Phe Lys Leu Glu Gln Asp Ile Ile Asn Ser Thr
                825                 830                 835 ata gat act tac tat tac aat aat ctt gtt aaa aaa gaa cat ttt ata        2717
Ile Asp Thr Tyr Tyr Tyr Asn Asn Leu Val Lys Lys Glu His Phe Ile
            840                 845                 850 aaa tta ttt cta gcc tac ata gtt aag agg tat gaa aaa aat ata gga        2765
Lys Leu Phe Leu Ala Tyr Ile Val Lys Arg Tyr Glu Lys Asn Ile Gly
        855                 860                 865 ata tta ttt ctt gat tat ccc act ctt ggt gaa tat ttc gtg aaa ttt        2813
Ile Leu Phe Leu Asp Tyr Pro Thr Leu Gly Glu Tyr Phe Val Lys Phe
    870                 875                 880 ata gat acg tgt atg atg gaa ata ttt gag atg aaa tca gat aag gct        2861
Ile Asp Thr Cys Met Met Glu Ile Phe Glu Met Lys Ser Asp Lys Ala
885                 890                 895                 900 ggt aat acg gat ata tat tct att ata ttt acg aat aag tat att cct        2909
Gly Asn Thr Asp Ile Tyr Ser Ile Ile Phe Thr Asn Lys Tyr Ile Pro
                905                 910                 915
```

```
atc cca tat ata acg tgt aaa aag cta aag aaa tac gaa tcc ttt gtt     2957
Ile Pro Tyr Ile Thr Cys Lys Lys Leu Lys Lys Tyr Glu Ser Phe Val
            920                 925                 930 gta tat gga acc gaa ata aaa tca ata ata aaa tct tca aag att aga     3005
Val Tyr Gly Thr Glu Ile Lys Ser Ile Ile Lys Ser Ser Lys Ile Arg
            935                 940                 945 tat gcg agt gtt ata aaa gta acg gag tat atc aca tct atc tgt tcg     3053
Tyr Ala Ser Val Ile Lys Val Thr Glu Tyr Ile Thr Ser Ile Cys Ser
            950                 955                 960 gaa gaa act agt tta tgg aac agc atc cca att gag ata aaa cat aag     3101
Glu Glu Thr Ser Leu Trp Asn Ser Ile Pro Ile Glu Ile Lys His Lys
965                 970                 975                 980 att att aat aat ata aac aat cat gat atg tat ata tta tat aaa aat     3149
Ile Ile Asn Asn Ile Asn Asn His Asp Met Tyr Ile Leu Tyr Lys Asn
                985                 990                 995 aga aaa aaa aaa taa                                                 3164
Arg Lys Lys Lys
            1000

<210> SEQ ID NO 2
<211> LENGTH: 77
<212> TYPE: PRT
<213> ORGANISM: Swinepox virus

<400> SEQUENCE: 2

Lys Leu Leu Asn Tyr Asp Asn Phe Leu Arg Leu Lys Asn Leu Val Met
1               5                   10                  15

Tyr Gly Ser His Ile Glu Asn Ile Ile Lys Asn Thr Tyr Met Tyr Tyr
            20                  25                  30

Ser Asn Ile Asp Lys Ala Ile Tyr Val Ile Met Lys His Cys Lys Lys
        35                  40                  45

His Ser Tyr Trp Met Arg Ile Pro Ile Glu Ile Gln Arg Tyr Ile Leu
    50                  55                  60

Leu His Leu Thr Met Lys Asp Leu Ser Ile Ile Leu Lys
65                  70                  75

<210> SEQ ID NO 3
<211> LENGTH: 430
<212> TYPE: PRT
<213> ORGANISM: Swinepox virus

<400> SEQUENCE: 3

Met Asp Asn Ile Arg Arg Ile Ile Ser Asn Ile Lys Gln Asp Asp Asn
1               5                   10                  15

Ile Ala Thr Asp Met Leu Ala Thr Phe Leu Ser Ser Ser Leu His Val
            20                  25                  30

Phe Lys Leu Lys Glu Leu Lys Glu Ile Val Leu Leu Leu Asn Lys
        35                  40                  45

Gly Ala Asn Leu Asn Gly Ile Ser Ile Tyr Asp Lys Thr Pro Phe His
    50                  55                  60

Cys Tyr Phe Thr Phe Asn Thr Asn Val Thr Ile Lys Val Ile Lys Phe
65                  70                  75                  80

Leu Ile Tyr His Gly Gly Asp Ile Asn Ser Val His Arg Cys Gly Asp
                85                  90                  95

Thr Ile Leu His Lys Tyr Leu Gly Asn Glu Asn Ile Asp Tyr Lys Val
            100                 105                 110

Val Glu Phe Leu Ile Arg Lys Gly Phe Asp Val Cys Lys Leu Asn Asn
        115                 120                 125
```

Ser Leu Lys Asn Pro Ile His Ile Phe Thr Ile Arg His Ile Asn Asn
    130                 135                 140

Thr Asn Leu Asn Ile Leu Asn Leu Leu Cys Ser His Ile Lys His Glu
145                 150                 155                 160

Tyr Asn Lys Asn Asp Glu Met Met Ser Ile Leu Asn Thr Met Leu Asn
                165                 170                 175

Tyr Cys His Asp Asp Tyr Thr Cys Phe Ser Ala Val Pro Tyr Thr Ile
            180                 185                 190

Asp Ile Thr Thr Ile Asn Tyr Arg Asp Lys Leu Gly Tyr Ser Pro Val
        195                 200                 205

Val Tyr Ala Ser Thr Thr Asp Lys Thr Ile Leu Val Asp Tyr Leu Ile
    210                 215                 220

Lys Leu Gly Ala Asn Met Asn Ile Thr Thr Asn Asp Gly Asn Thr Cys
225                 230                 235                 240

Gly Ser Phe Ala Val Met Asn Cys Asn Arg Asp Ile Asn Arg Leu Phe
                245                 250                 255

Leu Asn Gln Asn Pro Asn Ile Glu Thr Ile Tyr Asn Thr Leu Lys Ile
            260                 265                 270

Leu Ser Glu Asn Ile Val Phe Ile Asp Gly Cys Asp Val Arg Thr Asn
        275                 280                 285

Met Val Lys Lys Ile Leu Met Tyr Gly Phe Thr Leu Asp Pro Leu Phe
    290                 295                 300

Tyr Lys Asn His Asp Ile Ile Val Glu Tyr Phe Ser Ser Ile Lys
305                 310                 315                 320

Lys Tyr Asn Lys Ile Ile Leu Gln Met Ile Asp Glu Lys Ile Gly Asn
                325                 330                 335

Arg Ser Val Tyr Asp Ile Ile Phe Thr Lys Ser Asn Thr Gly Met Asp
            340                 345                 350

Val Arg Tyr Val Cys Asn Asp Ile Ile Lys Tyr Ala Ser Val Lys
        355                 360                 365

Tyr Tyr Gly Ser Leu Ile Lys Arg Leu Ile Tyr His Ser Lys Lys Arg
    370                 375                 380

Lys Arg Asn Ile Leu Lys Ala Ile His Ala Met Glu Asn Asn Thr Thr
385                 390                 395                 400

Leu Trp Asn Tyr Leu Pro Leu Glu Val Lys Met Tyr Ile Met Asp Phe
                405                 410                 415

Leu Pro Asp Thr Asp Ile Thr Asn Ile Leu Phe Met Lys Lys
            420                 425                 430

<210> SEQ ID NO 4
<211> LENGTH: 493
<212> TYPE: PRT
<213> ORGANISM: Swinepox virus

<400> SEQUENCE: 4

Met Asp Asn Leu Tyr Arg Tyr Ile Thr Val Ser Asp Thr Val Asp Val
 1               5                  10                  15

Asp Asn Val Arg Lys Leu Leu Ser Ser Cys Asn Ile Asp Val Val Ser
             20                  25                  30

Thr Ile Phe Gln Lys Tyr Leu His Arg Asn Asp Ile Lys Leu Asp Ile
         35                  40                  45

Val Glu Glu Phe Val Asn Asn Gly Ala Lys Leu Asn Gly Lys Asp Phe
     50                  55                  60

Asn Asp Lys Asn Ile Pro Leu Cys Thr Leu Leu Ser Asn Lys Phe Ile

```
                65                  70                  75                  80
Asp Tyr Asn Ser Ala Ile Asp Ile Thr Ser Phe Met Ile Thr His Gly
                    85                  90                  95
Ala Asp Ile Asn Lys Arg Asn Lys Asp Gly Arg Thr Pro Ile Phe Cys
                100                 105                 110
Leu Leu His Asn Ser Thr Leu Asn Asn Leu Glu Phe Val Ser Phe Met
                115                 120                 125
Ile Asp His Gly Ala Asp Ile Thr Ile Val Asp Gly Phe Gly Phe Thr
            130                 135                 140
Ser Leu Gln Ile Tyr Leu Gln Ser Ser Asn Val Gln Leu Asp Leu Val
145                 150                 155                 160
Glu Leu Leu Ile Gln Lys Gly Val Asp Val Asn Ile His Asn Asn Trp
                165                 170                 175
Phe Tyr Tyr Asn Thr Leu His Cys Tyr Ile Lys Lys Asn Tyr Asn Arg
                180                 185                 190
Ile Asn Met Asp Ile Ile Lys Tyr Ile Met Asp Asn Gly Phe Thr Ile
                195                 200                 205
Asn Glu Asn Lys Phe Thr Lys Ser Thr Phe Leu Asp Ile Leu Val Ser
    210                 215                 220
Ile Ile Asp Ser Lys Asn Phe Asp Ser Asn Val Val Asp Phe Ile Leu
225                 230                 235                 240
Lys Tyr Ile Asp Ile Asn Glu Lys Asn Ile Phe Asp Phe Thr Pro Leu
                245                 250                 255
Tyr Cys Ser Val Asp Ala Asn Asn Glu Lys Met Cys Ser Tyr Leu Leu
                260                 265                 270
Lys Lys Asn Ala Asp Pro Asn Ile Ile Thr Val Phe Gly Glu Thr Cys
                275                 280                 285
Ile Leu Thr Ala Ile Asn Asn His Asn Lys Asn Ile Leu Tyr Lys Leu
            290                 295                 300
Leu Asn Tyr Asp Ile Asp Ile Asn Thr Ile Gln Asn Thr Leu Phe Lys
305                 310                 315                 320
Leu Glu Gln Asp Ile Ile Asn Ser Thr Ile Asp Thr Tyr Tyr Tyr Asn
                325                 330                 335
Asn Leu Val Lys Lys Glu His Phe Ile Lys Leu Phe Leu Ala Tyr Ile
                340                 345                 350
Val Lys Arg Tyr Glu Lys Asn Ile Gly Ile Leu Phe Leu Asp Tyr Pro
                355                 360                 365
Thr Leu Gly Glu Tyr Phe Val Lys Phe Ile Asp Thr Cys Met Met Glu
                370                 375                 380
Ile Phe Glu Met Lys Ser Asp Lys Ala Gly Asn Thr Asp Ile Tyr Ser
385                 390                 395                 400
Ile Ile Phe Thr Asn Lys Tyr Ile Pro Ile Pro Tyr Ile Thr Cys Lys
                405                 410                 415
Lys Leu Lys Lys Tyr Glu Ser Phe Val Val Tyr Gly Thr Glu Ile Lys
                420                 425                 430
Ser Ile Ile Lys Ser Ser Lys Ile Arg Tyr Ala Ser Val Ile Lys Val
            435                 440                 445
Thr Glu Tyr Ile Thr Ser Ile Cys Ser Glu Glu Thr Ser Leu Trp Asn
450                 455                 460
Ser Ile Pro Ile Glu Ile Lys His Lys Ile Ile Asn Asn Ile Asn Asn
465                 470                 475                 480
His Asp Met Tyr Ile Leu Tyr Lys Asn Arg Lys Lys Lys
                485                 490
```

<210> SEQ ID NO 5
<211> LENGTH: 3295
<212> TYPE: DNA
<213> ORGANISM: Porcine reproductive and respiratory syndrome virus

<400> SEQUENCE: 5

| | | | | | |
|---|---|---|---|---|---|
| gaattcccgg | gccctgtcat | tgaaccaact | ttaggcctga | attgaaatga | aatgggtcc | 60 |
| atgcaaagcc | tttttgacaa | aattggccaa | ctttttgtgg | atgctttcac | ggagttcttg | 120 |
| gtgtccattg | ttgatatcat | tatatttttg | gccattttgt | ttggcttcac | catcgccggt | 180 |
| tggttggtgg | tcttttgcat | cagattggtt | tgctccgcga | tactccgtac | gcgccctgcc | 240 |
| attcactctg | agcaattaca | gaagatctta | tgaagccttt | ctttcccagt | gccaagtgga | 300 |
| cattcccacc | tggggaacta | acatcctttt | ggggatgttt | tggcaccata | aggtgtcaac | 360 |
| cctgattgat | gagatggtgt | cgcgtcgaat | gtaccgcatc | atggaaaaag | caggacaggc | 420 |
| tgcctggaaa | caggtggtga | gcgaggctac | gctgtctcgc | attagtagtt | tggatgtggt | 480 |
| ggctcatttt | cagcatcttg | ccgccattga | agccgagacc | tgtaaatatt | tggcctcccg | 540 |
| gctgcccatg | ctacacaacc | tgcgcatgac | agggtcaaat | gtaaccatag | tgtataatag | 600 |
| tactttgcat | caggtgtttg | ctattttttcc | aaccctggt | tcccggccaa | agcttcatga | 660 |
| ttttcagcaa | tggttaatag | ctgtacattc | ctccatattt | tcctctgttg | cagcttcttg | 720 |
| tactctcttt | gttgtgctgt | ggttgcgggt | tccaatacta | cgtactgttt | ttggtttccg | 780 |
| ctggttaggg | gcaattttttc | tttcgaactc | acagtgaatt | acacggtgtg | tccaccttgc | 840 |
| ctcacccggc | aagcagccgc | agaggcctac | gaacccggta | ggtctctttg | gtgcaggata | 900 |
| gggtatgacc | gatgtgggga | ggacgatcat | gacgagctag | ggtttatggt | accgtctggc | 960 |
| ctctccagcg | aaggccactt | gaccagtgtt | tacgcctggt | tggcgttctt | gtccttcagc | 1020 |
| tacacggccc | agttccatcc | cgagatattc | gggataggga | atgtgagtcg | agtttatgtt | 1080 |
| gacatcgaac | atcaactcat | ctgcgccgaa | catgacgggc | agaacaccac | cttgcctcgt | 1140 |
| catgacaaca | tttcagccgt | gtttcagacc | tattaccaac | atcaagtcga | cggcggcaat | 1200 |
| tggttcacc | tagaatggct | gcgtcccttc | ttttcctcat | ggttggtttt | aaatgtctct | 1260 |
| tggtttctca | ggcgttcgcc | tgcaaaccat | gtttcagttc | gagtcttgca | gacattaaga | 1320 |
| ccaacaccac | cgcagcggca | agctttgctg | tcctccaaga | catcagttgc | cttaggcatc | 1380 |
| gcaactcggc | ctctgaggcg | attcgcaaaa | tccctcagtg | ccgtacggcg | atagggacac | 1440 |
| ccgtgtatat | taccaccaca | gccaatgtga | cagatgagaa | ttatttacat | tcttctgatc | 1500 |
| tcctcatgct | ttcttcttgc | cttttctatg | cttctgagat | gagtgaaaag | ggatttaagg | 1560 |
| tggtatttgg | caatgtgtca | ggcatcgtgg | ctgtgtgtgt | caattttacc | agctacgtcc | 1620 |
| aacatgtcag | ggagtttacc | caacgctcct | tgatggtcga | ccatgtgcgg | ctgctccatt | 1680 |
| tcatgacacc | tgagaccatg | aggtgggcaa | ctgttttagc | ctgtcttttt | gccattctgt | 1740 |
| tggcaatttg | aatgtttaag | tatgttgggg | aaatgcttga | ccgcgggctg | ttgctcgcga | 1800 |
| ttgctttctt | tgtggtgtat | cgtgccgttc | tgttttgctg | tgctcgtcaa | cgccaacagc | 1860 |
| aacagcagct | ctcatctaca | gttgatttac | aacttgacgc | tatgtgagct | gaatggcaca | 1920 |
| gattggctat | ctaataaatt | tgattgggca | gtggagagtt | ttgtcatctt | tcccgttttg | 1980 |
| actcacattg | tctcctatgg | tgccctcact | accagccatt | tccttgacac | agtcgcttta | 2040 |
| gtcactgtgt | ctaccgccgg | gtttgttcac | gggcggtatg | tcctgagcag | catctacgcg | 2100 |

-continued

```
gtctgtgccc tggctgcgtt gacttgcttc gtcattaggt ttgcaaagaa ttgcatgtcc    2160
tggcgctact catgtaccag atatactaac tttcttctgg acactaaggg cagactctat    2220
cgttggcggt cgcctgtcat catagagaaa aggggcaaag ttgaggtcga aggtcatctg    2280
atcgacctca aaagagttgt gcttgatggt tccgtggcaa ccctataac cagagtttca     2340 gcggaacaat gggtcgtcc ttagatgact tttgttatga tagcacggct ccacaaaagg    2400
tgcttttggc gttttctatt acctacacgc cagtgatgat atatgcccta aaagtgagtc    2460
gcggccgact gttagggctt ctgcaccttt tgatcttcct gaactgtgct ttcaccttcg    2520
ggtacatgac attcgcgcac tttcagagta caaataaggt cgcgctcact atgggagcag    2580
tagttgcact cctttggggg gtgtattcag ccatagaaac ctggaaattc atcacctcca    2640
gatgccgttt gtgcttgcta ggccgcaagt acattctggc ccctgcccac cacgttgaga    2700
gtgccgcagg ctttcatccg attgcggcaa atgataacca cgcatttgtc gtccggcgtc    2760
ccggctccac tacggtcaac ggcacattgg tgcccgggtt gaaaggcctc gtgttgggtg    2820
gcagaaaagc tgttaaacag ggagtggtaa accttgtcaa atatgccaaa taacaacggc    2880
aagcagcaga agagaaagaa ggggatggc cagccagtca atcagctgtg ccagatgctg     2940
ggtaagatca tcgcccagca aaaccagtcc agaggcaagg gaccgggaaa gaaaaataag    3000
aagaaaaacc cggagaagcc ccattttcct ctagcgactg aagatgatgt cagacatcac    3060
tttaccccta gtgagcggca attgtgtctg tcgtcaatcc agactgcctt taatcaaggc    3120
gctgggactt gcaccctgtc agattcaggg aggataagtt acactgtgga gtttagtttg    3180
cctacgcatc atactgtgcg cctgatccgc gtcacagcat caccctcagc atgatgggct    3240
ggcattcttg aggcatctca gtgtttgaat tggaagaatg cgtggtgaag gatcc         3295
```

<210> SEQ ID NO 6
<211> LENGTH: 256
<212> TYPE: PRT
<213> ORGANISM: Porcine reproductive and respiratory syndrome virus

<400> SEQUENCE: 6

```
Met Lys Trp Gly Pro Cys Lys Ala Phe Leu Thr Lys Leu Ala Asn Phe
  1               5                  10                  15

Leu Trp Met Leu Ser Arg Ser Ser Trp Cys Pro Leu Leu Ile Ser Leu
             20                  25                  30

Tyr Phe Trp Pro Phe Cys Leu Ala Ser Pro Ser Pro Val Gly Trp Trp
         35                  40                  45

Ser Phe Ala Ser Asp Trp Phe Ala Pro Arg Tyr Ser Val Arg Ala Leu
     50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Thr Trp Gly Thr Lys His Pro Leu Gly
                 85                  90                  95

Met Phe Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
```

```
            165                 170                 175
Ser Asn Val Thr Ile Val Tyr Asn Ser Thr Leu His Gln Val Phe Ala
                180                 185                 190

Ile Phe Pro Thr Pro Gly Ser Arg Pro Lys Leu His Asp Phe Gln Gln
            195                 200                 205

Trp Leu Ile Ala Val His Ser Ser Ile Phe Ser Val Ala Ala Ser
    210                 215                 220

Cys Thr Leu Phe Val Val Leu Trp Leu Arg Val Pro Ile Leu Arg Thr
225                 230                 235                 240

Val Phe Gly Phe Arg Trp Leu Gly Ala Ile Phe Leu Ser Asn Ser Gln
                245                 250                 255

<210> SEQ ID NO 7
<211> LENGTH: 254
<212> TYPE: PRT
<213> ORGANISM: Porcine reproductive and respiratory syndrome virus

<400> SEQUENCE: 7

Met Val Asn Ser Cys Thr Phe Leu His Ile Phe Leu Cys Cys Ser Phe
  1               5                  10                  15

Leu Tyr Ser Leu Cys Cys Ala Val Val Ala Gly Ser Asn Thr Thr Tyr
                 20                  25                  30

Cys Phe Trp Phe Pro Leu Val Arg Gly Asn Phe Ser Phe Glu Leu Thr
             35                  40                  45

Val Asn Tyr Thr Val Cys Pro Pro Cys Leu Thr Arg Gln Ala Ala Ala
         50                  55                  60

Glu Ala Tyr Glu Pro Gly Arg Ser Leu Trp Cys Arg Ile Gly Tyr Asp
 65                  70                  75                  80

Arg Cys Gly Glu Asp Asp His Asp Glu Leu Gly Phe Met Val Pro Ser
                 85                  90                  95

Gly Leu Ser Ser Glu Gly His Leu Thr Ser Val Tyr Ala Trp Leu Ala
                100                 105                 110

Phe Leu Ser Phe Ser Tyr Thr Ala Gln Phe His Pro Glu Ile Phe Gly
            115                 120                 125

Ile Gly Asn Val Ser Arg Val Tyr Val Asp Ile Glu His Gln Leu Ile
        130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Asn His Val
        195                 200                 205

Ser Val Arg Val Leu Gln Thr Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250

<210> SEQ ID NO 8
<211> LENGTH: 178
<212> TYPE: PRT
<213> ORGANISM: Porcine reproductive and respiratory syndrome virus
```

```
<400> SEQUENCE: 8

Met Ala Ala Ser Leu Leu Phe Leu Met Val Gly Phe Lys Cys Leu Leu
 1               5                  10                  15

Val Ser Gln Ala Phe Ala Cys Lys Pro Cys Phe Ser Ser Ser Leu Ala
            20                  25                  30

Asp Ile Lys Thr Asn Thr Thr Ala Ala Ser Phe Ala Val Leu Gln
        35                  40                  45

Asp Ile Ser Cys Leu Arg His Arg Asn Ser Ala Ser Glu Ala Ile Arg
    50                  55                  60

Lys Ile Pro Gln Cys Arg Thr Ala Ile Gly Thr Pro Val Tyr Ile Thr
65                  70                  75                  80

Thr Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Arg Glu Phe Thr Gln Arg
    130                 135                 140

Ser Leu Met Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile

<210> SEQ ID NO 9
<211> LENGTH: 200
<212> TYPE: PRT
<213> ORGANISM: Porcine reproductive and respiratory syndrome virus

<400> SEQUENCE: 9

Met Leu Gly Lys Cys Leu Thr Ala Gly Cys Cys Ser Arg Leu Leu Ser
 1               5                  10                  15

Leu Trp Cys Ile Val Pro Phe Cys Phe Ala Val Leu Val Asn Ala Asn
            20                  25                  30

Ser Asn Ser Ser Ser His Leu Gln Leu Ile Tyr Asn Leu Thr Leu Cys
        35                  40                  45

Glu Leu Asn Gly Thr Asp Trp Leu Ser Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
```

```
                    180                 185                 190

Ser Ala Glu Gln Trp Gly Arg Pro
            195                 200

<210> SEQ ID NO 10
<211> LENGTH: 174
<212> TYPE: PRT
<213> ORGANISM: Porcine reproductive and respiratory syndrome virus

<400> SEQUENCE: 10

Met Gly Ser Ser Leu Asp Asp Phe Cys Tyr Asp Ser Thr Ala Pro Gln
  1               5                  10                  15

Lys Val Leu Leu Ala Phe Ser Ile Thr Tyr Thr Pro Val Met Ile Tyr
                 20                  25                  30

Ala Leu Lys Val Ser Arg Gly Arg Leu Leu Gly Leu Leu His Leu Leu
             35                  40                  45

Ile Phe Leu Asn Cys Ala Phe Thr Phe Gly Tyr Met Thr Phe Ala His
 50                  55                  60

Phe Gln Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Lys Gly Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 11
<211> LENGTH: 123
<212> TYPE: PRT
<213> ORGANISM: Porcine reproductive and respiratory syndrome virus

<400> SEQUENCE: 11

Met Pro Asn Asn Asn Gly Lys Gln Gln Lys Arg Lys Lys Gly Asp Gly
  1               5                  10                  15

Gln Pro Val Asn Gln Leu Cys Gln Met Leu Gly Lys Ile Ile Ala Gln
                 20                  25                  30

Gln Asn Gln Ser Arg Gly Lys Gly Pro Gly Lys Lys Asn Lys Lys Lys
             35                  40                  45

Asn Pro Glu Lys Pro His Phe Pro Leu Ala Thr Glu Asp Asp Val Arg
 50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120
```

```
<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 12
gcggatccgg cgcgccggat tttcctacat ctacact                              37

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 13
ctaaaattga attgtaat                                                   18

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 14
ttggcgcgcc ctagatctgt gtagttgatt gatttg                               36

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 15
tacggcgcgc cgggaaatgc taaagccaag cccaca                               36

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 16
ttcggatcct gctcagacag tattgtgtat gttatcaaga gc                        42

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 17
ccatgaattc cttccctgaa tgcaaggagg gcttc                                35

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: primer
```

<400> SEQUENCE: 18
cgggatcctc acccgggcag cgcgctgta                                29

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 19
cggaattcac aagggccgac attggcc                                  27

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 20
atcgggatcc cgttattctt cgctgatggt gg                            32

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 21
atcggaattc gcggtgcctg ttgctctgga tg                            32

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 22
cttcggatcc tcatgccccc ccgacgtcgg ccatc                         35

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 23
tcatgaattc ggccgctcgc ggcggtgctg aacgc                         35

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 24
cgggatccct agggcgcgga gccgagggc                                29

<210> SEQ ID NO 25
<211> LENGTH: 30

```
<212> TYPE: DNA
<213> ORGANISM: Artificial Sequence
<220> FEATURE:
<223> OTHER INFORMATION: Description of Artificial Sequence: primer

<400> SEQUENCE: 25
cggaattcag gcccgctggg gcgagcgtgg                                            30

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 26
cttcggatcc tcatgccccc ccgacgtcgg ccatc                                      35

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 27
tcatgaattc ggccgctcgc ggcggtgctg aacgc                                      35

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 28
cgggatcctt aatataattt tctaggtgct agttg                                      35

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 29
cggaattcga tgagtgatgg agcagttcaa                                            30

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 30
cgggatcctt aatataattt tctaggtgct agttg                                      35

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 31
```

```
cggaattcga tgagtgatgg agcagttcaa                                        30
```

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 32

```
cgggatcctt aatataattt tctaggtgct agttg                                  35
```

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 33

```
cggaattcta tgtgtttttt tataggactt                                        30
```

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 34

```
cgggatcctt aatataattt tctaggtgct agttg                                  35
```

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 35

```
cggaattcta tgtgtttttt tataggactt                                        30
```

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 36

```
cgtcagatct caggaggtca taagatgcca ttagc                                  35
```

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 37

```
cgttgaattc gatgacttgc cagacttaca acttg                                  35
```

<210> SEQ ID NO 38
<211> LENGTH: 33
<212> TYPE: DNA
<213> ORGANISM: Artificial Sequence

```
<220> FEATURE:
<223> OTHER INFORMATION: Description of Artificial Sequence: primer

<400> SEQUENCE: 38
cgtcgaattc gatgtctgga gcctctagtg gga                                    33

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 39
cgtcggatcc ggctcaaata gccgatactc ttctt                                  35

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 40
cgtcgaattc aatggaaagt ccaacgcacc caaaa                                  35

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 41
cgtcggatcc ggggactaaa tggaatcata ca                                     32

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 42
cgggaattcg ggtcgtcct tagatgactt ctgcc                                   35

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 43
gcggatcctt gttatgtggc atatttgaca aggtttac                               38

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 44
aatgaattcg aaatggggtc catgcaaagc cttttg                                 37
```

```
<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 45
caaggatccc acaccgtgta attcactgtg agttcg                                 36

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 46
gtcgaattcg ccaaataaca acggcaagca gcagaag                                37

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 47
caaggatccc agcccatcat gctgagggtg atg                                    33

<210> SEQ ID NO 48
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 48
ttcgaattcg gctaatagct gtacattcct ccatattt                               38

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 49
ggggatccta tcgccgtacg gcactgaggg                                        30

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 50
ccgaattcgg ctgcgtccct tcttttcctc atgg                                   34

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence: primer
```

<400> SEQUENCE: 51
ctggatcctt caaattgcca acagaatggc aaaaagac                                    38

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 52
ttgaattcgt tggagaaatg cttgaccgcg ggc                                         33

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 53
gaaggatcct aaggacgacc ccattgttcc gctg                                        34

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 54
atgaaggccc tgtaccccgt cacga                                                  25

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 55
cgggatccgg ctacagggcg tcgggtcct c                                            31

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 56
ccggatccgg cgcgcgacgt gacccggctc                                             30

<210> SEQ ID NO 57
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 57
ccggatccgc ggacggagat aaaacgccac ccac                                        34

<210> SEQ ID NO 58

<211> LENGTH: 677
<212> TYPE: PRT
<213> ORGANISM: Swinepox virus

<400> SEQUENCE: 58

Met Pro Ser Tyr Met Tyr Pro Lys Asn Ala Arg Lys Val Ile Ser Lys
1 5 10 15

Ile Ile Ser Leu Gln Leu Asp Ile Lys Lys Leu Pro Lys Lys Tyr Ile
20 25 30

Asn Thr Met Leu Glu Phe Gly Leu His Gly Asn Leu Pro Ala Cys Met
35 40 45

Tyr Lys Asp Ala Val Ser Tyr Asp Ile Asn Asn Ile Arg Phe Leu Pro
50 55 60

Tyr Asn Cys Val Met Val Lys Asp Leu Ile Asn Val Ile Lys Ser Ser
65 70 75 80

Ser Val Ile Asp Thr Arg Leu His Gln Ser Val Leu Lys His Arg Arg
85 90 95

Ala Leu Ile Asp Tyr Gly Asp Gln Asp Ile Ile Thr Leu Met Ile Ile
100 105 110

Asn Lys Leu Leu Ser Ile Asp Asp Ile Ser Tyr Ile Leu Asp Lys Lys
115 120 125

Ile Ile His Val Thr Lys Ile Leu Lys Ile Asp Pro Thr Val Ala Asn
130 135 140

Ser Asn Met Lys Leu Asn Lys Ile Glu Leu Val Asp Val Ile Thr Ser
145 150 155 160

Ile Pro Lys Ser Ser Tyr Thr Tyr Leu Tyr Asn Asn Met Ile Ile Asp
165 170 175

Leu Asp Thr Leu Leu Tyr Leu Ser Asp Ala Phe His Ile Pro Pro Thr
180 185 190

His Ile Ser Leu Arg Ser Leu Arg Asp Ile Asn Arg Ile Ile Glu Leu
195 200 205

Leu Lys Lys Tyr Pro Asn Asn Asn Ile Ile Asp Tyr Ile Ser Asp Ser
210 215 220

Ile Lys Ser Asn Ser Ser Phe Ile His Ile Leu His Met Ile Ile Ser
225 230 235 240

Asn Met Phe Pro Ala Ile Ile Pro Ser Val Asn Asp Phe Ile Ser Thr
245 250 255

Val Val Asp Lys Asp Arg Leu Ile Asn Met Tyr Gly Ile Lys Cys Val
260 265 270

Ala Met Phe Ser Tyr Asp Ile Asn Met Ile Asp Leu Glu Ser Leu Asp
275 280 285

Asp Ser Asp Tyr Ile Phe Ile Glu Lys Asn Ile Ser Ile Tyr Asp Val
290 295 300

Lys Cys Arg Asp Phe Ala Asn Met Ile Arg Asp Lys Val Lys Arg Glu
305 310 315 320

Lys Asn Arg Ile Leu Thr Thr Lys Cys Glu Asp Ile Ile Arg Tyr Ile
325 330 335

Lys Leu Phe Ser Lys Asn Arg Ile Asn Asp Glu Asn Asn Lys Val Glu
340 345 350

Glu Val Leu Ile His Ile Asp Asn Val Ser Lys Asn Asn Lys Leu Ser
355 360 365

Leu Ser Asp Ile Ser Ser Leu Met Asp Gln Phe Arg Leu Asn Pro Cys
370 375 380

Thr Ile Arg Asn Ile Leu Leu Ser Ser Ala Thr Ile Lys Ser Lys Leu

```
                385               390                395                400
Leu Ala Leu Arg Ala Val Lys Asn Trp Lys Cys Tyr Ser Leu Thr Asn
                    405                410                415

Val Ser Met Tyr Lys Lys Ile Lys Gly Val Ile Val Met Asp Met Val
                    420                425                430

Asp Tyr Ile Ser Thr Asn Ile Leu Lys Tyr His Lys Gln Leu Tyr Asp
                    435                440                445

Lys Met Ser Thr Phe Glu Tyr Lys Arg Asp Ile Lys Ser Cys Lys Cys
                    450                455                460

Ser Ile Cys Ser Asp Ser Ile Thr His His Ile Tyr Glu Thr Thr Ser
465                 470                475                480

Cys Ile Asn Tyr Lys Ser Thr Asp Asn Asp Leu Met Ile Val Leu Phe
                    485                490                495

Asn Leu Thr Arg Tyr Leu Met His Gly Met Ile His Pro Asn Leu Ile
                    500                505                510

Ser Val Lys Gly Trp Gly Pro Leu Ile Gly Leu Leu Thr Gly Asp Ile
                    515                520                525

Gly Ile Asn Leu Lys Leu Tyr Ser Thr Met Asn Ile Asn Gly Leu Arg
                    530                535                540

Tyr Gly Asp Ile Thr Leu Ser Ser Tyr Asp Met Ser Asn Lys Leu Val
545                 550                555                560

Ser Ile Ile Asn Thr Pro Ile Tyr Glu Leu Ile Pro Phe Thr Thr Cys
                    565                570                575

Cys Ser Leu Asn Glu Tyr Tyr Ser Lys Ile Val Ile Leu Ile Asn Val
                    580                585                590

Ile Leu Glu Tyr Met Ile Ser Ile Ile Leu Tyr Arg Ile Leu Ile Val
                    595                600                605

Lys Arg Phe Asn Asn Ile Lys Glu Phe Ile Ser Lys Val Val Asn Thr
                    610                615                620

Val Leu Glu Ser Ser Gly Ile Tyr Phe Cys Gln Met Arg Val His Glu
625                 630                635                640

Gln Ile Glu Leu Glu Ile Asp Glu Leu Ile Ile Asn Gly Ser Met Pro
                    645                650                655

Val Gln Leu Met His Leu Leu Leu Lys Val Ala Thr Ile Ile Leu Glu
                    660                665                670

Glu Ile Lys Glu Ile
            675

<210> SEQ ID NO 59
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 59
tcgaagatct tctcatgcaa aggtggaacc gttc                            34

<210> SEQ ID NO 60
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 60
tcgaagatct catgcctatg ttcaccatcc acac                            34
```

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 61
acgtcggatc ccttaccaaa ccacgtctta ctcttgtttt cc                42

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 62
acataggatc ccatgggaga aaacataaca cagtggaacc                40

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 63
cgtggatcct caattacaag aggtatcgtc tac                33

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 64
catagatctt gtggtgctgt ccgacttcgc a                31

<210> SEQ ID NO 65
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 65
tgcaggatcc tcatttacta aaggaaagat tgttgat                37

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 66
ctctggatcc tacagccatg aggatgatca tcagc                35

<210> SEQ ID NO 67
<211> LENGTH: 40
<212> TYPE: DNA
<213> ORGANISM: Artificial Sequence
<220> FEATURE:

<223> OTHER INFORMATION: Description of Artificial Sequence: primer

<400> SEQUENCE: 67
cgtcggatcc ctcacagttc cacatcattg tctttgggat              40

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 68
cttaggatcc catggctctt agcaaggtca aactaaatga c            41

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 69
cgttggatcc ctagatctgt gtagttgatt gatttgtgtg a            41

<210> SEQ ID NO 70
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 70
ctctggatcc tcatacccat catcttaaat tcaagacatt a            41

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 71
cgcgaattcg ctcgcagcgc tattggc                            27

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 72
gtaggagtgg ctgctgaag                                     19

<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 73
gaagcatgcc cgttcttatc aatagtttag tcgaaaata               39

```
<210> SEQ ID NO 74
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 74
cataagatct ggcattgtgt tattatacta acaaaaataa g                    41

<210> SEQ ID NO 75
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 75
ccgtagtcga caaagatcga cttattaata tgtatgggat t                    41

<210> SEQ ID NO 76
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 76
gcctgaagct tctagtacag tatttacgac ttttgaaat                       39

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 77
cggaattcct ctggttcgcc gt                                         22

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 78
gacggtggat ccggtaggcg gt                                         22

<210> SEQ ID NO 79
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 79
cacgaattct gacattttca acagtccaca ggcgc                           35

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: primer
```

```
<400> SEQUENCE: 80
gctgttggac atcacgggcc agg                                               23

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 81
acccggaaca tatggtcagc tccat                                             25

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 82
ggcgcgccag gcgaaggccg gggatacgg                                         29

<210> SEQ ID NO 83
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 83
gcgtgaattc ggggaatgga caggggcgag at                                     32

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 84
gagccagatc tgctcttttt actttccc                                          28

<210> SEQ ID NO 85
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 85
gcccggatcc tatggcagaa gggtttgcag c                                      31

<210> SEQ ID NO 86
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 86
ccgtggatcc ggcactccat cattcctcct c                                      31

<210> SEQ ID NO 87
<211> LENGTH: 33
```

```
<212> TYPE: DNA
<213> ORGANISM: Artificial Sequence
<220> FEATURE:
<223> OTHER INFORMATION: Description of Artificial Sequence: primer

<400> SEQUENCE: 87
gccgaattcg ctaatcctca aagcaaatgc aat                                    33

<210> SEQ ID NO 88
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 88
ggtgaattct ttatttagtt actaaatgca atattattt                              39

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 89
gccgaattcc aaaaacaagg accaacgcac                                        30

<210> SEQ ID NO 90
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 90
gccgaattca ctactggcgt ggtgtgttg                                         29

<210> SEQ ID NO 91
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 91
catgaattct caaggcacca aacgatcata tgaac                                  35

<210> SEQ ID NO 92
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 92
atttgaattc aattgtcata ctcctctcgc attgtct                                37

<210> SEQ ID NO 93
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 93
```
ccgaggatcc ggcaatacta ttagtcttgc tatgtacat                          39

<210> SEQ ID NO 94
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 94
ctctggatcc taatttaaat acatattctg cactgts                            37

<210> SEQ ID NO 95
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 95
aatgaattca aatcaaaaaa taataaccat tgggtcaat                          39

<210> SEQ ID NO 96
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 96
ggaagatcta cttgtcaatg gtgaatggca gatcag                             36

<210> SEQ ID NO 97
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 97
ctctgggatc ctaattttaa atacatattc tgcactgta                          39

<210> SEQ ID NO 98
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 98
aatgaattca aatcaaaaaa taataacatt gggtcaat                           38

<210> SEQ ID NO 99
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 99
aatgaattcg aaatgggtcc atgcaaagcc tttttg                             36

<210> SEQ ID NO 100
<211> LENGTH: 38
<212> TYPE: DNA
<213> ORGANISM: Artificial Sequence

```
<220> FEATURE:
<223> OTHER INFORMATION: Description of Artificial Sequence: primer

<400> SEQUENCE: 100
gcctgaagct tctagtacag tatttacgac ttttgaat                              38

<210> SEQ ID NO 101
<211> LENGTH: 129
<212> TYPE: PRT
<213> ORGANISM: Vaccinia virus

<400> SEQUENCE: 101
```

Met Phe Met Tyr Pro Glu Phe Ala Arg Lys Ala Leu Ser Lys Leu Ile
 1               5                  10                  15

Ser Lys Lys Leu Asn Ile Glu Lys Val Ser Ser Lys His Gln Leu Val
            20                  25                  30

Leu Leu Asp Tyr Gly Leu His Gly Leu Leu Pro Lys Ser Leu Tyr Leu
        35                  40                  45

Glu Ala Ile Asn Ser Asp Ile Leu Asn Val Arg Phe Phe Pro Pro Glu
    50                  55                  60

Ile Ile Asn Val Thr Asp Ile Val Lys Ala Leu Gln Asn Ser Cys Arg
65                  70                  75                  80

Val Asp Glu Tyr Leu Lys Ala Val Ser Leu Tyr His Lys Asn Ser Leu
                85                  90                  95

Met Val Ser Gly Pro Asn Val Val Lys Leu Met Ile Glu Tyr Asn Leu
            100                 105                 110

Leu Thr His Ser Asp Leu Glu Trp Leu Ile Asn Glu Asn Val Val Lys
        115                 120                 125

Ala

```
<210> SEQ ID NO 102
<211> LENGTH: 132
<212> TYPE: PRT
<213> ORGANISM: Swinepox virus

<400> SEQUENCE: 102
```

Met Pro Ser Tyr Met Tyr Pro Lys Asn Ala Arg Lys Val Ile Ser Lys
 1               5                  10                  15

Ile Ile Ser Leu Gln Leu Asp Ile Lys Lys Leu Pro Lys Lys Tyr Ile
            20                  25                  30

Asn Thr Met Leu Glu Phe Gly Leu His Gly Asn Leu Pro Ala Cys Met
        35                  40                  45

Tyr Lys Asp Ala Val Ser Tyr Asp Ile Asn Asn Ile Arg Phe Leu Pro
    50                  55                  60

Tyr Asn Cys Val Met Val Lys Asp Leu Ile Asn Val Ile Lys Ser Ser
65                  70                  75                  80

Ser Val Ile Asp Thr Arg Leu His Gln Ser Val Leu Lys His Arg Arg
                85                  90                  95

Ala Leu Ile Asp Tyr Gly Asp Gln Asp Ile Ile Thr Leu Met Ile Ile
            100                 105                 110

Asn Lys Leu Leu Ser Ile Asp Asp Ile Ser Tyr Ile Leu Asp Lys Lys
        115                 120                 125

Ile Ile His Val
    130

```
<210> SEQ ID NO 103
<211> LENGTH: 101
```

```
<212> TYPE: PRT
<213> ORGANISM: Vaccinia virus

<400> SEQUENCE: 103

Val Leu Asn Asp Gln Tyr Ala Lys Ile Val Ile Phe Phe Asn Thr Ile
 1               5                  10                  15

Ile Glu Tyr Ile Ile Ala Thr Ile Tyr Tyr Arg Leu Thr Val Leu Asn
                20                  25                  30

Asn Tyr Thr Asn Val Lys His Phe Val Ser Lys Val Leu His Thr Val
            35                  40                  45

Met Glu Ala Cys Gly Val Leu Phe Ser Tyr Ile Lys Val Asn Asp Lys
    50                  55                  60

Ile Glu His Glu Leu Glu Glu Met Val Asp Lys Gly Thr Val Pro Ser
65                  70                  75                  80

Tyr Leu Tyr His Leu Ser Ile Asn Val Ile Ser Ile Ile Leu Asp Asp
                85                  90                  95

Ile Asn Gly Thr Arg
            100

<210> SEQ ID NO 104
<211> LENGTH: 100
<212> TYPE: PRT
<213> ORGANISM: Swinepox virus

<400> SEQUENCE: 104

Ser Leu Asn Glu Tyr Tyr Ser Lys Ile Val Ile Leu Ile Asn Val Ile
 1               5                  10                  15

Leu Glu Tyr Met Ile Ser Ile Ile Leu Tyr Arg Ile Leu Ile Val Lys
                20                  25                  30

Arg Phe Asn Asn Ile Lys Glu Phe Ile Ser Lys Val Val Asn Thr Val
            35                  40                  45

Leu Glu Ser Ser Gly Ile Tyr Phe Cys Gln Met Arg Val His Glu Gln
    50                  55                  60

Ile Glu Leu Glu Ile Asp Glu Leu Ile Ile Asn Gly Ser Met Pro Val
65                  70                  75                  80

Gln Leu Met His Leu Leu Leu Lys Val Ala Thr Ile Ile Leu Glu Glu
                85                  90                  95

Ile Lys Glu Ile
            100

<210> SEQ ID NO 105
<211> LENGTH: 102
<212> TYPE: DNA
<213> ORGANISM: Artificial Sequence
<220> FEATURE:
<223> OTHER INFORMATION: Description of Artificial Sequence: Homology
      vector 520-17.5

<400> SEQUENCE: 105
cacatacgat ttaggtgaca ctatagaata caagctttat accattatag atacattacc     60
ttgtccgacg tgtagaattc atgccaaaga agaattaact aa                      102

<210> SEQ ID NO 106
<211> LENGTH: 102
<212> TYPE: DNA
<213> ORGANISM: Artificial Sequence
<220> FEATURE:
<223> OTHER INFORMATION: Description of Artificial Sequence: Homology
      vector 520-17.5
```

```
<400> SEQUENCE: 106
gtagtcgact ctagaaaaaa ttgaaaaact attctaattt attgcacgga gatcttttt     60 tttttttttt ttttggcat ataaatgaat tcggatcccg tc                       102

<210> SEQ ID NO 107
<211> LENGTH: 103
<212> TYPE: DNA
<213> ORGANISM: Artificial Sequence
<220> FEATURE:
<223> OTHER INFORMATION: Description of Artificial Sequence: Homology
      vector 520-17.5

<400> SEQUENCE: 107
agcccgtcag tatcggcgga aatccagctg agcgccggtc gctaccatta ccagttggtc    60
tggtgtcaaa aagatccata attaattaac ccgggtcgaa gac                     103

<210> SEQ ID NO 108
<211> LENGTH: 45
<212> TYPE: DNA
<213> ORGANISM: Artificial Sequence
<220> FEATURE:
<223> OTHER INFORMATION: Description of Artificial Sequence: Homology
      vector 520-17.5

<400> SEQUENCE: 108
agatccccgg gcgagctcga attcgtaatc atggtcatag tttcc                    45

<210> SEQ ID NO 109
<211> LENGTH: 57
<212> TYPE: DNA
<213> ORGANISM: Artificial Sequence
<220> FEATURE:
<223> OTHER INFORMATION: Description of Artificial Sequence: Homology
      vector 538-46.16

<400> SEQUENCE: 109
cacatacgat ttaggtgaca ctatagaata caagctttat accattatag atacatt       57

<210> SEQ ID NO 110
<211> LENGTH: 102
<212> TYPE: DNA
<213> ORGANISM: Artificial Sequence
<220> FEATURE:
<223> OTHER INFORMATION: Description of Artificial Sequence: Homology
      vector 538-46.16

<400> SEQUENCE: 110
aagctggtag atttccatgt agggccgcct gcaggtcgac tctagaattt cattttgttt    60
ttttctatgc tataaatgaa ttcggatccc gtcgttttac aa                      102

<210> SEQ ID NO 111
<211> LENGTH: 206
<212> TYPE: DNA
<213> ORGANISM: Artificial Sequence
<220> FEATURE:
<223> OTHER INFORMATION: Description of Artificial Sequence: Homology
      vector 538-46.16

<400> SEQUENCE: 111
gtatcggcgg aaatccagct gagcgccggt cgctaccatt accagttggt ctggtgtcaa    60
aaagatccat aattaattaa cccggccgcc tgcaggtgga ctctagaaaa aattgaaaaa   120
ctattctaat ttattgcacg gagatctttt tttttttttt tttttttggc atataaatga   180
```
attcgctcgc agcgctattg gcggcg    206

<210> SEQ ID NO 112
<211> LENGTH: 101
<212> TYPE: DNA
<213> ORGANISM: Artificial Sequence
<220> FEATURE:
<223> OTHER INFORMATION: Description of Artificial Sequence: Homology
      vector 538-46.16

<400> SEQUENCE: 112
cgcgtgcacc acgagggact ctagaggatc cataattaat taattaattt ttatcccggg    60
tcgacctgca ggcggccggg tcgacctgca ggcggccaga c    101

<210> SEQ ID NO 113
<211> LENGTH: 57
<212> TYPE: DNA
<213> ORGANISM: Artificial Sequence
<220> FEATURE:
<223> OTHER INFORMATION: Description of Artificial Sequence: Homology
      vector 538-46.16

<400> SEQUENCE: 113
agatccccgg gcgagctcga attcgtaatc atggtcatag ctgtttcctg tgtgaaa    57

<210> SEQ ID NO 114
<211> LENGTH: 51
<212> TYPE: DNA
<213> ORGANISM: Artificial Sequence
<220> FEATURE:
<223> OTHER INFORMATION: Description of Artificial Sequence: Homology
      vector 570-91.64

<400> SEQUENCE: 114
acaggaaaca gctatgacca tgattacgaa ttcgagctcg cccggggatc t    51

<210> SEQ ID NO 115
<211> LENGTH: 104
<212> TYPE: DNA
<213> ORGANISM: Artificial Sequence
<220> FEATURE:
<223> OTHER INFORMATION: Description of Artificial Sequence: Homology
      vector 570-91.64

<400> SEQUENCE: 115
aaatatataa ataccatgtt agaatttggt ctgctgcagg tcgactctag aatttcattt    60 tgttttttc tatgctataa atgaattcgg atcccgtcgt ttta    104

<210> SEQ ID NO 116
<211> LENGTH: 180
<212> TYPE: DNA
<213> ORGANISM: Artificial Sequence
<220> FEATURE:
<223> OTHER INFORMATION: Description of Artificial Sequence: Homology
      vector 570-91.64

<400> SEQUENCE: 116
gaaatccagc tgagcgccgg tcgctaccat taccagttgg tctggtgtca aaagatcca    60 taattaatta acccggtcga ctctagattt tttttttttt ttttttggc atataaatag    120 atctgtatcc taaaattgaa ttgtaattat cgataataaa tgaattccgg catggcctcg    180

<210> SEQ ID NO 117
<211> LENGTH: 109
<212> TYPE: DNA

<210> SEQ ID NO 118
<211> LENGTH: 51
<212> TYPE: DNA
<213> ORGANISM: Artificial Sequence
<220> FEATURE:
<223> OTHER INFORMATION: Description of Artificial Sequence: Homology
vector 570-91.64

<400> SEQUENCE: 117
ccatgctcta gaggatcccc gggcgagctc gaattcggat ccataattaa ttaattaatt    60
tttatcccgg gtcgaccggg tcgacctgca gcctacatgg aaatctacc                109

<210> SEQ ID NO 118
<211> LENGTH: 51
<212> TYPE: DNA
<213> ORGANISM: Artificial Sequence
<220> FEATURE:
<223> OTHER INFORMATION: Description of Artificial Sequence: Homology
vector 570-91.64

<400> SEQUENCE: 118
taatgtatct ataatggtat aaagcttgta ttctatagtg tcacctaaat c              51

<210> SEQ ID NO 119
<211> LENGTH: 51
<212> TYPE: DNA
<213> ORGANISM: Artificial Sequence
<220> FEATURE:
<223> OTHER INFORMATION: Description of Artificial Sequence: Homology
vector 727-54.60

<400> SEQUENCE: 119
acaggaaaca gctatgacca tgattacgaa ttcgagctcg cccgggatc t               51

<210> SEQ ID NO 120
<211> LENGTH: 168
<212> TYPE: DNA
<213> ORGANISM: Artificial Sequence
<220> FEATURE:
<223> OTHER INFORMATION: Description of Artificial Sequence: Homology
vector 727-54.60

<400> SEQUENCE: 120
gtattgcggc cgcctgcagg tcgactctag attttttttt tttttttttt tggcatataa    60
atagatctgt atcctaaaat tgaattgtaa ttatcgataa taaatgaatt cacccgctgg   120
tggcggtctt tggcgcgggc cccgtgggca tcggcccggg caccacgg                168

<210> SEQ ID NO 121
<211> LENGTH: 112
<212> TYPE: DNA
<213> ORGANISM: Artificial Sequence
<220> FEATURE:
<223> OTHER INFORMATION: Description of Artificial Sequence: Homology
vector 727-54.60

<400> SEQUENCE: 121
gagctcgaat tcggatccat aattaattaa tttttatccc ggcgcgcctc gactctagaa    60
tttcattttg ttttttttcta tgctataaat gaattcggat cccgtcgttt ta          112

<210> SEQ ID NO 122
<211> LENGTH: 116
<212> TYPE: DNA
<213> ORGANISM: Artificial Sequence
<220> FEATURE:
<223> OTHER INFORMATION: Description of Artificial Sequence: Homology
vector 727-54.60

<400> SEQUENCE: 122

```
gaaatccagc tgagcgccgg tcgctaccat taccagttgg tctggtgtca aaaagatcca        60
taattaatta acccgggtcg aggcgcgccg ggtcgacctg caggcggccg ctatac           116
```

<210> SEQ ID NO 123
<211> LENGTH: 51
<212> TYPE: DNA
<213> ORGANISM: Artificial Sequence
<220> FEATURE:
<223> OTHER INFORMATION: Description of Artificial Sequence: Homology
      vector 727-54.60

<400> SEQUENCE: 123

```
taatgtatct ataatggtat aaagcttgta ttctatagtg tcacctaaat c                 51
```

<210> SEQ ID NO 124
<211> LENGTH: 27
<212> TYPE: DNA
<213> ORGANISM: Artificial Sequence
<220> FEATURE:
<223> OTHER INFORMATION: Description of Artificial Sequence: Homology
      vector 779-94.31

<400> SEQUENCE: 124

```
gaatacaagc tagcttaaga aagaatg                                            27
```

<210> SEQ ID NO 125
<211> LENGTH: 198
<212> TYPE: DNA
<213> ORGANISM: Artificial Sequence
<220> FEATURE:
<223> OTHER INFORMATION: Description of Artificial Sequence: Homology
      vector 779-94.31

<400> SEQUENCE: 125

```
gaatcgtcta gatccccaag cttggcctcg agggccgcgg ccgcctgcag gtcgactcta        60 gattttttttt ttttttttttt ttggcatata aatagatctg tatcctaaaa ttgaattgta     120
attatcgata taaatgaat tcacccgctg gtggcggtct ttggcgcggg ccccgtgggc       180
atcggcccgg gcaccacg                                                    198
```

<210> SEQ ID NO 126
<211> LENGTH: 88
<212> TYPE: DNA
<213> ORGANISM: Artificial Sequence
<220> FEATURE:
<223> OTHER INFORMATION: Description of Artificial Sequence: Homology
      vector 779-94.31

<400> SEQUENCE: 126

```
gagctcgaat tcgagctcgc ccggggatcc tctagaattt cattttgttt ttttctatgc        60
tataaatgaa ttcggatccc gtcgtttt                                           88
```

<210> SEQ ID NO 127
<211> LENGTH: 129
<212> TYPE: DNA
<213> ORGANISM: Artificial Sequence
<220> FEATURE:
<223> OTHER INFORMATION: Description of Artificial Sequence: Homology
      vector 779-94.31

<400> SEQUENCE: 127

```
gaaatccagc tgagcgccgg tcgctaccat taccagttgg tctggtgtca aaaagatcca        60
taattaatta acccgggtcg acctgcaggg cggccgcggc cctcgaggcc aagcttgggg      120
```

```
atctaataa                                                         129

<210> SEQ ID NO 128
<211> LENGTH: 36
<212> TYPE: DNA
<213> ORGANISM: Artificial Sequence
<220> FEATURE:
<223> OTHER INFORMATION: Description of Artificial Sequence: Homology
      vector 779-94.31

<400> SEQUENCE: 128
ttttaaaaat acgacttact gcaggtcgac tctaga                            36

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: homology
      vector 789-41.7

<400> SEQUENCE: 129
gcccggggat cttgaagatg aatgcat                                      27

<210> SEQ ID NO 130
<211> LENGTH: 117
<212> TYPE: DNA
<213> ORGANISM: Artificial Sequence
<220> FEATURE:
<223> OTHER INFORMATION: Description of Artificial Sequence: homology
      vector 789-41.7

<400> SEQUENCE: 130
atttggtctg ctgcaggtcg actctagaaa aaattgaaaa actattctaa tttattgcac    60
ggagatcttt tttttttttt ttttttttgg catataaatg aattcgctcg cagcgct     117

<210> SEQ ID NO 131
<211> LENGTH: 90
<212> TYPE: DNA
<213> ORGANISM: Artificial Sequence
<220> FEATURE:
<223> OTHER INFORMATION: Description of Artificial Sequence: homology
      vector 789-41.7

<400> SEQUENCE: 131
gcgtgcacca cgagggactc tagaggatcc ataattaatt aattaatttt tatcccgggt    60
cgacctgcag cctacatgga aatctaccag                                    90

<210> SEQ ID NO 132
<211> LENGTH: 186
<212> TYPE: DNA
<213> ORGANISM: Artificial Sequence
<220> FEATURE:
<223> OTHER INFORMATION: Description of Artificial Sequence: homology
      vector 789-41.7

<400> SEQUENCE: 132
gccgtatcat acaagcttgg cctcgagggc cgcggccgcc tgcaggtcga ctctagattt    60
tttttttttt tttttttggc atataaatag atctgtatcc taaaattgaa ttgtaattat   120
cgataataaa tgaattcacc cgctggtggc ggtctttggc gcgggccccg tgggcatcgg   180
cccggg                                                             186
```

<210> SEQ ID NO 133
<211> LENGTH: 88
<212> TYPE: DNA
<213> ORGANISM: Artificial Sequence
<220> FEATURE:
<223> OTHER INFORMATION: Description of Artificial Sequence: homology
      vector 789-41.7

<400> SEQUENCE: 133
gagctcgaat tcgagctcgc ccggggatcc tctagaattt cattttgttt ttttctatgc    60
tataaatgaa ttcggatccc gtcgtttt                                       88

<210> SEQ ID NO 134
<211> LENGTH: 129
<212> TYPE: DNA
<213> ORGANISM: Artificial Sequence
<220> FEATURE:
<223> OTHER INFORMATION: Description of Artificial Sequence: homology
      vector 789-41.7

<400> SEQUENCE: 134
gaaatccagc tgagcgccgg tcgctaccat taccagttgg tctggtgtca aaaagatcca    60
taattaatta acccgggtcg acctgcaggg cggccgcggc cctcgaggcc aagcttgtat   120
gataatatc                                                           129

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: homology
      vector 789-41.7

<400> SEQUENCE: 135
tataatggta taaagctagc ttgtattcta                                     30

<210> SEQ ID NO 136
<211> LENGTH: 27
<212> TYPE: DNA
<213> ORGANISM: Artificial Sequence
<220> FEATURE:
<223> OTHER INFORMATION: Description of Artificial Sequence: Homology
      vector 789-41.27

<400> SEQUENCE: 136
gaatacaagc tagctttata ccattat                                        27

<210> SEQ ID NO 137
<211> LENGTH: 186
<212> TYPE: DNA
<213> ORGANISM: Artificial Sequence
<220> FEATURE:
<223> OTHER INFORMATION: Description of Artificial Sequence: Homology
      vector 789-41.27

<400> SEQUENCE: 137
atattatcat acaagcttgg cctcgagggc cgcggccgcc tgcaggtcga ctctagattt    60
tttttttttt ttttttggc atataaatag atctgtatcc taaaattgaa ttgtaattat   120
cgataataaa tgaattcacc cgctggtggc ggtctttggc gcgggccccg tgggcatcgg   180
cccggg                                                              186

<210> SEQ ID NO 138
<211> LENGTH: 88

```
<212> TYPE: DNA
<213> ORGANISM: Artificial Sequence
<220> FEATURE:
<223> OTHER INFORMATION: Description of Artificial Sequence: Homology
      vector 789-41.27

<400> SEQUENCE: 138
gagctcgaat tcgagctcgc ccggggatcc tctagaattt cattttgttt ttttctatgc     60
tataaatgaa ttcggatccc gtcgtttt                                        88

<210> SEQ ID NO 139
<211> LENGTH: 129
<212> TYPE: DNA
<213> ORGANISM: Artificial Sequence
<220> FEATURE:
<223> OTHER INFORMATION: Description of Artificial Sequence: Homology
      vector 789-41.27

<400> SEQUENCE: 139
gaaatccagc tgagcgccgg tcgctaccat taccagttgg tctggtgtca aaagatcca     60 taattaatta acccgggtcg acctgcaggg cggccgcggc cctcgaggcc aagcttgtat    120
gatacggca                                                            129

<210> SEQ ID NO 140
<211> LENGTH: 123
<212> TYPE: DNA
<213> ORGANISM: Artificial Sequence
<220> FEATURE:
<223> OTHER INFORMATION: Description of Artificial Sequence: Homology
      vector 789-41.27

<400> SEQUENCE: 140
tgtaggctgc aggtcgactc tagaaaaaat tgaaaaacta ttctaattta ttgcacggag    60 atctttttt tttttttttt ttttggcata taatgaatt ccggcatggc ctcgctcgcg     120
cgt                                                                   123

<210> SEQ ID NO 141
<211> LENGTH: 90
<212> TYPE: DNA
<213> ORGANISM: Artificial Sequence
<220> FEATURE:
<223> OTHER INFORMATION: Description of Artificial Sequence: Homology
      vector 789-41.27

<400> SEQUENCE: 141
ccatgctcta gaggatcccc gggcgagctc gaattcggat ccataattaa ttaattaatt    60
tttatcccgg gtcgacctgc agcagaccaa                                      90

<210> SEQ ID NO 142
<211> LENGTH: 36
<212> TYPE: DNA
<213> ORGANISM: Artificial Sequence
<220> FEATURE:
<223> OTHER INFORMATION: Description of Artificial Sequence: Homology
      vector 789-41.27

<400> SEQUENCE: 142
cattcatctt caagatcccc gggcgagctc gaattc                               36

<210> SEQ ID NO 143
<211> LENGTH: 27
<212> TYPE: DNA
<213> ORGANISM: Artificial Sequence
```

<220> FEATURE:
<223> OTHER INFORMATION: Description of Artificial Sequence: Homology
      vector 789-41.47

<400> SEQUENCE: 143
gcccggggat cttgaagatg aatgcat                                            27

<210> SEQ ID NO 144
<211> LENGTH: 117
<212> TYPE: DNA
<213> ORGANISM: Artificial Sequence
<220> FEATURE:
<223> OTHER INFORMATION: Description of Artificial Sequence: Homology
      vector 789-41.47

<400> SEQUENCE: 144
atttggtctg ctgcaggtcg actctagaaa aaattgaaaa actattctaa tttattgcac        60
ggagatcttt tttttttttt ttttttttgg catataaatg aattcgctcg cagcgct          117

<210> SEQ ID NO 145
<211> LENGTH: 90
<212> TYPE: DNA
<213> ORGANISM: Artificial Sequence
<220> FEATURE:
<223> OTHER INFORMATION: Description of Artificial Sequence: Homology
      vector 789-41.47

<400> SEQUENCE: 145
gcgtgcacca cgagggactc tagaggatcc ataattaatt aattaatttt tatcccgggt        60
cgacctgcag cctacatgga aatctaccag                                         90

<210> SEQ ID NO 146
<211> LENGTH: 109
<212> TYPE: DNA
<213> ORGANISM: Artificial Sequence
<220> FEATURE:
<223> OTHER INFORMATION: Description of Artificial Sequence: Homology
      vector 789-41.47

<400> SEQUENCE: 146
gccgtatcat acaagcttgg cctcgagggc cgcggccgcc tgcaggtcga ctctagaatt        60
tcattttgtt ttttctatg ctataaatga attcggatcc cgtcgtttt                    109

<210> SEQ ID NO 147
<211> LENGTH: 177
<212> TYPE: DNA
<213> ORGANISM: Artificial Sequence
<220> FEATURE:
<223> OTHER INFORMATION: Description of Artificial Sequence: Homology
      vector 789-41.47

<400> SEQUENCE: 147
gaaatccagc tgagcgccgg tcgctaccat taccagttgg tctggtgtca aaaagatcca        60
taattaatta acccggtcga ctctagaaaa aattgaaaaa ctattctaat ttattgcacg       120
gagatctttt tttttttttt ttttttggc atataaatga attccggcat ggcctcg          177

<210> SEQ ID NO 148
<211> LENGTH: 135
<212> TYPE: DNA
<213> ORGANISM: Artificial Sequence
<220> FEATURE:
<223> OTHER INFORMATION: Description of Artificial Sequence: Homology
      vector 789-41.47

```
<400> SEQUENCE: 148
ccatgctcta gaggatcccc gggcgagctc gaattcggat ccataattaa ttaattaatt      60
tttatcccgg gtcgaccggg tcgacctgca gggcggccgc ggccctcgag gccaagcttg     120
tatgataata tcaaa                                                     135

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Homology
      vector 789-41.47

<400> SEQUENCE: 149
tataatggta taaagctagc ttgtattcta                                      30

<210> SEQ ID NO 150
<211> LENGTH: 27
<212> TYPE: DNA
<213> ORGANISM: Artificial Sequence
<220> FEATURE:
<223> OTHER INFORMATION: Description of Artificial Sequence: Homology
      vector 789-41.73

<400> SEQUENCE: 150
gcccggggat cttgaagatg aatgcat                                         27

<210> SEQ ID NO 151
<211> LENGTH: 120
<212> TYPE: DNA
<213> ORGANISM: Artificial Sequence
<220> FEATURE:
<223> OTHER INFORMATION: Description of Artificial Sequence: Homology
      vector 789-41.73

<400> SEQUENCE: 151
atttggtctg ctgcaggtcg actctagatt tttttttttt tttttttttgg catataaata     60 gatctgtatc ctaaaattga attgtaatta tcgataataa atgaattcgc tcgcagcgct    120

<210> SEQ ID NO 152
<211> LENGTH: 88
<212> TYPE: DNA
<213> ORGANISM: Artificial Sequence
<220> FEATURE:
<223> OTHER INFORMATION: Description of Artificial Sequence: Homology
      vector 789-41.73

<400> SEQUENCE: 152
gagctcgaat tcgagctcgc ccggggatcc tctagaattt cattttgttt ttttctatgc      60
tataaatgaa ttcggatccc gtcgtttt                                        88

<210> SEQ ID NO 153
<211> LENGTH: 129
<212> TYPE: DNA
<213> ORGANISM: Artificial Sequence
<220> FEATURE:
<223> OTHER INFORMATION: Description of Artificial Sequence: Homology
      vector 789-41.73

<400> SEQUENCE: 153
gaaatccagc tgagcgccgg tcgctaccat taccagttgg tctggtgtca aaaagatcca     60
taattaatta acccgggtcg acctgcaggg cggccgcggc cctcgaggcc aagcttgtat    120
```

```
gatacggca                                                              129

<210> SEQ ID NO 154
<211> LENGTH: 186
<212> TYPE: DNA
<213> ORGANISM: Artificial Sequence
<220> FEATURE:
<223> OTHER INFORMATION: Description of Artificial Sequence: Homology
      vector 789-41.73

<400> SEQUENCE: 154
gccgtatcat acaagcttgg cctcgagggc cgcggccgcc tgcaggtcga ctctagattt      60
tttttttttt tttttttggc atataaatag atctgtatcc taaaattgaa ttgtaattat    120
cgataataaa tgaattcacc cgctggtggc ggtctttggc gcgggcccg tgggcatcgg     180 cccggg                                                                186

<210> SEQ ID NO 155
<211> LENGTH: 88
<212> TYPE: DNA
<213> ORGANISM: Artificial Sequence
<220> FEATURE:
<223> OTHER INFORMATION: Description of Artificial Sequence: Homology
      vector 789-41.73

<400> SEQUENCE: 155
gagctcgaat tcgagctcgc ccggggatcc tctagaattt cattttgttt ttttctatgc      60
tataaatgaa ttcggatccc gtcgtttt                                         88

<210> SEQ ID NO 156
<211> LENGTH: 129
<212> TYPE: DNA
<213> ORGANISM: Artificial Sequence
<220> FEATURE:
<223> OTHER INFORMATION: Description of Artificial Sequence: Homology
      vector 789-41.73

<400> SEQUENCE: 156
gaaatccagc tgagcgccgg tcgctaccat taccagttgg tctggtgtca aaaagatcca      60
taattaatta acccgggtcg acctgcaggg cggccgcggc cctcgaggcc aagcttgtat    120
gataatatc                                                              129

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Homology
      vector 789-41.73

<400> SEQUENCE: 157
tataatggta taaagctagc ttgtattcta                                       30

<210> SEQ ID NO 158
<211> LENGTH:
<212> TYPE:
<213> ORGANISM:

<400> SEQUENCE: 158

000

<210> SEQ ID NO 159
<211> LENGTH:
```

```
<212> TYPE:
<213> ORGANISM:

<400> SEQUENCE: 159

000

<210> SEQ ID NO 160
<211> LENGTH:
<212> TYPE:
<213> ORGANISM:

<400> SEQUENCE: 160

000

<210> SEQ ID NO 161
<211> LENGTH:
<212> TYPE:
<213> ORGANISM:

<400> SEQUENCE: 161

000

<210> SEQ ID NO 162
<211> LENGTH:
<212> TYPE:
<213> ORGANISM:

<400> SEQUENCE: 162

000

<210> SEQ ID NO 163
<211> LENGTH:
<212> TYPE:
<213> ORGANISM:

<400> SEQUENCE: 163

000

<210> SEQ ID NO 164
<211> LENGTH:
<212> TYPE:
<213> ORGANISM:

<400> SEQUENCE: 164

000

<210> SEQ ID NO 165
<211> LENGTH:
<212> TYPE:
<213> ORGANISM:

<400> SEQUENCE: 165

000

<210> SEQ ID NO 166
<211> LENGTH:
<212> TYPE:
<213> ORGANISM:

<400> SEQUENCE: 166

000

<210> SEQ ID NO 167
```

-continued

<211> LENGTH:
<212> TYPE:
<213> ORGANISM:

<400> SEQUENCE: 167

000

<210> SEQ ID NO 168
<211> LENGTH:
<212> TYPE:
<213> ORGANISM:

<400> SEQUENCE: 168

000

<210> SEQ ID NO 169
<211> LENGTH:
<212> TYPE:
<213> ORGANISM:

<400> SEQUENCE: 169

000

<210> SEQ ID NO 170
<211> LENGTH:
<212> TYPE:
<213> ORGANISM:

<400> SEQUENCE: 170

000

<210> SEQ ID NO 171
<211> LENGTH:
<212> TYPE:
<213> ORGANISM:

<400> SEQUENCE: 171

000

<210> SEQ ID NO 172
<211> LENGTH:
<212> TYPE:
<213> ORGANISM:

<400> SEQUENCE: 172

000

<210> SEQ ID NO 173
<211> LENGTH:
<212> TYPE:
<213> ORGANISM:

<400> SEQUENCE: 173

000

<210> SEQ ID NO 174
<211> LENGTH:
<212> TYPE:
<213> ORGANISM:

<400> SEQUENCE: 174

000

```
<210> SEQ ID NO 175
<211> LENGTH:
<212> TYPE:
<213> ORGANISM:

<400> SEQUENCE: 175

000

<210> SEQ ID NO 176
<211> LENGTH:
<212> TYPE:
<213> ORGANISM:

<400> SEQUENCE: 176

000

<210> SEQ ID NO 177
<211> LENGTH:
<212> TYPE:
<213> ORGANISM:

<400> SEQUENCE: 177

000

<210> SEQ ID NO 178
<211> LENGTH:
<212> TYPE:
<213> ORGANISM:

<400> SEQUENCE: 178

000

<210> SEQ ID NO 179
<211> LENGTH:
<212> TYPE:
<213> ORGANISM:

<400> SEQUENCE: 179

000

<210> SEQ ID NO 180
<211> LENGTH:
<212> TYPE:
<213> ORGANISM:

<400> SEQUENCE: 180

000

<210> SEQ ID NO 181
<211> LENGTH:
<212> TYPE:
<213> ORGANISM:

<400> SEQUENCE: 181

000

<210> SEQ ID NO 182
<211> LENGTH:
<212> TYPE:
<213> ORGANISM:

<400> SEQUENCE: 182

000
```

-continued

<210> SEQ ID NO 183
<211> LENGTH:
<212> TYPE:
<213> ORGANISM:

<400> SEQUENCE: 183

000

<210> SEQ ID NO 184
<211> LENGTH:
<212> TYPE:
<213> ORGANISM:

<400> SEQUENCE: 184

000

<210> SEQ ID NO 185
<211> LENGTH:
<212> TYPE:
<213> ORGANISM:

<400> SEQUENCE: 185

000

<210> SEQ ID NO 186
<211> LENGTH:
<212> TYPE:
<213> ORGANISM:

<400> SEQUENCE: 186

000

<210> SEQ ID NO 187
<211> LENGTH:
<212> TYPE:
<213> ORGANISM:

<400> SEQUENCE: 187

000

<210> SEQ ID NO 188
<211> LENGTH:
<212> TYPE:
<213> ORGANISM:

<400> SEQUENCE: 188

000

<210> SEQ ID NO 189
<211> LENGTH: 3942
<212> TYPE: DNA
<213> ORGANISM: Swinepox virus
<220> FEATURE:
<221> NAME/KEY: CDS
<222> LOCATION: (1)..(369)
<221> NAME/KEY: CDS
<222> LOCATION: (370)..(597)
<221> NAME/KEY: CDS
<222> LOCATION: (598)..(1539)
<221> NAME/KEY: CDS
<222> LOCATION: (1675)..(3708)

<400> SEQUENCE: 189 tgt ttg ttc att aat aag atg ggt gga gct att ata gaa tac aag ata 48
Cys Leu Phe Ile Asn Lys Met Gly Gly Ala Ile Ile Glu Tyr Lys Ile -continued

```
  1                  5                    10                   15
cct ggt tcc aaa tct ata acc aaa tct att tcc gaa gaa cta gaa aat        96
Pro Gly Ser Lys Ser Ile Thr Lys Ser Ile Ser Glu Glu Leu Glu Asn
                 20                  25                  30 tta aca aag cga gat aaa cca ata tct aaa att ata gtt att cct att       144
Leu Thr Lys Arg Asp Lys Pro Ile Ser Lys Ile Ile Val Ile Pro Ile
             35                  40                  45 gta tgt tac aga aat gca aat agt ata aag gtt aca ttt gca cta aaa       192
Val Cys Tyr Arg Asn Ala Asn Ser Ile Lys Val Thr Phe Ala Leu Lys
         50                  55                  60 aag ttt atc ata gat aag gag ttt agt aca aat gta ata gac gta gat       240
Lys Phe Ile Ile Asp Lys Glu Phe Ser Thr Asn Val Ile Asp Val Asp
 65              70                  75                  80 ggt aaa cat gaa aaa atg tcc atg aat gaa aca tgc gaa gag gat gtt       288
Gly Lys His Glu Lys Met Ser Met Asn Glu Thr Cys Glu Glu Asp Val
                 85                  90                  95 gct aga gga ttg gga att ata gat ctt gaa gat gaa tgc ata gag gaa       336
Ala Arg Gly Leu Gly Ile Ile Asp Leu Glu Asp Glu Cys Ile Glu Glu
            100                 105                 110 gat gat gtc gat acg tca tta ttt aat gta taa atg gat aaa ttg tat       384
Asp Asp Val Asp Thr Ser Leu Phe Asn Val     Met Asp Lys Leu Tyr
        115                 120                 125 gcg gca ata ttc ggc gtt ttt atg aca tct aaa gat gat gat ttt aat       432
Ala Ala Ile Phe Gly Val Phe Met Thr Ser Lys Asp Asp Asp Phe Asn
    130                 135                 140 aac ttt ata gaa gtt gta aaa tct gta tta aca gat aca tca tct aat       480
Asn Phe Ile Glu Val Val Lys Ser Val Leu Thr Asp Thr Ser Ser Asn
145                 150                 155                 160 cat aca ata tcg tcg tcc aat aat aat aca tgg ata tat ata ttt cta       528
His Thr Ile Ser Ser Ser Asn Asn Asn Thr Trp Ile Tyr Ile Phe Leu
                165                 170                 175 gcg ata tta ttt ggt gtt atg gta tta tta gtt ttt att ttg tat tta       576
Ala Ile Leu Phe Gly Val Met Val Leu Leu Val Phe Ile Leu Tyr Leu
            180                 185                 190 aaa gtt act aaa cca act taa atg gag gaa gca gat aac caa ctc gtt       624
Lys Val Thr Lys Pro Thr     Met Glu Glu Ala Asp Asn Gln Leu Val
        195                 200                 205 tta aat agt att agt gct aga gca tta aag gca ttt ttt gta tct aaa       672
Leu Asn Ser Ile Ser Ala Arg Ala Leu Lys Ala Phe Phe Val Ser Lys
    210                 215                 220 att aat gat atg gtc gat gaa tta gtt acc aaa aaa tat cca cca aag       720
Ile Asn Asp Met Val Asp Glu Leu Val Thr Lys Lys Tyr Pro Pro Lys
225                 230                 235                 240 aag aaa tca caa ata aaa ctc ata gat aca cga att cct att gat ctt       768
Lys Lys Ser Gln Ile Lys Leu Ile Asp Thr Arg Ile Pro Ile Asp Leu
                245                 250                 255 att aat caa caa ttc gtt aaa aga ttt aaa cta gaa aat tat aaa aat       816
Ile Asn Gln Gln Phe Val Lys Arg Phe Lys Leu Glu Asn Tyr Lys Asn
            260                 265                 270 gga att tta tcc gtt ctt atc aat agt tta gtc gaa aat aat tac ttt       864
Gly Ile Leu Ser Val Leu Ile Asn Ser Leu Val Glu Asn Asn Tyr Phe
        275                 280                 285 gaa caa gat ggt aaa ctt aat agc agt gat att gat gaa tta gtg ctc       912
Glu Gln Asp Gly Lys Leu Asn Ser Ser Asp Ile Asp Glu Leu Val Leu
    290                 295                 300 aca gac ata gag aaa aag att tta tcg ttg att cct aga tgt tct cct       960
Thr Asp Ile Glu Lys Lys Ile Leu Ser Leu Ile Pro Arg Cys Ser Pro
305                 310                 315                 320 ctt tat ata gat atc agt gac gtt aaa gtt ctc gca tct agg tta aaa      1008
```

```
Leu Tyr Ile Asp Ile Ser Asp Val Lys Val Leu Ala Ser Arg Leu Lys
            325                 330                 335 aaa agt gct aaa tca ttt acg ttt aat gat cat gaa tat att ata caa      1056
Lys Ser Ala Lys Ser Phe Thr Phe Asn Asp His Glu Tyr Ile Ile Gln
        340                 345                 350 tct gat aaa ata gag gaa tta ata aat agt tta tct aga aac cat gat      1104
Ser Asp Lys Ile Glu Glu Leu Ile Asn Ser Leu Ser Arg Asn His Asp
            355                 360                 365 att ata cta gat gaa aaa agt tct att aaa gac agc ata tat ata cta      1152
Ile Ile Leu Asp Glu Lys Ser Ser Ile Lys Asp Ser Ile Tyr Ile Leu
        370                 375                 380 tct gat gat ctt ttg aat ata ctt cgt gaa aga tta ttt aga tgt cca      1200
Ser Asp Asp Leu Leu Asn Ile Leu Arg Glu Arg Leu Phe Arg Cys Pro
385                 390                 395                 400 cag gtt aaa gat aat act att tct aga aca cgt cta tat gat tat ttt      1248
Gln Val Lys Asp Asn Thr Ile Ser Arg Thr Arg Leu Tyr Asp Tyr Phe
            405                 410                 415 act aga gtg tca aag aaa gaa gaa gcg aaa ata tac gtt ata ttg aaa      1296
Thr Arg Val Ser Lys Lys Glu Glu Ala Lys Ile Tyr Val Ile Leu Lys
        420                 425                 430 gat tta aag att gct gat ata ctc ggt atc gaa aca gta acg ata gga      1344
Asp Leu Lys Ile Ala Asp Ile Leu Gly Ile Glu Thr Val Thr Ile Gly
            435                 440                 445 tca ttt gta tat acg aaa tat agc atg ttg att aat tca att tcg tct      1392
Ser Phe Val Tyr Thr Lys Tyr Ser Met Leu Ile Asn Ser Ile Ser Ser
        450                 455                 460 aat gtt gat aga tat tca aaa agg ttc cat gac tct ttt tat gaa gat      1440
Asn Val Asp Arg Tyr Ser Lys Arg Phe His Asp Ser Phe Tyr Glu Asp
465                 470                 475                 480 att gcg gaa ttt ata aag gat aat gaa aaa att aat gta tcc aga gtt      1488
Ile Ala Glu Phe Ile Lys Asp Asn Glu Lys Ile Asn Val Ser Arg Val
            485                 490                 495 gtt gaa tgc ctt atc gta cct aat att aat ata gag tta tta act gaa      1536
Val Glu Cys Leu Ile Val Pro Asn Ile Asn Ile Glu Leu Leu Thr Glu
        500                 505                 510 taa gtatatataa atgattgttt ttataatgtt tgttatcgca tttagttttg           1589
ctgtatggtt atcatataca tttttaaggc cgtatatgat aaatgaaaat atataagcac    1649
ttatttttgt tagtataata acaca atg ccg tcg tat atg tat ccg aag aac      1701
                              Met Pro Ser Tyr Met Tyr Pro Lys Asn
                                              515                 520 gca aga aaa gta att tca aag att ata tca tta caa ctt gat att aaa      1749
Ala Arg Lys Val Ile Ser Lys Ile Ile Ser Leu Gln Leu Asp Ile Lys
        525                 530                 535 aaa ctt cct aaa aaa tat ata aat acc atg tta gaa ttt ggt cta cat      1797
Lys Leu Pro Lys Lys Tyr Ile Asn Thr Met Leu Glu Phe Gly Leu His
540                 545                 550 gga aat cta cca gct tgt atg tat aaa gat gcc gta tca tat gat ata      1845
Gly Asn Leu Pro Ala Cys Met Tyr Lys Asp Ala Val Ser Tyr Asp Ile
555                 560                 565                 570 aat aat ata aga ttt tta cct tat aat tgt gtt atg gtt aaa gat tta      1893
Asn Asn Ile Arg Phe Leu Pro Tyr Asn Cys Val Met Val Lys Asp Leu
            575                 580                 585 ata aat gtt ata aaa tca tca tct gta ata gat act aga tta cat caa      1941
Ile Asn Val Ile Lys Ser Ser Ser Val Ile Asp Thr Arg Leu His Gln
        590                 595                 600 tct gta tta aaa cat cgt aga gcg tta ata gat tac ggc gat caa gac      1989
Ser Val Leu Lys His Arg Arg Ala Leu Ile Asp Tyr Gly Asp Gln Asp
            605                 610                 615
```

```
att atc act tta atg atc att aat aag tta cta tcg ata gat gat ata        2037
Ile Ile Thr Leu Met Ile Ile Asn Lys Leu Leu Ser Ile Asp Asp Ile
620                 625                 630 tcc tat ata tta gat aaa aaa ata att cat gta aca aaa ata tta aaa        2085
Ser Tyr Ile Leu Asp Lys Lys Ile Ile His Val Thr Lys Ile Leu Lys
635                 640                 645                 650 ata gac cct aca gta gcc aat tca aac atg aaa ctg aat aag ata gag        2133
Ile Asp Pro Thr Val Ala Asn Ser Asn Met Lys Leu Asn Lys Ile Glu
                655                 660                 665 ctt gta gat gta ata aca tca ata cct aag tct tcc tat aca tat tta        2181
Leu Val Asp Val Ile Thr Ser Ile Pro Lys Ser Ser Tyr Thr Tyr Leu
        670                 675                 680 tat aat aat atg atc att gat ctc gat aca tta tta tat tta tcc gat        2229
Tyr Asn Asn Met Ile Ile Asp Leu Asp Thr Leu Leu Tyr Leu Ser Asp
            685                 690                 695 gca ttc cac ata ccc ccc aca cat ata tca tta cgt tca ctt aga gat        2277
Ala Phe His Ile Pro Pro Thr His Ile Ser Leu Arg Ser Leu Arg Asp
700                 705                 710 ata aac agg att att gaa ttg ctt aaa aaa tat ccg aat aat aat att        2325
Ile Asn Arg Ile Ile Glu Leu Leu Lys Lys Tyr Pro Asn Asn Asn Ile
715                 720                 725                 730 att gat tat ata tcc gat agc ata aaa tca aat agt tca ttc att cac        2373
Ile Asp Tyr Ile Ser Asp Ser Ile Lys Ser Asn Ser Ser Phe Ile His
                735                 740                 745 ata ctt cat atg ata ata tca aat atg ttt cct gct ata atc cct agt        2421
Ile Leu His Met Ile Ile Ser Asn Met Phe Pro Ala Ile Ile Pro Ser
        750                 755                 760 gta aac gat ttt ata tct acc gta gtt gat aaa gat cga ctt att aat        2469
Val Asn Asp Phe Ile Ser Thr Val Val Asp Lys Asp Arg Leu Ile Asn
            765                 770                 775 atg tat ggg att aag tgt gtt gct atg ttt tcg tac gat ata aac atg        2517
Met Tyr Gly Ile Lys Cys Val Ala Met Phe Ser Tyr Asp Ile Asn Met
780                 785                 790 atc gat tta gag tca tta gat gac tca gat tac ata ttt ata gaa aaa        2565
Ile Asp Leu Glu Ser Leu Asp Asp Ser Asp Tyr Ile Phe Ile Glu Lys
795                 800                 805                 810 aat ata tct ata tac gac gtt aaa tgt aga gat ttt gcg aat atg att        2613
Asn Ile Ser Ile Tyr Asp Val Lys Cys Arg Asp Phe Ala Asn Met Ile
                815                 820                 825 aga gat aag gtt aaa aga gaa aag aat aga ata tta act acg aaa tgt        2661
Arg Asp Lys Val Lys Arg Glu Lys Asn Arg Ile Leu Thr Thr Lys Cys
        830                 835                 840 gaa gat att ata aga tat ata aaa tta ttc agt aaa aat aga ata aac        2709
Glu Asp Ile Ile Arg Tyr Ile Lys Leu Phe Ser Lys Asn Arg Ile Asn
            845                 850                 855 gat gaa aat aat aag gtg gag gag gtg ttg ata cat att gat aat gta        2757
Asp Glu Asn Asn Lys Val Glu Glu Val Leu Ile His Ile Asp Asn Val
860                 865                 870 tct aaa aat aat aaa tta tca ctg tct gat ata tca tct tta atg gat        2805
Ser Lys Asn Asn Lys Leu Ser Leu Ser Asp Ile Ser Ser Leu Met Asp
875                 880                 885                 890 caa ttt cgt tta aat cca tgt acc ata aga aat ata tta tta tct tca        2853
Gln Phe Arg Leu Asn Pro Cys Thr Ile Arg Asn Ile Leu Leu Ser Ser
                895                 900                 905 gca act ata aaa tca aaa cta tta gcg tta cgg gca gta aaa aac tgg        2901
Ala Thr Ile Lys Ser Lys Leu Leu Ala Leu Arg Ala Val Lys Asn Trp
        910                 915                 920 aaa tgt tat tca ttg aca aat gta tca atg tat aaa aaa ata aag ggt        2949
Lys Cys Tyr Ser Leu Thr Asn Val Ser Met Tyr Lys Lys Ile Lys Gly
            925                 930                 935
```

```
gtt atc gta atg gat atg gtt gat tat ata tct act aac att ctt aaa        2997
Val Ile Val Met Asp Met Val Asp Tyr Ile Ser Thr Asn Ile Leu Lys
    940                 945                 950 tac cat aaa caa tta tat gat aaa atg agt acg ttt gaa tat aaa cga        3045
Tyr His Lys Gln Leu Tyr Asp Lys Met Ser Thr Phe Glu Tyr Lys Arg
955                 960                 965                 970 gat att aaa tca tgt aaa tgc tcg ata tgt tcc gac tct ata aca cat        3093
Asp Ile Lys Ser Cys Lys Cys Ser Ile Cys Ser Asp Ser Ile Thr His
                975                 980                 985 cat ata tat gaa aca aca tca tgt ata aat tat aaa tct acc gat aat        3141
His Ile Tyr Glu Thr Thr Ser Cys Ile Asn Tyr Lys Ser Thr Asp Asn
            990                 995                 1000 gat ctt atg ata gta ttg ttc aat cta act aga tat tta atg cat ggg        3189
Asp Leu Met Ile Val Leu Phe Asn Leu Thr Arg Tyr Leu Met His Gly
        1005                1010                1015 atg ata cat cct aat ctt ata agc gta aaa gga tgg ggt ccc ctt att        3237
Met Ile His Pro Asn Leu Ile Ser Val Lys Gly Trp Gly Pro Leu Ile
    1020                1025                1030 gga tta tta acg ggt gat ata ggt att aat tta aaa cta tat tcc acc        3285
Gly Leu Leu Thr Gly Asp Ile Gly Ile Asn Leu Lys Leu Tyr Ser Thr
1035                1040                1045                1050 atg aat ata aat ggg cta cgg tat gga gat att acg tta tct tca tac        3333
Met Asn Ile Asn Gly Leu Arg Tyr Gly Asp Ile Thr Leu Ser Ser Tyr
                1055                1060                1065 gat atg agt aat aaa tta gtc tct att att aat aca ccc ata tat gag        3381
Asp Met Ser Asn Lys Leu Val Ser Ile Ile Asn Thr Pro Ile Tyr Glu
            1070                1075                1080 tta ata ccg ttt act aca tgt tgt tca ctc aat gaa tat tat tca aaa        3429
Leu Ile Pro Phe Thr Thr Cys Cys Ser Leu Asn Glu Tyr Tyr Ser Lys
        1085                1090                1095 att gtg att tta ata aat gtt att tta gaa tat atg ata tct att ata        3477
Ile Val Ile Leu Ile Asn Val Ile Leu Glu Tyr Met Ile Ser Ile Ile
    1100                1105                1110 tta tat aga ata ttg atc gta aaa aga ttt aat aac att aaa gaa ttt        3525
Leu Tyr Arg Ile Leu Ile Val Lys Arg Phe Asn Asn Ile Lys Glu Phe
1115                1120                1125                1130 att tca aaa gtc gta aat act gta cta gaa tca tca ggc ata tat ttt        3573
Ile Ser Lys Val Val Asn Thr Val Leu Glu Ser Ser Gly Ile Tyr Phe
                1135                1140                1145 tgt cag atg cgt gta cat gaa caa att gaa ttg gaa ata gat gag ctc        3621
Cys Gln Met Arg Val His Glu Gln Ile Glu Leu Glu Ile Asp Glu Leu
            1150                1155                1160 att att aat gga tct atg cct gta cag ctt atg cat tta ctt cta aag        3669
Ile Ile Asn Gly Ser Met Pro Val Gln Leu Met His Leu Leu Leu Lys
        1165                1170                1175 gta gct acc ata ata tta gag gaa atc aaa gaa ata taa cgtattttt         3718
Val Ala Thr Ile Ile Leu Glu Glu Ile Lys Glu Ile
    1180                1185                1190 cttttaaata aataaaaata cttttttttt taaacaaggg gtgctacctt gtctaattgt     3778
atcttgtatt ttggatctga tgcaagatta ttaaataatc gtatgaaaaa gtagtagata    3838
tagtttatat cgttactgga catgatatta tgtttagtta attcttcttt ggcatgaatt    3898
ctacacgtcg gacaaggtaa tgtatctata atggtataaa gctt                     3942
```

<210> SEQ ID NO 190
<211> LENGTH: 122
<212> TYPE: PRT
<213> ORGANISM: Swinepox virus

```
-continued

<400> SEQUENCE: 190

Cys Leu Phe Ile Asn Lys Met Gly Gly Ala Ile Ile Glu Tyr Lys Ile
 1               5                  10                 15

Pro Gly Ser Lys Ser Ile Thr Lys Ser Ile Ser Glu Glu Leu Glu Asn
            20                  25                  30

Leu Thr Lys Arg Asp Lys Pro Ile Ser Lys Ile Val Ile Pro Ile
        35                  40                  45

Val Cys Tyr Arg Asn Ala Asn Ser Ile Lys Val Thr Phe Ala Leu Lys
 50                  55                  60

Lys Phe Ile Ile Asp Lys Glu Phe Ser Thr Asn Val Ile Asp Val Asp
65                  70                  75                  80

Gly Lys His Glu Lys Met Ser Met Asn Glu Thr Cys Glu Glu Asp Val
                85                  90                  95

Ala Arg Gly Leu Gly Ile Ile Asp Leu Glu Asp Glu Cys Ile Glu Glu
            100                 105                 110

Asp Asp Val Asp Thr Ser Leu Phe Asn Val
            115                 120

<210> SEQ ID NO 191
<211> LENGTH: 75
<212> TYPE: PRT
<213> ORGANISM: Swinepox virus

<400> SEQUENCE: 191

Met Asp Lys Leu Tyr Ala Ala Ile Phe Gly Val Phe Met Thr Ser Lys
 1               5                  10                 15

Asp Asp Asp Phe Asn Asn Phe Ile Glu Val Val Lys Ser Val Leu Thr
            20                  25                  30

Asp Thr Ser Ser Asn His Thr Ile Ser Ser Ser Asn Asn Asn Thr Trp
        35                  40                  45

Ile Tyr Ile Phe Leu Ala Ile Leu Phe Gly Val Met Val Leu Leu Val
 50                  55                  60

Phe Ile Leu Tyr Leu Lys Val Thr Lys Pro Thr
65                  70                  75

<210> SEQ ID NO 192
<211> LENGTH: 313
<212> TYPE: PRT
<213> ORGANISM: Swinepox virus

<400> SEQUENCE: 192

Met Glu Glu Ala Asp Asn Gln Leu Val Leu Asn Ser Ile Ser Ala Arg
 1               5                  10                 15

Ala Leu Lys Ala Phe Phe Val Ser Lys Ile Asn Asp Met Val Asp Glu
            20                  25                  30

Leu Val Thr Lys Lys Tyr Pro Pro Lys Lys Ser Gln Ile Lys Leu
        35                  40                  45

Ile Asp Thr Arg Ile Pro Ile Asp Leu Ile Asn Gln Gln Phe Val Lys
 50                  55                  60

Arg Phe Lys Leu Glu Asn Tyr Lys Asn Gly Ile Leu Ser Val Leu Ile
65                  70                  75                  80

Asn Ser Leu Val Glu Asn Asn Tyr Phe Glu Gln Asp Gly Lys Leu Asn
                85                  90                  95

Ser Ser Asp Ile Asp Glu Leu Val Leu Thr Asp Ile Glu Lys Lys Ile
            100                 105                 110

Leu Ser Leu Ile Pro Arg Cys Ser Pro Leu Tyr Ile Asp Ile Ser Asp
```

-continued

```
        115                 120                 125

Val Lys Val Leu Ala Ser Arg Leu Lys Lys Ser Ala Lys Ser Phe Thr
    130                 135                 140

Phe Asn Asp His Glu Tyr Ile Ile Gln Ser Asp Lys Ile Glu Glu Leu
145                 150                 155                 160

Ile Asn Ser Leu Ser Arg Asn His Asp Ile Ile Leu Asp Glu Lys Ser
                165                 170                 175

Ser Ile Lys Asp Ser Ile Tyr Ile Leu Ser Asp Asp Leu Leu Asn Ile
            180                 185                 190

Leu Arg Glu Arg Leu Phe Arg Cys Pro Gln Val Lys Asp Asn Thr Ile
        195                 200                 205

Ser Arg Thr Arg Leu Tyr Asp Tyr Phe Thr Arg Val Ser Lys Lys Glu
    210                 215                 220

Glu Ala Lys Ile Tyr Val Ile Leu Lys Asp Leu Lys Ile Ala Asp Ile
225                 230                 235                 240

Leu Gly Ile Glu Thr Val Thr Ile Gly Ser Phe Val Tyr Thr Lys Tyr
                245                 250                 255

Ser Met Leu Ile Asn Ser Ile Ser Ser Asn Val Asp Arg Tyr Ser Lys
            260                 265                 270

Arg Phe His Asp Ser Phe Tyr Glu Asp Ile Ala Glu Phe Ile Lys Asp
        275                 280                 285

Asn Glu Lys Ile Asn Val Ser Arg Val Val Glu Cys Leu Ile Val Pro
    290                 295                 300

Asn Ile Asn Ile Glu Leu Leu Thr Glu
305                 310

<210> SEQ ID NO 193
<211> LENGTH: 677
<212> TYPE: PRT
<213> ORGANISM: Swinepox virus

<400> SEQUENCE: 193

Met Pro Ser Tyr Met Tyr Pro Lys Asn Ala Arg Lys Val Ile Ser Lys
  1               5                  10                  15

Ile Ile Ser Leu Gln Leu Asp Ile Lys Lys Leu Pro Lys Lys Tyr Ile
            20                  25                  30

Asn Thr Met Leu Glu Phe Gly Leu His Gly Asn Leu Pro Ala Cys Met
        35                  40                  45

Tyr Lys Asp Ala Val Ser Tyr Asp Ile Asn Asn Ile Arg Phe Leu Pro
    50                  55                  60

Tyr Asn Cys Val Met Val Lys Asp Leu Ile Asn Val Ile Lys Ser Ser
 65                  70                  75                  80

Ser Val Ile Asp Thr Arg Leu His Gln Ser Val Leu Lys His Arg Arg
                 85                  90                  95

Ala Leu Ile Asp Tyr Gly Asp Gln Asp Ile Ile Thr Leu Met Ile Ile
            100                 105                 110

Asn Lys Leu Leu Ser Ile Asp Asp Ile Ser Tyr Ile Leu Asp Lys Lys
        115                 120                 125

Ile Ile His Val Thr Lys Ile Leu Lys Ile Asp Pro Thr Val Ala Asn
    130                 135                 140

Ser Asn Met Lys Leu Asn Lys Ile Glu Leu Val Asp Val Ile Thr Ser
145                 150                 155                 160

Ile Pro Lys Ser Ser Tyr Thr Tyr Leu Tyr Asn Asn Met Ile Ile Asp
                165                 170                 175
```

-continued

```
Leu Asp Thr Leu Leu Tyr Leu Ser Asp Ala Phe His Ile Pro Pro Thr
            180                 185                 190
His Ile Ser Leu Arg Ser Leu Arg Asp Ile Asn Arg Ile Ile Glu Leu
            195                 200                 205
Leu Lys Lys Tyr Pro Asn Asn Asn Ile Ile Asp Tyr Ile Ser Asp Ser
        210                 215                 220
Ile Lys Ser Asn Ser Ser Phe Ile His Ile Leu His Met Ile Ile Ser
225                 230                 235                 240
Asn Met Phe Pro Ala Ile Ile Pro Ser Val Asn Asp Phe Ile Ser Thr
                245                 250                 255
Val Val Asp Lys Asp Arg Leu Ile Asn Met Tyr Gly Ile Lys Cys Val
                260                 265                 270
Ala Met Phe Ser Tyr Asp Ile Asn Met Ile Asp Leu Glu Ser Leu Asp
            275                 280                 285
Asp Ser Asp Tyr Ile Phe Ile Glu Lys Asn Ile Ser Ile Tyr Asp Val
            290                 295                 300
Lys Cys Arg Asp Phe Ala Asn Met Ile Arg Asp Lys Val Lys Arg Glu
305                 310                 315                 320
Lys Asn Arg Ile Leu Thr Thr Lys Cys Glu Asp Ile Ile Arg Tyr Ile
                325                 330                 335
Lys Leu Phe Ser Lys Asn Arg Ile Asn Asp Glu Asn Asn Lys Val Glu
                340                 345                 350
Glu Val Leu Ile His Ile Asp Asn Val Ser Lys Asn Asn Lys Leu Ser
            355                 360                 365
Leu Ser Asp Ile Ser Ser Leu Met Asp Gln Phe Arg Leu Asn Pro Cys
        370                 375                 380
Thr Ile Arg Asn Ile Leu Leu Ser Ser Ala Thr Ile Lys Ser Lys Leu
385                 390                 395                 400
Leu Ala Leu Arg Ala Val Lys Asn Trp Lys Cys Tyr Ser Leu Thr Asn
                405                 410                 415
Val Ser Met Tyr Lys Lys Ile Lys Gly Val Ile Val Met Asp Met Val
                420                 425                 430
Asp Tyr Ile Ser Thr Asn Ile Leu Lys Tyr His Lys Gln Leu Tyr Asp
            435                 440                 445
Lys Met Ser Thr Phe Glu Tyr Lys Arg Asp Ile Lys Ser Cys Lys Cys
        450                 455                 460
Ser Ile Cys Ser Asp Ser Ile Thr His His Ile Tyr Glu Thr Thr Ser
465                 470                 475                 480
Cys Ile Asn Tyr Lys Ser Thr Asp Asn Asp Leu Met Ile Val Leu Phe
                485                 490                 495
Asn Leu Thr Arg Tyr Leu Met His Gly Met Ile His Pro Asn Leu Ile
                500                 505                 510
Ser Val Lys Gly Trp Gly Pro Leu Ile Gly Leu Leu Thr Gly Asp Ile
            515                 520                 525
Gly Ile Asn Leu Lys Leu Tyr Ser Thr Met Asn Ile Asn Gly Leu Arg
        530                 535                 540
Tyr Gly Asp Ile Thr Leu Ser Ser Tyr Asp Met Ser Asn Lys Leu Val
545                 550                 555                 560
Ser Ile Ile Asn Thr Pro Ile Tyr Glu Leu Ile Pro Phe Thr Thr Cys
                565                 570                 575
Cys Ser Leu Asn Glu Tyr Tyr Ser Lys Ile Val Ile Leu Ile Asn Val
            580                 585                 590
Ile Leu Glu Tyr Met Ile Ser Ile Ile Leu Tyr Arg Ile Leu Ile Val
```

```
                595                 600                 605
Lys Arg Phe Asn Asn Ile Lys Glu Phe Ile Ser Lys Val Val Asn Thr
        610                 615                 620

Val Leu Glu Ser Ser Gly Ile Tyr Phe Cys Gln Met Arg Val His Glu
625                 630                 635                 640

Gln Ile Glu Leu Glu Ile Asp Glu Leu Ile Ile Asn Gly Ser Met Pro
                645                 650                 655

Val Gln Leu Met His Leu Leu Leu Lys Val Ala Thr Ile Ile Leu Glu
        660                 665                 670

Glu Ile Lys Glu Ile
        675

<210> SEQ ID NO 194
<211> LENGTH: 64
<212> TYPE: PRT
<213> ORGANISM: Swinepox virus

<400> SEQUENCE: 194

Lys Leu Tyr Thr Ile Ile Asp Thr Leu Pro Cys Pro Thr Cys Arg Ile
  1               5                   10                  15

His Ala Lys Glu Glu Leu Thr Lys His Asn Ile Met Ser Ser Asn Asp
            20                  25                  30

Ile Asn Tyr Ile Tyr Tyr Phe Phe Ile Arg Leu Phe Asn Asn Leu Ala
        35                  40                  45

Ser Asp Pro Lys Tyr Lys Ile Gln Leu Asp Lys Val Ala Pro Leu Val
    50                  55                  60

<210> SEQ ID NO 195
<211> LENGTH: 583
<212> TYPE: DNA
<213> ORGANISM: Swinepox virus

```
gtt gct gta tgt aat cta gga tct att tcg tgg agt aaa ttt gtt aat        433
Val Ala Val Cys Asn Leu Gly Ser Ile Ser Trp Ser Lys Phe Val Asn
    130                 135                 140 aat aac gta ttt atg ttc gac aag ttg aga ata att acg aaa ata cta        481
Asn Asn Val Phe Met Phe Asp Lys Leu Arg Ile Ile Thr Lys Ile Leu
145                 150                 155                 160 gtt aaa aat cta aat aaa ata ata gat atc aat tat tat cca gtg ata        529
Val Lys Asn Leu Asn Lys Ile Ile Asp Ile Asn Tyr Tyr Pro Val Ile
                165                 170                 175 gaa tcg tct aga tct aat aag aaa cat aga ccc ata ggt atc ggg gtt        577
Glu Ser Ser Arg Ser Asn Lys Lys His Arg Pro Ile Gly Ile Gly Val
            180                 185                 190 cag ggt                                                                 583
Gln Gly
```

<210> SEQ ID NO 196
<211> LENGTH: 194
<212> TYPE: PRT
<213> ORGANISM: Swinepox virus

<400> SEQUENCE: 196

```
Ser Leu Arg Lys Asn Val Gly Asn Glu Glu Tyr Arg Thr Lys Asp Leu
  1               5                  10                  15

Phe Thr Ala Leu Trp Val Pro Asp Leu Phe Met Glu Arg Val Glu Lys
             20                  25                  30

Asp Glu Glu Trp Ser Leu Met Cys Pro Cys Glu Cys Pro Gly Leu Cys
         35                  40                  45

Asp Val Trp Gly Asn Asp Phe Asn Lys Leu Tyr Ile Glu Tyr Glu Thr
     50                  55                  60

Lys Lys Lys Ile Lys Ala Ile Ala Lys Ala Arg Ser Leu Trp Lys Ser
 65                  70                  75                  80

Ile Ile Glu Ala Gln Ile Glu Gln Gly Thr Pro Tyr Ile Leu Tyr Lys
                 85                  90                  95

Asp Ser Cys Asn Lys Lys Ser Asn Gln Ser Asn Leu Gly Thr Ile Arg
            100                 105                 110

Ser Ser Asn Leu Cys Thr Glu Ile Ile Gln Phe Ser Asn Glu Asp Glu
        115                 120                 125

Val Ala Val Cys Asn Leu Gly Ser Ile Ser Trp Ser Lys Phe Val Asn
    130                 135                 140

Asn Asn Val Phe Met Phe Asp Lys Leu Arg Ile Ile Thr Lys Ile Leu
145                 150                 155                 160

Val Lys Asn Leu Asn Lys Ile Ile Asp Ile Asn Tyr Tyr Pro Val Ile
                165                 170                 175

Glu Ser Ser Arg Ser Asn Lys Lys His Arg Pro Ile Gly Ile Gly Val
            180                 185                 190

Gln Gly
```

<210> SEQ ID NO 197
<211> LENGTH: 51
<212> TYPE: DNA
<213> ORGANISM: Artificial Sequence
<220> FEATURE:
<223> OTHER INFORMATION: Description of Artificial Sequence: Homology
      vector 751-07.A1

<400> SEQUENCE: 197
acaggaaaca gctatgacca tgattacgaa ttcgagctcg cccgggatc t            51

<210> SEQ ID NO 198
<211> LENGTH: 141
<212> TYPE: DNA
<213> ORGANISM: Artificial Sequence
<220> FEATURE:
<223> OTHER INFORMATION: Description of Artificial Sequence: Homology
      vector 751-07.A1

<400> SEQUENCE: 198

```
gtatagcggc cgcctgcagg tcgactctag attttttttt tttttttttt tggcatataa      60
atagatctgt atcctaaaat tgaattgtaa ttatcgataa taaatgaatt ccatgtgctg     120
cctcacccct gtgctggcgc t                                               141
```

<210> SEQ ID NO 199
<211> LENGTH: 120
<212> TYPE: DNA
<213> ORGANISM: Artificial Sequence
<220> FEATURE:
<223> OTHER INFORMATION: Description of Artificial Sequence: Homology
      vector 751-07.A1

<400> SEQUENCE: 199

```
tcgcccgcct ctgacgcccc ggatccataa ttaattaatt tttatcccgg cgcgcctcga      60
ctctagaatt tcattttgtt tttttctatg ctataaatga attcggatcc cgtcgtttta     120
```

<210> SEQ ID NO 200
<211> LENGTH: 116
<212> TYPE: DNA
<213> ORGANISM: Artificial Sequence
<220> FEATURE:
<223> OTHER INFORMATION: Description of Artificial Sequence: Homology
      vector 751-07.A1

<400> SEQUENCE: 200

```
gaaatccagc tgagcgccgg tcgctaccat taccagttgg tctggtgtca aaaagatcca      60
taattaatta acccgggtcg aggcgcgccg ggtcgacctg caggcggccg ctatac         116
```

<210> SEQ ID NO 201
<211> LENGTH: 51
<212> TYPE: DNA
<213> ORGANISM: Artificial Sequence
<220> FEATURE:
<223> OTHER INFORMATION: Description of Artificial Sequence: Homology
      vector 751-07.A1

<400> SEQUENCE: 201

```
taatgtatct ataatggtat aaagcttgta ttctatagtg tcacctaaat c               51
```

<210> SEQ ID NO 202
<211> LENGTH: 51
<212> TYPE: DNA
<213> ORGANISM: Artificial Sequence
<220> FEATURE:
<223> OTHER INFORMATION: Description of Artificial Sequence: Homology
      vector 751-56.A1

<400> SEQUENCE: 202

```
acaggaaaca gctatgacca tgattacgaa ttcgagctcg cccggggatc t               51
```

<210> SEQ ID NO 203
<211> LENGTH: 138
<212> TYPE: DNA
<213> ORGANISM: Artificial Sequence
<220> FEATURE:

```
<223> OTHER INFORMATION: Description of Artificial Sequence: Homology
      vector 751-56.A1

<400> SEQUENCE: 203
gtatagcggc cgcctgcagg tcgactctag atttttttttt ttttttttttt tggcatataa      60 atagatctgt atcctaaaat tgaattgtaa ttatcgataa taaatgaatt cgatggctgt      120
gcctgcaagc ccacagca                                                    138

<210> SEQ ID NO 204
<211> LENGTH: 120
<212> TYPE: DNA
<213> ORGANISM: Artificial Sequence
<220> FEATURE:
<223> OTHER INFORMATION: Description of Artificial Sequence: Homology
      vector 751-56.A1

<400> SEQUENCE: 204
cttagcccca aacgcacctc agatccataa ttaattaatt tttatcccgg cgcgcctcga      60
ctctagaatt tcattttgtt tttttctatg ctataaatga attcggatcc cgtcgtttta    120

<210> SEQ ID NO 205
<211> LENGTH: 116
<212> TYPE: DNA
<213> ORGANISM: Artificial Sequence
<220> FEATURE:
<223> OTHER INFORMATION: Description of Artificial Sequence: Homology
      vector 751-56.A1

<400> SEQUENCE: 205
gaaatccagc tgagcgccgg tcgctaccat taccagttgg tctggtgtca aaaagatcca      60
taattaatta acccgggtcg aggcgcgccg ggtcgacctg caggcggccg ctatac         116

<210> SEQ ID NO 206
<211> LENGTH: 51
<212> TYPE: DNA
<213> ORGANISM: Artificial Sequence
<220> FEATURE:
<223> OTHER INFORMATION: Description of Artificial Sequence: Homology
      vector 751-56.A1

<400> SEQUENCE: 206
taatgtatct ataatggtat aaagcttgta ttctatagtg tcacctaaat c               51

<210> SEQ ID NO 207
<211> LENGTH: 45
<212> TYPE: DNA
<213> ORGANISM: Artificial Sequence
<220> FEATURE:
<223> OTHER INFORMATION: Description of Artificial Sequence: Homology
      vector 752-22.1

<400> SEQUENCE: 207
caaggaatgg tgcatgcccg ttcttatcaa tagtttagtc gaaaa                      45

<210> SEQ ID NO 208
<211> LENGTH: 57
<212> TYPE: DNA
<213> ORGANISM: Artificial Sequence
<220> FEATURE:
<223> OTHER INFORMATION: Description of Artificial Sequence: Homology
      vector 752-22.1

<400> SEQUENCE: 208
tatataagca cttatttttg ttagtataat aacacaatgc cagatcccgt cgttttta        57
```

<210> SEQ ID NO 209
<211> LENGTH: 249
<212> TYPE: DNA
<213> ORGANISM: Artificial Sequence
<220> FEATURE:
<223> OTHER INFORMATION: Description of Artificial Sequence: Homology vector 752-22.1

<400> SEQUENCE: 209

| | |
|---|---|
| tccagctgag cgccggtcgc taccattacc agttggtctg gtgtcaaaaa gatccataat | 60 |
| taattaacca gcggccgcct gcaggtcgac tctagatttt ttttttttt tttttggca | 120 |
| tataaataga tctgtatcct aaaattgaat tgtaattatc gataataaat gaattcggat | 180 |
| ccataattaa ttaattttta tcccggcgcg ccgggtcgac ctgcaggcgg ccgctgggtc | 240 |
| gacaaagat | 249 |

<210> SEQ ID NO 210
<211> LENGTH: 45
<212> TYPE: DNA
<213> ORGANISM: Artificial Sequence
<220> FEATURE:
<223> OTHER INFORMATION: Description of Artificial Sequence: Homology vector 752-22.1

<400> SEQUENCE: 210

| | |
|---|---|
| caaaagtcgt aaatactgta ctagaagctt ggcgtaatca tggtc | 45 |

<210> SEQ ID NO 211
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 211

| | |
|---|---|
| cgacggatcc gaggtgcgtt tggggctaag tgc | 33 |

<210> SEQ ID NO 212
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 212

| | |
|---|---|
| ccacggatcc agcacaacgc gagtcccacc atggct | 36 |

<210> SEQ ID NO 213
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 213

| | |
|---|---|
| ccacgaattc gatggctgtg cctgcaagcc cacag | 35 |

<210> SEQ ID NO 214
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 214
cgaagatctg aggtgcgttt ggggctaagt gc                                32

<210> SEQ ID NO 215
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 215
cgcaggatcc ggggcgtcag aggcgggcga ggtg                              34

<210> SEQ ID NO 216
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 216
gagcggatcc tgcaggagga gacacagagc tg                                32

<210> SEQ ID NO 217
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 217
gcgcgaattc catgtgctgc ctcacccctg tg                                32

<210> SEQ ID NO 218
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 218
cgcaggatcc ggggcgtcag aggcgggcga ggtg                              34

<210> SEQ ID NO 219
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 219
ggggaattca atgcaaccca ccgcgccgcc cc                                32

<210> SEQ ID NO 220
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 220
gggggatcct agggcgcgcc cgccggctcg ct                                32

<210> SEQ ID NO 221
<211> LENGTH: 5785

<212> TYPE: DNA
<213> ORGANISM: Swinepox virus

<400> SEQUENCE: 221

| | | | | | |
|---|---|---|---|---|---|
| aagcttaaga | aagaatgtag | ggaacgaaga | atatagaacc | aaagatttat | ttactgcatt | 60 |
| atgggtacct | gatttattta | tggaacgcgt | agaaaaagat | gaagaatggt | ctctaatgtg | 120 |
| tccatgcgaa | tgtccaggat | tatgcgatgt | atggggaat | gattttaaca | aattatatat | 180 |
| agaatacgaa | acaagaaaaa | aaattaaagc | gatcgctaaa | gcaagaagtt | tatgcaaatc | 240 |
| tattatcgag | gctcaaatag | aacaaggaac | gccgtatata | ctatataaag | attcttgtaa | 300 |
| taaaaaatcc | aatcaaagca | atttgggaac | aattagatcg | agtaatctct | gtacagagat | 360 |
| tatacaattt | agtaacgagg | atgaagttgc | tgtatgtaat | ctaggatcta | tttcgtggag | 420 |
| taaatttgtt | aataataacg | tatttatgtt | cgacaagttg | agaataatta | cgaaaatact | 480 |
| agttaaaaat | ctaaataaaa | taatagatat | caattattat | ccagtgatag | aatcgtctag | 540 |
| atctaataag | aaacatagac | ccataggtat | cggtgttcag | ggtttggctg | atgtgtttat | 600 |
| attattgggc | tatgcattcg | atagcgaaga | agcaaaaata | ttaaatatac | aaatttccga | 660 |
| aacaatatat | tatgccgcac | tagaatctag | ttgcgaacta | gctaaaattt | acggacctta | 720 |
| tgagacatat | aacgattctc | cagcgagtaa | aggtattcta | caatatgata | tgtggttaaa | 780 |
| gaacccaaca | gatttatggg | attggaatga | actaaaaaag | agaattaata | cacatggatt | 840 |
| gagaaatagc | cttctaatag | caccaatgcc | tactgcatct | acatctcaaa | tattaagtaa | 900 |
| taatgagtcc | accgaaccat | atactagcaa | tatatataca | agaagagtat | tatctggaga | 960 |
| ttttcaggtt | gtaaatccac | acctattgag | agaactaata | agtagaaata | tgtggaataa | 1020 |
| tgacataaag | aatacaattg | tgttacataa | tggttctatt | caacatttag | atttaccaga | 1080 |
| taatataaaa | ccaatatata | aaacggtttg | ggagatatct | ccaaaatgta | ttttagaaat | 1140 |
| ggcagccgac | agaggtgcgt | ttatagatcc | aagtcaatca | atgacaatat | atatagataa | 1200 |
| tcctacatac | gcaaaactga | ccagtatgca | tttttacgga | tggagattgg | ggctaaaaac | 1260 |
| tgggatgtat | tatatgagaa | caaaatcggc | atcaaatcct | ataaaattca | cagttgagtg | 1320 |
| tagtaattgt | tctgcataat | ttttataaaa | atgaaatact | atctcatgta | tcttaatata | 1380 |
| ttaaaaatgc | gtaaaagtgg | cattccaaaa | caacccgttc | ccaaaaaaga | ttatgttcaa | 1440 |
| actgataata | ataaaaaaca | acaaataaca | acgtgttcag | aagtcgttga | gtatcttaaa | 1500 |
| tcactaagta | agagcaccga | aaaatgtata | gaaaatgtaa | tattaacgcc | ttctcaatat | 1560 |
| ccttcttgtt | catcgataac | tattaattta | acagactatc | tatcatctaa | aatgacatct | 1620 |
| acatatatag | cattagaagg | tgagtctaaa | atatacaaga | ataaaaagaa | tgaaagtaga | 1680 |
| tcgttagatc | aatatttttt | aaaaatacga | cttactgcag | caagtcctat | aatgtatcaa | 1740 |
| ttattagatt | gtatatattc | taatattaga | gataataaac | atataccccc | ttccttatca | 1800 |
| aatatatcta | tatcggactt | agaagagaaa | acgcttaacc | agggggtgttt | gttcattaat | 1860 |
| aagatgggtg | gagctattat | agaatacaag | atacctggtt | ccaaatctat | aacaaaatct | 1920 |
| atttccgaag | aactagaaaa | tttaacaaag | cgagataaac | aaatatctaa | aattatagtt | 1980 |
| attcctattg | tatgttacag | aaatgcaaat | agtataaagg | ttacatttgc | actaaaaaag | 2040 |
| tttatcatag | ataaggagtt | tagtacaaat | gtaatagacg | tagatggtaa | acatgaaaaa | 2100 |
| atgtccatga | atgaaacatg | cgaagaggat | gttgctagag | gattgggaat | tatagatctt | 2160 |
| gaagatgaat | gcatagagga | agatgatgtc | gatacgtcat | tatttaatgt | ataaatggat | 2220 |

-continued

```
aaattgtatg cggcaatatt cggcgttttt atgacatcta aagatgatga ttttaataac   2280
tttatagaag ttgtaaaatc tgtattaaca gatacatcat ctaatcatac aatatcgtcg   2340
tccaataata atacatggat atatatattt ctagcgatat tatttggtgt tatggtatta   2400
ttagttttta ttttgtattt aaaagttact aaaccaactt aaatggagga agcagataac   2460
caactcgttt aaatagtat tagtgctaga gcattaaagg cattttttgt atctaaaatt   2520
aatgatatgg tcgatgaatt agttaccaaa aaatatccac caaagaagaa atcacaaata   2580
aaactcatag atacacgaat tcctattgat cttattaatc aacaattcgt taaaagattt   2640
aaactagaaa attataaaaa tggaaatttta tccgttctta tcaatagttt agtcgaaaat   2700
aattactttg aacaagatgg taaacttaat agcagtgata ttgatgaatt agtgctcaca   2760
gacatagaga aaaagatttt atcgttgatt cctagatgtt ctcctcttta tatagatatc   2820
agtgacgtta aagttctcgc atctaggtta aaaaagtgct aaatcattta cgtttaatga   2880
tcatgaatat attatacaat ctgataaaat agaggaatta ataaatagtt tatctagaaa   2940
ccatgatatt atactagatg aaaaaagttc tattaaagac agcatatata tactatctga   3000
tgatcttttg aatatacttc gtgaaagatt atttagatgt ccacaggtta aagataatac   3060
tatttctaga acacgtctat atgattattt tactagagtg tcaaagaaag aagaagcgaa   3120
aatatacgtt atattgaaag atttaaagat tgctgatata ctcggtatcg aaacagtaac   3180
gataggatca tttgtatata cgaaatatag catgttgatt aattcaattt cgtctaatgt   3240
tgatagatat tcaaaaaggt tccatgactc ttttatgaa gatattgcgg aatttataaa   3300
ggataatgaa aaaattaatg tatccagagt tgttgaatgc cttatcgtac ctaatattaa   3360
tatagagtta ttaactgaat aagtatatat aaatgattgt ttttataatg tttgttatcg   3420
catttagttt tgctgtatgg ttatcatata catttttaag gccgtatatg ataaatgaaa   3480
atatataagc acttattttt gttagtataa taacacaatg ccgtcgtata tgtatccgaa   3540
gaacgcaaga aaagtaattt caaagattat atcattacaa cttgatatta aaaaacttcc   3600
taaaaaatat ataaatacca tgttagaatt tggtctacac ggaaatctac cagcttgtat   3660
gtataaagat gccgtatcat atgatataaa taatataaga ttttttacctt ataattgtgt   3720 tatggttaaa gatttaataa atgttataaa atcatcatct gtaatagata ctagattaca   3780
tcaatctgta ttaaaacatc gtagagcgtt aatagattac ggcgatcaag acattatcac   3840
tttaatgatc attaataagt tactatcgat agatgatata tcctatatat tagataaaaa   3900
aataattcat gtaacaaaaa tattaaaaat agaccctaca gtagccaatt caaacatgaa   3960
actgaataag atagagcttg tagatgtaat aacatcaata cctaagtctt cctatacata   4020
tttatataat aaatgatca ttgatctcga tacattatta tatttatccg atgcattcca   4080
catacccccc acacatatat cattacgttc acttagagat ataaacagga ttattgaatt   4140
gcttaaaaaa tatccgaata ataatattat tgattatata tccgatagca taaaatcaaa   4200
tagttcattc attcacatac ttcatatgat aatatcaaat atgttcctg ctataatccc   4260 tagtgtaaac gattttatat ctaccgtagt tgataaagat cgacttatta atatgtatgg   4320
gattaagtgt gttgctatgt tttcgtacga tataaacatg atcgatttag agtcattaga   4380
tgactcagat tacatatttta tagaaaaaaa tatatctata tacgacgtta aatgtagaga   4440
ttttgcgaat atgattagag ataaggttaa aagagaaaag aatagaatat taactacgaa   4500
atgtgaagat attataagat atataaaatt attcagtaaa aatagaataa acgatgaaaa   4560
taataaggtg gaggaggtgt tgatacatat tgataatgta tctaaaaata ataaattatc   4620
```

```
actgtctgat atatcatctt taatggatca atttcgttta aatccatgta ccataagaaa    4680
tatattatta tcttcagcaa ctataaaatc aaaactatta gcgttacggg cagtaaaaaa    4740
ctggaaatgt tattcattga caaatgtatc aatgtataaa aaaataaagg gtgttatcgt    4800
aatggatatg gttgattata tatctactaa cattcttaaa taccataaac aattatatga    4860
taaaatgagt acgtttgaat ataaacgaga tattaaatca tgtaaatgct cgatatgttc    4920
cgactctata acacatcata tatgaaac aacatcatgt ataaattata aatctaccga    4980
```

```
actgtctgat atatcatctt taatggatca atttcgttta aatccatgta ccataagaaa    4680
tatattatta tcttcagcaa ctataaaatc aaaactatta gcgttacggg cagtaaaaaa    4740
ctggaaatgt tattcattga caaatgtatc aatgtataaa aaaataaagg gtgttatcgt    4800
aatggatatg gttgattata tatctactaa cattcttaaa taccataaac aattatatga    4860
taaaatgagt acgtttgaat ataaacgaga tattaaatca tgtaaatgct cgatatgttc    4920
cgactctata acacatcata tatgaaac  aacatcatgt ataaattata aatctaccga    4980
taatgatctt atgatagtat tgttcaatct aactagatat ttaatgcatg ggatgataca    5040
tcctaatctt ataagcgtaa aaggatgggg tccccttatt ggattattaa cgggtgatat    5100
aggtattaat ttaaaactat attccaccat gaatataaat gggctacggt atggagatat    5160
tacgttatct tcatacgata tgagtaataa attagtctct attattaata cacccatata    5220
tgagttaata ccgtttacta catgttgttc actcaatgaa tattattcaa aaattgtgat    5280
tttaataaat gttatttttag aatatatgat atctattata ttatatagaa tattgatcgt    5340
aaaaagattt aataacatta aagaatttat ttcaaaagtc gtaaatactg tactagaatc    5400
atcaggcata tattttttgtc agatgcgtgt acatgaacaa attgaattgg aaatagatga    5460
gctcattatt aatggatcta tgcctgtaca gcttatgcat ttacttctaa aggtagctac    5520
cataatatta gaggaaatca agaaatata acgtatttt tcttttaaat aaataaaaat    5580
actttttttt ttaaacaagg ggtgctacct tgtctaattg tatcttgtat tttggatctg    5640
atgcaagatt attaaataat cgtatgaaaa agtagtagat atagtttata tcgttactgg    5700
acatgatatt atgtttagtt aattcttctt tggcatgaat tctacacgtc ggacaaggta    5760
atgtatctat aatggtataa agctt                                        5785
```

<210> SEQ ID NO 222
<211> LENGTH: 722
<212> TYPE: DNA
<213> ORGANISM: Swinepox virus

<400> SEQUENCE: 222

```
ttttgatttt acgccattat

-continued

<213> ORGANISM: Swinepox virus

<400> SEQUENCE: 223
aaacaatgcg ctttaatatc aaacatgcag gtggaatagg attgtcgata agtaatatac 60
gagctaaggg tacttatata tccggtataa acggcaaatc tatggtatag tacctatgtt 120
aagaatatat aataacacag ttagatatat taatcaggga ggtgataaaa gaccaggagc 180
aatgtcgatt tatatagaac catggcacgc tgatatattc gattttctaa gctt 234

<210> SEQ ID NO 224
<211> LENGTH: 1025
<212> TYPE: DNA
<213> ORGANISM: Swinepox virus

<400> SEQUENCE: 224
ggttgctcct aacttaataa gataatccac caagatagtt ttatccgtgg tagatgcata 60
cacaacagga gaatatccta atttatctct atagtttatg gttgtgatat ctatagtata 120
tgggaccgcc gaaaaacatg tataatcgtc gtgacaatag tttaacatcg tgtttaatat 180
cgacatcatt tcatcatttt tattatattc atgttttata tgcgaacaaa gcaaattcaa 240
tatatttaaa ttagtgttat tgatgtgtct aattgtaaat atatgaatag gattcttcag 300
actattattt agtttacata catcaaatcc ttttcttatt aaaaactcaa caactttata 360
atctatattc tcattaccaa ggtatttatg caatatggtg tctccacatc tatgtacact 420
gttaatgtca ccaccatgat aaataagaaa ctttattact ttaattgtaa cattcgtatt 480
aaatgtaaaa taacaatgaa atggtgtttt atcatatata gatatcccat ttaaattagc 540
acctttatta agcagtaata atacaatttc tttcaactct tttaatttaa atacgtgcaa 600
cgatgaactt aaaaatgtag ctaacatatc agtggctata ttatcatcct gttttatatt 660
tgatattatt cttcttatat tatccatttc cttcttacaa actatttaaa cgataaccaa 720
aatgtattca tgggctacta ataatagcca cattactaga aaaaaaattt tttttcaata 780
ttatgacatt attacttaag tattattgat aagtccttca ttgttaaatg taataatata 840
tatcgttgta tttctatagg aatcctcatc cagtaactat gtttcttgca gtgcttcata 900
attacataaa tcgctttatc aatgttagaa taatacatat atgtattttt gataatattt 960
tctatatgtg atccatacat tactaaattt tttaatctta aaaaattatc ataattgaga 1020
agctt 1025

<210> SEQ ID NO 225
<211> LENGTH: 305
<212> TYPE: DNA
<213> ORGANISM: Swinepox virus

<400> SEQUENCE: 225
aagcttggat gagcaataag agtatacaaa atttagtgtt tcaattcgct catggatcag 60
aagtagaata tataggtcaa tacgatatga gatttttaaa taatatacct attcatgata 120
agtttgatgt gtttttaaat aagcacatac tatcgtatgt acttagagat aaaataaaga 180
aatcagacca cagatatgta atgtttggat tttggttatt tatctcattg gaaatgtgtt 240
atattcgata aggaacatca tatgtctgtt tctatgattc aggaggaatt accaaacgaa 300
ttcca 305

<210> SEQ ID NO 226
<211> LENGTH: 1721

<212> TYPE: DNA
<213> ORGANISM: Swinepox virus
<220> FEATURE:
<221> NAME/KEY: CDS
<222> LOCATION: (1)..(1707)

<400> S

```
gat aca cca gtc cac gat tgt aat acg act tgt caa aca ccc aaa ggt    912
Asp Thr Pro Val His Asp Cys Asn Thr Thr Cys Gln Thr Pro Lys Gly
    290                 295                 300 gct ata aac acc agc ctt cca ttt cag aat ata cat cca gtc aca att    960
Ala Ile Asn Thr Ser Leu Pro Phe Gln Asn Ile His Pro Val Thr Ile
305                 310                 315                 320 gga gaa tgt cca aaa tat gtc aaa agc aca aaa ttg aga atg gct aca   1008
Gly Glu Cys Pro Lys Tyr Val Lys Ser Thr Lys Leu Arg Met Ala Thr
                325                 330                 335 gga tta agg aat atc ccg tct att caa tct aga ggc ctg ttt gga gcc   1056
Gly Leu Arg Asn Ile Pro Ser Ile Gln Ser Arg Gly Leu Phe Gly Ala
            340                 345                 350 att gct ggc ttt att gag ggg gga tgg aca gga atg ata gat ggc tgg   1104
Ile Ala Gly Phe Ile Glu Gly Gly Trp Thr Gly Met Ile Asp Gly Trp
        355                 360                 365 tac ggt tat cac cat cag aat gag cag gga tca gga tat gca gcc gac   1152
Tyr Gly Tyr His His Gln Asn Glu Gln Gly Ser Gly Tyr Ala Ala Asp
    370                 375                 380 cga aag agc aca cag aat gcc att gac ggg atc act aac aaa gta aac   1200
Arg Lys Ser Thr Gln Asn Ala Ile Asp Gly Ile Thr Asn Lys Val Asn
385                 390                 395                 400 tct gtt att gaa aag atg aac aca caa ttc aca gca gtg ggt aaa gaa   1248
Ser Val Ile Glu Lys Met Asn Thr Gln Phe Thr Ala Val Gly Lys Glu
                405                 410                 415 ttc aac cac ctg gaa aaa aga ata gag aat tta aac aaa aag gtt gat   1296
Phe Asn His Leu Glu Lys Arg Ile Glu Asn Leu Asn Lys Lys Val Asp
            420                 425                 430 gat ggt ttt ctg gat gtt tgg act tac aat gcc gaa ctg ttg gtt cta   1344
Asp Gly Phe Leu Asp Val Trp Thr Tyr Asn Ala Glu Leu Leu Val Leu
        435                 440                 445 ttg gaa aat gaa aga act ttg gat tat cac gat tca aat gtg aag aac   1392
Leu Glu Asn Glu Arg Thr Leu Asp Tyr His Asp Ser Asn Val Lys Asn
    450                 455                 460 cta tat gag aaa gta aga agc cag cta aaa aac aat gcc aag gaa att   1440
Leu Tyr Glu Lys Val Arg Ser Gln Leu Lys Asn Asn Ala Lys Glu Ile
465                 470                 475                 480 gga aat ggc tgc ttt gaa ttt tac cac aaa tgt gat gac acg tgc atg   1488
Gly Asn Gly Cys Phe Glu Phe Tyr His Lys Cys Asp Asp Thr Cys Met
                485                 490                 495 gag agc gtc aaa aat ggg act tat gat tac cca aaa tac tca gag gaa   1536
Glu Ser Val Lys Asn Gly Thr Tyr Asp Tyr Pro Lys Tyr Ser Glu Glu
            500                 505                 510 gca aaa cta aac aga gag gag ata gat ggg gta aag ctg gaa tca aca   1584
Ala Lys Leu Asn Arg Glu Glu Ile Asp Gly Val Lys Leu Glu Ser Thr
        515                 520                 525 agg att tac cag att ttg gcg atc tat tca act gtc gcc agt tca ttg   1632
Arg Ile Tyr Gln Ile Leu Ala Ile Tyr Ser Thr Val Ala Ser Ser Leu
    530                 535                 540 gta ctg tta gtc tcc ctg ggg gca atc agt ttc tgg atg tgc tcc aat   1680
Val Leu Leu Val Ser Leu Gly Ala Ile Ser Phe Trp Met Cys Ser Asn
545                 550                 555                 560 ggg tct tta cag tgc aga ata tgt att taaaattagg atcc                1721
Gly Ser Leu Gln Cys Arg Ile Cys Ile
                565

<210> SEQ ID NO 227
<211> LENGTH: 569
<212> TYPE: PRT
<213> ORGANISM: Swinepox virus
```

<400> SEQUENCE: 227

| | | | | | | | | | | | | | | |
|---|---|---|---|---|---|---|---|---|---|---|---|---|---|---|
|Met|Asn|Ser|Asp|Pro|Ala|Ile|Leu|Leu|Val|Leu|Leu|Cys|Thr|Phe|Thr|
|1| | | |5| | | |10| | | | |15| |
|Thr|Ala|Asn|Ala|Asp|Thr|Leu|Cys|Ile|Gly|Tyr|His|Ala|Asn|Asn|Ser|
| | | |20| | | | |25| | | |30| | | |
|Thr|Asp|Thr|Val|Asp|Thr|Val|Leu|Glu|Lys|Asn|Val|Thr|Val|Thr|His|
| | |35| | | | |40| | | | |45| | | |
|Ser|Val|Asn|Leu|Leu|Glu|Asp|Arg|His|Asn|Gly|Lys|Leu|Cys|Lys|Leu|
| |50| | | | |55| | | | |60| | | | |
|Arg|Gly|Val|Ala|Pro|Leu|His|Leu|Gly|Lys|Cys|Asn|Ile|Ala|Gly|Trp|
|65| | | | |70| | | | |75| | | | |80|
|Leu|Leu|Gly|Asn|Pro|Glu|Cys|Glu|Leu|Leu|Phe|Thr|Ala|Ser|Ser|Trp|
| | | | |85| | | | |90| | | | |95| |
|Ser|Tyr|Ile|Val|Glu|Thr|Ser|Asn|Ser|Asp|Asn|Gly|Thr|Cys|Tyr|Pro|
| | | |100| | | | |105| | | | |110| | |
|Gly|Asp|Phe|Ile|Asn|Tyr|Glu|Glu|Leu|Arg|Glu|Gln|Leu|Ser|Ser|Val|
| | |115| | | | |120| | | | |125| | | |
|Ser|Ser|Phe|Glu|Arg|Phe|Glu|Ile|Phe|Pro|Lys|Ala|Ser|Ser|Trp|Pro|
| |130| | | | |135| | | | |140| | | | |
|Asn|His|Glu|Thr|Asn|Ile|Gly|Val|Thr|Ala|Ala|Cys|Pro|Tyr|Ala|Gly|
|145| | | | |150| | | | |155| | | | |160|
|Ala|Asn|Ser|Phe|Tyr|Arg|Asn|Leu|Ile|Trp|Leu|Val|Lys|Lys|Gly|Asn|
| | | | |165| | | | |170| | | | |175| |
|Ser|Tyr|Pro|Lys|Leu|Ser|Lys|Ser|Tyr|Ile|Asn|Asn|Lys|Glu|Lys|Glu|
| | | |180| | | | |185| | | | |190| | |
|Val|Leu|Val|Leu|Trp|Gly|Ile|His|His|Pro|Pro|Thr|Ser|Thr|Asp|Gln|
| | |195| | | | |200| | | | |205| | | |
|Gln|Ser|Leu|Tyr|Gln|Asn|Ala|Asp|Ala|Tyr|Val|Phe|Val|Gly|Ser|Ser|
| |210| | | | |215| | | | |220| | | | |
|Lys|Tyr|Asn|Lys|Lys|Phe|Lys|Pro|Glu|Ile|Ala|Thr|Arg|Pro|Lys|Val|
|225| | | | |230| | | | |235| | | | |240|
|Arg|Gly|Gln|Ala|Gly|Arg|Met|Asn|Tyr|Tyr|Trp|Thr|Leu|Val|Lys|Pro|
| | | | |245| | | | |250| | | | |255| |
|Gly|Asp|Thr|Ile|Thr|Phe|Glu|Ala|Thr|Gly|Asn|Leu|Val|Val|Pro|Arg|
| | | |260| | | | |265| | | | |270| | |
|Tyr|Ala|Phe|Ala|Met|Lys|Arg|Gly|Ser|Gly|Ser|Gly|Ile|Ile|Ile|Ser|
| | | |275| | | | |280| | | | |285| | |
|Asp|Thr|Pro|Val|His|Asp|Cys|Asn|Thr|Thr|Cys|Gln|Thr|Pro|Lys|Gly|
| |290| | | | |295| | | | |300| | | | |
|Ala|Ile|Asn|Thr|Ser|Leu|Pro|Phe|Gln|Asn|Ile|His|Pro|Val|Thr|Ile|
|305| | | | |310| | | | |315| | | | |320|
|Gly|Glu|Cys|Pro|Lys|Tyr|Val|Lys|Ser|Thr|Lys|Leu|Arg|Met|Ala|Thr|
| | | | |325| | | | |330| | | | |335| |
|Gly|Leu|Arg|Asn|Ile|Pro|Ser|Ile|Gln|Ser|Arg|Gly|Leu|Phe|Gly|Ala|
| | | |340| | | | |345| | | | |350| | |
|Ile|Ala|Gly|Phe|Ile|Glu|Gly|Gly|Trp|Thr|Gly|Met|Ile|Asp|Gly|Trp|
| | |355| | | | |360| | | | |365| | | |
|Tyr|Gly|Tyr|His|His|Gln|Asn|Glu|Gln|Gly|Ser|Gly|Tyr|Ala|Ala|Asp|
| |370| | | | |375| | | | |380| | | | |
|Arg|Lys|Ser|Thr|Gln|Asn|Ala|Ile|Asp|Gly|Ile|Thr|Asn|Lys|Val|Asn|
|385| | | | |390| | | | |395| | | | |400|
|Ser|Val|Ile|Glu|Lys|Met|Asn|Thr|Gln|Phe|Thr|Ala|Val|Gly|Lys|Glu|
| | | | |405| | | | |410| | | | |415| |

```
Phe Asn His Leu Glu Lys Arg Ile Glu Asn Leu Asn Lys Lys Val Asp
            420                 425                 430

Asp Gly Phe Leu Asp Val Trp Thr Tyr Asn Ala Glu Leu Leu Val Leu
        435                 440                 445

Leu Glu Asn Glu Arg Thr Leu Asp Tyr His Asp Ser Asn Val Lys Asn
    450                 455                 460

Leu Tyr Glu Lys Val Arg Ser Gln Leu Lys Asn Asn Ala Lys Glu Ile
465                 470                 475                 480

Gly Asn Gly Cys Phe Glu Phe Tyr His Lys Cys Asp Asp Thr Cys Met
                485                 490                 495

Glu Ser Val Lys Asn Gly Thr Tyr Asp Tyr Pro Lys Tyr Ser Glu Glu
            500                 505                 510

Ala Lys Leu Asn Arg Glu Glu Ile Asp Gly Val Lys Leu Glu Ser Thr
        515                 520                 525

Arg Ile Tyr Gln Ile Leu Ala Ile Tyr Ser Thr Val Ala Ser Ser Leu
    530                 535                 540

Val Leu Val Ser Leu Gly Ala Ile Ser Phe Trp Met Cys Ser Asn
545                 550                 555                 560

Gly Ser Leu Gln Cys Arg Ile Cys Ile
                565

<210> SEQ ID NO 228
<211> LENGTH: 1414
<212> TYPE: DNA
<213> ORGANISM: Swinepox virus
<220> FEATURE:
<221

```
                                                                -continued

Pro Asn Gly Thr Val Lys Asp Arg Ser Pro Tyr Arg Thr Leu Met Ser
145                 150                 155                 160 tgc ccg atc ggt gaa gct cca tct ccg tat aat tca aga ttc gaa tca      528
Cys Pro Ile Gly Glu Ala Pro Ser Pro Tyr Asn Ser Arg Phe Glu Ser
            165                 170                 175 gtt gct tgg tca gca agt gca tgc cat gat gga atg gga tgg cta aca      576
Val Ala Trp Ser Ala Ser Ala Cys His Asp Gly Met Gly Trp Leu Thr
        180                 185                 190 atc ggg att tcc ggt cca gat aat gga gca gtg gct gtt ttg aaa tac      624
Ile Gly Ile Ser Gly Pro Asp Asn Gly Ala Val Ala Val Leu Lys Tyr
            195                 200                 205 aat ggt ata ata aca gat aca ata aaa agt tgg aga aac aaa ata cta      672
Asn Gly Ile Ile Thr Asp Thr Ile Lys Ser Trp Arg Asn Lys Ile Leu
        210                 215                 220 aga aca caa gag tca gaa tgt gtt tgt ata aac ggt tca tgt ttt act      720
Arg Thr Gln Glu Ser Glu Cys Val Cys Ile Asn Gly Ser Cys Phe Thr
225                 230                 235                 240 ata atg act gat ggc cca agc aat ggg caa gcc tcg tac aaa ata ttc      768
Ile Met Thr Asp Gly Pro Ser Asn Gly Gln Ala Ser Tyr Lys Ile Phe
                245                 250                 255 aaa atg gag aaa ggg aag att att aag tca gtt gag ctg gat gca cct      816
Lys Met Glu Lys Gly Lys Ile Ile Lys Ser Val Glu Leu Asp Ala Pro
            260                 265                 270 aat tac cac tat gag gaa tgc tcc tgt tac cct gat aca ggc aaa gtg      864
Asn Tyr His Tyr Glu Glu Cys Ser Cys Tyr Pro Asp Thr Gly Lys Val
        275                 280                 285 gtg tgt gtg tgc aga gac aat tgg cat gct tca aat cga ccg tgg gtc      912
Val Cys Val Cys Arg Asp Asn Trp His Ala Ser Asn Arg Pro Trp Val
    290                 295                 300 tct ttc gat cag aat ctt gat tat cag ata ggg tac ata tgc agt ggg      960
Ser Phe Asp Gln Asn Leu Asp Tyr Gln Ile Gly Tyr Ile Cys Ser Gly
305                 310                 315                 320 gtt ttc ggt gat aat ccg cgt tct aat gat ggg aaa ggc aat tgt ggc     1008
Val Phe Gly Asp Asn Pro Arg Ser Asn Asp Gly Lys Gly Asn Cys Gly
                325                 330                 335 cca gta ctt tct aat gga gca aat gga gtg aaa gga ttc tca ttt aga     1056
Pro Val Leu Ser Asn Gly Ala Asn Gly Val Lys Gly Phe Ser Phe Arg
            340                 345                 350 tat ggc aat ggt gtt tgg ata gga aga act aaa agt atc agc tct aga     1104
Tyr Gly Asn Gly Val Trp Ile Gly Arg Thr Lys Ser Ile Ser Ser Arg
        355                 360                 365 agt gga ttt gag atg att tgg gat cca aat gga tgg acg gaa act gat     1152
Ser Gly Phe Glu Met Ile Trp Asp Pro Asn Gly Trp Thr Glu Thr Asp
    370                 375                 380 agt agt ttc tct ata aag cag gat att ata gca tta act gat tgg tca     1200
Ser Ser Phe Ser Ile Lys Gln Asp Ile Ile Ala Leu Thr Asp Trp Ser
385                 390                 395                 400 gga tac agt gga agt ttt gtc caa cat cct gaa tta aca gga atg aac     1248
Gly Tyr Ser Gly Ser Phe Val Gln His Pro Glu Leu Thr Gly Met Asn
                405                 410                 415 tgc ata agg cct tgt ttt tgg gta gag tta atc aga gga caa ccc aag     1296
Cys Ile Arg Pro Cys Phe Trp Val Glu Leu Ile Arg Gly Gln Pro Lys
            420                 425                 430 gag agc aca atc tgg act agt gga agc agc att tct ttc tgt ggc gtg     1344
Glu Ser Thr Ile Trp Thr Ser Gly Ser Ser Ile Ser Phe Cys Gly Val
        435                 440                 445 gac aat gaa acc gca agc tgg tca tgg cca gac gga gct gat ctg cca     1392
Asp Asn Glu Thr Ala Ser Trp Ser Trp Pro Asp Gly Ala Asp Leu Pro
    450                 455                 460
```

```
ttc acc att gac aag tagatct                                              1414
Phe Thr Ile Asp Lys
465
```

<210> SEQ ID NO 229
<211> LENGTH: 469
<212> TYPE: PRT
<213> ORGANISM: Swinepox virus

<400> SEQUENCE: 229

```
Met Asn Ser Asn Gln Lys Ile Ile Thr Ile Gly Ser Ile Cys Leu Ile
1               5                   10                  15

Val Gly Ile Val Ser Leu Leu Gln Ile Gly Asn Ile Val Ser Leu
            20                  25                  30

Trp Ile Ser His Ser Ile Gln Thr Gly Glu Lys Asn His Ser Glu Ile
            35                  40                  45

Cys Asn Gln Asn Ile Ile Thr Tyr Glu Asn Asn Thr Trp Val Asn Gln
        50                  55                  60

Thr Tyr Val Asn Ile Ser Asn Thr Asn Ile Ala Asp Gly Gln Gly Val
65                  70                  75                  80

Thr Ser Ile Ile Leu Ala Gly Asn Pro Pro Leu Cys Pro Ile Ile Gly
                85                  90                  95

Trp Ala Ile Tyr Ser Lys Asn Asn Ser Ile Arg Ile Gly Pro Lys Gly
            100                 105                 110

Asn Ile Phe Val Ile Lys Lys Pro Ser Ile Ser Cys Ser His Leu Glu
        115                 120                 125

Cys Lys Thr Phe Phe Leu Thr Gln Gly Ala Leu Leu Asn Asp Arg His
130                 135                 140

Pro Asn Gly Thr Val Lys Asp Arg Ser Pro Tyr Arg Thr Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Lys Ile Leu
    210                 215                 220

Arg Thr Gln Glu Ser Glu Cys Val Cys Ile Asn Gly Ser Cys Phe Thr
225                 230                 235                 240

Ile Met Thr Asp Gly Pro Ser Asn Gly Gln Ala Ser Tyr Lys Ile Phe
                245                 250                 255

Lys Met Glu Lys Gly Lys Ile Ile Lys Ser Val Glu Leu Asp Ala Pro
            260                 265                 270

Asn Tyr His Tyr Glu Glu Cys Ser Cys Tyr Pro Asp Thr Gly Lys Val
        275                 280                 285

Val Cys Val Cys Arg Asp Asn Trp His Ala Ser Asn Arg Pro Trp Val
    290                 295                 300

Ser Phe Asp Gln Asn Leu Asp Tyr Gln Ile Gly Tyr Ile Cys Ser Gly
305                 310                 315                 320

Val Phe Gly Asp Asn Pro Arg Ser Asn Asp Gly Lys Gly Asn Cys Gly
                325                 330                 335

Pro Val Leu Ser Asn Gly Ala Asn Gly Val Lys Gly Phe Ser Phe Arg
            340                 345                 350

Tyr Gly Asn Gly Val Trp Ile Gly Arg Thr Lys Ser Ile Ser Ser Arg
```

```
            355                 360                 365
Ser Gly Phe Glu Met Ile Trp Asp Pro Asn Gly Trp Thr Glu Thr Asp
    370                 375                 380

Ser Ser Phe Ser Ile Lys Gln Asp Ile Ile Ala Leu Thr Asp Trp Ser
385                 390                 395                 400

Gly Tyr Ser Gly Ser Phe Val Gln His Pro Glu Leu Thr Gly Met Asn
                405                 410                 415

Cys Ile Arg Pro Cys Phe Trp Val Glu Leu Ile Arg Gly Gln Pro Lys
            420                 425                 430

Glu Ser Thr Ile Trp Thr Ser Gly Ser Ile Ser Phe Cys Gly Val
        435                 440                 445

Asp Asn Glu Thr Ala Ser Trp Ser Trp Pro Asp Gly Ala Asp Leu Pro
450                 455                 460

Phe Thr Ile Asp Lys
465

<210> SEQ ID NO 230
<211> LENGTH: 1501
<212> TYPE: DNA
<213> ORGANISM: Swinepox virus
<220> FEATURE:
<221> NAME/KEY: CDS
<222> LOCATION: (1)..(1494)

<400> SEQUENCE: 230 atg aat tct caa ggc acc aaa cga tca tat gaa caa atg gag act ggt      48
Met Asn Ser Gln Gly Thr Lys Arg Ser Tyr Glu Gln Met Glu Thr Gly

```
                Gly Ala Ala Gly Ala Ala Val Lys Gly Val Gly Thr Ile Ala Met Glu
                            180                 185                 190 tta atc aga atg atc aaa cgt gga atc aat gac cga aac ttc tgg agg              624
Leu Ile Arg Met Ile Lys Arg Gly Ile Asn Asp Arg Asn Phe Trp Arg
            195                 200                 205 ggt gaa aat gga cga agg aca agg att gca tat gaa aga atg tgc aat              672
Gly Glu Asn Gly Arg Arg Thr Arg Ile Ala Tyr Glu Arg Met Cys Asn
        210                 215                 220 att ctc aaa gga aaa ttt cag aca gct gcc cag agg gca atg atg gat              720
Ile Leu Lys Gly Lys Phe Gln Thr Ala Ala Gln Arg Ala Met Met Asp
225                 230                 235                 240 caa gta aga gaa agt cga aac cca gga aac gct gaa att gaa gat ctc              768
Gln Val Arg Glu Ser Arg Asn Pro Gly Asn Ala Glu Ile Glu Asp Leu
                245                 250                 255 att ttc ctg gca cgg tca gca ctt att cta agg ggg tca gtt gca cat              816
Ile Phe Leu Ala Arg Ser Ala Leu Ile Leu Arg Gly Ser Val Ala His
            260                 265                 270 aag tcc tgc ctg cct gct tgt gtg tat ggg ctt gca gta gca agt ggg              864
Lys Ser Cys Leu Pro Ala Cys Val Tyr Gly Leu Ala Val Ala Ser Gly
        275                 280                 285 cat gac ttt gaa aga gaa gga tat tca ctg gtc ggg ata gac ccc ttc              912
His Asp Phe Glu Arg Glu Gly Tyr Ser Leu Val Gly Ile Asp Pro Phe
    290                 295                 300 aaa tta ctt caa aac agt caa gtg ttc agc ctg atc aga cca aat gaa              960
Lys Leu Leu Gln Asn Ser Gln Val Phe Ser Leu Ile Arg Pro Asn Glu
305                 310                 315                 320 aac cca gct cac aag agt caa ttg gtg tgg atg gca tgc cat tct gct             1008
Asn Pro Ala His Lys Ser Gln Leu Val Trp Met Ala Cys His Ser Ala
                325                 330                 335 gca ttt gag gat tta aga ata tca agt ttc ata aga ggg aag aaa gtg             1056
Ala Phe Glu Asp Leu Arg Ile Ser Ser Phe Ile Arg Gly Lys Lys Val
            340                 345                 350 gtt cca aga gga aag ctt tcc aca aga ggg gtt cag att gct tca aat             1104
Val Pro Arg Gly Lys Leu Ser Thr Arg Gly Val Gln Ile Ala Ser Asn
        355                 360                 365 gag aat gtg gaa gct atg gac tct agt acc cta aaa cta aga agc aga             1152
Glu Asn Val Glu Ala Met Asp Ser Ser Thr Leu Lys Leu Arg Ser Arg
    370                 375                 380 tat tgg gcc ata agg acc aga agt gga gga aat acc aac caa cag aag             1200
Tyr Trp Ala Ile Arg Thr Arg Ser Gly Gly Asn Thr Asn Gln Gln Lys
385                 390                 395                 400 gca tct gcg ggc cag atc agt gtg caa cct aca ttc tca gtg caa cgg             1248
Ala Ser Ala Gly Gln Ile Ser Val Gln Pro Thr Phe Ser Val Gln Arg
                405                 410                 415 aat ctc cct ttt gaa aga gca acc gtt atg gca gct ttc agc ggg aat             1296
Asn Leu Pro Phe Glu Arg Ala Thr Val Met Ala Ala Phe Ser Gly Asn
            420                 425                 430 aat gag gga cgg aca tca gac atg cga acg gaa gtt ata agg atg atg             1344
Asn Glu Gly Arg Thr Ser Asp Met Arg Thr Glu Val Ile Arg Met Met
        435                 440                 445 gaa agt gca aag cca gaa gat ttg tcc ttc cag ggg cgg gga gtc ttc             1392
Glu Ser Ala Lys Pro Glu Asp Leu Ser Phe Gln Gly Arg Gly Val Phe
    450                 455                 460 gag ctc tcg gac gaa aag gca acg aac ccg atc gtg cct tcc ttt gac             1440
Glu Leu Ser Asp Glu Lys Ala Thr Asn Pro Ile Val Pro Ser Phe Asp
465                 470                 475                 480 atg agt aat gaa ggg tct tat ttc ttc gga gac aat gca gag gag tat             1488
Met Ser Asn Glu Gly Ser Tyr Phe Phe Gly Asp Asn Ala Glu Glu Tyr
                485                 490                 495
```

```
gac aat tgaattc                                                                  1501
Asp Asn
```

<210> SEQ ID NO 231
<211> LENGTH: 498
<212> TYPE: PRT
<213> ORGANISM: Swinepox virus

<400> SEQUENCE: 231

```
Met Asn Ser Gln Gly Thr Lys Arg Ser Tyr Glu Gln Met Glu Thr Gly
  1               5                  10                  15

Gly Glu Arg Gln Asp Ala Thr Glu Ile Arg Ala Ser Val Gly Arg Met
                 20                  25                  30

Ile Gly Gly Ile Gly Arg Phe Tyr Ile Gln Met Cys Thr Glu Leu Lys
             35                  40                  45

Leu Ser Asp Tyr Glu Gly Arg Leu Ile Gln Asn Ser Ile Thr Ile Glu
         50                  55                  60

Arg Met Val Leu Ser Ala Phe Asp Glu Arg Arg Asn Lys Tyr Leu Glu
 65                  70                  75                  80

Glu His Pro Ser Ala Gly Lys Asp Pro Lys Lys Thr Gly Gly Pro Ile
                 85                  90                  95

Tyr Arg Arg Val Asp Gly Lys Trp Met Arg Glu Leu Ile Leu Tyr Asp
                100                 105                 110

Lys Glu Glu Ile Arg Arg Val Trp Arg Gln Ala Asn Asn Gly Glu Asp
            115                 120                 125

Ala Thr Ala Gly Leu Thr His Ile Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Ile Ala Met Glu
                180                 185                 190

Leu Ile Arg Met Ile Lys Arg Gly Ile Asn Asp Arg Asn Phe Trp Arg
            195                 200                 205

Gly Glu Asn Gly Arg Arg Thr Arg Ile Ala Tyr Glu Arg Met Cys Asn
        210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Leu Ala Val Ala Ser Gly
            275                 280                 285

His Asp Phe Glu Arg Glu Gly Tyr Ser Leu Val Gly Ile Asp Pro Phe
        290                 295                 300

Lys Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Ile Ser Ser Phe Ile Arg Gly Lys Lys Val
                340                 345                 350

Val Pro Arg Gly Lys Leu Ser Thr Arg Gly Val Gln Ile Ala Ser Asn
            355                 360                 365
```

```
Glu Asn Val Glu Ala Met Asp Ser Ser Thr Leu Lys Leu Arg Ser Arg
    370             375             380
Tyr Trp Ala Ile Arg Thr Arg Ser Gly Gly Asn Thr Asn Gln Gln Lys
385             390             395             400
Ala Ser Ala Gly Gln Ile Ser Val Gln Pro Thr Phe Ser Val Gln Arg
                405             410             415
Asn Leu Pro Phe Glu Arg Ala Thr Val Met Ala Ala Phe Ser Gly Asn
            420             425             430
Asn Glu Gly Arg Thr Ser Asp Met Arg Thr Glu Val Ile Arg Met Met
            435             440             445
Glu Ser Ala Lys Pro Glu Asp Leu Ser Phe Gln Gly Arg Gly Val Phe
    450             455             460
Glu Leu Ser Asp Glu Lys Ala Thr Asn Pro Ile Val Pro Ser Phe Asp
465             470             475             480
Met Ser Asn Glu Gly Ser Tyr Phe Phe Gly Asp Asn Ala Glu Glu Tyr
            485             490             495
Asp Asn
```

What is claimed is:

1. A recombinant swinepox virus comprising a foreign DNA inserted into a swinepox virus genome, wherein the foreign DNA is inserted within an approximately 3.2 kb subfragment of the HindIII K fragment of the swinepox virus genomic DNA, wherein the approximately 3.2 kb subfragment of the HindIII K fragment comprises the nucleic acid sequence of SEQ. ID NO: 1, and wherein the foreign DNA is expressed in a host cell infected by the swinepox virus.

2. The recombinant swinepox virus of claim 1, wherein the foreign DNA is inserted into an open reading frame within the region corresponding to the 3.2 kB subfragment.

3. The recombinant swinepox virus of claim 2, wherein the foreign DNA is inserted into a B18R gene.

4. The recombinant swinepox virus of claim 2, wherein the foreign DNA is inserted into a B4R gene.

5. The recombinant swinepox virus of claim 1, wherein the foreign DNA is inserted into an EcoRI site within the region corresponding to the 3.2 Kb subfragment.

6. The recombinant swinepox virus of claim 1, wherein the foreign DNA encodes a polypeptide.

7. The recombinant swinepox virus of claim 6, wherein the polypeptide is antigenic.

8. The recombinant swinepox virus of claim 1, wherein the foreign DNA encodes a detectable marker.

9. The recombinant swinepox virus of claim 8, wherein the detectable marker is *E. coli* beta-galactosidase.

10. The recombinant swinepox virus of claim 8, wherein the detectable marker is *E. coli* beta-glucuronidase.

11. The recombinant swinepox virus of claim 1, wherein the foreign DNA encodes a cytokine.

12. The recombinant swinepox virus of claim 11, wherein the cytokine is chicken myelomonocytic growth factor (cMGF) or chicken interferon (cIFN).

13. The recombinant swinepox virus of claim 11, wherein the cytokine is selected from a group consisting of interleukin-2, interleukin-6, interleukin-12, interferons, and granulocyte-macrophage colony stimulating factor.

14. The recombinant swinepox virus of claim 6, wherein the polypeptide is derived from the group consisting of: human herpesvirus, herpes simplex virus-1, herpes simplex virus-2, human cytomegalovirus, Epstein-Barr virus, Varicell-Zoster virus, human herpesvirus-6, human herpesvirus-7, human influenza, human immunodeficiency virus, rabies virus, measles virus, hepatitis B virus and hepatitis C virus.

15. The recombinant swinepox virus of claim 7, wherein the antigenic polypeptide is hepatitis B virus core protein or hepatitis B virus surface protein.

16. The recombinant swinepox virus of claim 6, wherein the polypeptide is equine influenza virus neuraminidase or equine influenza virus hemagglutinin.

17. The recombinant swinepox virus of claim 6, wherein the polypeptide is selected from the group consisting of: equine influenza virus type A/A1 aska 91 neuraminidase, equine influenza virus type A/Kentucky 92 neuraminidase, equine influenza virus type A/Prague 56 neuraminidase, equine influenza virus type A/Miami 63 neuraminidase, equine influenza virus type A/Kentucky 81 neuraminidase, herpesvirus type 1 glycoprotein B, and equine herpesvirus type 1 glycoprotein D.

18. The recombinant swinepox virus of claim 6, wherein the polypeptide is selected from the group consisting of: hog cholera virus glycoprotein E1, hog cholera virus glycoprotein E2, swine influenza virus hemagglutinin, swine influenza virus neuraminidase, swine influenza virus matrix, swine influenza virus nucleoprotein, pseudorabies virus glycoprotein B, pseudorabies virus glycoprotein C, pseudorabies virus glycoprotein D, and PRRS virus ORF7.

19. The recombinant swinepox virus of claim 6, wherein the polypeptide is selected from the group consisting of: Infectious bovine rhinotracheitis virus gE, bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and bovine parainfluenza virus type 3 hemagglutinin neuraminidase.

20. The recombinant swinepox virus of claim 6, wherein the polypeptide is bovine viral diarrhea virus (BVDV) glycoprotein 48 or bovine viral diarrhea virus glycoprotein 53.

21. The recombinant swinepox virus of claim 6, wherein the polypeptide is selected from the group consisting of:

feline immunodeficiency virus gag, feline immunodeficiency virus env, Infectious laryngotracheitis virus glycoprotein B, infectious laryngotracheitis virus glycoprotein I, infectious laryngotracheitis virus glycoprotein D, infectious bovine rhinotracheitis virus glycoprotein G, infectious bovine rhinotracheitis virus glycoprotein E, pseudorabies virus glycoprotein 50, pseudorabies virus II glycoprotein B, pseudoraties virus III glycoprotein C, pseudorabies virus glycoprotein E, pseudorabies virus glycoprotein H, marek's disease virus glycoprotein A, marek's disease virus glycoprotein B, marek's disease virus glycoprotein D, newcastle disease virus hemagglutinin, newcastle disease virus neuraminidase, newcastle disease virus fusion, infectious bursal disease virus VP2, infectious bursal disease virus VP3, infectious bursal disease virus VP4, infectious bursal disease virus polyprotein, infectious bronchitis virus spike, infectious bronchitis virus matrix, and chick anemia virus.

22. The recombinant swinepox virus of claim 6, which is designated S-SPV-120.

23. The recombinant swinepox virus of claim 6, which is designated S-SPV-121.

24. The recombinant swinepox virus of claim 6, which is designated S-SPV-122.

25. The recombinant swinepox virus of claim 6, further comprising a second foreign DNA inserted into a swinepox virus genomic DNA, wherein the second foreign DNA is inserted within the larger HindIII to BglII subfragment of the HindIII M fragment of the swinepox virus genomic DNA and is capable of being expressed in a swinepox virus infected host cell.

26. The recombinant swinepox virus of claim 25, wherein the second foreign DNA encodes a polypeptide.

27. The recombinant swinepox virus of claim 25, wherein the foreign DNA encodes a cytokine.

28. The recombinant swinepox virus of claim 26, wherein the polypeptide is swine influenza virus hemagglutinin, swine influenza virus neuraminidase, swine influenza virus matrix, swine influenza virus nucleoprotein, pseudorabies virus glycoprotein B, pseudorabies virus glycoprotein C, pseudorabies virus glycoprotein D, porcine respiratory and reproductive virus ORF2, porcine respiratory and reproductive virus ORF3, porcine respiratory and reproductive virus ORF4, porcine respiratory and reproductive virus ORF5, porcine respiratory and reproductive virus ORF6, porcine respiratory and reproductive virus ORF7, Bovine Viral Diarrhea Virus glycoprotein 45, or Bovine Viral Diarrhea Virus glycoprotein 48.

29. The recombinant swinepox virus of claim 26, which is designated S-SPV-131.

30. The recombinant swinepox virus of claim 26, which is designated S-SPV-132.

31. The recombinant swinepox virus of claim 26, wherein the polypeptide is feline immunodeficiency virus gag/protease, feline immunodeficiency virus envelope, feline leukemia virus gag/protease, feline leukemia virus envelope, canine parvovirus VP2, or canine parvovirus VP1/2.

32. The recombinant swinepox virus of claim 26, which is designated S-SPV-127.

33. The recombinant swinepox virus of claim 26, which is designated S-SPV-128.

34. The recombinant swinepox virus of claim 1, wherein the foreign DNA is under the control of an endogenous poxvirus promoter selected from the group consisting of pox O1L promoter, pox I4L promoter, pox I3L promoter, pox I2L promoter, pox I1L promoter, and pox E10R promoter.

35. The recombinant swinepox virus of claim 1, wherein the foreign DNA is under control of a heterologous promoter selected from the group consisting of: pox synthetic late promoter 1, pox synthetic late promoter 2 early promoter 2, and pox synthetic early promoter 2.

36. The recombinant swinepox virus of claim 1, designated S-SPV-059.

37. A homology vector for producing a recombinant swinepox virus by inserting foreign DNA into a swinepox viral genome which comprises:
   a) double stranded foreign DNA not usually present within the swinepox virus genome;
   b) at one end the foreign DNA, double-stranded swinepox virus DNA homologous to the virus genome located at one side of an approximately 3.2 kb subfragment of the HindIII K fragment of the coding region of the swinepox virus genome;
   c) at the other end of the foreign DNA, double-stranded swinepox virus DNA homologous to the virus genome located at the other side of an approximately 3.2 kb subfragment of the HindIII K fragment of the coding region of the swinepox virus genome;
   wherein the approximately 3.2 kb subfragment of the HindIII K fragment comprises the nucleic acid sequence of SEQ. ID NO: 1.

38. The homology vector of claim 37, wherein the foreign DNA encodes a cytokine.

39. The homology vector of claim 38, wherein the cytokine is chicken myelomonocytic growth factor (cMGF) or chicken interferon (cIFN).

40. The homology vector of claim 37, wherein the foreign DNA encodes a polypeptide.

41. A homology vector of claim 40, wherein the polypeptide is antigenic.

42. The homology vector of claim 37, wherein the foreign DNA is under control of a promoter.

43. An immunogenic composition which comprises an effective immunizing amount of the recombinant swinepox virus of claim 1, and a suitable carrier.

44. A method of immunizing an animal against an animal pathogen which comprises administering to the animal an effective immunizing dose of the vaccine of claim 43.

* * * * *

UNITED STATES PATENT AND TRADEMARK OFFICE
CERTIFICATE OF CORRECTION

PATENT NO. : 6,221,361 B1
DATED : April 24, 2001
INVENTOR(S) : Mark D. Cochran and David E. Junker It is certified that error appears in the above-identified patent and that said Letters Patent is hereby corrected as shown below:

<u>Column 269,</u>
Line 24, change the claim reference number "6" to read -- 1 --.

Signed and Sealed this

Sixteenth Day of September, 2003

JAMES E. ROGAN
*Director of the United States Patent and Trademark Office*